(12) United States Patent
Benenato et al.

(10) Patent No.: US 12,312,293 B2
(45) Date of Patent: *May 27, 2025

(54) BRANCHED TAIL LIPID COMPOUNDS AND COMPOSITIONS FOR INTRACELLULAR DELIVERY OF THERAPEUTIC AGENTS

(71) Applicant: ModernaTX, Inc., Cambridge, MA (US)

(72) Inventors: Kerry E. Benenato, Cambridge, MA (US); Mark Cornebise, Arlington, MA (US); Edward Hennessy, Cambridge, MA (US); Ellalahewage S. Kumarasinghe, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 162 days.

This patent is subject to a terminal disclaimer.

(21) Appl. No.: 18/164,136

(22) Filed: Feb. 3, 2023

(65) Prior Publication Data

US 2023/0286903 A1    Sep. 14, 2023

Related U.S. Application Data

(63) Continuation of application No. 17/324,426, filed on May 19, 2021, now Pat. No. 11,597,698, which is a continuation of application No. 17/025,779, filed on Sep. 18, 2020, now Pat. No. 11,066,355.

(60) Provisional application No. 62/902,927, filed on Sep. 19, 2019.

(51) Int. Cl.
| | |
|---|---|
| C07C 229/24 | (2006.01) |
| A61K 9/127 | (2006.01) |
| A61K 9/1272 | (2025.01) |
| A61K 31/713 | (2006.01) |
| A61K 47/54 | (2017.01) |
| A61K 48/00 | (2006.01) |

(52) U.S. Cl.
CPC .......... *C07C 229/24* (2013.01); *A61K 9/1272* (2013.01); *A61K 31/713* (2013.01); *A61K 47/543* (2017.08); *A61K 48/0033* (2013.01); *A61K 48/005* (2013.01)

(58) Field of Classification Search
CPC .... C07C 229/24; A61K 47/543; A61K 9/1272
See application file for complete search history.

(56) References Cited

U.S. PATENT DOCUMENTS

| | | | |
|---|---|---|---|
| 3,324,182 A | 6/1967 | De et al. | |
| 3,799,876 A | 3/1974 | White et al. | |
| 3,872,171 A | 3/1975 | Cronin et al. | |
| 4,125,544 A | 11/1978 | Dygos | |
| 4,957,735 A | 9/1990 | Huang | |
| 5,807,861 A | 9/1998 | Klein et al. | |
| 6,143,276 A | 11/2000 | Unger | |
| 6,303,378 B1 | 10/2001 | Bridenbaugh et al. | |
| 6,395,253 B2 | 5/2002 | Levy et al. | |
| 6,652,886 B2 | 11/2003 | Ahn et al. | |
| 6,696,038 B1 | 2/2004 | Mahato et al. | |
| 7,268,120 B1 | 9/2007 | Horton et al. | |
| 7,371,404 B2 | 5/2008 | Panzner et al. | |
| 7,943,168 B2 | 5/2011 | Schlesinger et al. | |
| 8,058,069 B2 | 11/2011 | Yaworski et al. | |
| 8,158,601 B2 | 4/2012 | Chen et al. | |
| 8,420,123 B2 | 4/2013 | Troiano et al. | |
| 8,440,614 B2 | 5/2013 | Castor | |
| 8,449,916 B1 | 5/2013 | Bellaire et al. | |
| 8,450,298 B2 | 5/2013 | Mahon et al. | |
| 8,460,696 B2 | 6/2013 | Slobodkin et al. | |
| 8,460,709 B2 | 6/2013 | Ausborn et al. | |
| 8,563,041 B2 | 10/2013 | Grayson et al. | |
| 8,568,784 B2 | 10/2013 | Lillard et al. | |
| 8,569,256 B2 | 10/2013 | Heyes et al. | |
| 8,580,297 B2 | 11/2013 | Essler et al. | |
| 8,603,499 B2 | 12/2013 | Zale et al. | |
| 8,603,500 B2 | 12/2013 | Zale et al. | |
| 8,603,501 B2 | 12/2013 | Zale et al. | |
| 8,603,534 B2 | 12/2013 | Zale et al. | |
| 8,603,535 B2 | 12/2013 | Troiano et al. | |
| 8,609,142 B2 | 12/2013 | Troiano et al. | |
| 8,613,951 B2 | 12/2013 | Zale et al. | |
| 8,613,954 B2 | 12/2013 | Zale et al. | |

(Continued)

FOREIGN PATENT DOCUMENTS

| | | |
|---|---|---|
| AU | 652831 B2 | 9/1994 |
| CN | 102068701 A | 5/2011 |

(Continued)

OTHER PUBLICATIONS

Abdelwahed, W., et al., "Freeze-drying of nanoparticles: formulation, process and storage considerations," Advanced Drug Delivery Reviews 58, pp. 1688-1713, Dec. 30, 2006, Epub Oct. 6, 2006.
Akinc, A., et al., "Targeted Delivery of RNAi Therapeutics with Endogenous and Exogenous Ligand-Based Mechanisms," Molecular Therapy : The Journal of the American Society of Gene Therapy 18(7):1357-1364, Academic Press, United States (2010).
Akinc et al., Development of Lipidoid-siRNA Formulations for Systemic Delivery to the Liver, Molecular Therapy, May 2009, vol. 17, No. 5, pp. 872-879.

(Continued)

*Primary Examiner* — Sikarl A Witherspoon
(74) *Attorney, Agent, or Firm* — COOLEY LLP

(57) ABSTRACT

The disclosure features novel lipids and compositions involving the same. Lipid nanoparticles (e.g., empty LNPs or loaded LNPs) include a novel lipid as well as additional lipids such as phospholipids, structural lipids, and PEG lipids. Lipid nanoparticles (e.g., empty LNPs or loaded LNPs) further including therapeutic and/or prophylactics such as RNA are useful in the delivery of therapeutic and/or prophylactics to mammalian cells or organs to, for example, regulate polypeptide, protein, or gene expression.

20 Claims, No Drawings

(56) References Cited

U.S. PATENT DOCUMENTS

| | | |
|---|---|---|
| 8,617,608 B2 | 12/2013 | Zale et al. |
| 8,618,240 B2 | 12/2013 | Podobinski et al. |
| 8,637,083 B2 | 1/2014 | Troiano et al. |
| 8,642,076 B2 | 2/2014 | Manoharan et al. |
| 8,652,487 B2 | 2/2014 | Maldonado |
| 8,652,528 B2 | 2/2014 | Troiano et al. |
| 8,663,599 B1 | 3/2014 | Sung et al. |
| 8,663,700 B2 | 3/2014 | Troiano et al. |
| 8,668,926 B1 | 3/2014 | Mousa et al. |
| 8,685,368 B2 | 4/2014 | Reineke |
| 8,691,750 B2 | 4/2014 | Constien et al. |
| 8,697,098 B2 | 4/2014 | Perumal et al. |
| 8,703,204 B2 | 4/2014 | Bloom et al. |
| 8,709,483 B2 | 4/2014 | Farokhzad et al. |
| 8,715,736 B2 | 5/2014 | Sachdeva et al. |
| 8,715,741 B2 | 5/2014 | Maitra et al. |
| 8,728,527 B2 | 5/2014 | Singh |
| 8,734,832 B2 | 5/2014 | O'Hagan et al. |
| 8,734,846 B2 | 5/2014 | Ali et al. |
| 8,734,853 B2 | 5/2014 | Sood et al. |
| 8,802,644 B2 | 8/2014 | Chen et al. |
| 9,006,487 B2 | 4/2015 | Anderson et al. |
| 9,029,590 B2 | 5/2015 | Colletti et al. |
| 9,394,234 B2 | 7/2016 | Chen et al. |
| 9,717,690 B2 | 8/2017 | Guild et al. |
| 9,738,593 B2 | 8/2017 | Ansell et al. |
| 9,867,888 B2 | 1/2018 | Benenato |
| 9,868,691 B2 | 1/2018 | Benenato |
| 9,868,692 B2 | 1/2018 | Benenato |
| 9,868,693 B2 | 1/2018 | Benenato |
| 10,106,490 B2 | 10/2018 | Du |
| 10,166,298 B2 | 1/2019 | Ansell et al. |
| 10,195,156 B2 | 2/2019 | Benenato et al. |
| 10,266,485 B2 | 4/2019 | Benenato |
| 10,392,341 B2 | 8/2019 | Benenato et al. |
| 10,442,756 B2 | 10/2019 | Benenato et al. |
| 10,799,463 B2 | 10/2020 | Benenato et al. |
| 10,857,105 B2 | 12/2020 | Benenato et al. |
| 11,001,861 B2 | 5/2021 | Martini et al. |
| 11,066,355 B2 | 7/2021 | Benenato et al. |
| 11,203,569 B2 | 12/2021 | Almarsson et al. |
| 11,220,476 B2 | 1/2022 | Benenato et al. |
| 11,504,337 B2 | 11/2022 | Martini et al. |
| 11,583,504 B2 | 2/2023 | Brader |
| 11,597,698 B2 | 3/2023 | Benenato et al. |
| 11,969,506 B2 | 4/2024 | Patel et al. |
| 12,077,501 B2 | 9/2024 | Benenato et al. |
| 12,144,895 B2 | 11/2024 | Brader |
| 12,151,995 B2 | 11/2024 | Benenato |
| 2003/0073619 A1 | 4/2003 | Mahato et al. |
| 2003/0092653 A1 | 5/2003 | Kisich et al. |
| 2004/0142474 A1 | 7/2004 | Mahato et al. |
| 2005/0222064 A1 | 10/2005 | Vargeese et al. |
| 2006/0008910 A1 | 1/2006 | MacLachlan et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2007/0252295 A1 | 11/2007 | Panzner et al. |
| 2009/0042825 A1 | 2/2009 | Matar et al. |
| 2009/0042829 A1 | 2/2009 | Matar et al. |
| 2010/0285112 A1 | 11/2010 | Novobrantseva et al. |
| 2010/0324120 A1 | 12/2010 | Chen et al. |
| 2011/0009641 A1 | 1/2011 | Anderson et al. |
| 2011/0200582 A1 | 8/2011 | Baryza et al. |
| 2011/0244026 A1 | 10/2011 | Guild et al. |
| 2012/0136073 A1 | 5/2012 | Yang et al. |
| 2012/0177724 A1 | 7/2012 | Irvine et al. |
| 2012/0178702 A1 | 7/2012 | Huang et al. |
| 2012/0226085 A1 | 9/2012 | Ishihara et al. |
| 2012/0295832 A1 | 11/2012 | Constien et al. |
| 2013/0017223 A1 | 1/2013 | Hope et al. |
| 2013/0064894 A1 | 3/2013 | Martin et al. |
| 2013/0065942 A1 | 3/2013 | Matar et al. |
| 2013/0090372 A1 | 4/2013 | Budzik et al. |
| 2013/0108685 A1 | 5/2013 | Kuboyama et al. |
| 2013/0115273 A1 | 5/2013 | Yang et al. |
| 2013/0115274 A1 | 5/2013 | Knopov et al. |
| 2013/0116307 A1 | 5/2013 | Heyes et al. |
| 2013/0122104 A1 | 5/2013 | Yaworski et al. |
| 2013/0123338 A1 | 5/2013 | Heyes et al. |
| 2013/0129785 A1 | 5/2013 | Manoharan et al. |
| 2013/0130348 A1 | 5/2013 | Gu et al. |
| 2013/0142868 A1 | 6/2013 | Hoekman et al. |
| 2013/0142876 A1 | 6/2013 | Howard et al. |
| 2013/0150625 A1 | 6/2013 | Budzik et al. |
| 2013/0156845 A1 | 6/2013 | Manoharan et al. |
| 2013/0156849 A1 | 6/2013 | De Fougerolles et al. |
| 2013/0164400 A1 | 6/2013 | Knopov et al. |
| 2013/0171241 A1 | 7/2013 | Geall |
| 2013/0172406 A1 | 7/2013 | Zale et al. |
| 2013/0178541 A1 | 7/2013 | Stanton et al. |
| 2013/0183244 A1 | 7/2013 | Hanes et al. |
| 2013/0183355 A1 | 7/2013 | Jain et al. |
| 2013/0183372 A1 | 7/2013 | Schutt et al. |
| 2013/0183373 A1 | 7/2013 | Schutt et al. |
| 2013/0183375 A1 | 7/2013 | Schutt et al. |
| 2013/0189351 A1 | 7/2013 | Geall |
| 2013/0195759 A1 | 8/2013 | Mirkin et al. |
| 2013/0195765 A1 | 8/2013 | Gho et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236500 A1 | 9/2013 | Zale et al. |
| 2013/0236533 A1 | 9/2013 | Von Andrian et al. |
| 2013/0236550 A1 | 9/2013 | Ausborn et al. |
| 2013/0243827 A1 | 9/2013 | Troiano et al. |
| 2013/0243848 A1 | 9/2013 | Lobovkina et al. |
| 2013/0243867 A1 | 9/2013 | Mohapatra et al. |
| 2013/0251766 A1 | 9/2013 | Zale et al. |
| 2013/0251816 A1 | 9/2013 | Zale et al. |
| 2013/0251817 A1 | 9/2013 | Zale et al. |
| 2013/0266617 A1 | 10/2013 | Mirosevich et al. |
| 2013/0273117 A1 | 10/2013 | Podobinski et al. |
| 2013/0274504 A1 | 10/2013 | Colletti et al. |
| 2013/0274523 A1 | 10/2013 | Bawiec, III et al. |
| 2013/0280334 A1 | 10/2013 | Karp et al. |
| 2013/0280339 A1 | 10/2013 | Zale et al. |
| 2013/0295183 A1 | 11/2013 | Troiano et al. |
| 2013/0295191 A1 | 11/2013 | Troiano et al. |
| 2013/0302432 A1 | 11/2013 | Zale et al. |
| 2013/0302433 A1 | 11/2013 | Troiano et al. |
| 2013/0315831 A1 | 11/2013 | Shi et al. |
| 2013/0330401 A1 | 12/2013 | Payne et al. |
| 2013/0338210 A1 | 12/2013 | Manoharan et al. |
| 2013/0344158 A1 | 12/2013 | Zale et al. |
| 2014/0017327 A1 | 1/2014 | Cheng et al. |
| 2014/0017329 A1 | 1/2014 | Mousa |
| 2014/0037573 A1 | 2/2014 | Eliasof et al. |
| 2014/0037660 A1 | 2/2014 | Fotin-Mleczek et al. |
| 2014/0037714 A1 | 2/2014 | Quay et al. |
| 2014/0039032 A1 | 2/2014 | Kuboyama et al. |
| 2014/0044772 A1 | 2/2014 | MacLachlan et al. |
| 2014/0044791 A1 | 2/2014 | Basilion et al. |
| 2014/0045913 A1 | 2/2014 | Kuboyama et al. |
| 2014/0050775 A1 | 2/2014 | Slobodkin et al. |
| 2014/0057109 A1 | 2/2014 | Menchen et al. |
| 2014/0065172 A1 | 3/2014 | Echeverri et al. |
| 2014/0065204 A1 | 3/2014 | Hayes et al. |
| 2014/0065228 A1 | 3/2014 | Yaworski et al. |
| 2014/0079774 A1 | 3/2014 | Brinker et al. |
| 2014/0093575 A1 | 4/2014 | Hammond et al. |
| 2014/0093579 A1 | 4/2014 | Zale et al. |
| 2014/0113137 A1 | 4/2014 | Podobinski et al. |
| 2014/0121263 A1 | 5/2014 | Fitzgerald et al. |
| 2014/0121393 A1 | 5/2014 | Manoharan et al. |
| 2014/0134260 A1 | 5/2014 | Heyes et al. |
| 2014/0141070 A1 | 5/2014 | Geall et al. |
| 2014/0141089 A1 | 5/2014 | Liang |
| 2014/0141483 A1 | 5/2014 | Bossard et al. |
| 2014/0142165 A1 | 5/2014 | Grayson et al. |
| 2014/0142254 A1 | 5/2014 | Fonnum et al. |
| 2014/0161830 A1 | 6/2014 | Anderson et al. |
| 2014/0288160 A1 | 9/2014 | Guild et al. |

(56) References Cited

U.S. PATENT DOCUMENTS

| | | |
|---|---|---|
| 2014/0308304 A1 | 10/2014 | Manoharan et al. |
| 2015/0174260 A1 | 6/2015 | Yang et al. |
| 2015/0174261 A1 | 6/2015 | Kuboyama et al. |
| 2015/0239926 A1 | 8/2015 | Payne et al. |
| 2015/0284317 A1 | 10/2015 | Colletti et al. |
| 2015/0343062 A1 | 12/2015 | Kuboyama et al. |
| 2015/0376115 A1 | 12/2015 | Ansell et al. |
| 2016/0002178 A1 | 1/2016 | Fenton et al. |
| 2016/0009657 A1 | 1/2016 | Anderson et al. |
| 2016/0151284 A1 | 6/2016 | Heyes et al. |
| 2016/0317458 A1 | 11/2016 | Brito et al. |
| 2016/0361411 A1 | 12/2016 | Gindy et al. |
| 2017/0119904 A1 | 5/2017 | Ansell et al. |
| 2018/0201572 A1 | 7/2018 | Benenato |
| 2018/0273467 A1 | 9/2018 | Benenato |
| 2018/0303925 A1 | 10/2018 | Weissman et al. |
| 2018/0333366 A1 | 11/2018 | Benenato et al. |
| 2018/0369419 A1 | 12/2018 | Benenato et al. |
| 2019/0016669 A1 | 1/2019 | Benenato et al. |
| 2019/0298657 A1 | 10/2019 | Martini et al. |
| 2019/0298658 A1 | 10/2019 | Benenato et al. |
| 2019/0314291 A1 | 10/2019 | Besin et al. |
| 2019/0314292 A1 | 10/2019 | Benenato et al. |
| 2019/0314524 A1 | 10/2019 | Ansell et al. |
| 2019/0336452 A1 | 11/2019 | Brader |
| 2019/0390181 A1 | 12/2019 | Benenato et al. |
| 2020/0069599 A1 | 3/2020 | Smith et al. |
| 2020/0129445 A1 | 4/2020 | Patel et al. |
| 2020/0131116 A1 | 4/2020 | Almarsson et al. |
| 2021/0087135 A1 | 3/2021 | Benenato et al. |
| 2021/0154148 A1 | 5/2021 | Benenato et al. |
| 2021/0161829 A1 | 6/2021 | Benenato et al. |
| 2021/0198200 A1 | 7/2021 | Benenato et al. |
| 2022/0073449 A1 | 3/2022 | Almarsson et al. |
| 2022/0106259 A1 | 4/2022 | Benenato et al. |
| 2022/0265857 A1 | 8/2022 | Besin et al. |
| 2022/0380299 A1 | 12/2022 | Benenato et al. |
| 2022/0409536 A1 | 12/2022 | Benenato et al. |
| 2023/0364024 A1 | 11/2023 | Brader |
| 2024/0124388 A1 | 4/2024 | Benenato et al. |
| 2024/0226026 A1 | 7/2024 | Benenato |

FOREIGN PATENT DOCUMENTS

| | | | |
|---|---|---|---|
| CN | 102204920 A | | 10/2011 |
| CN | 102813929 A | | 12/2012 |
| CN | 104644555 A | | 5/2015 |
| EP | 0737750 A2 | | 10/1996 |
| EP | 2073848 B1 | | 8/2013 |
| EP | 1404860 B1 | | 11/2013 |
| JP | 2000169864 A | | 6/2000 |
| WO | WO-9314778 A1 | | 8/1993 |
| WO | WO-1999014346 A2 | | 3/1999 |
| WO | WO-9915580 A1 | | 4/1999 |
| WO | WO-9952503 A2 | | 10/1999 |
| WO | WO-9954344 A1 | | 10/1999 |
| WO | WO-03086280 A2 | | 10/2003 |
| WO | WO-2005034979 A2 | | 4/2005 |
| WO | WO-2006063249 A2 | | 6/2006 |
| WO | WO-2008042973 A2 | | 4/2008 |
| WO | WO-2009024599 A1 | | 2/2009 |
| WO | WO-2009053686 A1 | | 4/2009 |
| WO | WO-2009086558 A1 | | 7/2009 |
| WO | WO-2009127060 A1 | | 10/2009 |
| WO | WO-2009129385 A1 | | 10/2009 |
| WO | WO-2009129395 A1 | | 10/2009 |
| WO | WO-2010030739 A1 | | 3/2010 |
| WO | WO-2010042877 A1 | | 4/2010 |
| WO | WO-2010053572 A2 | | 5/2010 |
| WO | WO-2010054406 A1 | | 5/2010 |
| WO | WO-2010060818 A1 | | 6/2010 |
| WO | WO-2010088537 A2 | | 8/2010 |
| WO | WO-2010129709 A1 | | 11/2010 |
| WO | WO-2010135207 A1 | | 11/2010 |
| WO | WO-2011017548 A1 | | 2/2011 |
| WO | WO-2011058990 A1 | | 5/2011 |
| WO | WO-2011068810 A1 | | 6/2011 |
| WO | WO-2011127255 A1 | | 10/2011 |
| WO | WO-2011136368 A1 | | 11/2011 |
| WO | WO-2012000104 A1 | | 1/2012 |
| WO | WO-2012006376 A2 | | 1/2012 |
| WO | WO-2012006378 A1 | | 1/2012 |
| WO | WO-2012030901 A1 | | 3/2012 |
| WO | WO-2012031043 A1 | | 3/2012 |
| WO | WO-2012031046 A2 | | 3/2012 |
| WO | WO-2012054365 A2 | | 4/2012 |
| WO | WO-2012129483 A1 | | 9/2012 |
| WO | WO-2012149252 A2 | | 11/2012 |
| WO | WO-2012149255 A2 | | 11/2012 |
| WO | WO-2012149265 A2 | | 11/2012 |
| WO | WO-2012149282 A2 | | 11/2012 |
| WO | WO-2012149301 A2 | | 11/2012 |
| WO | WO-2012149376 A2 | | 11/2012 |
| WO | WO-2012149393 A2 | | 11/2012 |
| WO | WO-2012153338 A2 | | 11/2012 |
| WO | WO-2012170889 A1 | | 12/2012 |
| WO | WO-2012170930 A1 | | 12/2012 |
| WO | WO-2013006825 A1 | | 1/2013 |
| WO | WO-2013006834 A1 | | 1/2013 |
| WO | WO-2013006837 A1 | | 1/2013 |
| WO | WO-2013006838 A1 | | 1/2013 |
| WO | WO-2013006842 A2 | | 1/2013 |
| WO | WO-2013016058 A1 | | 1/2013 |
| WO | WO-2013033438 A2 | | 3/2013 |
| WO | WO-2013033563 A1 | | 3/2013 |
| WO | WO-2013036835 A1 | | 3/2013 |
| WO | WO-2013049328 A1 | | 4/2013 |
| WO | WO-2013052167 A2 | | 4/2013 |
| WO | WO-2013056132 A2 | | 4/2013 |
| WO | WO-2013057715 A1 | | 4/2013 |
| WO | WO-2013059496 A1 | | 4/2013 |
| WO | WO-2013059922 A1 | | 5/2013 |
| WO | WO-2013064911 A2 | | 5/2013 |
| WO | WO-2013066903 A1 | | 5/2013 |
| WO | WO-2013067537 A1 | | 5/2013 |
| WO | WO-2013070872 A1 | | 5/2013 |
| WO | WO-2013072929 A2 | | 5/2013 |
| WO | WO-2013086322 A1 | | 6/2013 |
| WO | WO-2013086354 A1 | | 6/2013 |
| WO | WO-2013086373 A1 | | 6/2013 |
| WO | WO-2013086526 A1 | | 6/2013 |
| WO | WO-2013087083 A1 | | 6/2013 |
| WO | WO-2013087791 A1 | | 6/2013 |
| WO | WO-2013093648 A2 | | 6/2013 |
| WO | WO-2013126803 A1 | | 8/2013 |
| WO | WO-2013135359 A1 | | 9/2013 |
| WO | WO-2013143555 A1 | | 10/2013 |
| WO | WO-2013143683 A1 | | 10/2013 |
| WO | WO-2013148186 A1 | | 10/2013 |
| WO | WO-2013148541 A1 | | 10/2013 |
| WO | WO-2013149141 A1 | | 10/2013 |
| WO | WO-2013151650 A1 | | 10/2013 |
| WO | WO-2013155487 A1 | | 10/2013 |
| WO | WO-2013158127 A1 | | 10/2013 |
| WO | WO-2013158579 A1 | | 10/2013 |
| WO | WO-2013155493 A9 | | 11/2013 |
| WO | WO-2013166498 A1 | | 11/2013 |
| WO | WO-2013173693 A1 | | 11/2013 |
| WO | WO-2013177419 A2 | | 11/2013 |
| WO | WO-2013177421 A2 | | 11/2013 |
| WO | WO-2013185069 A1 | | 12/2013 |
| WO | WO-2014007398 A1 | | 1/2014 |
| WO | WO-2014008334 A1 | | 1/2014 |
| WO | WO-2014026284 A1 | | 2/2014 |
| WO | WO-2014028487 A1 | | 2/2014 |
| WO | WO-2014028763 A1 | | 2/2014 |
| WO | WO-2014047649 A1 | | 3/2014 |
| WO | WO-2014048969 A1 | | 4/2014 |
| WO | WO-2014052634 A1 | | 4/2014 |
| WO | WO-2014054026 A1 | | 4/2014 |
| WO | WO-2014071072 A2 | | 5/2014 |
| WO | WO-2014072997 A1 | | 5/2014 |
| WO | WO-2014089486 A1 | | 6/2014 |
| WO | WO-2014144196 A1 | | 9/2014 |

(56) References Cited

FOREIGN PATENT DOCUMENTS

| | | |
|---|---|---|
| WO | WO-2014160243 A1 | 10/2014 |
| WO | WO-2014172045 A1 | 10/2014 |
| WO | WO-2014182661 A2 | 11/2014 |
| WO | WO-2014210356 A1 | 12/2014 |
| WO | WO-2015011633 A1 | 1/2015 |
| WO | WO-2015095346 A1 | 6/2015 |
| WO | WO-2015130584 A2 | 9/2015 |
| WO | WO-2015154002 A1 | 10/2015 |
| WO | WO-2015199952 A1 | 12/2015 |
| WO | WO-2016004202 A1 | 1/2016 |
| WO | WO-2016004318 A1 | 1/2016 |
| WO | WO-2016118697 A1 | 7/2016 |
| WO | WO-2016118724 A1 | 7/2016 |
| WO | WO-2016176330 A1 | 11/2016 |
| WO | WO-2017004143 A1 | 1/2017 |
| WO | WO-2017010573 A1 | 1/2017 |
| WO | WO-2017015630 A2 | 1/2017 |
| WO | WO-2017031232 A1 | 2/2017 |
| WO | WO-2017049245 A2 | 3/2017 |
| WO | WO-2017070616 A2 | 4/2017 |
| WO | WO-2017070626 A2 | 4/2017 |
| WO | WO-2017075531 A1 | 5/2017 |
| WO | WO-2017099823 A1 | 6/2017 |
| WO | WO-2017100744 A1 | 6/2017 |
| WO | WO-2017112865 A1 | 6/2017 |
| WO | WO-2017117528 A1 | 7/2017 |
| WO | WO-2017127750 A1 | 7/2017 |
| WO | WO-2017176974 A1 | 10/2017 |
| WO | WO-2017180917 A2 | 10/2017 |
| WO | WO-2017192470 A1 | 11/2017 |
| WO | WO-2017201317 A1 | 11/2017 |
| WO | WO-2017201325 A1 | 11/2017 |
| WO | WO-2017201328 A1 | 11/2017 |
| WO | WO-2017201332 A1 | 11/2017 |
| WO | WO-2017201333 A1 | 11/2017 |
| WO | WO-2017201340 A2 | 11/2017 |
| WO | WO-2017201342 A1 | 11/2017 |
| WO | WO-2017201346 A1 | 11/2017 |
| WO | WO-2017201347 A1 | 11/2017 |
| WO | WO-2017201348 A1 | 11/2017 |
| WO | WO-2017201349 A1 | 11/2017 |
| WO | WO-2017201350 A1 | 11/2017 |
| WO | WO-2017201352 A1 | 11/2017 |
| WO | WO-2017218704 A1 | 12/2017 |
| WO | WO-2018078053 A1 | 5/2018 |
| WO | WO-2018081480 A1 | 5/2018 |
| WO | WO-2018081638 A1 | 5/2018 |
| WO | WO-2018089540 A1 | 5/2018 |
| WO | WO-2018144775 A1 | 8/2018 |
| WO | WO-2018170260 A1 | 9/2018 |
| WO | WO-2018170270 A1 | 9/2018 |
| WO | WO-2018170306 A1 | 9/2018 |
| WO | WO-2018170322 A1 | 9/2018 |
| WO | WO-2018170336 A1 | 9/2018 |
| WO | WO-2018191719 A1 | 10/2018 |
| WO | WO-2018200943 A1 | 11/2018 |
| WO | WO-2018225871 A1 | 12/2018 |
| WO | WO-2018232120 A1 | 12/2018 |
| WO | WO-2019036008 A1 | 2/2019 |
| WO | WO-2019036030 A1 | 2/2019 |
| WO | WO-2019046809 A1 | 3/2019 |
| WO | WO-2019089828 A1 | 5/2019 |
| WO | WO-2019152557 A1 | 8/2019 |
| WO | WO-2019193183 A2 | 10/2019 |
| WO | WO-2019202035 A1 | 10/2019 |
| WO | WO-2020002525 A1 | 1/2020 |
| WO | WO-2020061367 A1 | 3/2020 |
| WO | WO-2020061457 A1 | 3/2020 |
| WO | WO-2020123300 A2 | 6/2020 |
| WO | WO-2021055833 A1 | 3/2021 |
| WO | WO-2021055835 A1 | 3/2021 |
| WO | WO-2021055849 A1 | 3/2021 |
| WO | WO-2021204175 A1 | 10/2021 |
| WO | WO-2022204288 A1 | 9/2022 |
| WO | WO-2023107669 A1 | 6/2023 |

OTHER PUBLICATIONS

Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003; 14(3):191-202.

Andries, O., et al., Comparison of the gene transfer efficiency of mRNA/GL67 and pDNA/GL67 complexes in respiratory cells. Mol Pharmaceutics. 2012; 9: 2136-2145.

Ashizawa et al., "Liposomal delivery of nucleic acid-based anti-cancer therapeutics: BP-100-1.01," Expert Opin. Drug Deliv., (2014) 12(7):1107-1120.

Bag, J., Recovery of normal protein synthesis in heat-shocked chicken myotubes by liposome-mediated transfer of mRNAs. Can. J. Biochem. Cell Biol. 1985; 63(3): 231-235.

Belliveau et al., "Microfluidic Synthesis of Highly Potent Limit-size Lipid Nanoparticles for In Vivo Delivery of siRNA," Molecular Therapy-Nucleic Acids, 2012, 1, e37, 9 pages.

Berge et al., "Pharmaceutical salts," Journal of Pharmaceutical Sciences, 1977, vol. 66, No. 1, pp. 1-19.

Bettinger, T. et al., Peptide-mediated RNA delivery: a novel approach for enhanced transfection of primary and post-mitotic cells. Nucleic Acids Res. Sep. 15, 2001;29(18):3882-91.

Bolhassani A., et al. , Improvement of Different Vaccine Delivery Systems For Cancer Therapy, Molecular Cancer, Biomed Central, London, GB, 2011, vol. 10, No. 3, pp. 1-20.

Bonehill, A., et al., Single-step antigen loading and activation of dendritic cells by mRNA electroporation for the purpose of therapeutic vaccination in melanoma patients. Clin Cancer Res. May 2009; 15(10): 3366-3375.

Bouxsein, N.F., et al., Structure and gene silencing activities of monovalent and pentavalent cationic lipid vectors complexed with siRNA. Biochem. 2007; 46(16): 4785-4792.

Bowman, "N-Substituted Amino-acids. Part II. The Reductive Alkylation of Amino-acids," Journal of the Chemical Society (1950), pp. 1346-1349.

Cao et al., "Approach on quantitative structure-activity relationship for design of a pH neutral carrier containing tertiary amino group," Analytica Chimica Acta (2007) 581: 19-26.

Chen, D., et al., Rapid discovery of potent siRNA-containing lipid nanoparticles enabled by controlled microfluidic formulation. J Am Chem Soc. 2012; 134: 6948-6951.

Chen, S. et al., "Development of lipid nanoparticle formulations of siRNA for hepatocyte gene silencing following subcutaneous administration," J Control Release, 2014, 196, 106-112.

Cun, Dongmei, et al., Preparation and characterization of poly(DL-lactide-co-glycolide) nanoparticles for siRNA delivery. International Journal of Pharmaceutics 390 (2010) 70-75.

Dahlman, James E. et al., In vivo endothelial siRNA delivery using polymeric nanoparticles with low molecular weight, Nature Nanotechnology, 2014, No vol. #, pp. 1-8.

Delehanty, James B., Peptides for Specific Intracellular Delivery and Targeting of Nanoparticles: Implications for Developing Nanoparticle-Mediated Drug Delivery, Future Science, Therapeutic Delivery, 2010, vol. 1, No. 3, pp. 411-433.

Dong et al., "Lipopeptide nanoparticles for potent and selective siRNA delivery in rodents and nonhuman primates," PNAS, Mar. 2014, vol. 111, No. 11, 3955-3960; 5753-5754.

El Ouahabi, A., et al., Double long-chain amidine liposome-mediated self replicating RNA transfection. FEBS Letters. Feb. 1996; 380(1-2): 108-112.

Felgner, PL Cationic lipid/polynucleotide condensates for in vitro and in vivo polynucleotide delivery—the cytofectins. J. of Liposome Research. 1993; 3(1): 3-16.

Felgner P.L., et al., "Lipofection: A Highly Efficient, Lipid-Mediated DNA-Transfection Procedure," Proceedings of the National Academy of Sciences USA, vol. 84 (21), Nov. 1987, pp. 7413-7417.

Felgner, PL Particulate systems and polymers for in vitro and in vivo delivery of polynucleotides. Adv. Drug Delivery Rev. 1990; 5(3): 163-187.

Gao, X. et al., Nonviral gene delivery: what we know and what is next. AAPS J. Mar. 23, 2007;9(1):E92-104.

(56) References Cited

OTHER PUBLICATIONS

Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
Hashiba et al., "pH-labile PEGylation of siRNA-loaded lipid nanoparticle improves active targeting and gene silencing activity in hepatocytes," Journal of Controlled Release (2017) vol. 262, 239-246.
He, K. et al., Synthesis and Separation of Diastereomers of Ribonucleoside 5'-(alpha-P-Borano)triphosphates. J Org Chern. Aug. 21, 1998 ;63(17):5769-5773.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Heurtaul T et al., "Physico-chemical stability of colloidal lipid particles," Biomaterials, 2003,24:4283-4300.
Hoerr, I. et al., In vivo application of RNA leads to induction of specific cytotoxic T lymphocytes and antibodies. EurJ Immunol. Jan. 2000;30(1): 1-7.
Jaiswal et al., "Nanostructured lipid carriers and their current application in targeted drug delivery," Artificial Cells, Nanomedicine, and Biotechnology (2016) 44: 27-40.
Jayaraman et al., "Maximizing the Potency of siRNA Lipid Nanoparticles for Hepatic Gene Silencing In Vivo," Angew. Chem. Int. Ed. 2012, 51, 8529-8533.
Juliano, R.L., et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kang, Hyunmin, Inhibition of MDR1 Gene Expression by Chimeric HNA Antisense Oligonucleotides, Nucleic Acids Research, 2004, vol. 32, No. 14, pp. 4411-4419.
Kariko et al., Phosphate-enhanced transfection of cationic lipid-complexed mRNA and plasmid DNA. Biochimica et Biophysica Acta. 1998. 1369:320-34.
Kariko, K., et al., In vivo protein expression from mRNA delivered into adult rat brain. J. of Neuroscience Methods. Jan. 2001; 105(1): 77-86.
Kariko K. et al., "Incorporation of pseudouridine into mRNA yields superior nonimmunogenic vector with increased translational capacity and biological stability," Molecular Therapy, Nature Publishing Group, vol. 16 (11):1833-1840 (2008).
Keown, WA, et al., [41] Methods for Introducing DNA into Mammalian Cells. Methods in Enzymology, 1990, 185:527-37.
Kirpotin, D.B., et al., Antibody targeting of long-circulating lipidic nanoparticles does not increase tumor localization but does increase internalization in animal models. Cancer Res. 2006; 66: 6732-6740.
Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8, No. 4, pp. 3232-3241.
Lai, S.K., et al., Mucus-penetrating nanoparticles for drug and gene delivery to mucosal tissues. Adv Drug Deliv Rev. Feb. 27, 2009; 61(2): 158-171.
Lai, S.K., et al., Rapid transport of large polymeric nanoparticles in fresh undiluted human mucus. PNAS. Jan. 30, 2007; 104(5): 1482-1487.
Lee, Justin B. et al., Lipid Nanoparticle siRNA Systems for Silencing The Androgen Receptor In Human Prostate Cancer in Vivo, International Journal of Cancer, 2012, vol. 131, pp. 781-790.
Lehto, T., et al., Cell-penetrating peptides for the delivery of nucleic acids. Expert Opin. Drug Deliv. Jul. 2012; 9(7): 823-836.
Leung et al., "Lipid Nanoparticles for Short Interfering RNA Delivery", Advances in Genetics, 2014, vol. 88, Chapter 4, pp. 71-110.
Lewis, David, Dynamic Polyconjugates (DPC) Technology: An elegant solution to the SIRNA delivery problem. Arrowhead Research Corp (NASDAQ: ARWR). Nov. 2011. 6 pages.
Lewis, R., et al., "Studies of the Thermotropie Phase Behavior of Phosphatidylcholines Containing 2-Alkyl Substituted Fatty Alkyl Chains: A New Class of Phosphatidylcholines Forming Inverted Nonlamellar Phases," Biophysical Journal, Apr. 1994, vol. 66, pp. 1088-1103.
Li, L. et al., Overcoming obstacles to develop effective and safe siRNA therapeutics. Expert Opin Biol Ther. May 2009; 9(5): 609-19.
Li, L. et al., Preparation and gene delivery of alkaline amino acids-based cationic liposomes. Arch Pharm Res. Jul. 2008;31(7):924-31. Epub Aug. 14, 2008.
Lian, T. et al., Trends and developments in liposome drug delivery systems. J Pharm Sci. Jun. 2001;90(6):667-80.
Lopez-Berestein, G. et al., Treatment of systemic fungal infections with liposomal amphotericin B. Arch Intern Med. Nov. 1989;149(11):2533-6.
Love et al., Lipid-like materials for low-dose, in vivo gene silencing, PNAS vol. 107 No. 5, pp. 1864-1869, Feb. 2, 2010, 7 pages.
Luten, D.B., "The Preparation of Aminonitriles and Their Quaternary Ammonium Derivatives", Journal of Organic Chemistry (1939), 3, pp. 588-597.
M. Kanapathipillai, et al., Nanoparticle targeting of anti-cancer drugs that alter intracellular signaling or influence the tumor microenvironment, Adv. Drug Deliv. Rev. (2014), pp. 1-12.
Magee, W .E. et al., Marked stimulation of lymphocyte-mediated attack on tumor cells by target-directed liposomes containing immune RNA, Cancer Res., 1978, 38(4):1173-6.
Malone, R.W. et al., Cationic liposome-mediated RNA transfection. Proc Natl Acad Sci U S A. Aug. 1989;86 (16):6077-81.
Martinon, F. et al., Induction of virus-specific cytotoxic T lymphocytes in vivo by liposome-entrapped mRNA. Eur J Immunol. Jul. 1993;23(7): 1719-22.
Maskarinec et al., "Direct Observation of Poloxamer 188 Insertion into Lipid Monolayers," Biophys J., Mar. 2002, vol. 82, 1453-1459.
Maurer, N., et al., Spontaneous entrapment of polynucleotides upon electrostatic interaction with ethanol- destabilized cationic liposomes. Biophys J. May 2001; 80(5): 2310-2326.
Midoux et al., Lipid-based mRNA vaccine delivery systems. Expert Rev Vaccines. Feb. 2015; 14(2):221-34. doi: 10.1586/14760584.2015.986104. Epub Dec. 26, 2014. Review .
Mishra, R.K. et al., Improved leishmanicidal effect of phosphorothioate antisense oligonucleotides by LDL-mediated delivery. Biochim Biophys Acta. Nov. 7, 1995;1264(2):229-37.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Mohtar et al., "Solid Lipid Nanoparticles of Atovaquone Based on 24 Full-Factorial Design," Iranian Journal of Pharmaceutical Research (2015) 14(4): 989-1000.
Morissette, S. L., "High-Throughput Crystallization: Polymorphs, Salts, Co-Crystals and Solvates of Pharmaceutical Solids," Advanced Drug Delivery Reviews, vol. 56, No. 3, Feb. 2004, pp. 275-300.
Müller et al., "Solid lipid nanoparticles (SLN) for controlled drug delivery a review of the state of the art," European Journal of Pharmaceutics and Biopharmaceutics, (2000) 50 161-177.
Müller et al., Solid lipid nanoparticles (SLN) as potential carrier for human use: interaction with human granulocytes, Journal of Controlled Release, 1997, 47: 261-269.
Nair, S. et al., Soluble proteins delivered to dendritic cells via pH-sensitive liposomes induce primary cytotoxic T lymphocyte responses in vitro. J Exp Med. Feb. 1, 1992; 175(2):609-12.
Ohgami, N., et al., "Analysis of Molecular Recognition of the Cholesterol-binding Proteins," Bulletin of Institute for Life and Health Sciences, Japan, 2008 vol. 4, pp. 35-40.
Okumura, K., et al., Bax mRNA therapy using cationic liposomes for human malignant melanoma. J Gene Med. 2008; 10: 910-917.
Oster, C.G., et al. Comparative study of DNA encapsulation into PLGA microparticles using modified double emulsion methods and spray drying techniques. Journal of Microencapsulation, May 2005; 22(3): 235-244.
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, pp. 1-10.

(56) References Cited

OTHER PUBLICATIONS

Pollard, C., et al., Type IIFN counteracts the induction of antigen-specific immune responses by lipid-based delivery of mRNA vaccines. Mol Ther. Jan. 2013; 21(1): 251-259.
Pulford, B., et al., Liposome-siRNA-peptide complexes cross the blood-brain barrier and significantly decrease PrP'C on neuronal cells and PrP'RES in infected cell cultures. PLoS ONE. 2010; 5(6): e11085, 13 pages.
Ramteke, K. H. et al., "Solid Lipid Nanoparticle: A Review," IOSR Journal of Pharmacy, Nov.-Dec. 2012, 2(60): 34-44.
Sabnis et al., "A Novel Amino Lipid Series for mRNA Delivery: Improved Endosomal Escape and Sustained Pharmacology and Safety in Non-human Primates," Molecular Therapy, Jun. 2018, vol. 26, No. 6, pp. 1509-1519.
Saha, A. et al., "Phosphate Bioisostere Containing Amphiphiles: A Novel Class of Squaramide-based Lipids," Chemical Communications, Jul. 19, 2016, vol. 52(60), pp. 9438-9441.
Sahay, G. et al., "Efficiency of siRNA delivery by lipid nanoparticles is limited by endocytic recycling," Nat Biotechnol. Jul. 2013 ; 31(7): 653-658.
Saito, R., et al., Distribution of liposomes into brain and rat brain tumor models by convection-enhanced delivery monitored with magnetic resonance imaging. Cancer Res. Apr. 2004; 64: 2572-2579.
Sakuma, S. et al., Mucoadhesion of polystyrene nanoparticles having surface hydrophilic polymeric chains in the gastrointestinal tract. Int J Pharm. Jan. 25, 1999;177(2):161-72.
Schott, J.W., et al., Viral and non-viral approaches for transient delivery of mRNA and proteins. Current Gene Ther. 2011; 11 (5): 382-398.
Semple, S.C., et al., Efficient encapsulation of antisense oligonucleotides in lipid vesicles using ionizable aminolipids: formation of novel small multilamellar vesicle structures. Biochim Biophys Acta. Feb. 9, 2001; 1510(1-2): 152-166.
Semple, S.C., et al., "Rational design of cationic lipids for siRNA delivery", Nature Biotechnology, 2010, vol. 28, No. 2, 172-176.
Shah et al., "Lipid Nanoparticles: Production, Characterization and Stability," Springer International Publishing, 2014, 23 pages.
Shea, R.G. et al., Synthesis, hybridization properties and antiviral activity of lipid-oligodeoxynucleotide conjugates. Nucleic Acids Res. Jul. 11, 1990;18(13):3777-83.
Strobel, I. et al., Human dendritic cells transfected with either RNA or DNA encoding influenza matrix protein M1 differ in their ability to stimulate cytotoxic T lymphocytes. Gene Ther. Dec. 2000; 7(23): 2028-2035.
Svinarchuk, F.P. et al., Inhibition of HIV proliferation in MT-4 cells by antisense oligonucleotide conjugated to lipophilic groups. Biochimie. 1993;75(1-2):49-54.
Tam et al., "Advances in Lipid Nanoparticles for siRNA Delivery," Pharmaceutics 2013, 5, 498-507; doi:10.3390/pharmaceutics5030498.
Tavernier, G. et al., "mRNA as gene therapeutic: How to control protein expression," Journal of Controlled Release, vol. 150 (3):238-247(2011).
Thess et al., "Sequence-engineered mRNA Without Chemical Nucleosside Modifications Enables an Effective Protein Therapy in Large Animals," Molecular Therapy, Jun. 30, 2015, pp. 1-9, with supplemental data, vol. 23, No. 9.
Torchilin, Vladimir et al., Multifunctional and Stimuli-Sensitive Pharmaceutical Nanocarriers, Eur J. Pharm Biopharm, 2009, vol. 71, No. 3, pp. 431-444.
Tracy, M., "Progress in the Development of LNP Delivery for siRNA Advancing LNPs to the Clinic," International Liposome Research Days Meeting, Vancouver, Canada. Aug. 2010, pp. 1-52.
Treat, J. et al., in Liposomes in the Therapy of Infectious Disease and Cancer, Lopez-Berestein and Fidler (eds.), Liss, New York, 1989. 353-65.
Uzgun, S., et al., PEGylation improves nanoparticle formation and transfection efficiency of messenger RNA. Pharm Res. Sep. 2011; 28(9); 2223-2232.
Van Tendeloo V., et al. "Highly efficient gene delivery by mRNA electroporation in human hematopoietic cells: superiority to lipofection and passive pulsing of mRNA and to electroporation of plasmid cDNA for tumor antigen loading of dendritic cells," Blood, vol. 98(1):49-56 (2001).
Wan et al., Lipid nanoparticle delivery systems for siRNA-based therapeutics. Drug Deliv Transl Res. Feb. 2014;4(1):74-83. doi: 10.1007/s13346-013-0161-z.
Wang Y. et al., "Systemic delivery of modified mRNA encoding herpes simplex virus 1 thymidine kinase for targeted cancer gene therapy", Molecular Therapy, vol. 21(2):358-367 (2012).
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Yadava, P. et al., "Effect of Lyophilization and Freeze-thawing on the Stability of siRNA-liposome Complexes," AAPS PharmSciTech, Jun. 2008, 9(2): 335-341.
Yamamoto et al., Current prospects for mRNA gene delivery, European Journal of Pharmaceutics and Biopharmaceutics 71 (2009) 484-489.
Zhang et al., "A novel cationic cardiolipin analogue for gene delivery," Pharmazie, 2006, 61: 10-14.
Zhang et al., "Biodegradable Amino-Ester Nanomaterials for Cas9 mRNA Delivery in Vitro and in Vivo," ACS Applied Materials & Interfaces, Aug. 2017, 9(30): 25481-25487.
Zhigaltsev, I.V., et al., Bottom-Up design and synthesis of limit size lipid nanoparticle systems with aqueous and triglyceride cores using millisecond microfluidic mixing. Langmuir. Feb. 21, 2012; 28(7): 3633-3640.
Zimmermann, E. et al., Electrolyte- and pH-stabilities of aqueous solid lipid nanoparticle (SLN) dispersions in artificial gastrointestinal media. Eur J Pharm Biopharm. Sep. 2001;52(2):203-10.
Zohra, F.T., et al., Drastic effect of nanoapatite particles on liposome-mediated mRNA delivery to mammalian cells. Analytical Biochem. Oct. 2005; 345(1): 164-166.
Zohra, F.T., et al., Effective delivery with enhanced translational activity synergistically accelerates mRNA-based transfection. Biochem Biophys Res Comm. Jun. 2007; 358(1): 373-378.
Abrams et al., "Evaluation of Efficacy, Biodistribution, and Inflammation for a Potent siRNA Nanoparticle: Effect of Dexamethasone Co-treatment," Molecular Therapy, Jan. 2010, vol. 18 , No. 1, 171-180.
Audic and Chaufer, "Caseinate Based Biodegradable Films with Improved Water Resistance," Journal of Applied Polymer Science, (2010) vol. 117, 1828-1836.
Burnett et al., Dialkylaminoalkanol Esters of p-Aminobenzoic Acid, Journal of the American Chemical Society, Nov. 1937, vol. 59, pp. 2248-2252.
Cornebise M et al., Discovery of a Novel Amino Lipid that Improves Lipid Nanoparticle Performance through Specific Interactions with mRNA, Advanced Functional Mater, 2022, vol. 32(8), 2106727, 12 pages.
Han et al., "An ionizable lipid toolbox for RNA delivery," Nature Communications, 2021, 12:7233, 6 pages.
Hassett et al., "Optimization of Lipid Nanoparticles for Intramuscular Administration of mRNA Vaccines", Molecular Therapy: Nucleic Acids, Apr. 2019, vol. 15, 11 pages.
Mahidhar et al., "Distance of hydroxyl functionality from the quaternized center influence DNA binding and in vitro gene delivery efficacies of cationic lipids with hydroxyalkyl headgroups," J. Med. Chem. 2004, 47, 23, 5721-5728.
Mann et al., "355. Triethylenediamine (1 : 4-diazabicyclo[2 : 2 : 2]octane) and hexaethylenetetramine. Part III. The interaction of 2 : 2' : 2"-trichlorotriethylamine hydrochloride and dimethylamine," Journal of the Chemical Society, (1957), pp. 1881-1899.
Rehse, K., et al., "Antiaggregatorische und anticoagulante Eigenschaften von Oligoaminen, 12. Mitt.+): Alkyl- und Arylalkylderivate von Putrescin, Spermidin und Spermin", Arch. Pharm. (Weinheim) 323, 287-294 (1990) (with English abstract).

(56) References Cited

OTHER PUBLICATIONS

Tao et al., "Mechanistically Probing Lipid-siRNA Nanoparticle-associated Toxicities Identifies Jak Inhibitors Effective in Mitigating Multifaceted Toxic Responses," Molecular Therapy, Mar. 2011, vol. 19, No. 3, 567-575.

BRANCHED TAIL LIPID COMPOUNDS AND COMPOSITIONS FOR INTRACELLULAR DELIVERY OF THERAPEUTIC AGENTS

RELATED APPLICATIONS

This application is a continuation of U.S. application Ser. No. 17/324,426, filed May 19, 2021, now U.S. Pat. No. 11,597,698, which is a continuation of U.S. application Ser. No. 17/025,779, filed Sep. 18, 2020, now U.S. Pat. No. 11,066,355, which claims priority to, and the benefit of, U.S. Provisional Application No. 62/902,927, filed Sep. 19, 2019, the entire contents of each of which are incorporated herein by reference.

FIELD OF DISCLOSURE

The present disclosure provides novel compounds, compositions comprising such compounds, and methods involving lipid nanoparticle compositions to deliver one or more therapeutic and/or prophylactics to and/or produce polypeptides in mammalian cells or organs. In addition to a novel lipid, lipid nanoparticle compositions of the disclosure may include one or more cationic and/or ionizable amino lipids, phospholipids including polyunsaturated lipids, PEG lipids, structural lipids, and/or therapeutic and/or prophylactics in specific fractions.

BACKGROUND OF THE DISCLOSURE

The effective targeted delivery of biologically active substances such as small molecule drugs, proteins, and nucleic acids represents a continuing medical challenge. In particular, the delivery of nucleic acids to cells is made difficult by the relative instability and low cell permeability of such species. Thus, there exists a need to develop methods and compositions to facilitate the delivery of therapeutic and/or prophylactics such as nucleic acids to cells.

Lipid-containing nanoparticle compositions, liposomes, and lipoplexes have proven effective as transport vehicles into cells and/or intracellular compartments for biologically active substances such as small molecule drugs, proteins, and nucleic acids. Such compositions generally include one or more "cationic" and/or amino (ionizable) lipids, phospholipids including polyunsaturated lipids, structural lipids (e.g., sterols), and/or lipids containing polyethylene glycol (PEG lipids). Cationic and/or ionizable lipids include, for example, amine-containing lipids that can be readily protonated. Though a variety of such lipid-containing nanoparticle compositions have been demonstrated, improvements in safety, efficacy, and specificity are still lacking.

SUMMARY OF THE DISCLOSURE

The present disclosure provides novel compounds and compositions and methods involving the same.

In some aspects, the disclosure relates to a compound of Formula (1-1):

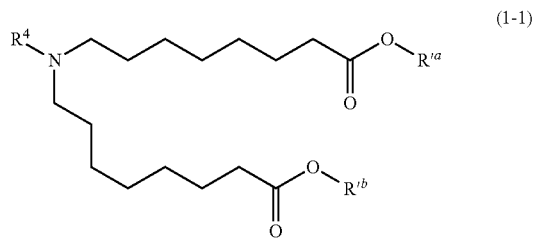

or its N-oxide, or a salt or isomer thereof, wherein $R^{\prime a}$ is $R^{\prime branched}$ or $R^{\prime cyclic}$; wherein $R^{\prime branched}$ is:

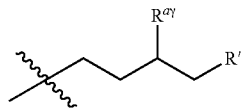

and $R^{\prime cyclic}$ is:

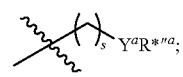

and $R^{\prime b}$ is:

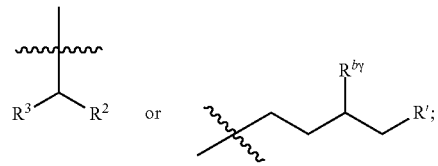

wherein

denotes a point of attachment;

wherein $R^{a\gamma}$ and $R^{b\gamma}$ are each independently a $C_{2-12}$ alkyl or $C_{2-12}$ alkenyl;

$R^2$ and $R^3$ are each independently selected from the group consisting of $C_{1-14}$ alkyl and $C_{2-14}$ alkenyl;

$R^4$ is $-(CH_2)_2OH$;

each R' independently is a $C_{1-12}$ alkyl or $C_{2-12}$ alkenyl;

$Y^a$ is a $C_{3-6}$ carbocycle;

$R^{*na}$ is selected from the group consisting of $C_{1-15}$ alkyl and $C_{2-15}$ alkenyl; and s is 2 or 3.

In some aspects, the disclosure relates to a compound of Formula (2-1):

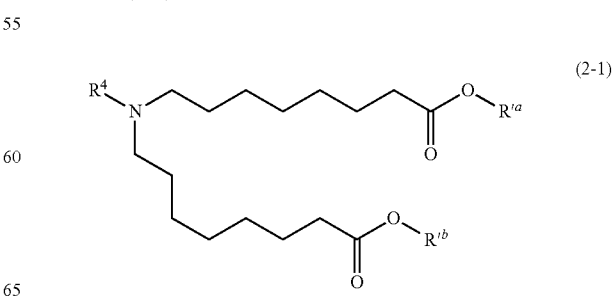

or its N-oxide, or a salt or isomer thereof,
wherein $R^{ia}$ is $R^{ibranched}$ or $R^{icyclic}$; wherein $R^{ibranched}$ is:

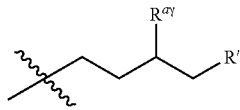

and $R^{icyclic}$ is:

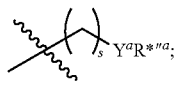

and
$R^{ib}$ is:

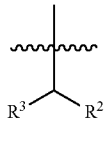 or 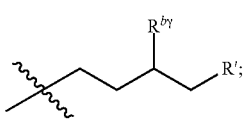

wherein

denotes a point of attachment;
wherein $R^{a\gamma}$ and $R^{b\gamma}$ are each independently a $C_{2-12}$ alkyl or $C_{2-12}$ alkenyl;
$R^2$ and $R^3$ are each independently selected from the group consisting of $C_{1-14}$ alkyl and $C_{2-14}$ alkenyl;
$R^4$ is

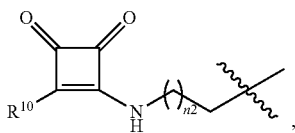

wherein

denotes a point of attachment; $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
each $R'$ independently is a $C_{1-12}$ alkyl or $C_{2-12}$ alkenyl;
$Y^a$ is a $C_{3-6}$ carbocycle;
$R^{*na}$ is selected from the group consisting of $C_{1-15}$ alkyl and $C_{2-15}$ alkenyl; and
s is 2 or 3.

In some aspects, the disclosure relates to a compound of Formula (A):

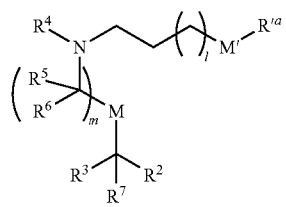

(A)

or its N-oxide, or a salt or isomer thereof,
wherein $R^{ia}$ is $R^{ibranched}$ or $R^{icyclic}$; wherein $R^{ibranched}$ is:

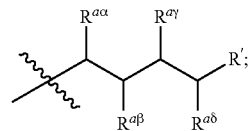

$R^{icyclic}$ is:

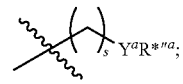

wherein

denotes a point of attachment;
wherein $R^{a\alpha}$ is H, and $R^{a\beta}$, $R^{a\gamma}$, and $R^{a\delta}$ are each independently selected from the group consisting of H, $C_{2-12}$ alkyl, and $C_{2-12}$ alkenyl, wherein at least one of $R^{a\beta}$, $R^{a\gamma}$, and $R^{a\delta}$ is selected from the group consisting of $C_{2-12}$ alkyl and $C_{2-12}$ alkenyl;
$R^2$ and $R^3$ are each $C_{1-14}$ alkyl;
$R^4$ is selected from the group consisting of —(CH$_2$)$_2$OH, —(CH$_2$)$_3$OH, —(CH$_2$)$_4$OH, —(CH$_2$)$_5$OH and

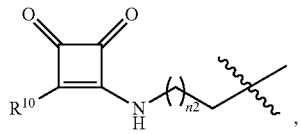

wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

$R^7$ is H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

In some aspects, the disclosure relates to a compound of Formula (B):

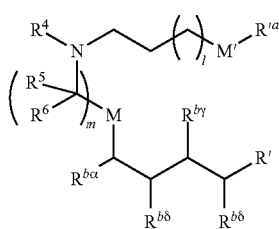

(B)

or its N-oxide, or a salt or isomer thereof, wherein $R'^a$ is $R'^{branched}$ or $R'^{cyclic}$; wherein $R'^{branched}$ is:

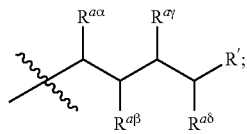

$R'^{cyclic}$ is:

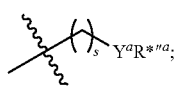

wherein

denotes a point of attachment;

wherein $R^{a\alpha}$ and $R^{a\beta}$ are each H, and $R^{a\gamma}$ and $R^{a\delta}$ are each independently selected from the group consisting of H, $C_{2-12}$ alkyl, and $C_{2-12}$ alkenyl, wherein at least one of $R^{a\gamma}$ and $R^{a\delta}$ is selected from the group consisting of $C_{2-12}$ alkyl and $C_{2-12}$ alkenyl;

$R^{b\alpha}$, $R^{b\beta}$, $R^{b\gamma}$, and $R^{b\delta}$ are each independently selected from the group consisting of H, $C_{2-30}$ alkyl, and $C_{5-20}$ alkenyl, wherein at least one of $R^{b\alpha}$, $R^{b\beta}$, $R^{b\gamma}$, and $R^{b\delta}$ is selected from the group consisting of $C_{2-30}$ alkyl and $C_{5-20}$ alkenyl;

$R^4$ is selected from the group consisting of —$(CH_2)_2OH$, —$(CH_2)_3OH$, —$(CH_2)_4OH$, —$(CH_2)_5OH$ and

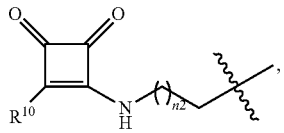

wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

In some aspects, the disclosure relates to a compound of Formula (A-a):

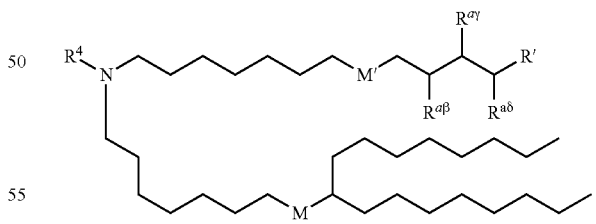

(A-a)

or its N-oxide, or a salt or isomer thereof, wherein $R^{a\beta}$, $R^{a\gamma}$ and $R^{a\delta}$ are each independently selected from the group consisting of H, $C_{2-12}$ alkyl, and $C_{2-12}$ alkenyl, wherein at least one of $R^{a\beta}$, $R^{a\gamma}$, and $R^{a\delta}$ is selected from the group consisting of $C_{2-12}$ alkyl and $C_{2-12}$ alkenyl;

$R^4$ is selected from the group consisting of —$(CH_2)_2OH$, —$(CH_2)_3OH$, —$(CH_2)_4OH$, and —$(CH_2)_5OH$;

M and M' are each independently selected from the group consisting of —C(O)O— and —OC(O)—; and R' is a $C_{1-12}$ alkyl or $C_{2-12}$ alkenyl.

In some aspects, the disclosure relates to a compound of Formula (A-b):

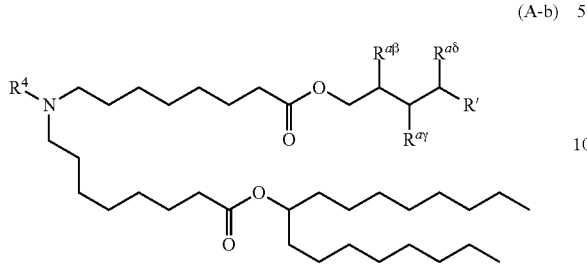

(A-b)

or its N-oxide, or a salt or isomer thereof, wherein $R^{a\beta}$, $R^{a\gamma}$ and $R^{a\delta}$ are each independently selected from the group consisting of H, $C_{2-12}$ alkyl, and $C_{2-12}$ alkenyl, wherein at least one of $R^{a\beta}$, $R^{a\gamma}$, and $R^{a\delta}$ is selected from the group consisting of $C_{2-12}$ alkyl and $C_{2-12}$ alkenyl;

$R^4$ is selected from the group consisting of —$(CH_2)_2OH$, —$(CH_2)_3OH$, —$(CH_2)_4OH$ and —$(CH_2)_5OH$; and R' is a $C_{1-12}$ alkyl or $C_{2-12}$ alkenyl.

DETAILED DESCRIPTION

The disclosure relates to novel lipids and lipid lipid nanoparticles (e.g., empty LNPs or loaded LNPs) including a novel lipid. The disclosure also provides methods of delivering a therapeutic and/or prophylactic to a mammalian cell, specifically delivering a therapeutic and/or prophylactic to a mammalian organ, producing a polypeptide of interest in a mammalian cell, improving levels of protein produced in a mammalian cell as compared to LNPs comprising other lipids, and treating a disease or disorder in a mammal in need thereof. For example, a method of producing a polypeptide of interest in a cell involves contacting a nanoparticle comprising an mRNA with a mammalian cell, whereby the mRNA may be translated to produce the polypeptide of interest. A method of delivering a therapeutic and/or prophylactic to a mammalian cell or organ may involve administration of a nanoparticle composition including the therapeutic and/or prophylactic to a subject, in which the administration involves contacting the cell or organ with the composition, whereby the therapeutic and/or prophylactic is delivered to the cell or organ. Such methods of delivery can be in vitro or in vivo.

The present disclosure provides lipids including a central amine moiety and at least one biodegradable group. The lipids described herein may be advantageously used in lipid nanoparticles (e.g., empty LNPs or loaded LNPs) for the delivery of therapeutic and/or prophylactics to mammalian cells or organs. For example, the lipids described herein have little or no immunogenicity. For example, the lipid compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c) has a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprise a reference lipid (e.g., MC3, KC2, or DLinDMA) and the same therapeutic or prophylactic agent.

In some aspects, the disclosure relates to a compound of Formula (A-1):

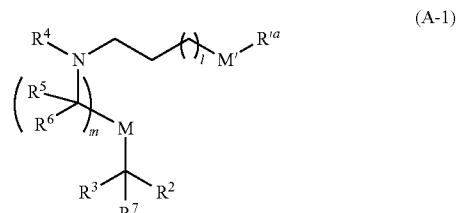

(A-1)

or its N-oxide, or a salt or isomer thereof, wherein $R'^a$ is $R'^{branched}$ or $R'^{cyclic}$; wherein $R'^{branched}$ is:

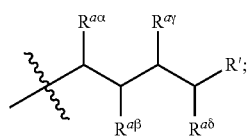

$R'^{cyclic}$ is:

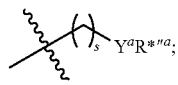

wherein

denotes a point of attachment;

wherein $R^{a\alpha}$, $R^{a\gamma}$ and $R^{a\delta}$ are each independently selected from the group consisting of H, $C_{2-12}$ alkyl, and $C_{2-12}$ alkenyl; and $R^{a\beta}$ is a $C_2$ alkyl, $C_3$ alkyl, $C_4$ alkyl, $C_5$ alkyl, or $C_6$ alkyl;

$R^2$ and $R^3$ are each $C_{1-14}$ alkyl;

$R^4$ is —$(CH_2)_2OH$ or

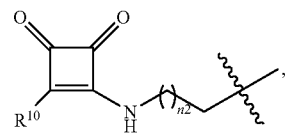

wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

$R^7$ is H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R*^{na}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

In some aspects, the disclosure relates to a compound of Formula (A-2):

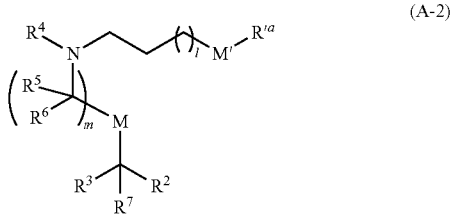

(A-2)

or its N-oxide, or a salt or isomer thereof, wherein $R^{'a}$ is $R^{'branched}$ or $R^{'cyclic}$; wherein $R^{'branched}$ is:

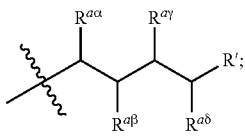

$R^{'cyclic}$ is:

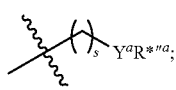

wherein

denotes a point of attachment;

wherein $R^{a\alpha}$, $R^{a\beta}$, and $R^{a\delta}$ are each independently selected from the group consisting of H, $C_{2-12}$ alkyl, and $C_{2-12}$ alkenyl; and $R^{a\gamma}$ is a $C_2$ alkyl, $C_3$ alkyl, $C_4$ alkyl, $C_5$ alkyl, or $C_6$ alkyl;

$R^2$ and $R^3$ are each $C_{1-14}$ alkyl;

$R^4$ is —$(CH_2)_2OH$ or

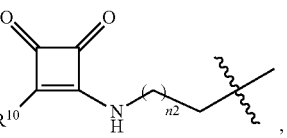

wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

$R^7$ is H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R*^{na}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

In some aspects, the disclosure relates to a compound of Formula (A-3):

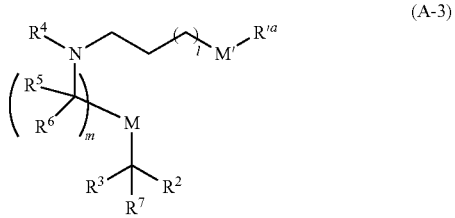

(A-3)

or its N-oxide, or a salt or isomer thereof, wherein $R^{'a}$ is $R^{'branched}$ or $R^{'cyclic}$; wherein $R^{'branched}$ is:

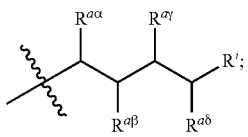

$R^{'cyclic}$ is:

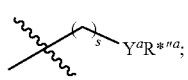

wherein

denotes a point of attachment;

wherein $R^{a\alpha}$, $R^{a\gamma}$ and $R^{a\beta}$ are each independently selected from the group consisting of H, $C_{2-12}$ alkyl, and $C_{2-12}$ alkenyl; and $R^{a\delta}$ is a $C_2$ alkyl, $C_3$ alkyl, $C_4$ alkyl, $C_5$ alkyl, or $C_6$ alkyl;

$R^2$ and $R^3$ are each $C_{1-14}$ alkyl;

$R^4$ is —$(CH_2)_2OH$ or

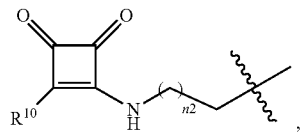

wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

$R^7$ is H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

In some embodiments, a compound of the disclosure has one of the following structures:

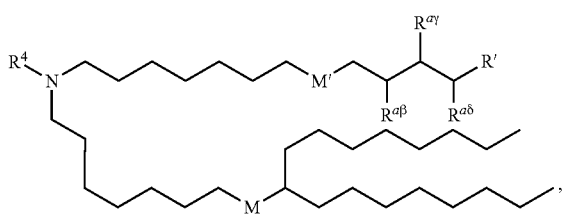

(IA)

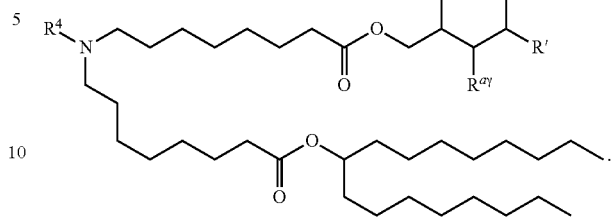

(IB)

In some aspects, the disclosure relates to a compound of Formula (B-1):

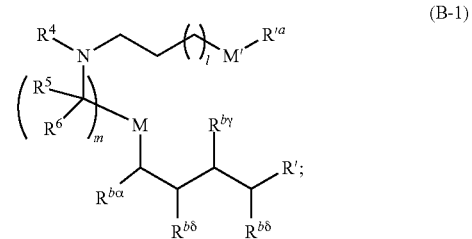

(B-1)

or its N-oxide, or a salt or isomer thereof, wherein $R'^a$ is $R'^{branched}$ or $R'^{cyclic}$; wherein $R'^{branched}$ is:

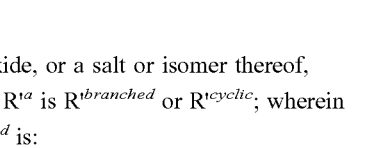

$R'^{cyclic}$ is:

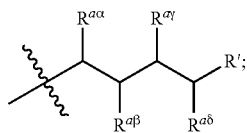

wherein

denotes a point of attachment;

wherein $R^{a\alpha}$, $R^{a\gamma}$, and $R^{a\delta}$ are each independently selected from the group consisting of H, $C_{2-12}$ alkyl, and $C_{2-12}$ alkenyl; and $R^{a\beta}$ is a $C_2$ alkyl, $C_3$ alkyl, $C_4$ alkyl, $C_5$ alkyl, or $C_6$ alkyl;

$R^{b\alpha}$, $R^{b\gamma}$, and $R^{b\delta}$ are each independently selected from the group consisting of H, $C_{2-30}$ alkyl, and $C_{5-20}$ alkenyl; and $R^{b\beta}$ is a $C_2$ alkyl, $C_3$ alkyl, $C_4$ alkyl, $C_5$ alkyl, or $C_6$ alkyl;

$R^4$ is

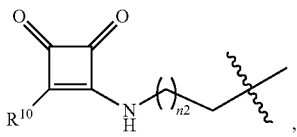, wherein

denotes a point of attachment;
wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

In some aspects, the disclosure relates to a compound of Formula (B-2):

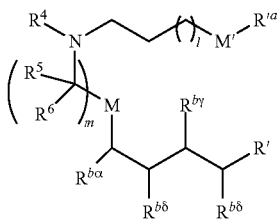

(B-2)

or its N-oxide, or a salt or isomer thereof,
wherein $R'^a$ is $R'^{branched}$ or $R'^{cyclic}$; wherein $R'^{branched}$ is:

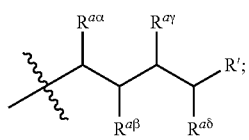

$R'^{cyclic}$ is:

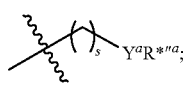

wherein

denotes a point of attachment;
wherein $R^{a\alpha}$, $R^{a\beta}$, and $R^{a\delta}$ are each independently selected from the group consisting of H, $C_{2-12}$ alkyl, and $C_{2-12}$ alkenyl; and $R^{a\gamma}$ is a $C_2$ alkyl, $C_3$ alkyl, $C_4$ alkyl, $C_5$ alkyl, or $C_6$ alkyl;

$R^{b\alpha}$, $R^{b\beta}$, and $R^{b\gamma}$ are each independently selected from the group consisting of H, $C_{2-30}$ alkyl, and $C_{5-20}$ alkenyl; and $R^{b\gamma}$ is a $C_2$ alkyl, $C_3$ alkyl, $C_4$ alkyl, $C_5$ alkyl, or $C_6$ alkyl;

$R^4$ is —$(CH_2)_2OH$ or

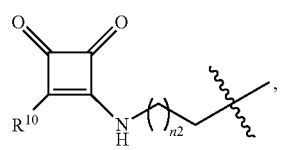, wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

In some aspects, the disclosure relates to a compound of Formula (B-3):

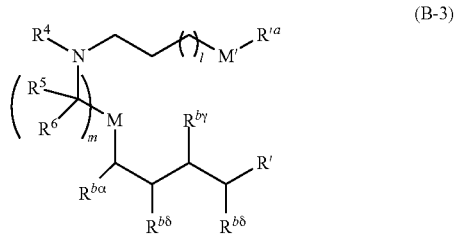

(B-3)

or its N-oxide, or a salt or isomer thereof,
wherein $R'^a$ is $R'^{branched}$ or $R'^{cyclic}$; wherein $R'^{branched}$ is:

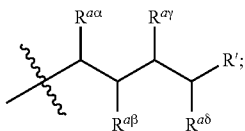

$R'^{cyclic}$ is:

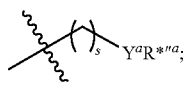

wherein

denotes a point of attachment;
wherein $R^{a\alpha}$, $R^{a\beta}$, and $R^{a\gamma}$ are each independently selected from the group consisting of H, $C_{2-12}$ alkyl, and $C_{2-12}$ alkenyl; and $R^{a\delta}$ is a $C_2$ alkyl, $C_3$ alkyl, $C_4$ alkyl, $C_5$ alkyl, or $C_6$ alkyl;
$R^{b\alpha}$, $R^{b\beta}$, and $R^{b\gamma}$ are each independently selected from the group consisting of H, $C_{2-30}$ alkyl, and $C_{5-20}$ alkenyl; and $R^{b\delta}$ is a $C_2$ alkyl, $C_3$ alkyl, $C_4$ alkyl, $C_5$ alkyl, or $C_6$ alkyl;
$R^4$ is —(CH$_2$)$_2$OH or

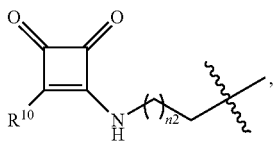

wherein

denotes a point of attachment;
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
$R^5$ and $R^6$ are each H;
M and M' are each independently selected from the group consisting of —C(O)O— and —OC(O)—;
R' is a $C_{1-12}$ alkyl or $C_{2-12}$ alkenyl;
$Y^a$ is a $C_{3-6}$ carbocycle;
$R^{*"a}$ is selected from the group consisting of $C_{1-15}$ alkyl and $C_{2-15}$ alkenyl;
l is selected from the group consisting of 1, 2, 3, 4, and 5;
s is 2 or 3; and
m is selected from the group consisting of 5, 6, 7, 8, 9, 10, 11, 12, and 13.

In some aspects, the disclosure relates to a compound of Formula (A-a1):

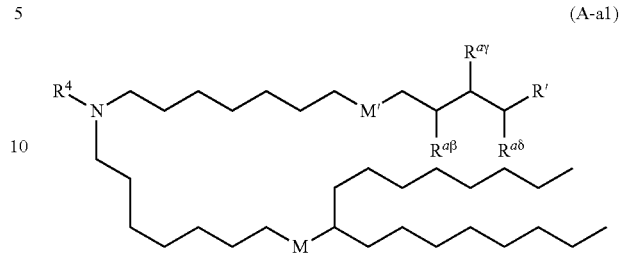

(A-a1)

or its N-oxide, or a salt or isomer thereof,
wherein $R^{a\gamma}$ and $R^{a\delta}$ are each independently selected from the group consisting of H, $C_{2-12}$ alkyl, and $C_{2-12}$ alkenyl; and $R^{a\beta}$ is a $C_2$ alkyl, $C_3$ alkyl, $C_4$ alkyl, $C_5$ alkyl, or $C_6$ alkyl;
$R^4$ is —(CH$_2$)$_2$OH or

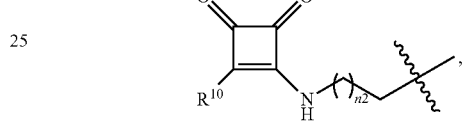

wherein

denotes a point of attachment;
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
M and M' are each independently selected from the group consisting of —C(O)O— and —OC(O)—; and
R' is a $C_{1-12}$ alkyl or $C_{2-12}$ alkenyl.

In some aspects, the disclosure relates to a compound of Formula (A-a2):

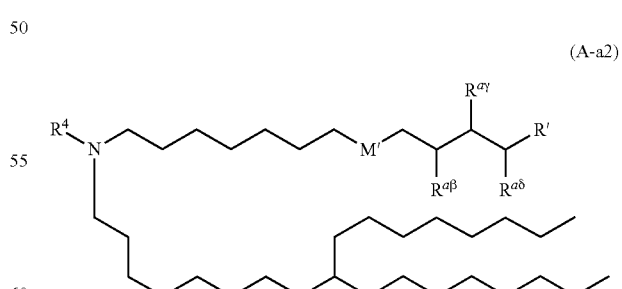

(A-a2)

or its N-oxide, or a salt or isomer thereof,
wherein $R^{a\beta}$ and $R^{a\delta}$ are each independently selected from the group consisting of H, $C_{2-12}$ alkyl, and $C_{2-12}$ alkenyl; and $R^{a\gamma}$ is a $C_2$ alkyl, $C_3$ alkyl, $C_4$ alkyl, $C_5$ alkyl, or $C_6$ alkyl;
$R^4$ is —(CH$_2$)$_2$OH or

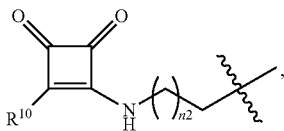

wherein

denotes a point of attachment;
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
M and M' are each independently selected from the group consisting of —C(O)O— and —OC(O)—; and
R' is a $C_{1-12}$ alkyl or $C_{2-12}$ alkenyl.

In some aspects, the disclosure relates to a compound of Formula (A-a3):

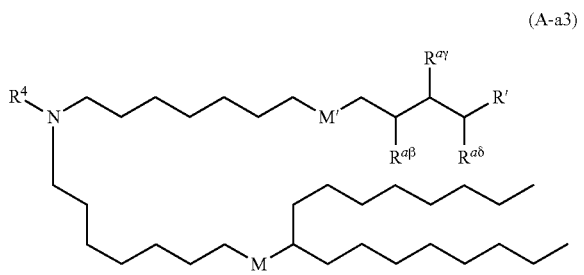

(A-a3)

or its N-oxide, or a salt or isomer thereof,
wherein $R^{a\beta}$ and $R^{a\gamma}$ are each independently selected from the group consisting of H, $C_{2-12}$ alkyl, and $C_{2-12}$ alkenyl; and $R^{a\delta}$ is a $C_2$ alkyl, $C_3$ alkyl, $C_4$ alkyl, $C_5$ alkyl, or $C_6$ alkyl;
$R^4$ is —$(CH_2)_2OH$ or

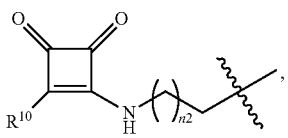

wherein

denotes a point of attachment;
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
M and M' are each independently selected from the group consisting of —C(O)O— and —OC(O)—; and
R' is a $C_{1-12}$ alkyl or $C_{2-12}$ alkenyl.

In some aspects, the disclosure relates to a compound of Formula (A-b1):

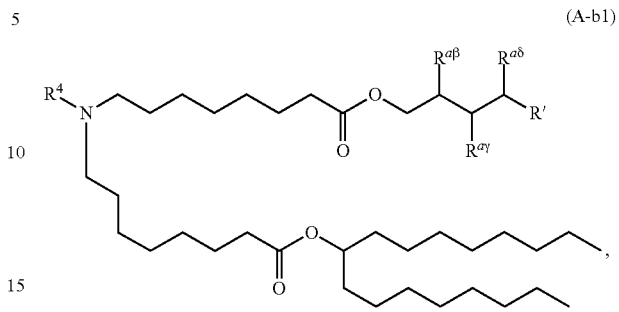

(A-b1)

or its N-oxide, or a salt or isomer thereof,
wherein $R^{a\gamma}$ and $R^{a\delta}$ are each independently selected from the group consisting of H, $C_{2-12}$ alkyl, and $C_{2-12}$ alkenyl; and $R^{a\beta}$ is a $C_2$ alkyl, $C_3$ alkyl, $C_4$ alkyl, $C_5$ alkyl, or $C_6$ alkyl;
$R^4$ is —$(CH_2)_2OH$ or

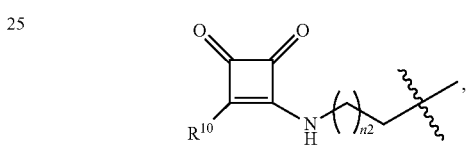

wherein

denotes a point of attachment;
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10; and
R' is a $C_{1-12}$ alkyl or $C_{2-12}$ alkenyl.

In some aspects, the disclosure relates to a compound of Formula (A-b2):

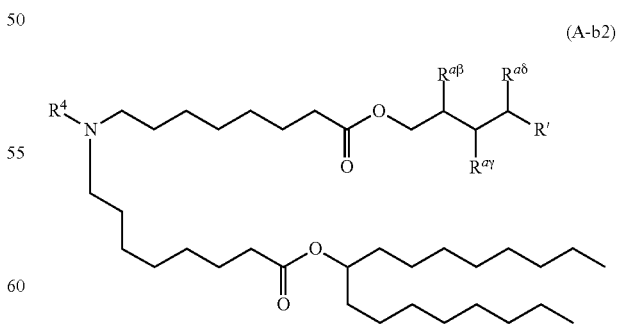

(A-b2)

or its N-oxide, or a salt or isomer thereof,
wherein $R^{a\beta}$ and $R^{a\delta}$ are each independently selected from the group consisting of H, $C_{2-12}$ alkyl, and $C_{2-12}$ alkenyl; and $R^{a\gamma}$ is a $C_2$ alkyl, $C_3$ alkyl, $C_4$ alkyl, $C_5$ alkyl, or $C_6$ alkyl;

$R^4$ is —$(CH_2)_2OH$ or

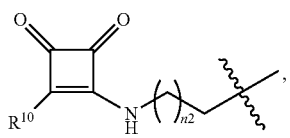

wherein

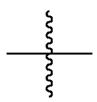

denotes a point of attachment; $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10; and R' is a $C_{1-12}$ alkyl or $C_{2-12}$ alkenyl.

In some aspects, the disclosure relates to a compound of Formula (A-b3):

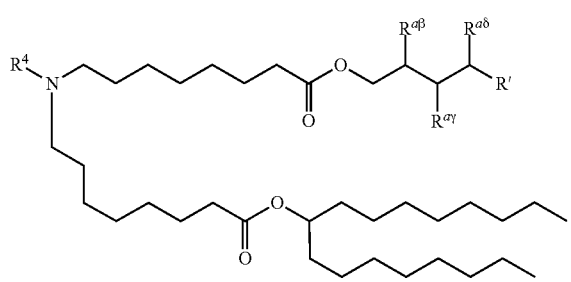

(A-b3)

or its N-oxide, or a salt or isomer thereof, wherein $R^{\alpha\beta}$ and $R^{\alpha\gamma}$ are each independently selected from the group consisting of H, $C_{2-12}$ alkyl, and $C_{2-12}$ alkenyl; and $R^{\alpha\delta}$ is a $C_2$ alkyl, $C_3$ alkyl, $C_4$ alkyl, $C_5$ alkyl, or $C_6$ alkyl;

$R^4$ is —$(CH_2)_2OH$ or

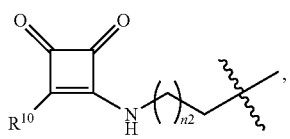

wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10; and R' is a $C_{1-12}$ alkyl or $C_{2-12}$ alkenyl.

In some aspects, the disclosure relates to a compound of Formula (A-c):

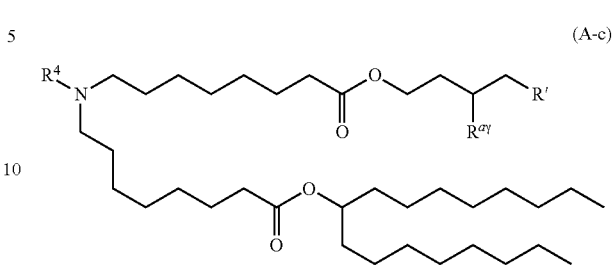

(A-c)

or its N-oxide, or a salt or isomer thereof, wherein $R^{\alpha\gamma}$ is a $C_2$ alkyl, $C_3$ alkyl, $C_4$ alkyl, $C_5$ alkyl, or $C_6$ alkyl;

$R^4$ is —$(CH_2)_2OH$ or

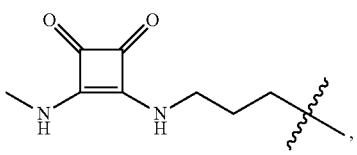 [SMILES: *CCCNc1c(NC)c(=O)c1=O]

wherein

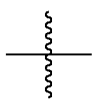

denotes a point of attachment; and R' is a $C_{1-12}$ alkyl.

In some aspects, the disclosure relates to a compound of Formula (B-c):

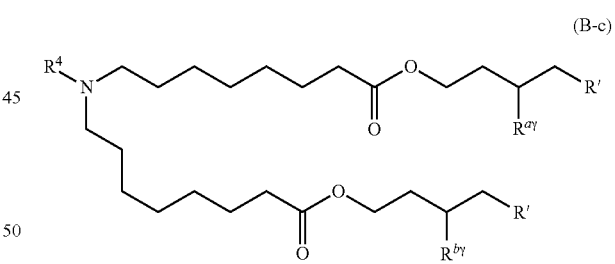

(B-c)

or its N-oxide, or a salt or isomer thereof, wherein $R^{\alpha\gamma}$ is a $C_2$ alkyl, $C_3$ alkyl, $C_4$ alkyl, $C_5$ alkyl, or $C_6$ alkyl;

$R^{b\gamma}$ is a $C_2$ alkyl, $C_3$ alkyl, $C_4$ alkyl, $C_5$ alkyl, or $C_6$ alkyl; and $R^4$ is —$(CH_2)_2OH$ or

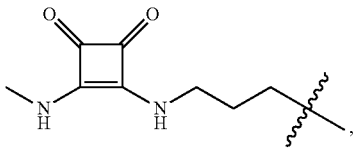 [SMILES: *CCCNc1c(NC)c(=O)c1=O]

wherein

denotes a point of attachment; and R' is a $C_{1-12}$ alkyl.

In some aspects, the disclosure relates to a compound of Formula (I-a):

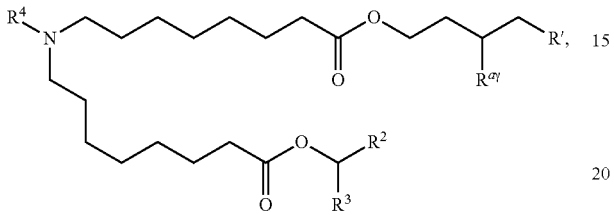

(I-a)

wherein $R^2$ and $R^3$ are each independently selected from the group consisting of $C_{1-14}$ alkyl and $C_{2-14}$ alkenyl; and $R^{\alpha\gamma}$ and $R^{b\gamma}$ are each independently a $C_{2-6}$ alkyl.

The compounds of any one of Formulae (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), and (B-c), include one or more of the following features when applicable.

In some embodiments, $R^4$ is

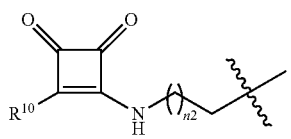

and n2 is 2. In some embodiments, $R^4$ is

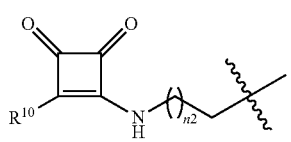

and n2 is 3. In some embodiments, $R^4$ is

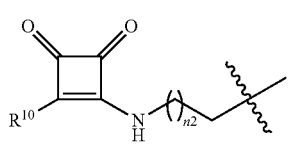

and n2 is 4.

In some embodiments, $R^{10}$ is —NH$_2$. In some embodiments, $R^{10}$ is —NH($C_{1-6}$ alkyl). In some embodiments, $R^{10}$ is —N($C_{1-6}$ alkyl)$_2$. In some embodiments, $R^{10}$ is —NH(CH$_3$). In some embodiments, $R^{10}$ is —N(CH$_3$)$_2$.

In some embodiments, $R^4$ is —(CH$_2$)$_2$OH, —(CH$_2$)$_3$OH, or —(CH$_2$)$_4$OH and M and M' are each —C(O)O—. In some embodiments, $R^4$ is —(CH$_2$)$_2$OH and M and M' are each —C(O)O—. In some embodiments, $R^4$ is —(CH$_2$)$_3$OH and M and M' are each —C(O)O—. In some embodiments, $R^4$ is —(CH$_2$)$_4$OH and M and M' are each —C(O)O—.

In some embodiments, $R^4$ is

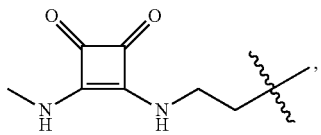 [SMILES: *CCNc1c(NC)c(=O)c1=O]

In some embodiments, $R^4$ is

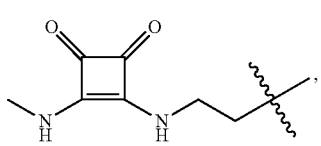 [SMILES: *CCNc1c(NC)c(=O)c1=O]

and M and M' are each —C(O)O—. In some embodiments, $R^4$ is

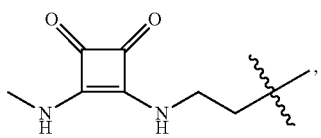 [SMILES: *CCNc1c(NC)c(=O)c1=O]

and M and M' are each —OC(O)—. In some embodiments, $R^4$ is

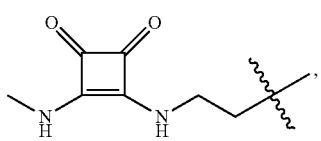 [SMILES: *CCNc1c(NC)c(=O)c1=O]

and M is —OC(O)— and M' —C(O)O—. In some embodiments, $R^4$ is

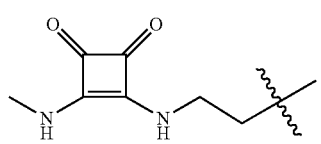 [SMILES: *CCNc1c(NC)c(=O)c1=O]

is —C(O)O— and M' is —OC(O)—.

In some embodiments, 1 is 1, 2, 3, or 4. In some embodiments, 1 is 5. In some embodiments, m is 5, 6, 7, 8, or 9. In some embodiments, m is 5. In some embodiments, m is 7.

In some embodiments, 1 is 5 and m is 5. In some embodiments, 1 is 5 and m is 7. In some embodiments, 1 is 5 and m is 5, 6, 7, 8, or 9. In some embodiments m is 5 and 1 is 1, 2, 3, or 4. In some embodiments m is 7 and 1 is 1, 2, 3, or 4.

In some embodiments, $R^5$, $R^6$, and $R^7$ are each H, and m is 5, 6, 7, 8, or 9. In some embodiments, $R^5$, $R^6$, and $R^7$ are each H, and m is 5. In some embodiments, $R^5$, $R^6$, and $R^7$ are each H, and m is 7.

In some embodiments, $R^2$ and $R^3$ are each independently $C_{1-14}$ alkyl or $C_{2-14}$ alkenyl. In some embodiments, $R^2$ and $R^3$ are each independently $C_{3-14}$ alkyl or $C_{3-14}$ alkenyl. In some embodiments, $R^2$ and $R^3$ are independently $C_{5-14}$ alkyl or $C_{5-14}$ alkenyl.

In some embodiments, $R^2$ and $R^3$ are each independently $C_{1-14}$ alkyl. In some embodiments, $R^2$ and $R^3$ are each independently $C_{3-14}$ alkyl. In some embodiments, $R^2$ and $R^3$ are each independently $C_{7-9}$ alkyl.

In some embodiments, $R^2$ and $R^3$ are each $C_7$ alkyl. In some embodiments, $R^2$ and $R^3$ are each $C_8$ alkyl. In some embodiments, $R^2$ and $R^3$ are each $C_9$ alkyl.

In some embodiments, $R'^a$ is $R'^{branched}$, $R^{a\alpha}$, $R^{a\gamma}$, and $R^{a\delta}$ are each H, and $R^{a\beta}$ is a $C_2$-$C_6$ alkyl. In some embodiments, $R'^a$ is $R'^{branched}$, $R^{a\alpha}$, $R^{a\beta}$ and $R^{a\delta}$ are each H, and $R^{a\gamma}$ is a $C_2$-$C_6$ alkyl. In some embodiments, $R'^a$ is $R'^{branched}$, $R^{a\alpha}$, $R^{a\beta}$, and $R^{a\gamma}$ are each H, and $R^{a\delta}$ is a $C_2$-$C_6$ alkyl.

In some embodiments, $R^{b\alpha}$, $R^{b\gamma}$, and $R^{b\delta}$ are each H, and $R^{b\beta}$ is a $C_2$-$C_6$ alkyl. In some embodiments, $R^{b\alpha}$, $R^{b\beta}$, and $R^{b\delta}$ are each H, and $R^{b\gamma}$ is a $C_2$-$C_6$ alkyl. In some embodiments, $R^{b\alpha}$, $R^{b\beta}$, and $R^{b\gamma}$ are each H, and $R^{b\delta}$ is a $C_2$-$C_6$ alkyl.

In some embodiments, $R^{a\alpha}$, $R^{a\gamma}$, and $R^{a\delta}$ are each H, $R^{a\beta}$ is a $C_2$-$C_6$ alkyl, $R^{b\alpha}$, $R^{b\gamma}$, and $R^{b\delta}$ are each H, and $R^{b\beta}$ is a $C_2$-$C_6$ alkyl. In some embodiments, $R^{a\alpha}$, $R^{a\gamma}$, and $R^{a\delta}$ are each H, $R^{a\beta}$ is a $C_2$-$C_6$ alkyl, $R^{b\alpha}$, $R^{b\beta}$, and $R^{b\delta}$ are each H, and $R^{b\gamma}$ is a $C_2$-$C_6$ alkyl. In some embodiments, $R^{a\alpha}$, $R^{a\gamma}$, and $R^{a\delta}$ are each H, $R^{a\beta}$ is a $C_2$-$C_6$ alkyl, $R^{b\alpha}$, $R^{b\beta}$, and $R^{b\gamma}$ are each H, and $R^{b\delta}$ is a $C_2$-$C_6$ alkyl.

In some embodiments, $R^{a\alpha}$, $R^{a\beta}$, and $R^{a\delta}$ are each H, $R^{a\gamma}$ is a $C_2$-$C_6$ alkyl, $R^{b\alpha}$, $R^{b\gamma}$, and $R^{b\delta}$ are each H, and $R^{b\beta}$ is a $C_2$-$C_6$ alkyl. In some embodiments, $R^{a\alpha}$, $R^{a\beta}$, and $R^{a\delta}$ are each H, $R^{a\gamma}$ is a $C_2$-$C_6$ alkyl, $R^{b\alpha}$, $R^{b\beta}$, and $R^{b\delta}$ are each H, and $R^{b\gamma}$ is a $C_2$-$C_6$ alkyl. In some embodiments, $R^{a\alpha}$, $R^{a\beta}$, and $R^{a\delta}$ are each H, $R^{a\gamma}$ is a $C_2$-$C_6$ alkyl, $R^{b\alpha}$, $R^{b\beta}$, and $R^{b\gamma}$ are each H, and $R^{b\delta}$ is a $C_2$-$C_6$ alkyl.

In some embodiments, $R^{a\alpha}$, $R^{a\beta}$, and $R^{a\gamma}$ are each H, $R^{a\delta}$ is a $C_2$-$C_6$ alkyl, $R^{b\alpha}$, $R^{b\gamma}$, and $R^{b\delta}$ are each H, and $R^{b\beta}$ is a $C_2$-$C_6$ alkyl. In some embodiments, $R^{a\alpha}$, $R^{a\beta}$, and $R^{a\gamma}$ are each H, $R^{a\delta}$ is a $C_2$-$C_6$ alkyl, $R^{b\alpha}$, $R^{b\beta}$, and $R^{b\delta}$ are each H, and $R^{b\gamma}$ is a $C_2$-$C_6$ alkyl. In some embodiments, $R^{a\alpha}$, $R^{a\beta}$, and $R^{a\gamma}$ are each H, $R^{a\delta}$ is a $C_2$-$C_6$ alkyl, $R^{b\alpha}$, $R^{b\beta}$, and $R^{b\gamma}$ are each H, and $R^{b\delta}$ is a $C_2$-$C_6$ alkyl.

In some embodiments, R' is a $C_{1-12}$ alkyl or $C_{2-12}$ alkenyl. In some embodiments, R' is a $C_2$ alkyl. In some embodiments, R' is a $C_3$ or $C_4$ alkyl. In some embodiments, R' is a $C_3$ alkyl. In some embodiments, R' is a $C_4$ alkyl. In some embodiments, R' is a $C_5$ alkyl.

In some embodiments, R' is $C_4$ alkyl or $C_4$ alkenyl. In some embodiments, R' is $C_5$ alkyl or $C_5$ alkenyl. In some embodiments, R' is $C_6$ alkyl or $C_6$ alkenyl. In some embodiments, R' is $C_7$ alkyl or $C_7$ alkenyl. In some embodiments, R' is $C_8$ alkyl or $C_8$ alkenyl. In some embodiments, R' is $C_9$ alkyl or $C_9$ alkenyl. In some embodiments, R' is $C_{10}$ alkyl or $C_{10}$ alkenyl. In some embodiments, R' is $C_{11}$ alkyl or $C_{11}$ alkenyl.

In some embodiments, $R'^a$ is $R'^{branched}$, $R^{a\alpha}$, $R^{a\gamma}$ and $R^{a\delta}$ are each H, $R^{a\beta}$ is a $C_2$-$C_6$ alkyl and R' is a $C_3$-$C_5$ alkyl. In some embodiments, $R'^a$ is $R'^{branched}$, $R^{a\alpha}$, $R^{a\gamma}$ and $R^{a\delta}$ are each H, $R^{a\beta}$ is a $C_2$-$C_6$ alkyl and R' is a $C_3$ alkyl. In some embodiments, $R'^a$ is $R'^{branched}$, $R^{a\alpha}$, $R^{a\gamma}$ and $R^{a\delta}$ are each H, $R^{a\beta}$ is a $C_2$-$C_6$ alkyl and R' is a $C_4$ alkyl.

In some embodiments, $R'^a$ is $R'^{branched}$, $R^{a\alpha}$, $R^{a\beta}$ and $R^{a\delta}$ are each H, $R^{a\gamma}$ is a $C_2$-$C_6$ alkyl, and R' is a $C_3$-$C_5$ alkyl. In some embodiments, $R'^a$ is $R'^{branched}$, $R^{a\alpha}$, $R^{a\beta}$ and $R^{a\delta}$ are each H, $R^{a\gamma}$ is a $C_2$-$C_6$ alkyl, and R' is a $C_3$ alkyl. In some embodiments, $R'^a$ is $R'^{branched}$, $R^{a\alpha}$, $R^{a\beta}$ and $R^{a\delta}$ are each H, $R^{b\gamma}$ is a $C_2$-$C_6$ alkyl, and R' is a $C_4$ alkyl.

In some embodiments, $R'^a$ is $R'^{branched}$, $R^{a\alpha}$, $R^{a\beta}$ and $R^{a\gamma}$ are each H, $R^{a\delta}$ is a $C_2$-$C_6$ alkyl and R' is a $C_3$-$C_5$ alkyl. In some embodiments, $R'^a$ is $R'^{branched}$, $R^{a\alpha}$, $R^{a\beta}$ and $R^{a\gamma}$ are each H, $R^{a\delta}$ is a $C_2$-$C_6$ alkyl and R' is a $C_3$ alkyl. In some embodiments, $R'^a$ is $R'^{branched}$, $R^{a\alpha}$, $R^{a\beta}$ and $R^{a\gamma}$ are each H, $R^{a\delta}$ is a $C_2$-$C_6$ alkyl and R' is a $C_4$ alkyl.

In some embodiments, $R*''^a$ is $C_2$-alkyl or $C_3$-alkyl.

In some embodiments, s is 2. In some embodiments, s is 3.

In some embodiments, s is 2 and $R*''^a$ is a $C_2$ alkyl or a $C_3$-alkyl.

In some embodiments, $Y^a R*''^a$ is

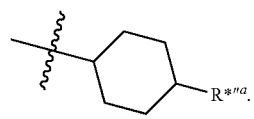

In some embodiments, $Y^a R*''^a$ is

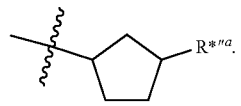

In some embodiments, s is 2, $Y^a R*''^a$ is

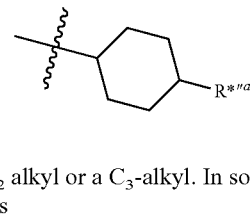

and $R*''^a$ is a $C_2$ alkyl or a $C_3$-alkyl. In some embodiments, s is 2, $Y^a R*''^a$ is

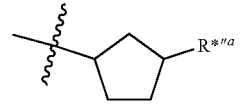

and $R*''^a$ is a $C_2$ alkyl or a $C_3$-alkyl.

In some embodiments the compound of any of the formulae described herein is suitable for making a nanoparticle composition for intramuscular administration.

In some embodiments, the compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c) is selected from the compounds of Table 1 and N-oxides, salts or isomers thereof.

TABLE 1
Amino Lipids.
| Cpd | Structure |
|---|---|
| 7 | 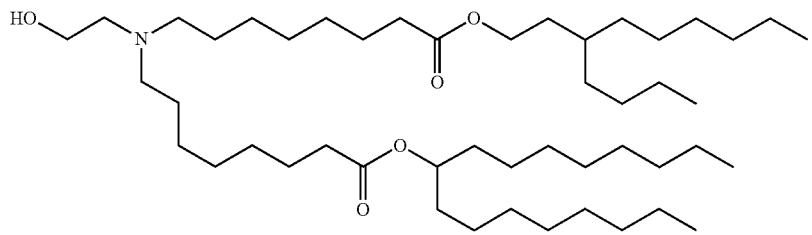 [SMILES: CCCCCCCCC(CCCCCCCC)OC(=O)CCCCCCCN(CCO)CCCCCCCC(=O)OCCC(CCCC)CCCCCC] |
| 8 | 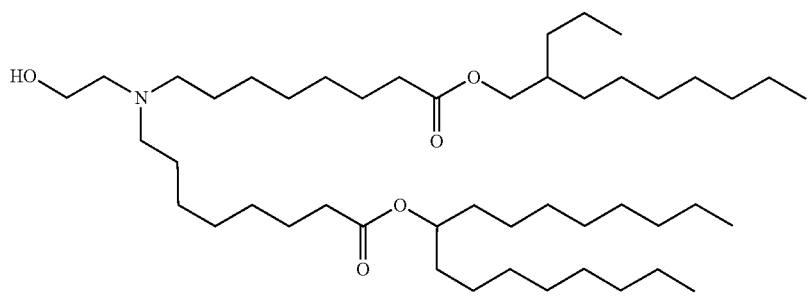 [SMILES: CCCCCCCCC(CCCCCCCC)OC(=O)CCCCCCCN(CCO)CCCCCCCC(=O)OCC(CCC)CCCCCCC] |
| 9 | 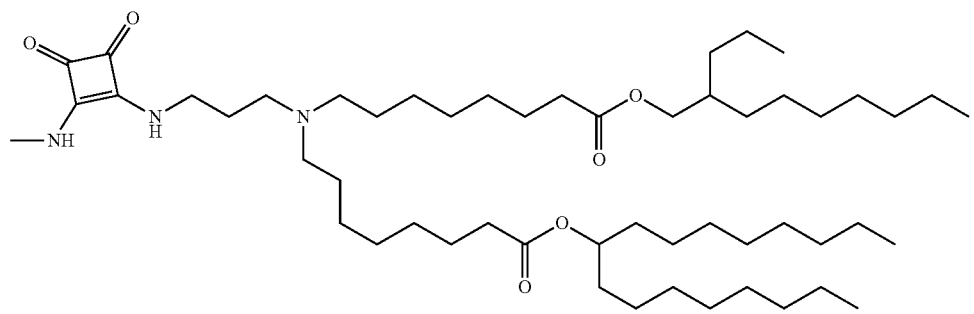 [SMILES: CCCCCCCCC(CCCCCCCC)OC(=O)CCCCCCCN(CCCCCCCC(=O)OCC(CCC)CCCCCCC)CCCNc1c(NC)c(=O)c1=O] |
| 10 | 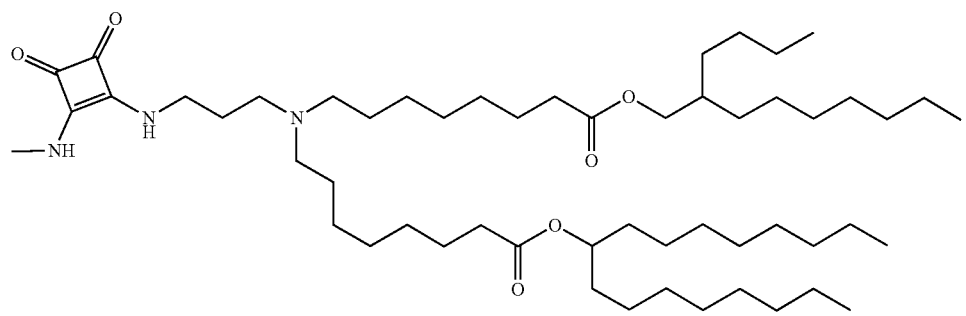 [SMILES: CCCCCCCCC(CCCCCCCC)OC(=O)CCCCCCCN(CCCCCCCC(=O)OCC(CCCC)CCCCCCC)CCCNc1c(NC)c(=O)c1=O] |
| 11 | 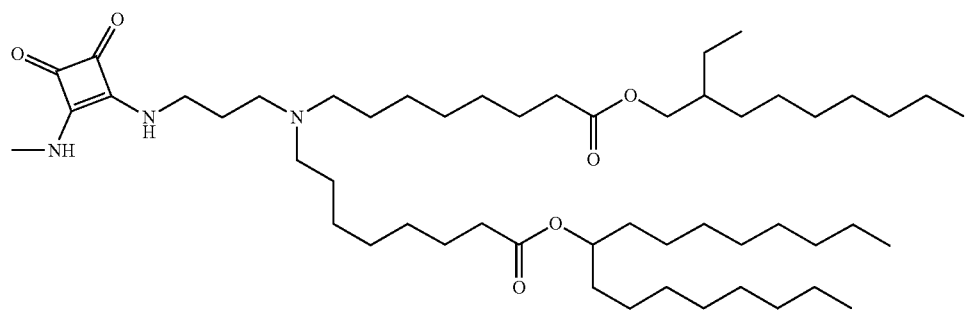 [SMILES: CCCCCCCCC(CCCCCCCC)OC(=O)CCCCCCCN(CCCCCCCC(=O)OCC(CC)CCCCCCC)CCCNc1c(NC)c(=O)c1=O] |

TABLE 1-continued
Amino Lipids.
| Cpd | Structure |
|---|---|
| 12 | 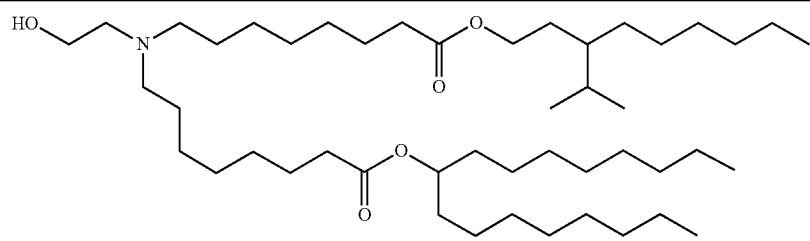 |
| 13 | 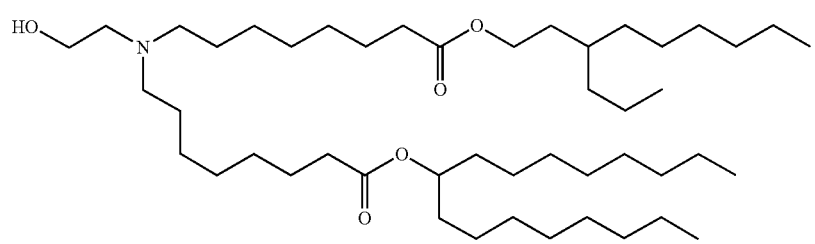 [SMILES: CCCCCCCCC(CCCCCCCC)OC(=O)CCCCCCCN(CCO)CCCCCCCC(=O)OCCC(CCC)CCCCCC] |
| 14 | 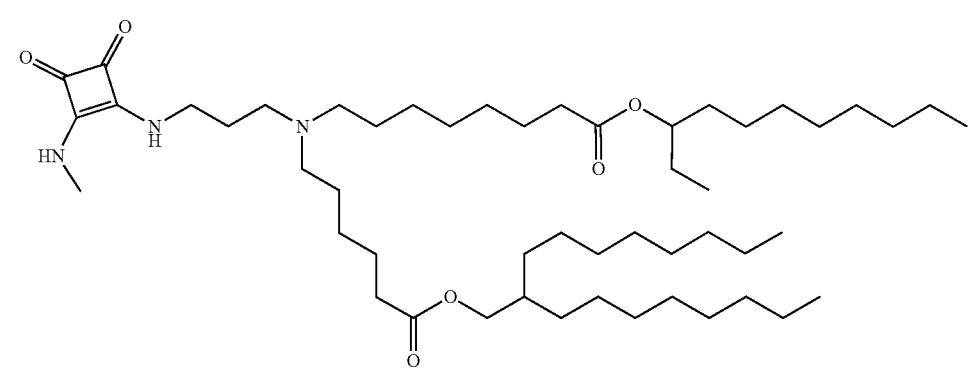 [SMILES: CCCCCCCCC(CCCCCCCC)COC(=O)CCCCCN(CCCCCCCC(=O)OC(CC)CCCCCCCC)CCCNc1c(NC)c(=O)c1=O] |
| 15 | 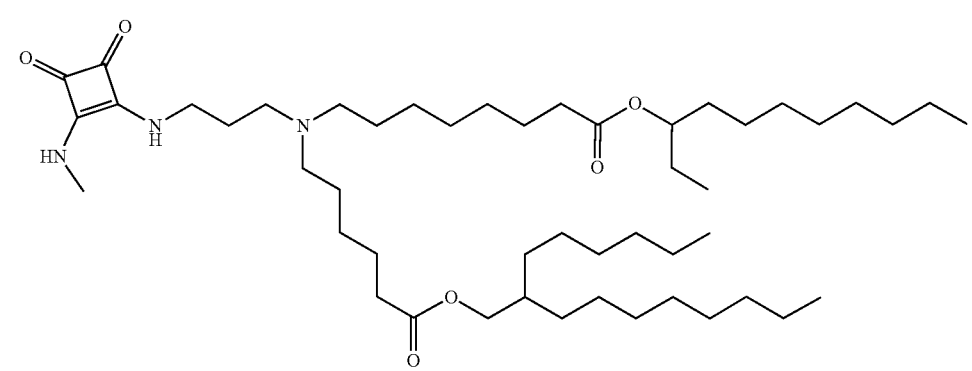 [SMILES: CCCCCCCCC(CCCCCC)COC(=O)CCCCCN(CCCCCCCC(=O)OC(CC)CCCCCCCC)CCCNc1c(NC)c(=O)c1=O] |
| 16 | 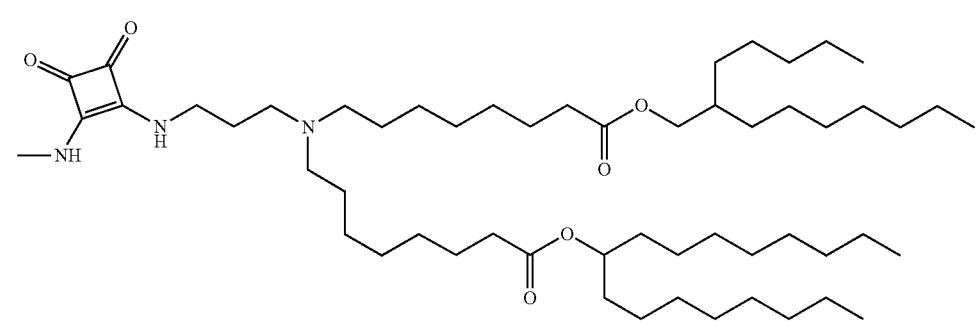 [SMILES: CCCCCCCCC(CCCCCCCC)OC(=O)CCCCCCCN(CCCCCCCC(=O)OCC(CCCCC)CCCCCCC)CCCNc1c(NC)c(=O)c1=O] |

TABLE 1-continued
Amino Lipids.
| Cpd | Structure |
|---|---|
| 17 | 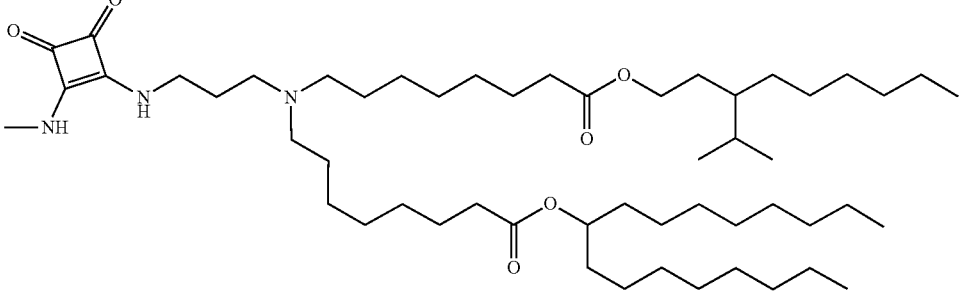 |
| 18 | 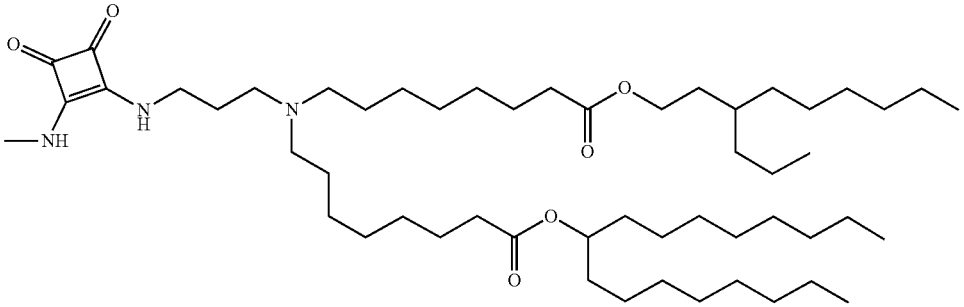 [SMILES: CCCCCCCCC(CCCCCCCC)OC(=O)CCCCCCCN(CCCCCCCC(=O)OCCC(CCC)CCCCCC)CCCNc1c(NC)c(=O)c1=O] |
| 19 | 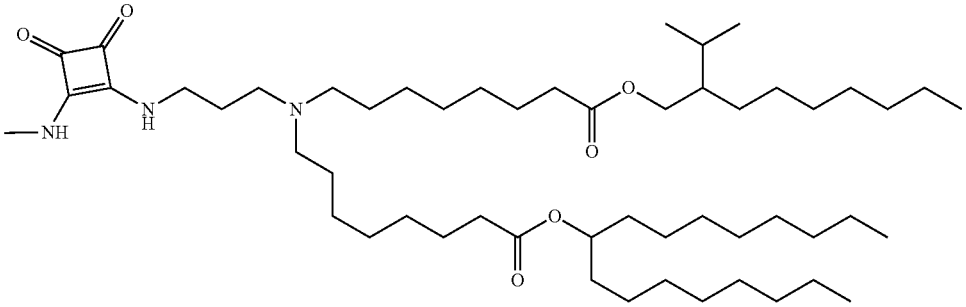 [SMILES: CCCCCCCCC(CCCCCCCC)OC(=O)CCCCCCCN(CCCCCCCC(=O)OCC(CCCCCCC)C(C)C)CCCNc1c(NC)c(=O)c1=O] |
| 20 | 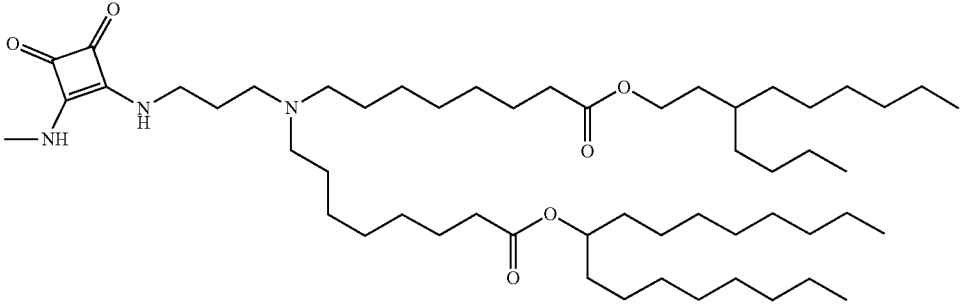 [SMILES: CCCCCCCCC(CCCCCCCC)OC(=O)CCCCCCCN(CCCCCCCC(=O)OCCC(CCCC)CCCCCC)CCCNc1c(NC)c(=O)c1=O] |
| 21 | 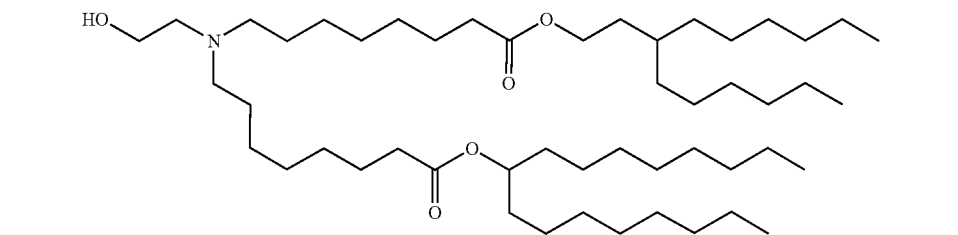 [SMILES: CCCCCCCCC(CCCCCCCC)OC(=O)CCCCCCCN(CCO)CCCCCCCC(=O)OCCC(CCCCCC)CCCCCC] |

TABLE 1-continued

Amino Lipids.

| Cpd | Structure |
|---|---|
| 22 | 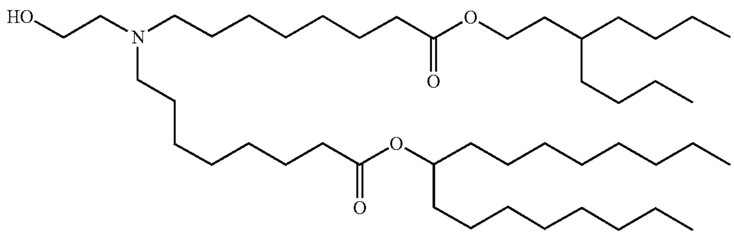 [SMILES: CCCCCCCCC(CCCCCCCC)OC(=O)CCCCCCCN(CCO)CCCCCCCC(=O)OCCC(CCCC)CCCC] |
| 23 | 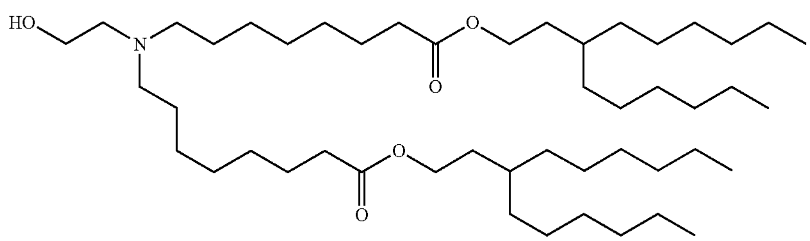 [SMILES: CCCCCCC(CCCCCC)CCOC(=O)CCCCCCCN(CCO)CCCCCCCC(=O)OCCC(CCCCCC)CCCCCC] |
| 24 | 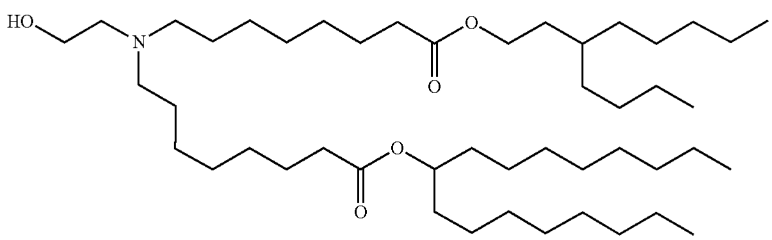 [SMILES: CCCCCCCCC(CCCCCCCC)OC(=O)CCCCCCCN(CCO)CCCCCCCC(=O)OCCC(CCCC)CCCCC] |
| 25 | 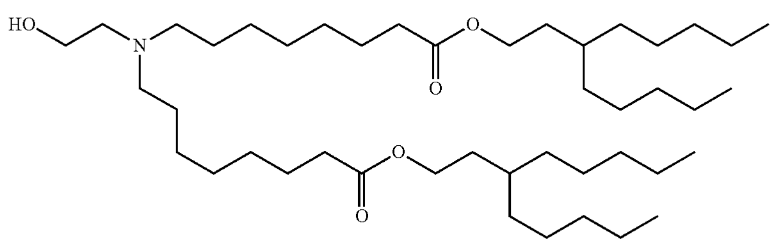 [SMILES: CCCCCC(CCCCC)CCOC(=O)CCCCCCCN(CCO)CCCCCCCC(=O)OCCC(CCCCC)CCCCC] |
| 26 | 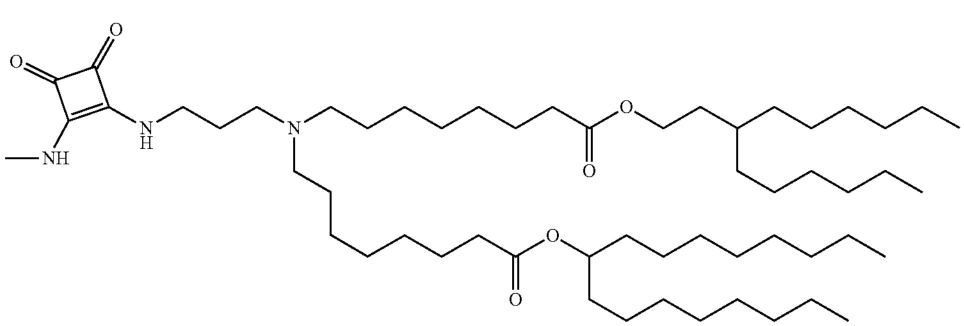 [SMILES: CCCCCCCCC(CCCCCCCC)OC(=O)CCCCCCCN(CCCCCCCC(=O)OCCC(CCCCCC)CCCCCC)CCCNc1c(NC)c(=O)c1=O] |

TABLE 1-continued

Amino Lipids.

| Cpd | Structure |
|---|---|
| 27 | 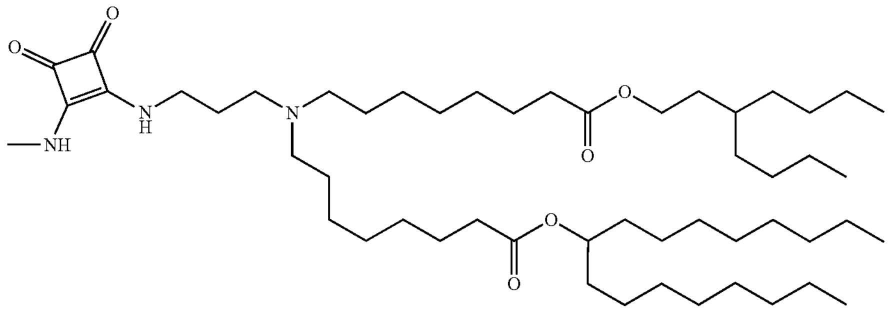 [SMILES: CCCCCCCCC(CCCCCCCC)OC(=O)CCCCCCCN(CCCCCCCC(=O)OCCC(CCCC)CCCC)CCCNc1c(NC)c(=O)c1=O] |
| 28 | 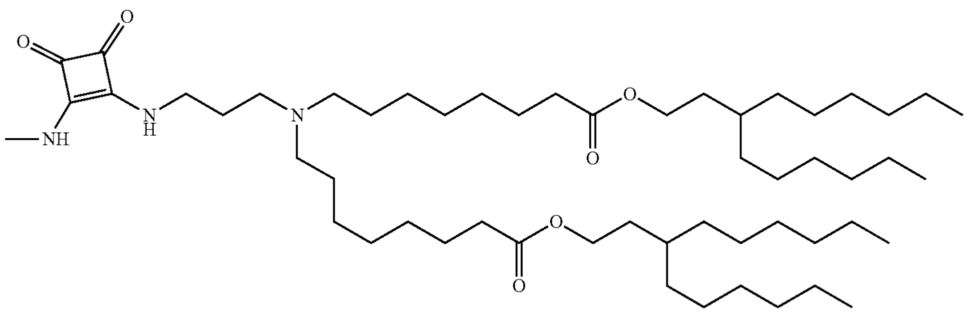 [SMILES: CCCCCCC(CCCCCC)CCOC(=O)CCCCCCCN(CCCCCCCC(=O)OCCC(CCCCCC)CCCCCC)CCCNc1c(NC)c(=O)c1=O] |
| 29 | 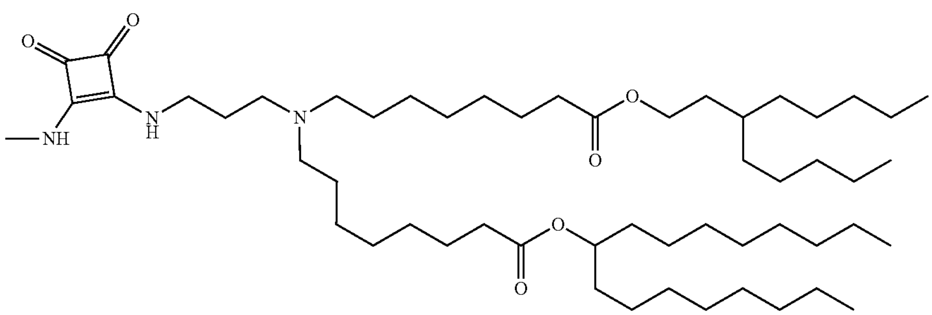 [SMILES: CCCCCCCCC(CCCCCCCC)OC(=O)CCCCCCCN(CCCCCCCC(=O)OCCC(CCCCC)CCCCC)CCCNc1c(NC)c(=O)c1=O] |
| 30 | 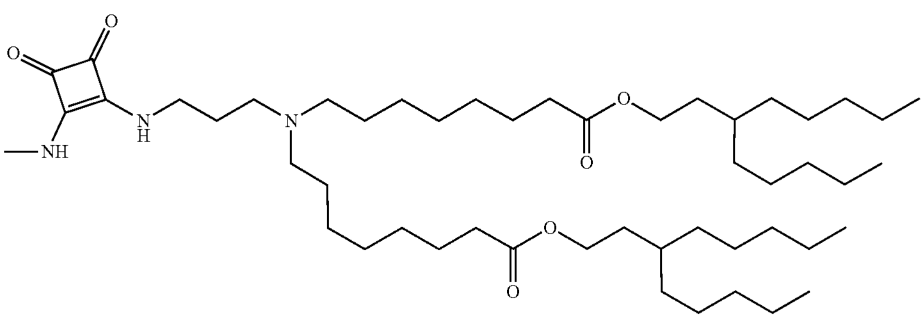 [SMILES: CCCCCC(CCCCC)CCOC(=O)CCCCCCCN(CCCCCCCC(=O)OCCC(CCCCC)CCCCC)CCCNc1c(NC)c(=O)c1=O] |
| 31 | 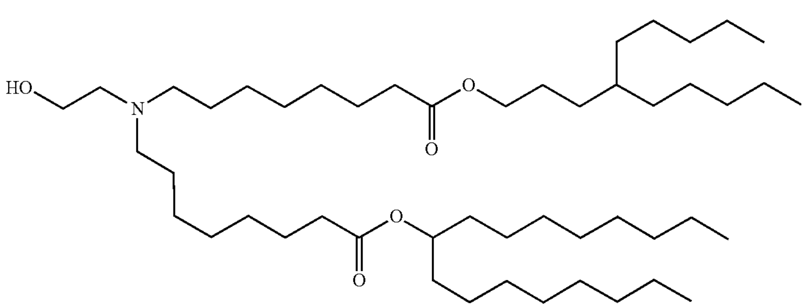 [SMILES: CCCCCCCCC(CCCCCCCC)OC(=O)CCCCCCCN(CCO)CCCCCCCC(=O)OCCCC(CCCCC)CCCCC] |

TABLE 1-continued

Amino Lipids.

| Cpd | Structure |
|---|---|
| 32 | 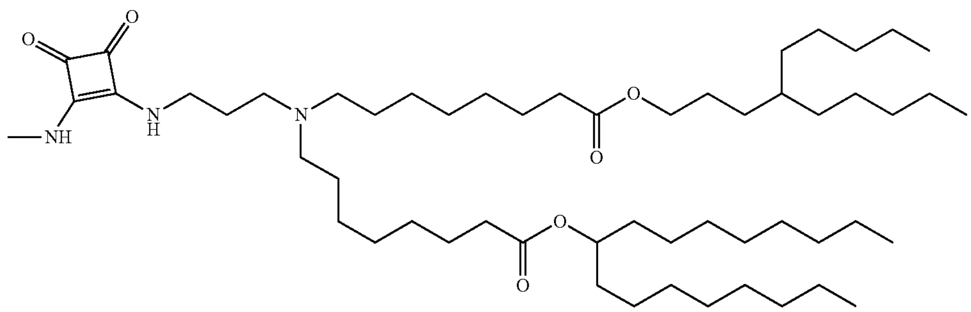 [SMILES: CCCCCCCCC(CCCCCCCC)OC(=O)CCCCCCCN(CCCCCCCC(=O)OCCCC(CCCCC)CCCCC)CCCNc1c(NC)c(=O)c1=O] |
| 33 | 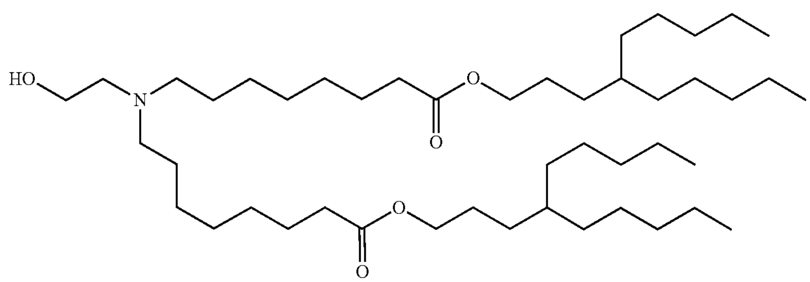 [SMILES: CCCCCC(CCCCC)CCCOC(=O)CCCCCCCN(CCO)CCCCCCCC(=O)OCCCC(CCCCC)CCCCC] |
| 34 | 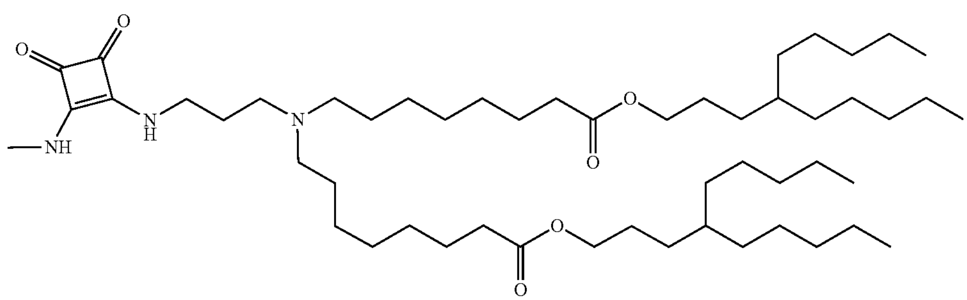 [SMILES: CCCCCC(CCCCC)CCCOC(=O)CCCCCCCN(CCCCCCCC(=O)OCCCC(CCCCC)CCCCC)CCCNc1c(NC)c(=O)c1=O] |
| 35 | 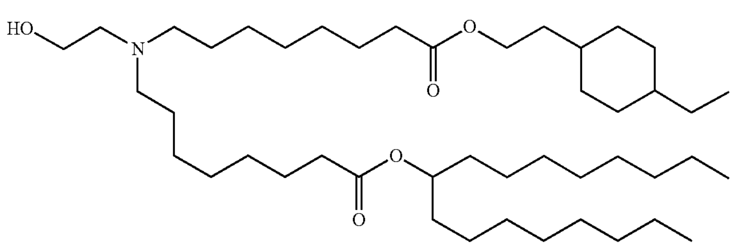 [SMILES: CCCCCCCCC(CCCCCCCC)OC(=O)CCCCCCCN(CCO)CCCCCCCC(=O)OCCC1CCC(CC)CC1] |
| 36 | 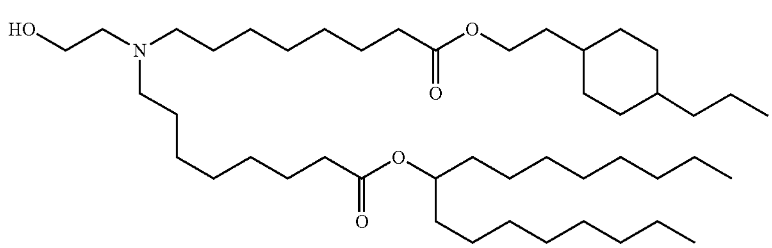 [SMILES: CCCCCCCCC(CCCCCCCC)OC(=O)CCCCCCCN(CCO)CCCCCCCC(=O)OCCC1CCC(CCC)CC1] |

TABLE 1-continued
Amino Lipids.
| Cpd | Structure |
|---|---|
| 37 | 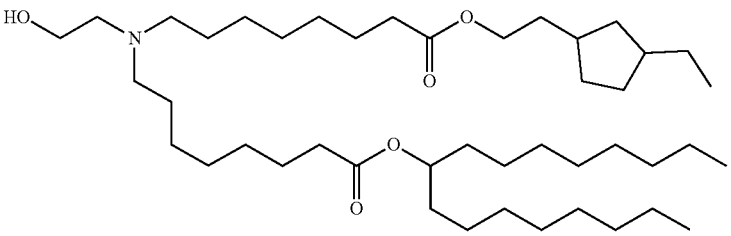 [SMILES: CCCCCCCCC(CCCCCCCC)OC(=O)CCCCCCCN(CCO)CCCCCCCC(=O)OCCC1CCC(CC)C1] |
| 38 | 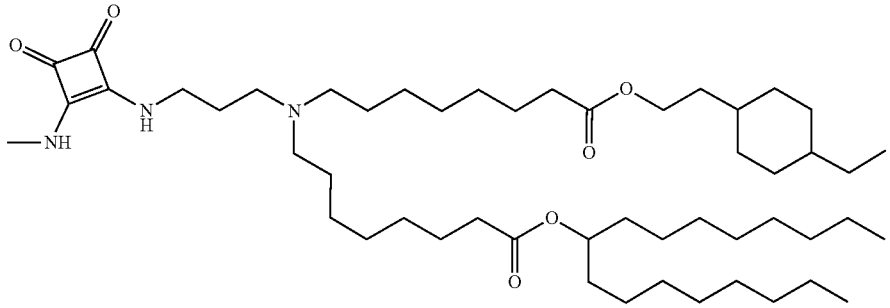 [SMILES: CCCCCCCCC(CCCCCCCC)OC(=O)CCCCCCCN(CCCCCCCC(=O)OCCC1CCC(CC)CC1)CCCNc1c(NC)c(=O)c1=O] |
| 39 | 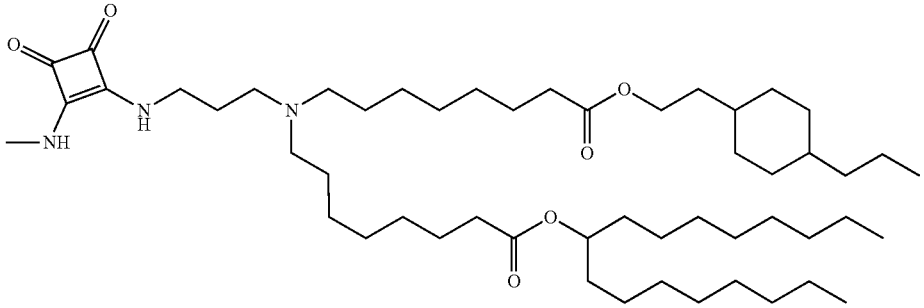 [SMILES: CCCCCCCCC(CCCCCCCC)OC(=O)CCCCCCCN(CCCCCCCC(=O)OCCC1CCC(CCC)CC1)CCCNc1c(NC)c(=O)c1=O] |
| 40 | 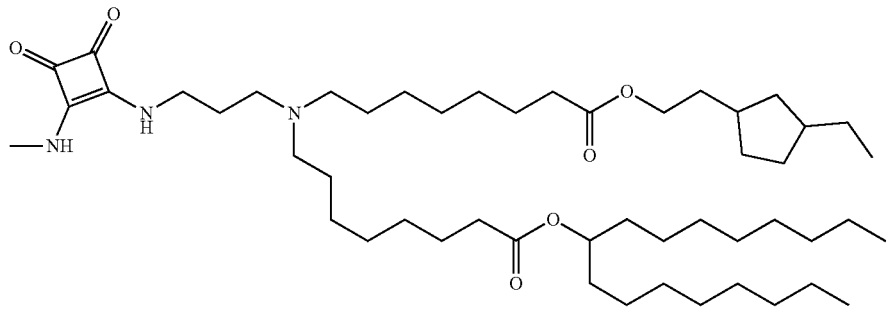 [SMILES: CCCCCCCCC(CCCCCCCC)OC(=O)CCCCCCCN(CCCCCCCC(=O)OCCC1CCC(CC)C1)CCCNc1c(NC)c(=O)c1=O] |
| 41 | 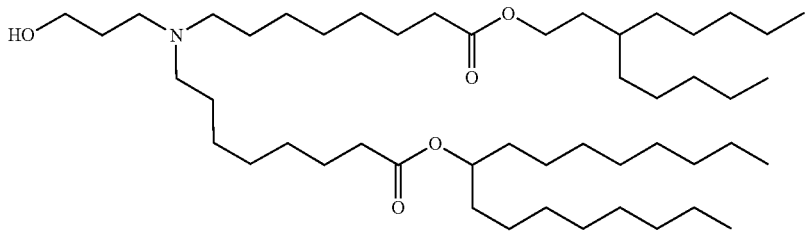 [SMILES: CCCCCCCCC(CCCCCCCC)OC(=O)CCCCCCCN(CCCO)CCCCCCCC(=O)OCCC(CCCCC)CCCCC] |

TABLE 1-continued

Amino Lipids.

| Cpd | Structure |
|---|---|
| 42 | 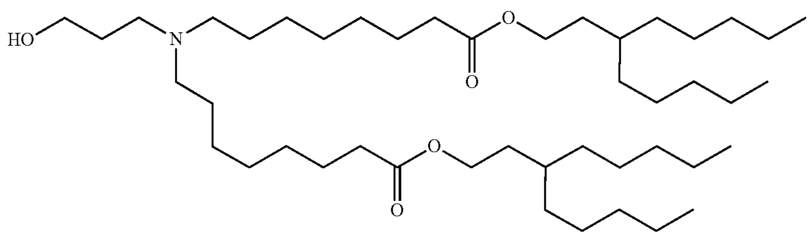 [SMILES: CCCCCC(CCCCC)CCOC(=O)CCCCCCCN(CCCO)CCCCCCCC(=O)OCCC(CCCCC)CCCCC] |
| 43 | 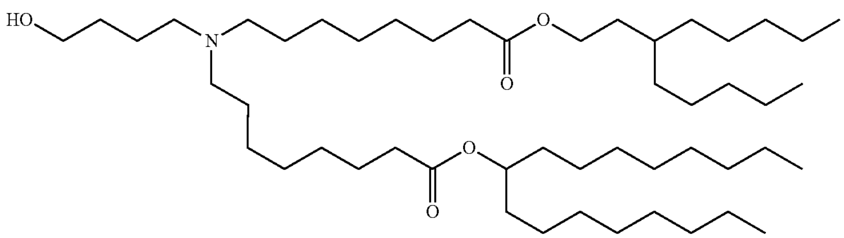 [SMILES: CCCCCCCCC(CCCCCCCC)OC(=O)CCCCCCCN(CCCCO)CCCCCCCC(=O)OCCC(CCCCC)CCCCC] |
| 44 | 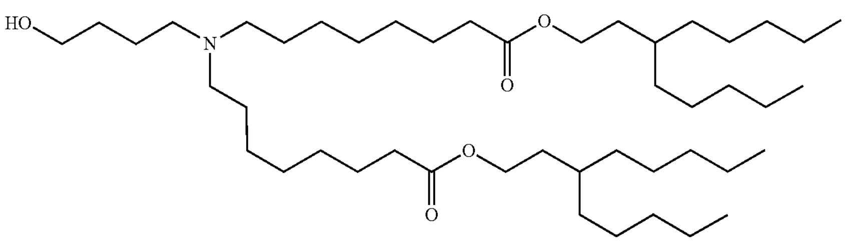 [SMILES: CCCCCC(CCCCC)CCOC(=O)CCCCCCCN(CCCCO)CCCCCCCC(=O)OCCC(CCCCC)CCCCC] |
| 45 | 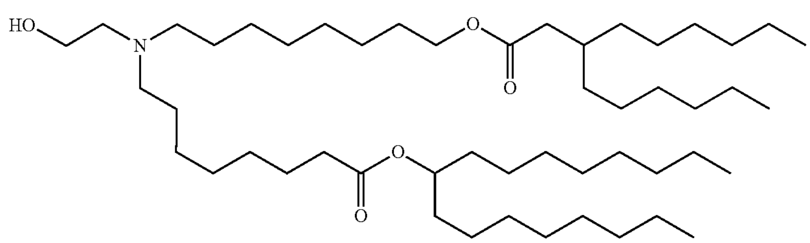 [SMILES: CCCCCCCCC(CCCCCCCC)OC(=O)CCCCCCCN(CCO)CCCCCCCCOC(=O)CC(CCCCCC)CCCCCC] |
| 46 | 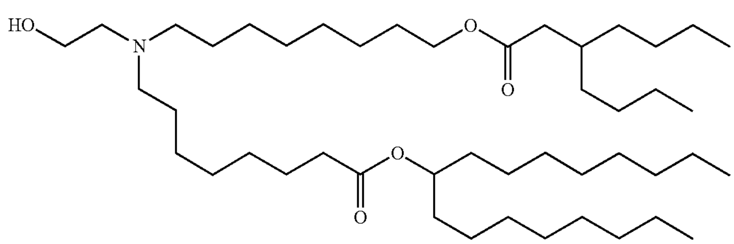 [SMILES: CCCCCCCCC(CCCCCCCC)OC(=O)CCCCCCCN(CCO)CCCCCCCCOC(=O)CC(CCCC)CCCC] |
| 47 | 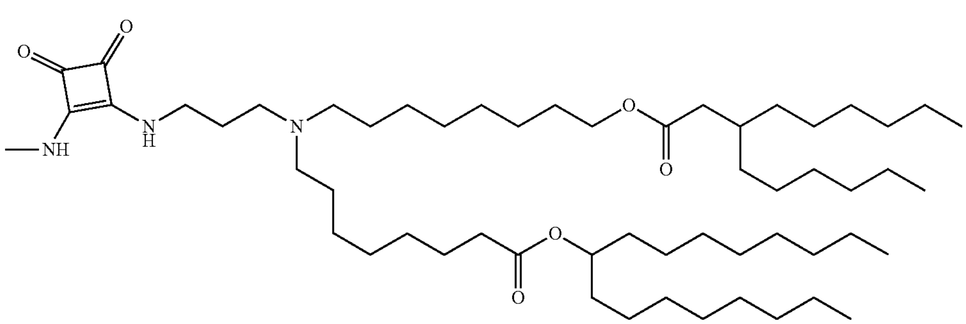 [SMILES: CCCCCCCCC(CCCCCCCC)OC(=O)CCCCCCCN(CCCCCCCCOC(=O)CC(CCCCCC)CCCCCC)CCCNc1c(NC)c(=O)c1=O] |

TABLE 1-continued
Amino Lipids.
| Cpd | Structure |
|---|---|
| 48 | 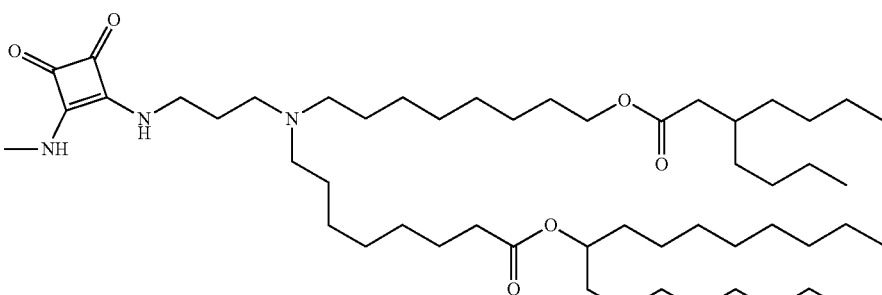 |
| 49 | 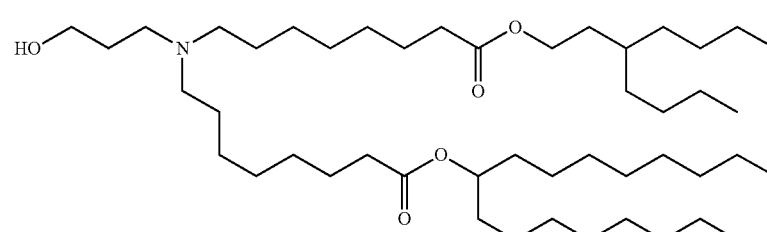 |
| 50 | 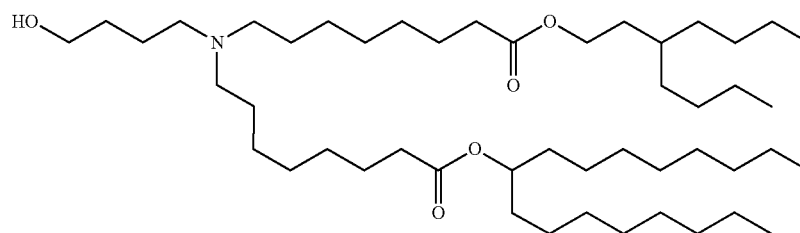 |
| 51 | 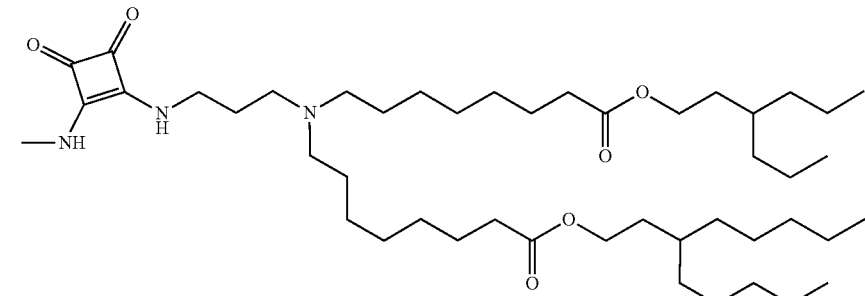 |
| 52 | 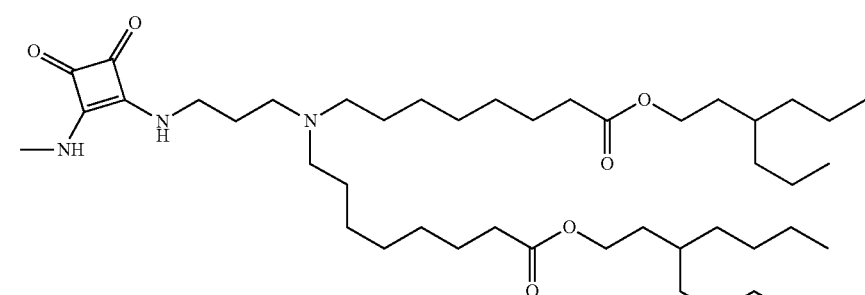 |

TABLE 1-continued

Amino Lipids.

| Cpd | Structure |
|---|---|
| 53 | 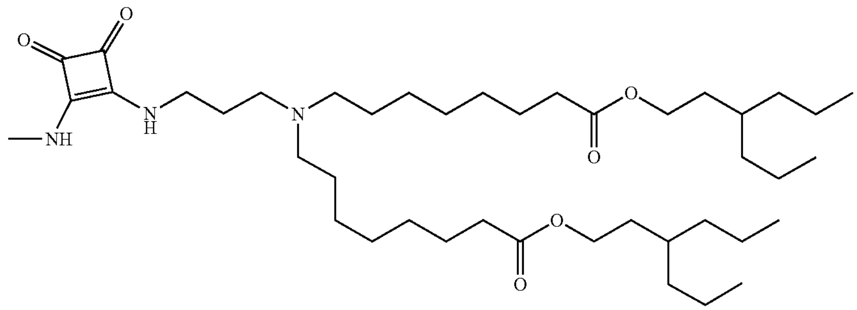 [SMILES: CCCC(CCC)CCOC(=O)CCCCCCCN(CCCCCCCC(=O)OCCC(CCC)CCC)CCCNc1c(NC)c(=O)c1=O] |
| 54 | 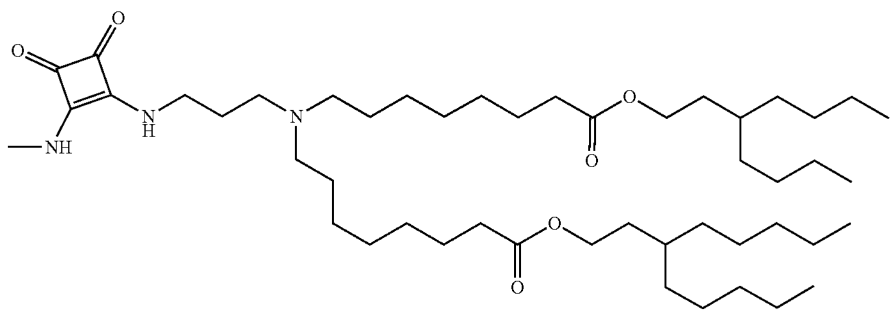 [SMILES: CCCCCC(CCCCC)CCOC(=O)CCCCCCCN(CCCCCCCC(=O)OCCC(CCCC)CCCC)CCCNc1c(NC)c(=O)c1=O] |
| 55 | 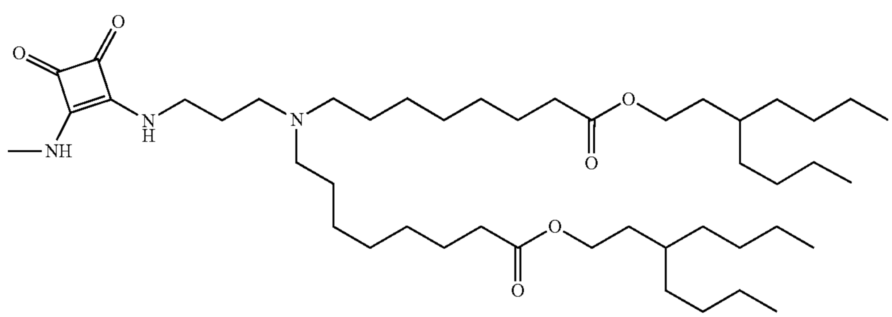 [SMILES: CCCCC(CCCC)CCOC(=O)CCCCCCCN(CCCCCCCC(=O)OCCC(CCCC)CCCC)CCCNc1c(NC)c(=O)c1=O] |
| 56 | 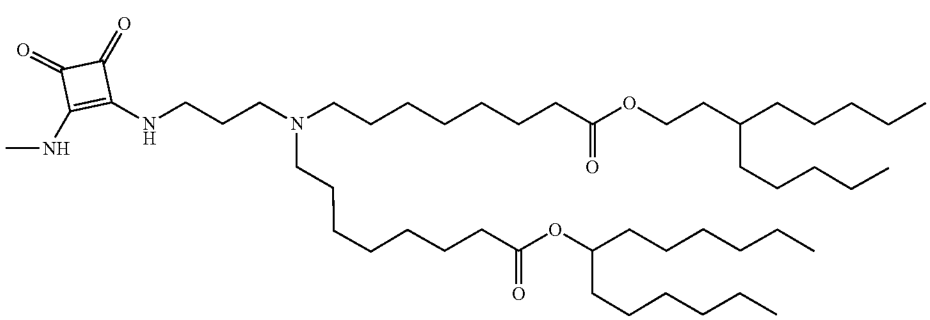 [SMILES: CCCCCCC(CCCCCC)OC(=O)CCCCCCCN(CCCCCCCC(=O)OCCC(CCCCC)CCCCC)CCCNc1c(NC)c(=O)c1=O] |
| 57 | 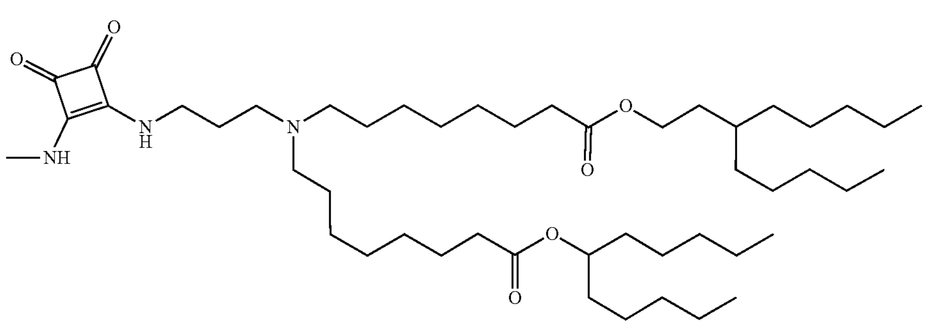 [SMILES: CCCCCC(CCCCC)CCOC(=O)CCCCCCCN(CCCCCCCC(=O)OC(CCCCC)CCCCC)CCCNc1c(NC)c(=O)c1=O] |

TABLE 1-continued

Amino Lipids.

| Cpd | Structure |
|---|---|
| 58 | 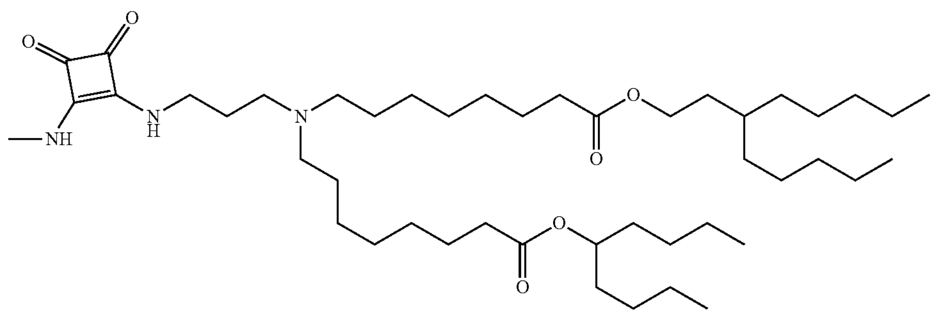 [SMILES: CCCCCC(CCCCC)CCOC(=O)CCCCCCCN(CCCCCCCC(=O)OC(CCCC)CCCC)CCCNc1c(NC)c(=O)c1=O] |
| 59 | 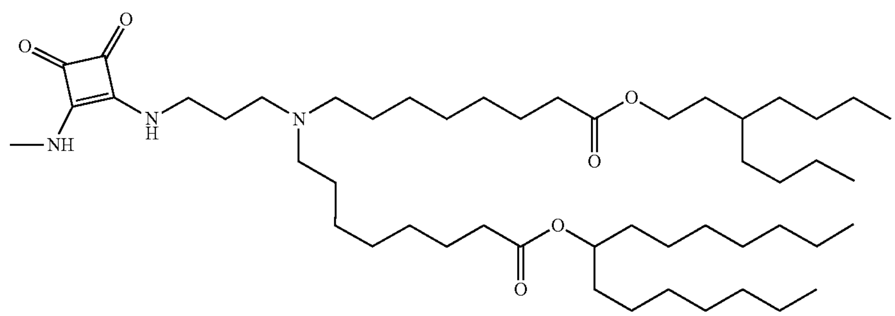 [SMILES: CCCCCCCC(CCCCCCC)OC(=O)CCCCCCCN(CCCCCCCC(=O)OCCC(CCCC)CCCC)CCCNc1c(NC)c(=O)c1=O] |
| 60 | 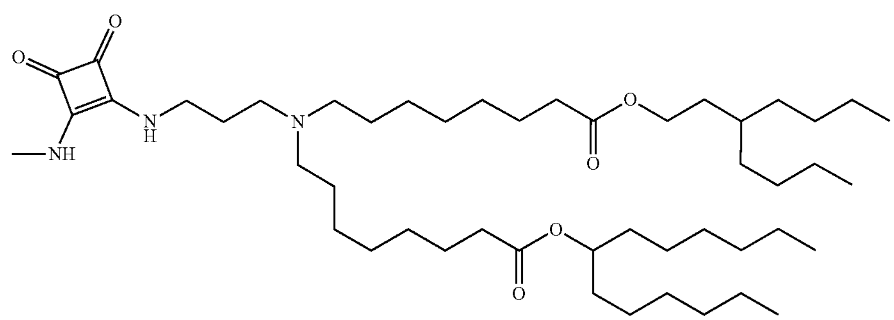 [SMILES: CCCCCCC(CCCCCC)OC(=O)CCCCCCCN(CCCCCCCC(=O)OCCC(CCCC)CCCC)CCCNc1c(NC)c(=O)c1=O] |
| 61 | 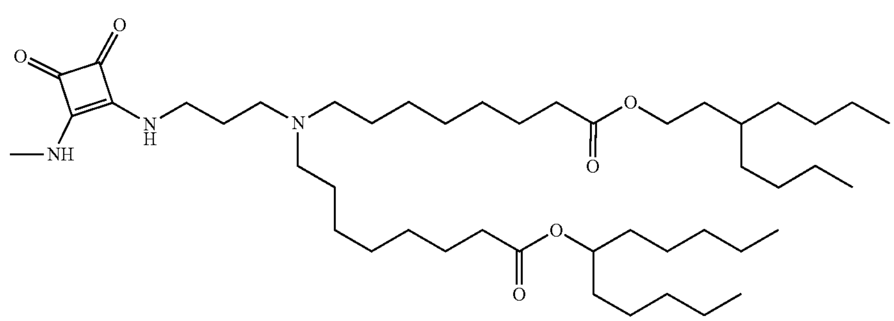 [SMILES: CCCCCC(CCCCC)OC(=O)CCCCCCCN(CCCCCCCC(=O)OCCC(CCCC)CCCC)CCCNc1c(NC)c(=O)c1=O] |

TABLE 1-continued

Amino Lipids.

| Cpd | Structure |
|---|---|
| 62 | 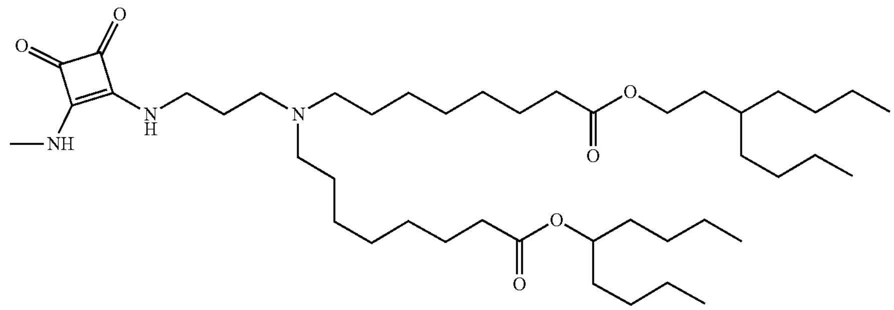 [SMILES: CCCCC(CCCC)CCOC(=O)CCCCCCCN(CCCCCCCC(=O)OC(CCCC)CCCC)CCCNc1c(NC)c(=O)c1=O] |
| 63 | 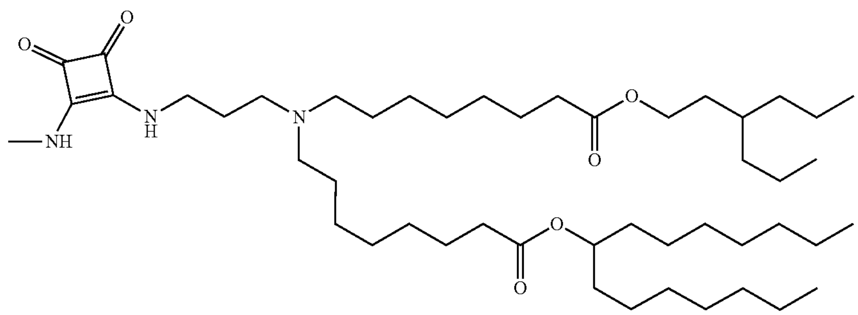 [SMILES: CCCCCCCC(CCCCCCC)OC(=O)CCCCCCCN(CCCCCCCC(=O)OCCC(CCC)CCC)CCCNc1c(NC)c(=O)c1=O] |
| 64 | 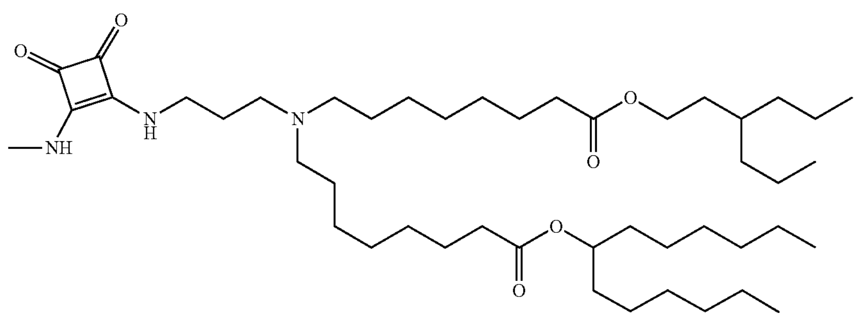 [SMILES: CCCCCCC(CCCCCC)OC(=O)CCCCCCCN(CCCCCCCC(=O)OCCC(CCC)CCC)CCCNc1c(NC)c(=O)c1=O] |
| 65 | 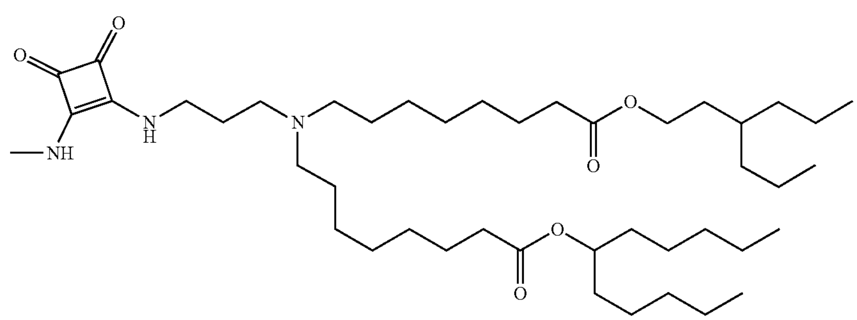 [SMILES: CCCCCC(CCCCC)OC(=O)CCCCCCCN(CCCCCCCC(=O)OCCC(CCC)CCC)CCCNc1c(NC)c(=O)c1=O] |
| 66 | 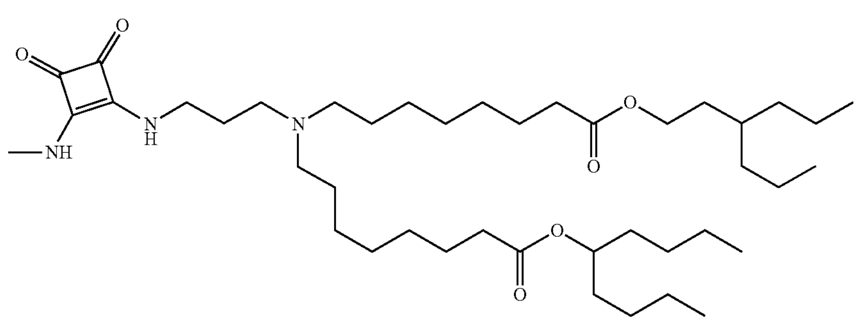 [SMILES: CCCCC(CCCC)OC(=O)CCCCCCCN(CCCCCCCC(=O)OCCC(CCC)CCC)CCCNc1c(NC)c(=O)c1=O] |

TABLE 1-continued

Amino Lipids.

| Cpd | Structure |
|---|---|
| 67 | 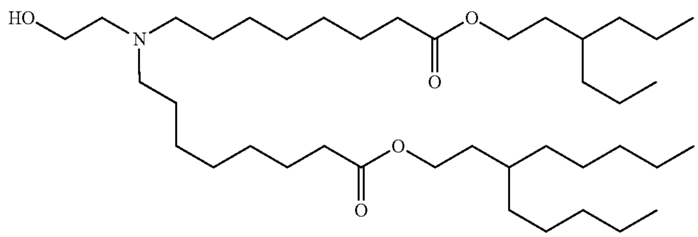 [SMILES: CCCCCC(CCCCC)CCOC(=O)CCCCCCCN(CCO)CCCCCCCC(=O)OCCC(CCC)CCC] |
| 68 | 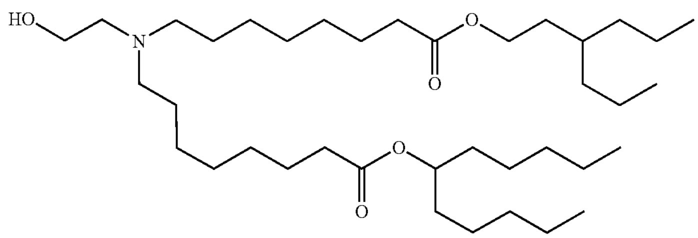 [SMILES: CCCCCC(CCCCC)OC(=O)CCCCCCCN(CCO)CCCCCCCC(=O)OCCC(CCC)CCC] |
| 69 | 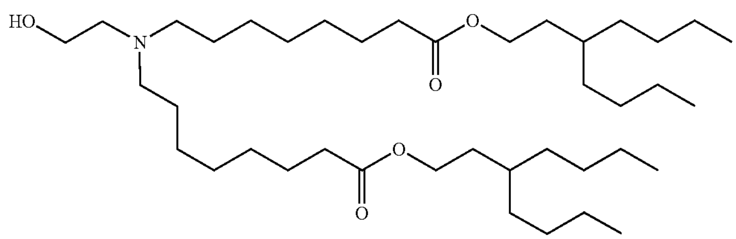 [SMILES: CCCCC(CCCC)CCOC(=O)CCCCCCCN(CCO)CCCCCCCC(=O)OCCC(CCCC)CCCC] |
| 70 | 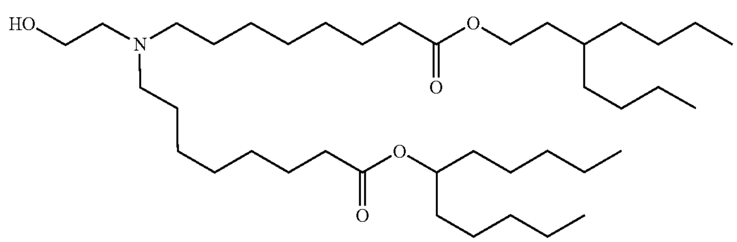 [SMILES: CCCCCC(CCCCC)OC(=O)CCCCCCCN(CCO)CCCCCCCC(=O)OCCC(CCCC)CCCC] |
| 71 | 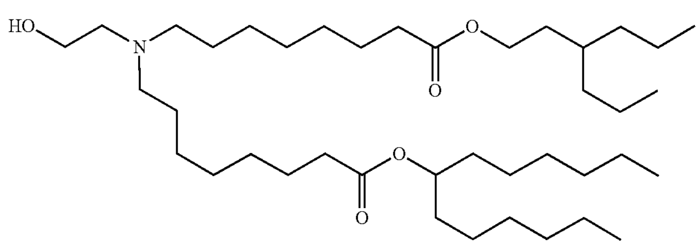 [SMILES: CCCCCCC(CCCCCC)OC(=O)CCCCCCCN(CCO)CCCCCCCC(=O)OCCC(CCC)CCC] |
| 72 | 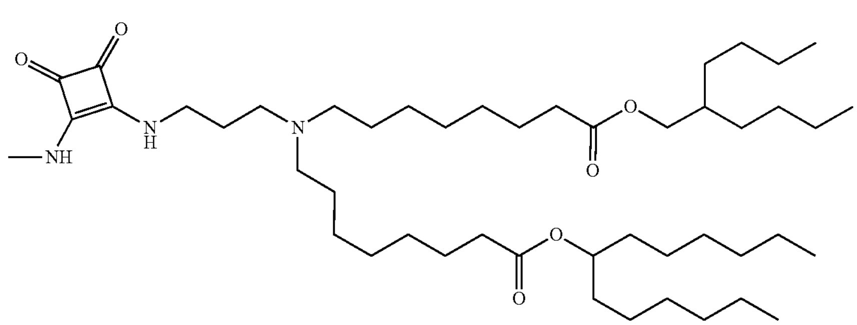 [SMILES: CCCCCCC(CCCCCC)OC(=O)CCCCCCCN(CCCCCCCC(=O)OCC(CCCC)CCCC)CCCNc1c(NC)c(=O)c1=O] |

TABLE 1-continued

Amino Lipids.

| Cpd | Structure |
|---|---|
| 73 | 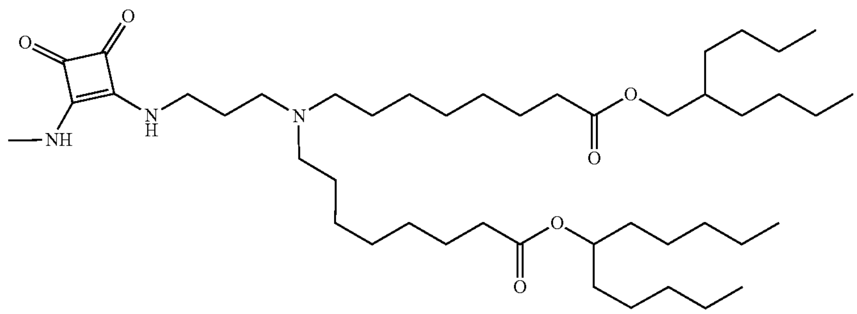 [SMILES: CCCCCC(CCCCC)OC(=O)CCCCCCCN(CCCCCCCC(=O)OCC(CCCC)CCCC)CCCNc1c(NC)c(=O)c1=O] |
| 74 | 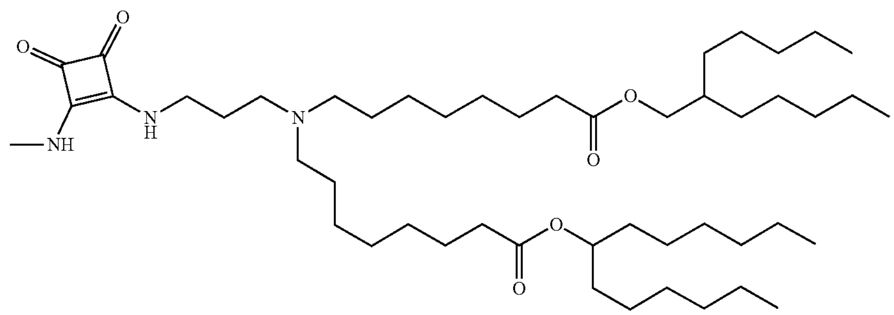 [SMILES: CCCCCCC(CCCCCC)OC(=O)CCCCCCCN(CCCCCCCC(=O)OCC(CCCCC)CCCCC)CCCNc1c(NC)c(=O)c1=O] |
| 75 | 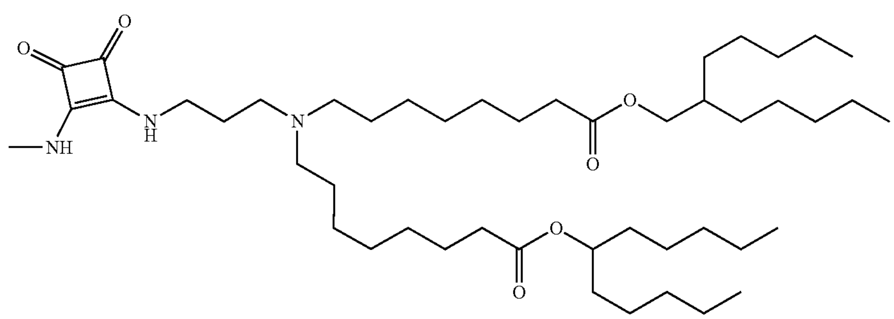 [SMILES: CCCCCC(CCCCC)COC(=O)CCCCCCCN(CCCCCCCC(=O)OC(CCCCC)CCCCC)CCCNc1c(NC)c(=O)c1=O] |
| 76 | 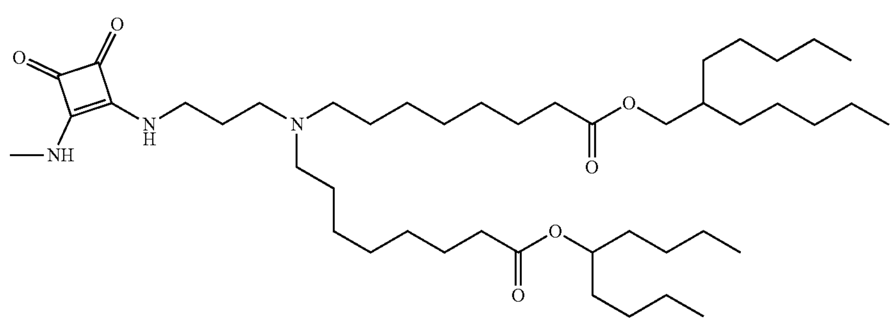 [SMILES: CCCCCC(CCCCC)COC(=O)CCCCCCCN(CCCCCCCC(=O)OC(CCCC)CCCC)CCCNc1c(NC)c(=O)c1=O] |
| 77 | 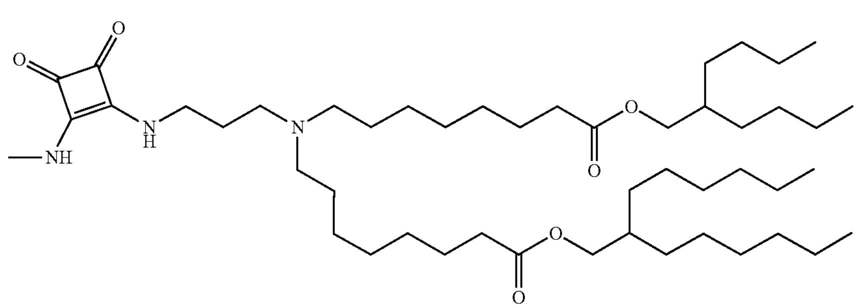 [SMILES: CCCCCCC(CCCCCC)COC(=O)CCCCCCCN(CCCCCCCC(=O)OCC(CCCC)CCCC)CCCNc1c(NC)c(=O)c1=O] |

TABLE 1-continued
Amino Lipids.
| Cpd | Structure |
|---|---|
| 78 | 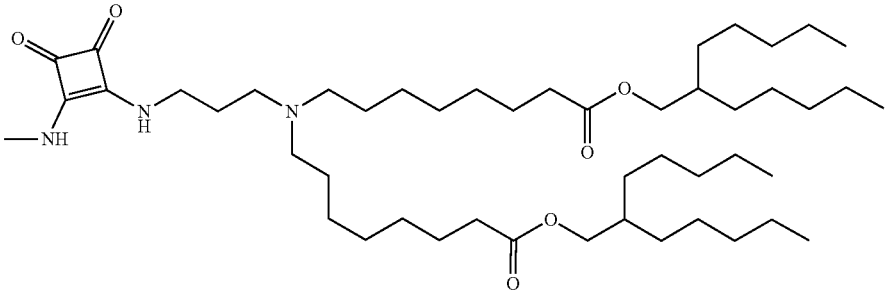 [SMILES: CCCCCC(CCCCC)COC(=O)CCCCCCCN(CCCCCCCC(=O)OCC(CCCCC)CCCCC)CCCNc1c(NC)c(=O)c1=O] |
| 79 | 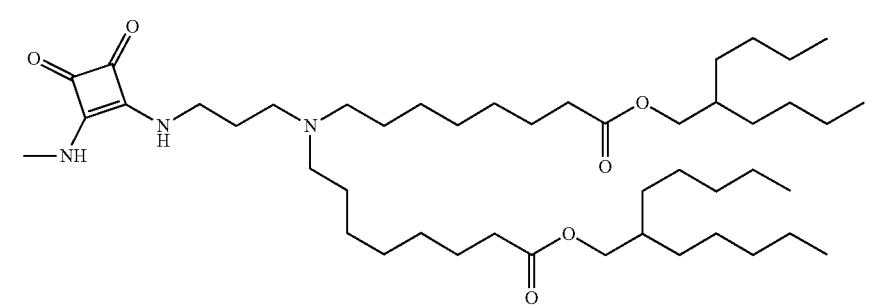 [SMILES: CCCCCC(CCCCC)COC(=O)CCCCCCCN(CCCCCCCC(=O)OCC(CCCC)CCCC)CCCNc1c(NC)c(=O)c1=O] |
| 80 | 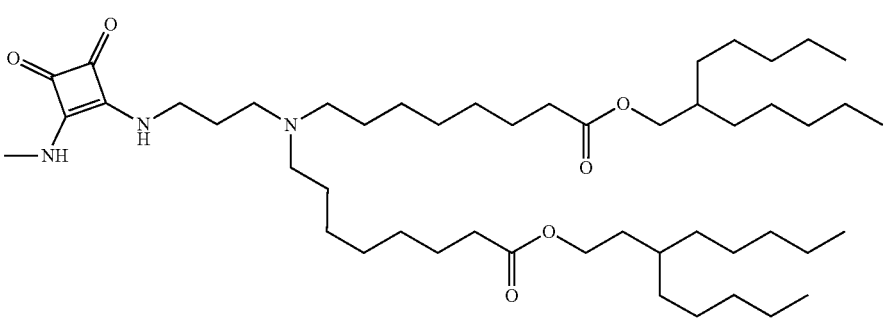 [SMILES: CCCCCC(CCCCC)CCOC(=O)CCCCCCCN(CCCCCCCC(=O)OCC(CCCCC)CCCCC)CCCNc1c(NC)c(=O)c1=O] |
| 81 | 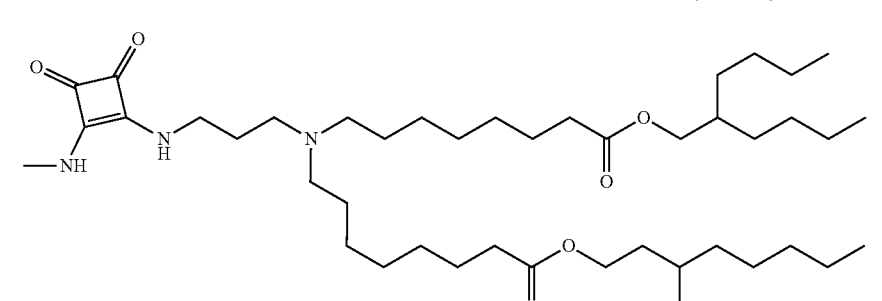 |
| 82 | 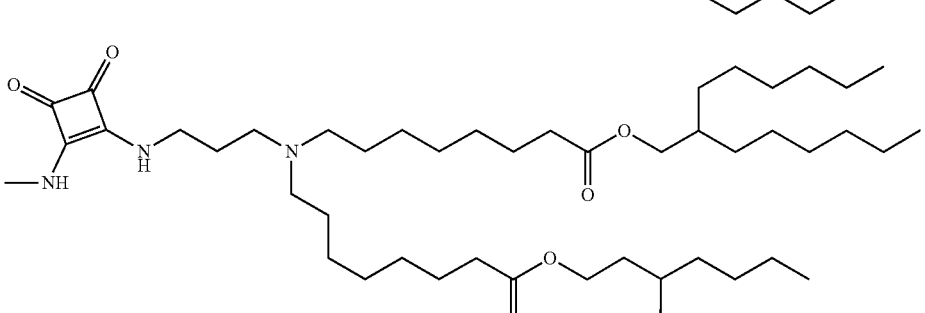 |

TABLE 1-continued

Amino Lipids.

| Cpd | Structure |
|---|---|
| 83 | 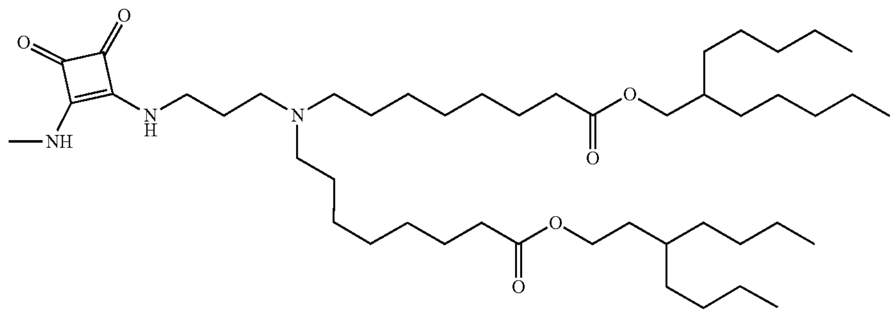 [SMILES: CCCCCC(CCCCC)COC(=O)CCCCCCCN(CCCCCCCC(=O)OCCC(CCCC)CCCC)CCCNc1c(NC)c(=O)c1=O] |
| 84 | 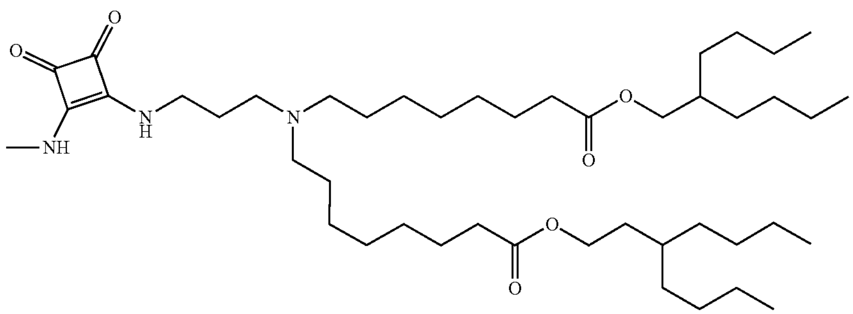 [SMILES: CCCCC(CCCC)CCOC(=O)CCCCCCCN(CCCCCCCC(=O)OCC(CCCC)CCCC)CCCNc1c(NC)c(=O)c1=O] |

The central amine moiety of a lipid according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

Definitions

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-14}$ alkenyl" means an optionally substituted linear or branched hydrocarbon including 2-14 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, Cis alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "$C_{3-6}$ carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles. In some embodiments, the carbocycle is a $C_{3-8}$ cycloalkyl. In some embodiments, the carbocycle is a $C_{3-6}$ cycloalkyl. In some embodiments, the carbocycle is a $C_{6-10}$ aryl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc. In some embodiments, an "aryl" is a $C_{6-10}$ carbocycle with aromatity (e.g., an "aryl" is a $C_{6-10}$ aryl).

As used herein, the term "heterocycle" or "heterocyclic group" means an optionally substituted mono- or multicyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles. In some embodiments, the heterocycle is a 4 to 12-membered heterocycloalkyl. In some embodiments, the heterocycle is a 5- or 6-membered heteroaryl.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen sulfur, and boron. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C=O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R"", in which each OR are alkoxy groups that can be the same or different and R"" is an alkyl or alkenyl group), a phosphate (e.g., $P(O)_4^{3-}$), a thiol (e.g., —SH), a sulfoxide (e.g., —S(O)R), a sulfinic acid (e.g., —S(O)OH), a sulfonic acid (e.g., —S(O)$_2$OH), a thial (e.g., —C(S)H), a sulfate (e.g., $S(O)_4^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a $C_{1-6}$ alkyl group may be further substituted with one, two, three, four, five, or six substituents as described herein.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

About, Approximately: As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean+/−10% of the recited value. For instance, a nanoparticle composition including a lipid component having about 40% of a given compound may include 30-50% of the compound.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of lipid nanoparticles (e.g., empty LNPs or loaded LNPs). Moreover, more than one mammalian cell may be contacted by a nanoparticle composition.

As used herein, the term "delivering" means providing an entity to a destination. For example, delivering a therapeutic and/or prophylactic to a subject may involve administering a nanoparticle composition including the therapeutic and/or prophylactic to the subject (e.g., by an intravenous, intramuscular, intradermal, or subcutaneous route). Administration of a nanoparticle composition to a mammal or mammalian cell may involve contacting one or more cells with the nanoparticle composition.

As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to the level of delivery of a therapeutic and/or prophylactic by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. It will be understood that the enhanced delivery of a nanoparticle to a target tissue need not be determined in a subject being treated, it may be determined in a surrogate such as an animal model (e.g., a rat model). In certain embodiments, a nanoparticle composition including a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c) has substantively the same level of delivery enhancement regardless of administration routes. For example, certain compounds disclosed herein exhibit similar delivery enhancement when they are used for delivering a therapeutic and/or prophylactic either intravenously or intramuscularly. In other embodiments, certain compounds disclosed herein exhibit a higher level of delivery enhancement when they are used for delivering a therapeutic and/or prophylactic intramuscularly than intravenously.

As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. For example, for renovascular targeting, a therapeutic and/or prophylactic is specifically provided to a mammalian kidney as compared to the liver and spleen if 1.5, 2-fold, 3-fold, 5-fold, 10-fold, 15 fold, or 20 fold more therapeutic and/or prophylactic per 1 g of tissue is delivered to a kidney compared to that delivered to the liver or spleen following systemic administration of the therapeutic and/or prophylactic. It will be understood that the ability of a nanoparticle to specifically deliver to a target tissue need not be determined in a subject being treated, it may be determined in a surrogate such as an animal model (e.g., a rat model).

As used herein, "encapsulation efficiency" refers to the amount of a therapeutic and/or prophylactic that becomes part of a nanoparticle composition, relative to the initial total amount of therapeutic and/or prophylactic used in the preparation of a nanoparticle composition. For example, if 97 mg of therapeutic and/or prophylactic are encapsulated in a nanoparticle composition out of a total 100 mg of therapeutic and/or prophylactic initially provided to the composition, the encapsulation efficiency may be given as 97%. As used herein, "encapsulation" may refer to complete, substantial, or partial enclosure, confinement, surrounding, or encasement.

As used herein, "encapsulation", "encapsulated", "loaded", and "associated" may refer to complete, substantial, or partial enclosure, confinement, surrounding, or encasement. As used herein, "encapsulation" or "association" may refer to the process of confining an individual nucleic acid molecule within a nanoparticle and/or establishing a physiochemical relationship between an individual nucleic acid molecule and a nanoparticle. As used herein, an "empty nanoparticle" may refer to a nanoparticle that is substantially free of a therapeutic or prophylactic agent. As used herein, an "empty nanoparticle" or an "empty lipid nanoparticle" may refer to a nanoparticle that is substantially free of a nucleic acid. As used herein, an "empty nanoparticle" or an "empty lipid nanoparticle" may refer to a nanoparticle that is substantially free of a nucleotide or a polypeptide. As used herein, an "empty nanoparticle" or an "empty lipid nanoparticle" may refer to a nanoparticle that consists substantially of only lipid components. As used herein, a "loaded nanoparticle" or a "loaded lipid nanoparticle" (also referred to as a "full nanoparticle" or a "full lipid nanoparticle") may refer to a nanoparticle comprising the components of the empty nanoparticle, and a therapeutic or prophylactic agent. As used herein, a "loaded nanoparticle" or a "loaded lipid nanoparticle" (also referred to as a "full nanoparticle" or a "full lipid nanoparticle") may refer to a nanoparticle comprising the components of the empty nanoparticle, and a nucleotide or polypeptide. As used herein, a "loaded nanoparticle" or a "loaded lipid nanoparticle" (also referred to as a "full nanoparticle" or a "full lipid nanoparticle") may refer to a nanoparticle comprising the components of the empty nanoparticle, and a nucleic acid.

As used herein, "expression" of a nucleic acid sequence refers to translation of an mRNA into a polypeptide or protein and/or post-translational modification of a polypeptide or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerization is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of tautomerism in di-substituted guanidine is shown below.

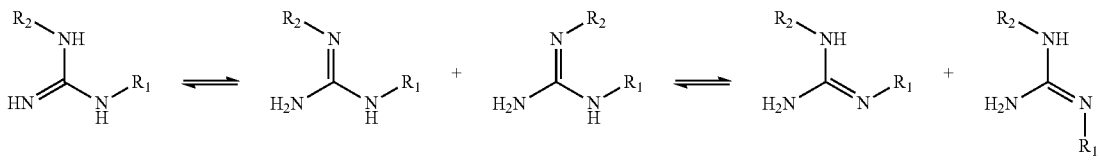

It is to be understood that the compounds of the disclosure may be depicted as different tautomers. It should also be understood that when compounds have tautomeric forms, all tautomeric forms are intended to be included in the scope of the disclosure, and the naming of the compounds does not exclude any tautomer form.

As used herein, a "lipid component" is that component of a nanoparticle composition that includes one or more lipids. For example, the lipid component may include one or more cationic/ionizable, PEGylated, structural, or other lipids, such as phospholipids.

As used herein, a "linker" is a moiety connecting two moieties, for example, the connection between two nucleosides of a cap species. A linker may include one or more groups including but not limited to phosphate groups (e.g., phosphates, boranophosphates, thiophosphates, selenophosphates, and phosphonates), alkyl groups, amidates, or glycerols. For example, two nucleosides of a cap analog may be linked at their 5' positions by a triphosphate group or by a chain including two phosphate moieties and a boranophosphate moiety.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, the "N:P ratio" is the molar ratio of ionizable (in the physiological pH range) nitrogen atoms in a lipid to phosphate groups in an RNA, e.g., in a nanoparticle composition including a lipid component and an RNA.

As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

As used herein, "naturally occurring" means existing in nature without artificial aid.

As used herein, "patient" refers to a subject who may seek or be in need of treatment, requires treatment, is receiving treatment, will receive treatment, or a subject who is under care by a trained professional for a particular disease or condition.

As used herein, a "PEG lipid" or "PEGylated lipid" refers to a lipid comprising a polyethylene glycol component.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, the "polydispersity index," or "PDI" is a ratio that describes the homogeneity of the particle size distribution of a system. A small value, e.g., less than 0.3, indicates a narrow particle size distribution.

As used herein, the term "polypeptide" or "polypeptide of interest" refers to a polymer of amino acid residues typically joined by peptide bonds that can be produced naturally (e.g., isolated or purified) or synthetically. The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art. The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest.

As used herein, a "DNA" refers to a desoxyribonucleic acid that may be naturally or non-naturally occurring. For example, a DNA may be a synthetic molecule, e.g., a synthetic DNA molecule produced in vitro. In some embodiments, the DNA molecule is a recombinant molecule. As used herein, a "recombinant DNA molecule" refers to a DNA molecule that does not exist as a natural product, but is produced using molecular biology techniques.

As used herein, a "single unit dose" is a dose of any therapeutic administered in one dose/at one time/single route/single point of contact, i.e., single administration event.

As used herein, a "split dose" is the division of single unit dose or total daily dose into two or more doses.

As used herein, a "total daily dose" is an amount given or prescribed in 24 hour period. It may be administered as a single unit dose.

As used herein, "size" or "mean size" in the context of lipid nanoparticles (e.g., empty LNPs or loaded LNPs) refers to the mean diameter of a nanoparticle composition.

As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, "targeted cells" refers to any one or more cells of interest. The cells may be found in vitro, in vivo, in situ, or in the tissue or organ of an organism. The organism may be an animal, preferably a mammal, more preferably a human and most preferably a patient.

As used herein "target tissue" refers to any one or more tissue types of interest in which the delivery of a therapeutic and/or prophylactic would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

The term "therapeutic agent" or "prophylactic agent" refers to any agent that, when administered to a subject, has a therapeutic, diagnostic, and/or prophylactic effect and/or elicits a desired biological and/or pharmacological effect. Therapeutic agents are also referred to as "actives" or "active agents." Such agents include, but are not limited to, cytotoxins, radioactive ions, chemotherapeutic agents, small molecule drugs, proteins, and nucleic acids.

As used herein, the term "therapeutically effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, "transfection" refers to the introduction of a species (e.g., an RNA) into a cell. Transfection may occur, for example, in vitro, ex vivo, or in vivo.

As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the "zeta potential" is the electrokinetic potential of a lipid, e.g., in a particle composition.

Nanoparticle Compositions

The disclosure also features lipid nanoparticles comprising a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c) as described herein.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter), e.g., when measured by dynamic light scattering (DLS), transmission electron microscopy, scanning electron microscopy, or another method. Nanoparticle compositions include, for example, lipid nanoparticles (LNPs; e.g., empty LNPs or loaded LNPs), liposomes, lipid vesicles, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or cross-linked to one another. Lipid bilayers may include one or more ligands, proteins, or channels.

Nanoparticle compositions comprise a lipid component including at least one compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c). For example, the lipid component of a nanoparticle composition may include one or more of compounds of Table 1. Nanoparticle compositions may also include a variety of other components. For example, the lipid component of a nanoparticle composition may include one or more other lipids in addition to a lipid according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c).

Cationic/Ionizable Lipids

The lipid nanoparticle (e.g., an empty LNP or a loaded LNP) may include one or more cationic and/or ionizable lipids (e.g., lipids that may have a positive or partial positive charge at physiological pH) in addition to a lipid according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c). Cationic and/or ionizable lipids may be selected from the non-limiting group consisting of 3-(didodecylamino)-$N_1,N_{1,4}$-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, a cationic lipid may also be a lipid including a cyclic amine group.

Structural Lipids

The lipid nanoparticle (e.g., an empty LNP or a loaded LNP) may include one or more structural lipids. Structural lipids can be selected from the group consisting of, but are not limited to, cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the structural lipid includes cholesterol and a corticosteroid (such as prednisolone, dexamethasone, prednisone, and hydrocortisone), or a combination thereof.

In some embodiments, the structural lipid is:

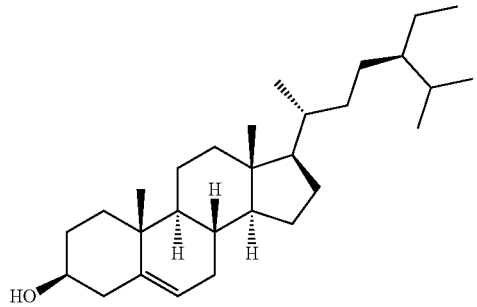

(SL-1)

Phospholipids

The lipid nanoparticle (e.g., an empty LNP or a loaded LNP) may include one or more phospholipids, such as one or more (poly)unsaturated lipids. Phospholipids may assemble into one or more lipid bilayers. In general, phospholipids may include a phospholipid moiety and one or more fatty acid moieties. For example, a phospholipid may be a lipid according to Formula (IV):

$$R^A \underset{O}{\overset{O}{\|}} O \underset{R^B \underset{O}{\overset{O}{\|}}}{} O \underset{O^-}{\overset{O}{\|}} OR^P, \quad (IV)$$

in which $R_p$ represents a phospholipid moiety and $R^A$ and $R_B$ represent fatty acid moieties with or without unsaturation that may be the same or different. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a lipid nanoparticle (e.g., an empty LNP or a loaded LNP) to facilitate membrane permeation or cellular recognition or in conjugating a lipid nanoparticle (e.g., an empty LNP or a loaded LNP) to a useful component such as a targeting or imaging moiety (e.g., a dye).

Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2- dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE), and mixtures thereof. In some embodiments, a lipid nanoparticle (e.g., an empty LNP or a loaded LNP) includes DSPC. In certain embodiments, a lipid nanoparticle (e.g., an empty LNP or a loaded LNP) includes DOPE. In some embodiments, a lipid nanoparticle (e.g., an empty LNP or a loaded LNP) includes both DSPC and DOPE.

PEG lipids

The lipid nanoparticle (e.g., an empty LNP or a loaded LNP) may include one or more PEG or PEG-modified lipids. Such species may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides (PEG-CER), PEG-modified dialkylamines, PEG-modified diacylglycerols (PEG-DEG), PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In certain embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, and a PEG-modified dialkylglycerol.

In certain embodiments, PEG lipid is selected from the group consisting of 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). For example, in some embodiments, the PEG lipid is PEG-DMG.

In certain embodiments, the PEG lipid is a compound of Formula (PL-I):

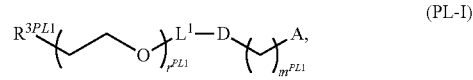
(PL-I)

or a salt thereof, wherein:
$R^{3PL1}$ is $-OR^{OPL1}$.
$R^{OPL1}$ is hydrogen, optionally substituted alkyl, or an oxygen protecting group;
$r^{PL1}$ is an integer between 1 and 100, inclusive;
$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^{NPL1})$, S, C(O), $C(O)N(R^{NPL1})$, $NR^{NPL1}C(O)$, C(O)O, OC(O), OC(O)O, $OC(O)N(R^{NPL1})$, $NR^{NPL1}C(O)O$, or $NR^{NPL1}C(O)N(R^{NPL1})$;
D is a moiety obtained by click chemistry or a moiety cleavable under physiological conditions;
$m^{PL1}$ is 0, 1, 2, 3, 4, 5, 6, 7, 8, 9, or 10;
A is of the formula:

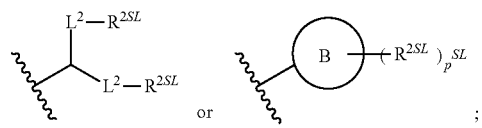

each instance of of $L^2$ is independently a bond or optionally substituted $C_{1-6}$ alkylene, wherein one methylene unit of the optionally substituted $C_{1-6}$ alkylene is optionally replaced with O, $N(R^{NPL1})$, S, C(O), $C(O)N(R^{NPL1})$, $NR^{NPL1}C(O)$, C(O)O, OC(O), OC(O)O, $-OC(O)N(R^{NPL1})$, $NR^{NPL1}C(O)O$, or $NR^{NPL1}C(O)N(R^{NPL1})$;
each instance of $R^{2SL}$ is independently optionally substituted $C_{1-30}$ alkyl, optionally substituted $C_{1-30}$ alkenyl, or optionally substituted $C_{1-30}$ alkynyl; optionally wherein one or more methylene units of $R^{2SL}$ are independently replaced with optionally substituted carbocyclylene, optionally substituted heterocyclylene, optionally substituted arylene, optionally substituted heteroarylene, $N(R^{NPL1})$, O, S, C(O), $C(O)N(R^{NPL1})$, $NR^{NPL1}C(O)$, $NR^{NPL1}C(O)N(R^{NPL1})$, $-C(O)O$, OC(O), OC(O)O, $OC(O)N(R^{NPL1})$, $NR^{NPL1}C(O)O$, C(O)S, SC(O), $C(=NR^{NPL1})$, $-C(=NR^{NPL1})N(R^{NPL1})$, $NR^{NPL1}C(=NR^{NPL1})$, $NR^{NPL1}C(=NR^{NPL1})N(R^{NPL1})$, C(S), $C(S)N(R^{NPL1})$, $NR^{NPL1}C(S)$, $NR^{NPL1}C(S)N(R^{NPL1})$, S(O), OS(O), S(O)O, OS(O)O, $OS(O)_2$, $S(O)_2O$, $OS(O)_2O$, $N(R^{NPL1})S(O)$, $S(O)N(R^{NPL1})$, $N(R^{NPL1})S(O)N(R^{NPL1})$, $OS(O)N(R^{NPL1})$, $N(R^{NPL1})S(O)O$, $S(O)_2$, $N(R^{NPL1})S(O)_2$, $S(O)_2N(R^{NPL1})$, $N(R^{NPL1})S(O)_2N(R^{NPL1})$, $OS(O)_2N(R^{NPL1})$, or $N(R^{NPL1})S(O)_2O$;
each instance of $R^{NPL1}$ is independently hydrogen, optionally substituted alkyl, or a nitrogen protecting group;
Ring B is optionally substituted carbocyclyl, optionally substituted heterocyclyl, optionally substituted aryl, or optionally substituted heteroaryl; and
$p^{SL}$ is 1 or 2.

In certain embodiments, the PEG lipid is a compound of Formula (PL-I—OH):

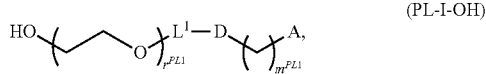
(PL-I-OH)

or a salt thereof.

In certain embodiments, the PEG lipid is a compound of Formula (PL-II-OH):

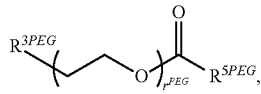 (PL-II-OH)

or a salt or isomer thereof, wherein:

$R^{3PEG}$ is —$OR^O$;
$R^O$ is hydrogen, $C_{1-6}$ alkyl or an oxygen protecting group;
$r^{PEG}$ is an integer between 1 and 100;
$R^{5PEG}$ is $C_{10-40}$ alkyl, $C_{10-40}$ alkenyl, or $C_{10-40}$ alkynyl; and optionally one or more methylene groups of $R^{5PEG}$ are independently replaced with $C_{3-10}$ carbocyclylene, 4 to 10 membered heterocyclylene, $C_{6-10}$ arylene, 4 to 10 membered heteroarylene, —N($R^{NPEG}$)—, —O—, —S—, —C(O)—, —C(O)N($R^{NPEG}$)—, —$NR^{NPEG}$C(O)—, —$NR^{NPEG}$C(O)N($R^{NPEG}$)—, C(O), —OC(O)—, —OC(O)O—, —OC(O)N($R^{NPEG}$)—, —$NR^{NPEG}$C(O)O—, —C(O)S—, —SC(O)—, —C(=$NR^{NPEG}$), —C(=$NR^{NPEG}$)N($R^{NPEG}$)—, —$NR^{NPEG}$C(=$NR^{NPEG}$)—, —$NR^{NPEG}$C(=$NR^{NPEG}$)N($R^{NPEG}$)—, C(S)—C(S)N($R^{NPEG}$)—, —$NR^{NPEG}$C(S)—, —$NR^{NPEG}$C(S)N($R^{NPEG}$), —S(O)—, —OS(O)—, —S(O)O—, —OS(O)O—, —OS(O)$_2$—, —S(O)$_2$O—, —OS(O)$_2$O—, —N($R^{NPEG}$)S(O)—, —S(O)N($R^{NPEG}$)—, —N($R^{NPEG}$)S(O)N($R^{NPEG}$)—, —OS(O)N($R^{NPEG}$)—, —N($R^{NPEG}$)S(O)O—, —S(O)$_2$—, —N($R^{NPEG}$)S(O)$_2$—, —S(O)$_2$N($R^{NPEG}$)—, —N($R^{NPEG}$)S(O)$_2$N($R^{NPEG}$)—, —OS(O)$_2$N($R^{NPEG}$)—, or —N($R^{NPEG}$)S(O)$_2$O—; and each instance of $R^{NPEG}$ is independently hydrogen, $C_{1-6}$ alkyl, or a nitrogen protecting group.

In certain embodiments, in the PEG lipid of Formula (PL-II-OH), r is an integer between 40 and 50. For example, r is selected from the group consisting of 40, 41, 42, 43, 44, 45, 46, 47, 48, 49 and 50. For example, r is 45.

In certain embodiments, in the PEG lipid of Formula (PL-II-OH), $R^5$ is $C_{17}$ alkyl.

In certain embodiments, the PEG lipid is a compound of Formula (PL-II):

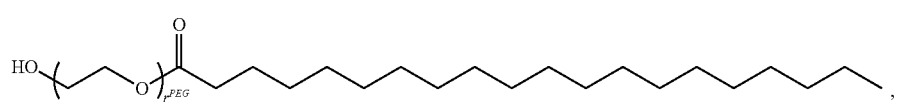 (PL-II)

wherein $r^{PEG}$ is an integer between 1 and 100.

In certain embodiments, the PEG lipid is a compound of Formula (PEG-1):

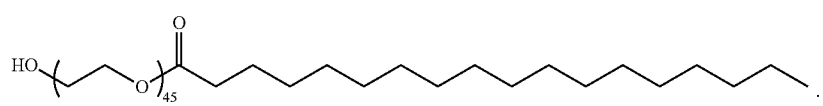 (PEG-1)

In certain embodiments, the PEG lipid is a compound of Formula (PL-III):

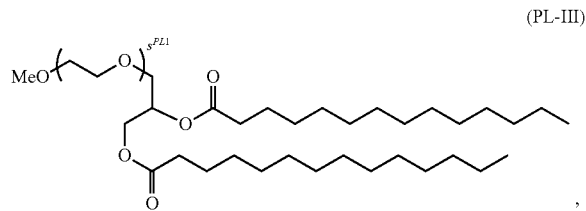

(PL-III)

or a salt or isomer thereof, wherein $S^{PL1}$ is an integer between 1 and 100.

In certain embodiments, the PEG lipid is a compound of following formula:

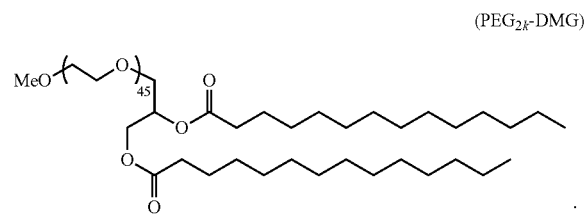

(PEG$_{2k}$-DMG)

In certain embodiments, the incorporation of lipids of one of formulae (PL-I), PL-I—OH), (PL-II), (PL-II-OH), (PL-III), PEG$_{2k}$-DMG, or PEG-1 in the nanoparticle formulation can improve the pharmacokinetics and/or biodistribution of the lipid nanoparticle formulations. For example, incorporation of lipids of one of formulae (PL-II-OH), (PL-IIa-OH), (PL-II), or PEG-lin the nanoparticle formulation can reduce the accelerated blood clearance (ABC) effect.

Adjuvants

In some embodiments, a lipid nanoparticle (e.g., an empty LNP or a loaded LNP) that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Therapeutic Agents

Lipid nanoparticles (e.g., empty LNPs or loaded LNPs) may include one or more therapeutic and/or prophylactics. The disclosure features methods of delivering a therapeutic and/or prophylactic to a mammalian cell or organ, producing a polypeptide of interest in a mammalian cell, and treating a disease or disorder in a mammal in need thereof comprising administering to a mammal and/or contacting a mammalian cell with a lipid nanoparticle (e.g., an empty LNP or a loaded LNP) including a therapeutic and/or prophylactic.

Therapeutic and/or prophylactics include biologically active substances and are alternately referred to as "active agents." A therapeutic and/or prophylactic may be a substance that, once delivered to a cell or organ, brings about a desirable change in the cell, organ, or other bodily tissue or system. Such species may be useful in the treatment of one or more diseases, disorders, or conditions. In some embodiments, a therapeutic and/or prophylactic is a small molecule drug useful in the treatment of a particular disease, disorder, or condition.

In some embodiments, a therapeutic and/or prophylactic is a vaccine, a compound (e.g., a polynucleotide or nucleic acid molecule that encodes a protein or polypeptide or peptide or a protein or polypeptide or protein) that elicits an immune response, and/or another therapeutic and/or prophylactic. Vaccines include compounds and preparations that are capable of providing immunity against one or more conditions related to infectious diseases and can include mRNAs encoding infectious disease derived antigens and/or epitopes. Vaccines also include compounds and preparations that direct an immune response against cancer cells and can include mRNAs encoding tumor cell derived antigens, epitopes, and/or neoepitopes. In some embodiments, a vaccine and/or a compound capable of eliciting an immune response is administered intramuscularly via a composition of the disclosure.

In other embodiments, a therapeutic and/or prophylactic is a protein, for example a protein needed to augment or replace a naturally-occurring protein of interest. Such proteins or polypeptides may be naturally occurring, or may be modified using methods known in the art, e.g., to increase half life. Exemplary proteins are intracellular, transmembrane, or secreted.

Polynucleotides and Nucleic Acids

In some embodiments, the therapeutic agent is an agent that enhances (i.e., increases, stimulates, upregulates) protein expression. Non-limiting examples of types of therapeutic agents that can be used for enhancing protein expression include RNAs, mRNAs, dsRNAs, CRISPR/Cas9 technology, ssDNAs and DNAs (e.g., expression vectors). The agent that upregulates protein expression may upregulate expression of a naturally occurring or non-naturally occurring protein (e.g., a chimeric protein that has been modified to improve half life, or one that comprises desirable amino acid changes). Exemplary proteins include intracellular, transmembrane, or secreted proteins, peptides, or polypeptides.

In some embodiments, the therapeutic agent is a DNA therapeutic agent. The DNA molecule can be a double-stranded DNA, a single-stranded DNA (ssDNA), or a molecule that is a partially double-stranded DNA, i.e., has a portion that is double-stranded and a portion that is single-stranded. In some cases the DNA molecule is triple-stranded or is partially triple-stranded, i.e., has a portion that is triple stranded and a portion that is double stranded. The DNA molecule can be a circular DNA molecule or a linear DNA molecule.

A DNA therapeutic agent can be a DNA molecule that is capable of transferring a gene into a cell, e.g., that encodes and can express a transcript. In other embodiments, the DNA molecule is a synthetic molecule, e.g., a synthetic DNA molecule produced in vitro. In some embodiments, the DNA molecule is a recombinant molecule. Non-limiting exemplary DNA therapeutic agents include plasmid expression vectors and viral expression vectors.

The DNA therapeutic agents described herein, e.g., DNA vectors, can include a variety of different features. The DNA therapeutic agents described herein, e.g., DNA vectors, can include a non-coding DNA sequence. For example, a DNA sequence can include at least one regulatory element for a gene, e.g., a promoter, enhancer, termination element, polyadenylation signal element, splicing signal element, and the like. In some embodiments, the non-coding DNA sequence is an intron. In some embodiments, the non-coding DNA sequence is a transposon. In some embodiments, a DNA sequence described herein can have a non-coding DNA sequence that is operatively linked to a gene that is transcriptionally active. In other embodiments, a DNA sequence described herein can have a non-coding DNA sequence that is not linked to a gene, i.e., the non-coding DNA does not regulate a gene on the DNA sequence.

In some embodiments, in the loaded LNP of the disclosure, the one or more therapeutic and/or prophylactic agents is a nucleic acid. In some embodiments, the one or more therapeutic and/or prophylactic agents is selected from the group consisting of a ribonucleic acid (RNA) and a deoxyribonucleic acid (DNA).

For example, in some embodiments, when the therapeutic and/or prophylactic agents is a DNA, the DNA is selected from the group consisting of a double-stranded DNA, a single-stranded DNA (ssDNA), a partially double-stranded DNA, a triple stranded DNA, and a partially triple-stranded DNA. In some embodiments, the DNA is selected from the group consisting of a circular DNA, a linear DNA, and mixtures thereof.

In some embodiments, in the loaded LNP of the disclosure, the one or more therapeutic and/or prophylactic agents is selected from the group consisting of a plasmid expression vector, a viral expression vector, and mixtures thereof.

For example, in some embodiments, when the therapeutic and/or prophylactic agents is a RNA, the RNA is selected from the group consisting of a single-stranded RNA, a double-stranded RNA (dsRNA), a partially double-stranded RNA, and mixtures thereof. In some embodiments, the RNA is selected from the group consisting of a circular RNA, a linear RNA, and mixtures thereof.

For example, in some embodiments, when the therapeutic and/or prophylactic agents is a RNA, the RNA is selected from the group consisting of a short interfering RNA (siRNA), an asymmetrical interfering RNA (aiRNA), a RNA interference (RNAi) molecule, a microRNA (miRNA), an antagomir, an antisense RNA, a ribozyme, a Dicer-substrate RNA (dsRNA), a small hairpin RNA (shRNA), a messenger RNA (mRNA), locked nucleic acids (LNAs) and CRISPR/Cas9 technology, and mixtures thereof.

For example, in some embodiments, when the therapeutic and/or prophylactic agents is a RNA, the RNA is selected from the group consisting of a small interfering RNA (siRNA), an asymmetrical interfering RNA (aiRNA), a microRNA (miRNA), a Dicer-substrate RNA (dsRNA), a small hairpin RNA (shRNA), a messenger RNA (mRNA), and mixtures thereof.

In some embodiments, the one or more therapeutic and/or prophylactic agents is an mRNA. In some embodiments, the one or more therapeutic and/or prophylactic agents is a modified mRNA (mmRNA).

In some embodiments, the one or more therapeutic and/or prophylactic agents is an mRNA that incorporates a microRNA binding site (miR binding site). Further, in some embodiments, an mRNA includes one or more of a stem loop, a chain terminating nucleoside, a polyA sequence, a polyadenylation signal, and/or a 5' cap structure.

An mRNA may be a naturally or non-naturally occurring mRNA. An mRNA may include one or more modified nucleobases, nucleosides, or nucleotides, as described below, in which case it may be referred to as a "modified mRNA" or "mmRNA." As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

An mRNA may include a 5' untranslated region (5'-UTR), a 3' untranslated region (3'-UTR), and/or a coding region (e.g., an open reading frame). An mRNA may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified. In some embodiments, all uracils or uridines are modified. When all nucleobases, nucleosides, or nucleotides are modified, e.g., all uracils or uridines, the mRNA can be referred to as "fully modified", e.g., for uracil or uridine.

In some embodiments, an mRNA as described herein may include a 5' cap structure, a chain terminating nucleotide, optionally a Kozak sequence (also known as a Kozak consensus sequence), a stem loop, a polyA sequence, and/or a polyadenylation signal.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., m7G(5')ppp(5')G, commonly written as m7GpppG. A cap species may also be an anti-reverse cap analog. A non-limiting list of possible cap species includes m7GpppG, m7Gpppm7G, m73'dGpppG, m27,O3'GpppG, m27,O3'GppppG, m27,O2'GppppG, m7Gpppm7G, m73'dGpppG, m27,O3'GpppG, m27,O3'GppppG, and m27,O2'GppppG.

An mRNA may instead or additionally include a chain terminating nucleoside. For example, a chain terminating nucleoside may include those nucleosides deoxygenated at the 2' and/or 3' positions of their sugar group. Such species may include 3' deoxyadenosine (cordycepin), 3' deoxyuridine, 3' deoxycytosine, 3' deoxyguanosine, 3' deoxythymine, and 2',3' dideoxynucleosides, such as 2',3' dideoxyadenosine, 2',3' dideoxyuridine, 2',3' dideoxycytosine, 2',3' dideoxyguanosine, and 2',3' dideoxythymine. In some embodiments, incorporation of a chain terminating nucleotide into an mRNA, for example at the 3'-terminus, may result in stabilization of the mRNA.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A poly A sequence may also comprise stabilizing nucleotides or analogs. For example, a poly A sequence can include deoxythymidine, e.g., inverted (or reverse linkage) deoxythymidine (dT), as a stabilizing nucleotide or analog. Detials on using inverted dT and other stabilizing poly A sequence modifications can be found, for example, in WO2017/049275 A2, the content of which is incoported herein by reference. A polyA sequence may be a tail located adjacent to a 3' untranslated region of an mRNA. In some embodiments, a polyA sequence may affect the nuclear export, translation, and/or stability of an mRNA.

An mRNA may instead or additionally include a microRNA binding site. MicroRNA binding sites (or miR binding sites) can be used to regulate mRNA expression in various tissues or cell types. In exemplary embodiments, miR binding sites are engineered into 3' UTR sequences of an mRNA to regulate, e.g., enhance degradation of mRNA in cells or tissues expressing the cognate miR. Such regulation is useful to regulate or control "off-target" expression ir mRNAs, i.e., expression in undesired cells or tissues in vivo. Details on using mir binding sites can be found, for example, in WO 2017/062513 A2, the content of which is incoported herein by reference.

In some embodiments, an mRNA is a bicistronic mRNA comprising a first coding region and a second coding region with an intervening sequence comprising an internal ribosome entry site (IRES) sequence that allows for internal translation initiation between the first and second coding regions, or with an intervening sequence encoding a self-cleaving peptide, such as a 2A peptide. IRES sequences and 2A peptides are typically used to enhance expression of multiple proteins from the same vector. A variety of IRES sequences are known and available in the art and may be used, including, e.g., the encephalomyocarditis virus IRES.

In some embodiments, an mRNA of the disclosure comprises one or more modified nucleobases, nucleosides, or nucleotides (termed "modified mRNAs" or "mmRNAs"). In some embodiments, modified mRNAs may have useful properties, including enhanced stability, intracellular retention, enhanced translation, and/or the lack of a substantial induction of the innate immune response of a cell into which the mRNA is introduced, as compared to a reference unmodified mRNA. Therefore, use of modified mRNAs may enhance the efficiency of protein production, intracellular retention of nucleic acids, as well as possess reduced immunogenicity.

In some embodiments, an mRNA includes one or more (e.g., 1, 2, 3 or 4) different modified nucleobases, nucleosides, or nucleotides. In some embodiments, an mRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified mRNA may have reduced degradation in a cell into which the mRNA is introduced, relative to a corresponding unmodified mRNA.

In some embodiments, the modified nucleobase is a modified uracil. Exemplary nucleobases and nucleosides having a modified uracil include pseudouridine ($\psi$), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridineor 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine ($\tau$m5U), 1-taurinomethyl-pseudouridine, 5-taurinomethyl-2-thio-uridine($\tau$m5s2U), 1-taurinomethyl-4-thio-pseudouridine, 5-methyl-uridine (m5U, i.e., having the nucleobase deoxythymine), 1-methyl-pseudouridine (m1$\psi$), 5-methyl-2-thio-uridine (m5s2U), 1-methyl-4-thio-pseudouridine (m1s4$\psi$), 4-thio-1-methyl-pseudouridine, 3-methyl-pseudouridine (m3$\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp3U), 1-methyl-3-(3-amino-3-carboxypropyl)pseudouridine (acp3 $\psi$), 5-(isopentenylaminomethyl)uridine (inm5U), 5-(isopentenylaminomethyl)-2-thio-uridine (inm5s2U), $\alpha$-thio-uridine, 2'-O-methyl-uridine (Um), 5,2'-O-dimethyl-uridine (m5Um), 2'-O-methyl-pseudouridine ($\psi$n), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), and 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include $\kappa$-aza-cytidine, 6-aza-cytidine, pseudoisocytidine, 3-methyl-cytidine (m3C), N4-acetyl-cytidine (ac4C), 5-formyl-cytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), $\alpha$-thio-cytidine, 2'-O-methyl-cytidine (Cm), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include $\alpha$-thio-adenosine, 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms2i6A), N6-(cis-hydroxyisopentenyl)adenosine (io6A), 2-methylthio-N6-

(cis-hydroxyisopentenyl)adenosine (ms2io6A), N6-glycinylcarbamoyl-adenosine (g6A), N6-threonylcarbamoyl-adenosine (t6A), N6-methyl-N6-threonylcarbamoyl-adenosine (m6t6A), 2-methylthio-N6-threonylcarbamoyl-adenosine (ms2g6A), N6,N6-dimethyl-adenosine (m62A), N6-hydroxynorvalylcarbamoyl-adenosine (hn6A), 2-methylthio-N6-hydroxynorvalylcarbamoyl-adenosine (ms2hn6A), N6-acetyl-adenosine (ac6A), 7-methyl-adenine, 2-methylthio-adenine, 2-methoxy-adenine, α-thio-adenosine, 2'-O-methyl-adenosine (Am), N6,2'-O-dimethyl-adenosine (m6Am), N6,N6,2'-O-trimethyl-adenosine (m62Am), 1,2'-O-dimethyl-adenosine (m1Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include α-thio-guanosine, inosine (I), 1-methyl-inosine (mlI), wyosine (imG), methylwyosine (mimG), 4-demethyl-wyosine (imG-14), isowyosine (imG2), wybutosine (yW), peroxywybutosine (o2yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine (m7G), 6-thio-7-methyl-guanosine, 7-methyl-inosine, 6-methoxy-guanosine, 1-methyl-guanosine (mlG), N2-methyl-guanosine (m2G), N2,N2-dimethyl-guanosine (m22G), N2,7-dimethyl-guanosine (m2,7G), N2, N2,7-dimethyl-guanosine (m2,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m2Gm), N2,N2-dimethyl-2'-O-methyl-guanosine (m22Gm), 1-methyl-2'-O-methyl-guanosine (mlGm), N2,7-dimethyl-2'-O-methyl-guanosine (m2,7Gm), 2'-O-methyl-inosine (Im), 1,2'-O-dimethyl-inosine (mlIm), 2'-O-ribosylguanosine (phosphate) (Gr(p)), 1-thio-guanosine, O6-methyl-guanosine, 2'-F-ara-guanosine, and 2'-F-guanosine.

In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is pseudouridine (ψ), N1-methylpseudouridine (m1ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.) In some embodiments, the modified nucleobase is N1-methylpseudouridine (m1ψ) and the mRNA of the disclosure is fully modified with N1-methylpseudouridine (m1ψ). In some embodiments, N1-methylpseudouridine (m1ψ) represents from 75-100% of the uracils in the mRNA. In some embodiments, N1-methylpseudouridine (m1ψ) represents 100% of the uracils in the mRNA.

In some embodiments, the modified nucleobase is a modified cytosine. Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified adenine. Exemplary nucleobases and nucleosides having a modified adenine include 7-deaza-adenine, 1-methyl-adenosine (m1A), 2-methyl-adenine (m2A), N6-methyl-adenosine (m6A). In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine (m1ψ), 5-methoxy-uridine (mo5U), 5-methyl-cytidine (m5C), pseudouridine (ψ), α-thio-guanosine, or α-thio-adenosine. In some embodiments, an mRNA of the disclosure includes a combination of one or more of the aforementioned modified nucleobases (e.g., a combination of 2, 3 or 4 of the aforementioned modified nucleobases.)

In some embodiments, the mRNA comprises pseudouridine (ψ). In some embodiments, the mRNA comprises pseudouridine (ψ) and 5-methyl-cytidine (m5C). In some embodiments, the mRNA comprises 1-methyl-pseudouridine (m1ψ). In some embodiments, the mRNA comprises 1-methyl-pseudouridine (m1ψ) and 5-methyl-cytidine (m5C). In some embodiments, the mRNA comprises 2-thiouridine (s2U). In some embodiments, the mRNA comprises 2-thiouridine and 5-methyl-cytidine (m5C). In some embodiments, the mRNA comprises 5-methoxy-uridine (mo5U). In some embodiments, the mRNA comprises 5-methoxy-uridine (mo5U) and 5-methyl-cytidine (m5C). In some embodiments, the mRNA comprises 2'-O-methyl uridine. In some embodiments, the mRNA comprises 2'-O-methyl uridine and 5-methyl-cytidine (m5C). In some embodiments, the mRNA comprises N6-methyl-adenosine (m6A). In some embodiments, the mRNA comprises N6-methyl-adenosine (m6A) and 5-methyl-cytidine (m5C).

In certain embodiments, an mRNA of the disclosure is uniformly modified (i.e., fully modified, modified throughout the entire sequence) for a particular modification. For example, an mRNA can be uniformly modified with N1-methylpseudouridine (m1ψ) or 5-methyl-cytidine (m5C), meaning that all uridines or all cytosine nucleosides in the mRNA sequence are replaced with N1-methylpseudouridine (m1ψ) or 5-methyl-cytidine (m5C). Similarly, mRNAs of the disclosure can be uniformly modified for any type of nucleoside residue present in the sequence by replacement with a modified residue such as those set forth above.

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

The mmRNAs of the disclosure can include a combination of modifications to the sugar, the nucleobase, and/or the internucleoside linkage. These combinations can include any one or more modifications described herein.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

The mRNAs of the present disclosure, or regions thereof, may be codon optimized. Codon optimization methods are known in the art and may be useful for a variety of purposes: matching codon frequencies in host organisms to ensure proper folding, bias GC content to increase mRNA stability or reduce secondary structures, minimize tandem repeat codons or base runs that may impair gene construction or expression, customize transcriptional and translational control regions, insert or remove proteins trafficking sequences, remove/add post translation modification sites in encoded proteins (e.g., glycosylation sites), add, remove or shuffle protein domains, insert or delete restriction sites, modify ribosome binding sites and mRNA degradation sites, adjust translation rates to allow the various domains of the protein to fold properly, or to reduce or eliminate problem secondary structures within the polynucleotide. Codon optimization tools, algorithms and services are known in the art; non-limiting examples include services from GeneArt (Life Technologies), DNA2.0 (Menlo Park, CA) and/or proprietary methods. In some embodiments, the mRNA sequence is optimized using optimization algorithms, e.g., to optimize expression in mammalian cells or enhance mRNA stability.

In certain embodiments, the present disclosure includes polynucleotides having at least 80%, at least 85%, at least 90%, at least 95%, at least 98%, or at least 99% sequence identity to any of the polynucleotide sequences described herein.

mRNAs of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In some embodiments, mRNAs are made using IVT enzymatic synthesis methods. Accordingly, the present disclosure also includes polynucleotides, e.g., DNA, constructs and vectors that may be used to in vitro transcribe an mRNA described herein.

Non-natural modified nucleobases may be introduced into polynucleotides, e.g., mRNA, during synthesis or post-synthesis. In certain embodiments, modifications may be on internucleoside linkages, purine or pyrimidine bases, or sugar. In particular embodiments, the modification may be introduced at the terminal of a polynucleotide chain or anywhere else in the polynucleotide chain; with chemical synthesis or with a polymerase enzyme.

Either enzymatic or chemical ligation methods may be used to conjugate polynucleotides or their regions with different functional moieties, such as targeting or delivery agents, fluorescent labels, liquids, nanoparticles, etc. Therapeutic Agents for Reducing Protein Expression In some embodiments, the therapeutic agent is a therapeutic agent that reduces (i.e., decreases, inhibits, down-regulates) protein expression. Non-limiting examples of types of therapeutic agents that can be used for reducing protein expression include mRNAs that incorporate a microRNA binding site(s) (miR binding site), microRNAs (miR-NAs), antagomirs, small (short) interfering RNAs (siRNAs) (including shortmers and dicer-substrate RNAs), RNA interference (RNAi) molecules, antisense RNAs, ribozymes, small hairpin RNAs (shRNAs), locked nucleic acids (LNAs) and CRISPR/Cas9 technology.

Peptide Polypeptide Therapeutic Agents

In some embodiments, the therapeutic agent is a peptide therapeutic agent. In some embodiments the therapeutic agent is a polypeptide therapeutic agent.

In some embodiments, the peptide or polypeptide is naturally-derived, e.g., isolated from a natural source. In other embodiments, the peptide or polypeptide is a synthetic molecule, e.g., a synthetic peptide or polypeptide produced in vitro. In some embodiments, the peptide or polypeptide is a recombinant molecule. In some embodiments, the peptide or polypeptide is a chimeric molecule. In some embodiments, the peptide or polypeptide is a fusion molecule. In some embodiments, the peptide or polypeptide therapeutic agent of the composition is a naturally occurring peptide or polypeptide. In some embodiments, the peptide or polypeptide therapeutic agent of the composition is a modified version of a naturally occurring peptide or polypeptide (e.g., contains less than 3, less than 5, less than 10, less than 15, less than 20, or less than 25 amino substitutions, deletions, or additions compared to its wild type, naturally occurring peptide or polypeptide counterpart).

In some embodiments, in the loaded LNP of the disclosure, the one or more therapeutic and/or prophylactic agents is a polynucleotide or a polypeptide.

Other Components

A lipid nanoparticle (e.g., an empty LNP or a loaded LNP) may include one or more components in addition to those described in the preceding sections. For example, a lipid nanoparticle (e.g., an empty LNP or a loaded LNP) may include one or more small hydrophobic molecules such as a vitamin (e.g., vitamin A or vitamin E) or a sterol.

Lipid nanoparticles (e.g., empty LNPs or loaded LNPs) may also include one or more permeability enhancer molecules, carbohydrates, polymers, surface altering agents, or other components. Carbohydrates may include simple sugars (e.g., glucose) and polysaccharides (e.g., glycogen and derivatives and analogs thereof).

A polymer may be included in and/or used to encapsulate or partially encapsulate a nanoparticle composition. A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. For example, a polymer may include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly (vinyl acetate), polyvinyl halides such as poly(vinyl chloride) (PVC), polyvinylpyrrolidone (PVP), polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, polyoxamines, poly(ortho)esters, poly(butyric acid), poly (valeric acid), poly(lactide-co-caprolactone), trimethylene carbonate, poly(N-acryloylmorpholine) (PAcM), poly(2-methyl-2-oxazoline) (PMOX), poly(2-ethyl-2-oxazoline) (PEOZ), and polyglycerol.

Surface altering agents may include, but are not limited to, anionic proteins (e.g., bovine serum albumin), surfactants (e.g., cationic surfactants such as dimethyldioctadecyl-ammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin 04, domase alfa, neltenexine, and erdosteine), and DNases (e.g., rhDNase). A surface altering agent may be disposed within a nanoparticle and/or on the surface of a lipid nanoparticle (e.g., an empty LNP or a loaded LNP) (e.g., by coating, adsorption, covalent linkage, or other process).

A lipid nanoparticle (e.g., an empty LNP or a loaded LNP) may also comprise one or more functionalized lipids. For example, a lipid may be functionalized with an alkyne group that, when exposed to an azide under appropriate reaction conditions, may undergo a cycloaddition reaction. In particular, a lipid bilayer may be functionalized in this fashion with one or more groups useful in facilitating membrane permeation, cellular recognition, or imaging. The surface of a lipid nanoparticle (e.g., an empty LNP or a loaded LNP) may also be conjugated with one or more useful antibodies. Functional groups and conjugates useful in targeted cell delivery, imaging, and membrane permeation are well known in the art.

In addition to these components, lipid nanoparticles (e.g., empty LNPs or loaded LNPs) may include any substance useful in pharmaceutical compositions. For example, the lipid nanoparticle (e.g., an empty LNP or a loaded LNP) may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included.

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN® 60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinylpyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER® 188, cetrimonium bromide, cetylpyridinium chloride, benzalkonium chloride, docusate sodium, and/or combinations thereof.

A binding agent may be starch (e.g. cornstarch and starch paste); gelatin; sugars (e.g. sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Examples of preservatives may include, but are not limited to, antioxidants, chelating agents, antimicrobial preservatives, antifungal preservatives, alcohol preservatives, acidic preservatives, and/or other preservatives. Examples of antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN®II, NEOLONE™, KATHON™, and/or EUXYL®.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g., HEPES), magnesium hydroxide, aluminum hydroxide, alginic acid, pyrogen-free water, isotonic saline, Ringer's solution, ethyl alcohol, and/or combinations thereof. Lubricating agents may selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

Examples of oils include, but are not limited to, almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, silicone oil, and/or combinations thereof.

Formulations

Lipid nanoparticles (e.g., empty LNPs or loaded LNPs) may include a lipid component and one or more additional components, such as a therapeutic and/or prophylactic. A lipid nanoparticle (e.g., an empty LNP or a loaded LNP) may be designed for one or more specific applications or targets. The elements of a lipid nanoparticle (e.g., an empty LNP or a loaded LNP) may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition may include, for example, a lipid according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid (such as an unsaturated lipid, e.g., DOPE or DSPC), a PEG lipid, and a structural lipid. The elements of the lipid component may be provided in specific fractions.

In some embodiments, the lipid component of a nanoparticle composition includes a lipid according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a PEG lipid, and a structural lipid. In certain embodiments, the lipid component of the nanoparticle composition includes about 30 mol % to about 60 mol % compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), about 0 mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the nanoparticle composition includes about 35 mol % to about 55 mol % compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), about 5 mol % to about 25 mol % phospholipid, about 30 mol % to about 40 mol % structural lipid, and about 0 mol % to about 10 mol % of PEG lipid. In a particular embodiment, the lipid component includes about 50 mol % said compound, about 10 mol % phospholipid, about 38.5 mol % structural lipid, and about 1.5 mol % of PEG lipid. In another particular embodiment, the lipid component includes about 40 mol % said compound, about 20 mol % phospholipid, about 38.5 mol % structural lipid, and about 1.5 mol % of PEG lipid. In some embodiments, the phospholipid may be DOPE or DSPC. In other embodiments, the PEG lipid may be PEG-1, or $PEG_{2k}$-DMG and/or the structural lipid may be cholesterol.

In some embodiments an empty lipid nanoparticle (empty LNP) comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, and a PEG lipid.

In some embodiments a loaded lipid nanoparticle (loaded LNP) comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, a PEG lipid, and one or more therapeutic and/or prophylactic agents.

In some embodiments, the empty LNP or loaded LNP comprises the compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), in an amount from about 40% to about 60%.

In some embodiments, the empty LNP or loaded LNP comprises the phospholipid in an amount from about 0% to about 20%. For example, in some embodiments, the empty LNP or loaded LNP comprises DSPC in an amount from about 0% to about 20%.

In some embodiments, the empty LNP or loaded LNP comprises the structural lipid in an amount from about 30% to about 50%. For example, in some embodiments, the empty LNP or loaded LNP comprises cholesterol in an amount from about 30% to about 50%.

In some embodiments, the empty LNP or loaded LNP comprises the PEG lipid in an amount from about 0% to about 5%. For example, in some embodiments, the empty LNP or loaded LNP comprises PEG-1 or $PEG_{2k}$-DMG in an amount from about 0% to about 5%.

In some embodiments, the empty LNP or loaded LNP comprises about 40 mol % to about 60 mol % of the compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), about 0 mol % to about 20 mol % phospholipid, about 30 mol % to about 50 mol % structural lipid, and about 0 mol % to about 5 mol % PEG lipid.

In some embodiments, the empty LNP or loaded LNP comprises about 40 mol % to about 60 mol % of the compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), about 0 mol % to about 20 mol % DSPC, about 30 mol % to about 50 mol % cholesterol, and about 0 mol % to about 5 mol % $PEG_{2k}$-DMG. In some embodiments, the empty LNP or loaded LNP comprises about 40 mol % to about 60 mol % of the compound of Table 1, about 0 mol % to about 20 mol % DSPC, about 30 mol % to about 50 mol % cholesterol, and about 0 mol % to about 5 mol % $PEG_{2k}$-DMG.

In some embodiments, the empty LNP or loaded LNP comprises about 40 mol % to about 60 mol % of the compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), about 0 mol % to about 20 mol % DSPC, about 30 mol % to about 50 mol % cholesterol, and about 0 mol % to about 5 mol % PEG-1. In some embodiments, the empty LNP or loaded LNP comprises about 40 mol % to about 60 mol % of the compound of Table 1, about 0 mol % to about 20 mol % DSPC, about 30 mol % to about 50 mol % cholesterol, and about 0 mol % to about 5 mol % PEG-1.

In some embodiments, the empty LNP or loaded LNP comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, and a PEG lipid, wherein the phospholipid is DSPC and the structural lipid is cholesterol. In some embodiments, the empty LNP or loaded LNP comprises a compound of Table 1, a phospholipid, a structural lipid, and a PEG lipid, wherein the phospholipid is DSPC and the structural lipid is cholesterol.

In some embodiments, the empty LNP or loaded LNP comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, and a PEG lipid, wherein the structural lipid is cholesterol and the PEG lipid is $PEG_{2k}$-DMG. In some embodiments, the empty LNP or loaded LNP comprises a compound of Table 1, a phospholipid, a structural lipid, and a PEG lipid, wherein the structural lipid is cholesterol and the PEG lipid is $PEG_{2k}$-DMG.

In some embodiments, the empty LNP or loaded LNP comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, and a PEG lipid, wherein the structural lipid is cholesterol and the PEG lipid is PEG-1. In some embodiments, the empty LNP or loaded LNP comprises a compound of Table 1 a phospholipid, a structural lipid, and a PEG lipid, wherein the structural lipid is cholesterol and the PEG lipid is PEG-1.

In some embodiments, the empty LNP or loaded LNP comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, and a PEG lipid, wherein the phospholipid is DSPC and the PEG lipid is PEG2k-DMG. In some embodiments, the empty LNP or loaded LNP comprises a compound of Table 1, a phospholipid, a structural lipid, and a PEG lipid, wherein the phospholipid is DSPC and the PEG lipid is $PEG_{2k}$-DMG.

In some embodiments, the empty LNP or loaded LNP comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, and a PEG lipid, wherein the phospholipid is DSPC and the PEG lipid is PEG-1. In some embodiments, the empty LNP or loaded LNP comprises a compound of Table 1, a phospholipid, a structural lipid, and a PEG lipid, wherein the phospholipid is DSPC and the PEG lipid is PEG-1.

In some embodiments, the empty LNP or loaded LNP comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, and a PEG lipid, wherein the phospholipid is DSPC, the structural lipid is cholesterol, and the PEG lipid is $PEG_{2k}$-DMG. In some embodiments, the empty LNP or loaded LNP comprises a compound of Table 1, a phospholipid, a structural lipid, and a PEG lipid, wherein the phospholipid is DSPC, the structural lipid is cholesterol, and the PEG lipid is $PEG_{2k}$-DMG.

In some embodiments, the empty LNP or loaded LNP comprises a compound of Formula (A-c), a phospholipid, a structural lipid, and a PEG lipid, wherein the phospholipid is DSPC, the structural lipid is cholesterol, and the PEG lipid is $PEG_{2k}$-DMG. In some embodiments, the empty LNP or loaded LNP comprises a compound of Table 1, a phospholipid, a structural lipid, and a PEG lipid, wherein the phospholipid is DSPC, the structural lipid is cholesterol, and the PEG lipid is $PEG_{2k}$-DMG.

In some embodiments, the empty LNP or loaded LNP comprises a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, and a PEG lipid, wherein the phospholipid is DSPC, the structural lipid is cholesterol, and the PEG lipid is PEG-1.

In some embodiments, the empty LNP or loaded LNP comprises a compound of Formula (A-c), a phospholipid, a structural lipid, and a PEG lipid, wherein the phospholipid is DSPC, the structural lipid is cholesterol, and the PEG lipid is PEG-1. In some embodiments, the empty LNP or loaded LNP comprises a compound of Table 1, a phospholipid, a structural lipid, and a PEG lipid, wherein the phospholipid is DSPC, the structural lipid is cholesterol, and the PEG lipid is PEG-1.

Lipid nanoparticles (e.g., empty LNPs or loaded LNPs) may be designed for one or more specific applications or targets. For example, a nanoparticle composition may be designed to deliver a therapeutic and/or prophylactic such as an RNA to a particular cell, tissue, organ, or system or group thereof in a mammal's body. Physiochemical properties of lipid nanoparticles (e.g., empty LNPs or loaded LNPs) may be altered in order to increase selectivity for particular bodily targets. For instance, particle sizes may be adjusted based on the fenestration sizes of different organs. The therapeutic and/or prophylactic included in a nanoparticle composition may also be selected based on the desired delivery target or targets. For example, a therapeutic and/or prophylactic may be selected for a particular indication, condition, disease, or disorder and/or for delivery to a particular cell, tissue, organ, or system or group thereof (e.g., localized or specific delivery). In certain embodiments, a nanoparticle composition may include an mRNA encoding a polypeptide of interest capable of being translated within a cell to produce the polypeptide of interest. Such a composition may be designed to be specifically delivered to a particular organ. In some embodiments, a composition may be designed to be specifically delivered to a mammalian liver.

The amount of a therapeutic and/or prophylactic in a nanoparticle composition may depend on the size, composition, desired target and/or application, or other properties of the nanoparticle composition as well as on the properties of the therapeutic and/or prophylactic. For example, the amount of an RNA useful in a nanoparticle composition may depend on the size, sequence, and other characteristics of the RNA. The relative amounts of a therapeutic and/or prophylactic and other elements (e.g., lipids) in a nanoparticle composition may also vary. In some embodiments, the wt/wt ratio of the lipid component to a therapeutic and/or prophylactic in a nanoparticle composition may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic and/or prophylactic may be from about 10:1 to about 40:1. In certain embodiments, the wt/wt ratio is about 20:1.

The amount of a therapeutic and/or prophylactic in a nanoparticle composition may, for example, be measured using absorption spectroscopy (e.g., ultraviolet-visible spectroscopy).

In some embodiments, a nanoparticle composition includes one or more RNAs, and the one or more RNAs, lipids, and amounts thereof may be selected to provide a specific N:P ratio. The N:P ratio of the composition refers to the molar ratio of nitrogen atoms in one or more lipids to the number of phosphate groups in an RNA. In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio may be from about 2:1 to about 8:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1. For example, the N:P ratio may be about 5.67:1.

Physical Properties

The characteristics of a lipid nanoparticle (e.g., an empty LNP or a loaded LNP) may depend on the components thereof. For example, a lipid nanoparticle (e.g., an empty LNP or a loaded LNP) including cholesterol as a structural lipid may have different characteristics than a lipid nanoparticle (e.g., an empty LNP or a loaded LNP) that includes a different structural lipid. Similarly, the characteristics of a lipid nanoparticle (e.g., an empty LNP or a loaded LNP) may depend on the absolute or relative amounts of its components. For instance, a lipid nanoparticle (e.g., an empty LNP or a loaded LNP) including a higher molar fraction of a phospholipid may have different characteristics than a lipid nanoparticle (e.g., an empty LNP or a loaded LNP) including a lower molar fraction of a phospholipid. Characteristics may also vary depending on the method and conditions of preparation of the nanoparticle composition.

Lipid nanoparticles (e.g., empty LNPs or loaded LNPs) may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a nanoparticle composition, such as particle size, polydispersity index, and zeta potential.

The mean size of a lipid nanoparticle (e.g., an empty LNP or a loaded LNP) may be between 10s of nm and 100s of nm, e.g., measured by dynamic light scattering (DLS). For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a lipid nanoparticle (e.g., an empty LNP or a loaded LNP) may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 150 nm, from about 70 nm to about 130 nm, from about 70 nm to about 100 nm, from about 70 nm to about 90 nm, from about 70 nm to about 80 nm, from about 80 nm to about 150 nm, from about 80 nm to about 130 nm, from about 80 nm to about 100 nm, from about 80 nm to about 90 nm, from about 90 nm to about 150 nm, from about 90 nm to about 130 nm, or from about 90 nm to about 100 nm. In certain embodiments, the mean size of a lipid nanoparticle (e.g., an empty LNP or a loaded LNP) may from about 70 nm to about 130 nm or be from about 70 nm to about 100 nm. In a particular embodiment, the mean size may be about 80 nm. In other embodiments, the mean size may be about 100 nm. In other embodiments, the mean size may be about 120 nm.

A lipid nanoparticle (e.g., an empty LNP or a loaded LNP) may be relatively homogenous. A polydispersity index may be used to indicate the homogeneity of a nanoparticle composition, e.g., the particle size distribution of the lipid nanoparticles (e.g., empty LNPs or loaded LNPs). A small (e.g., less than 0.3) polydispersity index generally indicates a narrow particle size distribution. A lipid nanoparticle (e.g., an empty LNP or a loaded LNP) may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a lipid nanoparticle (e.g., an empty LNP or a loaded LNP) may be from about 0.10 to about 0.20.

The zeta potential of a lipid nanoparticle (e.g., an empty LNP or a loaded LNP) may be used to indicate the electrokinetic potential of the composition. For example, the zeta potential may describe the surface charge of a nanoparticle composition. Lipid nanoparticles (e.g., empty LNPs or loaded LNPs) with relatively low charges, positive or negative, are generally desirable, as more highly charged species may interact undesirably with cells, tissues, and other elements in the body. In some embodiments, the zeta potential of a lipid nanoparticle (e.g., an empty LNP or a loaded LNP) may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic describes the amount of therapeutic and/or prophylactic that is encapsulated or otherwise associated with a lipid nanoparticle (e.g., an empty LNP or a loaded LNP) after preparation, relative to the initial amount provided. The encapsulation efficiency is desirably high (e.g., close to 100%). The encapsulation efficiency may be measured, for example, by comparing the amount of therapeutic and/or prophylactic in a solution containing the lipid nanoparticle (e.g., an empty LNP or a loaded LNP) before and after breaking up the lipid nanoparticle (e.g., an empty LNP or a loaded LNP) with one or more organic solvents or detergents. Fluorescence may be used to measure the amount of free therapeutic and/or prophylactic (e.g., RNA) in a solution. For the lipid nanoparticles (e.g., empty LNPs or loaded LNPs) described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%. In some embodiments, the encapsulation efficiency of the therapeutic and/or prophylactic agent is between 80% and 100%.

Pharmaceutical Compositions

Lipid nanoparticles (e.g., empty LNPs or loaded LNPs) may be formulated in whole or in part as pharmaceutical compositions. Pharmaceutical compositions may include one or more lipid nanoparticles (e.g., empty LNPs or loaded LNPs). In one embodiment, a pharmaceutical composition comprises a population of lipid nanoparticles (e.g., empty LNPs or loaded LNPs). For example, a pharmaceutical composition may include one or more lipid nanoparticles (e.g., empty LNPs or loaded LNPs) including one or more different therapeutic and/or prophylactics. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy*, $21^{st}$ Edition, A. R. Gennaro; Lippincott, Williams & Wilkins, Baltimore, MD, 2006. Conventional excipients and accessory ingredients may be used in any pharmaceutical composition, except insofar as any conventional excipient or accessory ingredient may be incompatible with one or more components of a nanoparticle composition. An excipient or accessory ingredient may be incompatible with a component of a lipid nanoparticle (e.g., an empty LNP or a loaded LNP) if its combination with the component may result in any undesirable biological effect or otherwise deleterious effect.

In some embodiments, one or more excipients or accessory ingredients may make up greater than 50% of the total mass or volume of a pharmaceutical composition including a nanoparticle composition. For example, the one or more excipients or accessory ingredients may make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Relative amounts of the one or more lipid nanoparticles (e.g., empty LNPs or loaded LNPs), the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition may comprise between 0.1% and 100% (wt/wt) of one or more lipid nanoparticles (e.g., empty LNPs or loaded LNPs).

In certain embodiments, the lipid nanoparticles (e.g., empty LNPs or loaded LNPs) and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising a compound of any of Formulae (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), and (B-c) is a solution that is refrigerated for storage and/or shipment at, for example, about −20° C., −30° C., −40° C., −50° C., −60° C., −70° C., or −80° C. In certain embodiments, the disclosure also relates to a method of increasing stability of the lipid nanoparticles (e.g., empty LNPs or loaded LNPs) and/or pharmaceutical compositions comprising a compound of any of Formulae (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), and (B-c) by storing the lipid nanoparticles (e.g., empty LNPs or loaded LNPs) and/or pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the lipid nanoparticles (e.g., empty LNPs or loaded LNPs) and/or pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In some embodiments, the formulation is stabilized for at least 4 weeks at about 4° C. In certain embodiments, the pharmaceutical composition of the disclosure comprises a lipid nanoparticle (e.g., an empty LNP or a loaded LNP) disclosed herein and a pharmaceutically acceptable carrier selected from one or more of Tris, an acetate (e.g., sodium acetate), an citrate (e.g., sodium citrate), saline, PBS, and sucrose. In certain embodiments, the pharmaceutical composition of the disclosure has a pH value between about 7 and 8 (e.g., 6.8 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a lipid nanoparticle (e.g., an empty LNP or a loaded LNP) disclosed herein, Tris, saline and sucrose, and has a pH of about 7.5-8, which is suitable for storage and/or shipment at, for example, about −20° C. For example, a pharmaceutical composition of the disclosure comprises a lipid nanoparticle (e.g., an empty LNP or a loaded LNP) disclosed herein and PBS and has a pH of about 7-7.8, suitable for storage and/or shipment at, for example, about 4° C. or lower. "Stability," "stabilized," and "stable" in the context of the present disclosure refers to the resistance of lipid nanoparticles (e.g., empty LNPs or loaded LNPs) and/or pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

In some embodiments, a pharmaceutical composition of the disclosure comprises a empty LNP or a loaded LNP, a cryoprotectant, a buffer, or a combination thereof.

In some embodiments, the cryoprotectant comprises one or more cryoprotective agents, and each of the one or more cryoprotective agents is independently a polyol (e.g., a diol or a triol such as propylene glycol (i.e., 1,2-propanediol), 1,3-propanediol, glycerol, (+/−)-2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a polymer (e.g., polyethylene glycol 200 (PEG 200), PEG 400, PEG 600, PEG 1000, PEG$_{2k}$-DMG, PEG 3350, PEG 4000, PEG 8000, PEG 10000, PEG 20000, polyethylene glycol monomethyl ether 550 (mPEG 550), mPEG 600, mPEG 2000, mPEG 3350, mPEG 4000, mPEG 5000, polyvinylpyrrolidone (e.g., polyvinylpyrrolidone K 15), pentaerythritol propoxylate, or polypropylene glycol P 400), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myo-inositol, D-(+)-raffinose pentahydrate, D-(+)-trehalose dihydrate, or D-(+)-glucose monohydrate), or a salt (e.g., lithium acetate, lithium chloride, lithium formate, lithium nitrate, lithium sulfate, magnesium acetate, sodium acetate, sodium chloride, sodium formate, sodium malonate, sodium nitrate, sodium sulfate, or any hydrate thereof), or any combination thereof. In some embodiments, the cryoprotectant comprises sucrose. In some embodiments, the cryoprotectant and/or excipient is sucrose. In some embodiments, the cryoprotectant comprises sodium acetate. In some embodiments, the cryoprotectant and/or excipient is sodium acetate. In some embodiments, the cryoprotectant comprises sucrose and sodium acetate.

In some embodiments, wherein the buffer is selected from the group consisting of an acetate buffer, a citrate buffer, a phosphate buffer, a tris buffer, and combinations thereof.

Lipid nanoparticles (e.g., empty LNPs or loaded LNPs) and/or pharmaceutical compositions including one or more lipid nanoparticles (e.g., empty LNPs or loaded LNPs) may be administered to any patient or subject, including those patients or subjects that may benefit from a therapeutic effect provided by the delivery of a therapeutic and/or prophylactic to one or more particular cells, tissues, organs, or systems or groups thereof. Although the descriptions provided herein of lipid nanoparticles (e.g., empty LNPs or loaded LNPs) and pharmaceutical compositions including lipid nanoparticles (e.g., empty LNPs or loaded LNPs) are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats. The subject lipid nanoparticles can also be employed for in vitro and ex vivo uses.

A pharmaceutical composition including one or more lipid nanoparticles (e.g., empty LNPs or loaded LNPs) may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage.

Pharmaceutical compositions may be prepared in a variety of forms suitable for a variety of routes and methods of administration. For example, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutic and/or prophylactics, additional agents such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, films, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato or tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay, silicates), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants, and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices. Intradermal compositions may be administered by devices which limit the effective penetration length of a needle into the skin. Jet injection devices which deliver liquid compositions to the dermis via a liquid jet injector and/or via a needle which pierces the stratum corneum and produces a jet which reaches the dermis are suitable. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (wt/wt) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (wt/wt) of the composition, and active ingredient may constitute 0.1% to 20% (wt/wt) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 µm to 500 µm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (wt/wt) and as much as 100% (wt/wt) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.10% to 20% (wt/wt) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (wt/wt) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this present disclosure.

mRNA Therapies mRNA as a drug modality has the potential to deliver secreted proteins as well as intracellular proteins and transmembrane proteins. mRNA as a drug modality has the potential to deliver transmembrane and intracellular proteins, i.e., targets that standard biologics are unable to access owing to their inability to cross the cell membrane when delivered in protein form. One major challenge to making mRNA based therapies a reality is the identification of an optimal delivery vehicle. Due to its large size, chemical instability and potential immunogenicity, mRNA requires a delivery vehicle that can offer protection from endo- and exo-nucleases, as well as shield the cargo from immune sentinels. Lipid nanoparticles (LNPs) have been identified as a leading option in this regard.

Key performance criteria for a lipid nanoparticle delivery system are to maximize cellular uptake and enable efficient release of mRNA from the endosome. In one embodiment, the subject LNPs comprising the novel lipids disclosed herein, demonstrate improvements in at least one of cellular uptake and endosomal release. At the same time the LNP must provide a stable drug product and be able to be dosed safely at therapeutically relevant levels. LNPs are multi-component systems which typically consist of an amino lipid, phospholipid, cholesterol, and a PEG-lipid. Each component is required for aspects of efficient delivery of the nucleic acid cargo and stability of the particle. The key component thought to drive cellular uptake, endosomal escape, and tolerability is the amino lipid. Cholesterol and the PEG-lipid contribute to the stability of the drug product both in vivo and on the shelf, while the phospholipid provides additional fusogenicity to the LNP, thus helping to drive endosomal escape and rendering the nucleic acid bioavailable in the cytosol of cells.

Several amino lipid series have been developed for oligonucleotide delivery over the past couple of decades, including the amino lipid MC3 (DLin-MC3-DMA). MC3-based LNPs have been shown to be effective in delivering mRNA. LNPs of this class are quickly opsonized by apolipoprotein E (ApoE) when delivered intravenously, which enables cellular uptake by the low density lipoprotein receptor (LDLr). However, concerns remain that MC3's long tissue half-life could contribute to unfavorable side effects hindering its use for chronic therapies. In addition, extensive literature evidence suggests that chronic dosing of lipid nanoparticles can produce several toxic sides effects including complement activation-related pseudo allergy (CARPA) and liver damage. Hence, to unleash the potential of mRNA and other nucleic acid, nucleoptide or peptide based therapies for humans, a class of LNPs with increased delivery efficiency along with a metabolic and toxicity profile that would enable chronic dosing in humans is needed.

The ability to treat a broad swath of diseases requires the flexibility to safely dose chronically at varying dose levels. Through systematic optimization of the amino lipid structure, the compounds of the disclosure were identified as compounds that balance chemical stability, improved efficiency of delivery due to improved endosomal escape, rapid in vivo metabolism, and a clean toxicity profile. The combination of these features provides a drug candidate that can be dosed chronically without activation of the immune system. Initial rodent screens led to the identification of a lead lipid with good delivery efficiency and pharmacokinetics. The lead LNP was profiled further in non-human primate for efficiency of delivery after single and repeat dosing. Finally, the optimized LNPs were evaluated in one-month repeat dose toxicity studies in rat and non-human primate. Without wishing to be bound by theory, the novel ionizable lipids of the instant disclosure have the improved cellular delivery, improved protein expression, and improved biodegradability properties that can lead to greater than 2 fold, 5 fold, 10 fold, 15 fold, or 20 fold increase in mRNA expression in cells as compared to LNPs which lack a lipid of the invention. In another embodiment, an LNP comprising a lipid of the invention can result in specific (e.g., preferential) delivery to a certain cell type or types as compared other cell types, thereby resulting in a greater than 2 fold, 5 fold, 10 fold, 15 fold, or 20 fold increase in mRNA expression in certain cells or tissues as compared to LNPs which lack a lipid of the invention. These improvements over the art allow for the safe and effective use of mRNA-based therapies in acute and chronic diseases.

Methods

In some aspects, the disclosure provides a method of delivering a therapeutic and/or prophylactic to a cell (e.g., a mammalian cell). This method includes the step of contacting the cell with a loaded LNP or a pharmaceutical composition of the disclosure, whereby the therapeutic and/or prophylactic is delivered to the cell. In some embodiments, the cell is in a subject and the contacting comprises administering the cell to the subject. In some embodiments, the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, a PEG lipid, and one or more therapeutic and/or prophylactic agents, whereby the therapeutic and/or prophylactic is delivered to the cell.

In some embodiments, the disclosure provides a method of delivering a therapeutic and/or prophylactic to a cell within a subject, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method of delivering a therapeutic and/or prophylactic to a cell within a subject, wherein the method comprises the step of administering to the subject a lipid nanoparticle comprising a compound of Formula (A-c), DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method of delivering a therapeutic and/or prophylactic to a cell within a subject, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of delivering a therapeutic and/or prophylactic to a cell within a subject, wherein the method comprises the step of administering to the subject a lipid nanoparticle comprising a compound of Formula (A-c), DSPC, cholesterol, and PEG-1, and one or more therapeutic and/or prophylactic agents selected from a nucleotide, a polypeptide, and a nucleic acid (e.g., an RNA).

In some aspects, the disclosure provides a method of delivering (e.g., specifically delivering) a therapeutic and/or prophylactic to a mammalian organ or tissue (e.g., a liver, kidney, spleen, or lung). This method includes the step of contacting the cell with a loaded LNP or a pharmaceutical composition of the disclosure, whereby the therapeutic and/or prophylactic is delivered to the target organ or tissue. In some embodiments, the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, a PEG lipid, and one or more therapeutic and/or prophylactic agents, whereby the therapeutic and/or prophylactic is delivered to the target organ or tissue.

In some embodiments, the disclosure provides a method of specifically delivering a therapeutic and/or prophylactic to an organ of a subject, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method of specifically delivering a therapeutic and/or prophylactic to an organ of a subject, wherein the method comprises the step of administering to the subject a lipid nanoparticle comprising a compound of Formula (A-c), DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method of specifically delivering a therapeutic and/or prophylactic to an organ of a subject, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of specifically delivering a therapeutic and/or prophylactic to an organ of a subject, wherein the method comprises the step of administering to the subject a lipid nanoparticle comprising a compound of Formula (A-c), DSPC, cholesterol, and PEG-1, and one or more therapeutic and/or prophylactic agents selected from a nucleotide, a polypeptide, and a nucleic acid (e.g., an RNA).

In some aspects, the disclosure features a method for the enhanced delivery of a therapeutic and/or prophylactic (e.g., an mRNA) to a target tissue (e.g., a liver, spleen, or lung). This method includes the step of contacting the cell with a loaded LNP or a pharmaceutical composition of the disclosure, whereby the therapeutic and/or prophylactic is delivered to the target tissue (e.g., a liver, kidney, spleen, or lung). In some embodiments, the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, a PEG lipid, and one or more therapeutic and/or prophylactic agents, whereby the therapeutic and/or prophylactic is delivered to the target tissue (e.g., a liver, kidney, spleen, or lung).

In some embodiments, the disclosure provides a method for the enhanced delivery of a therapeutic and/or prophylactic to a target tissue, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method for the enhanced delivery of a therapeutic and/or prophylactic to a target tissue, wherein the method comprises the step of administering to the subject a lipid nanoparticle comprising a compound of Formula (A-c), DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method for the enhanced delivery of a therapeutic and/or prophylactic to a target tissue, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method for the enhanced delivery of a therapeutic and/or prophylactic to a target tissue, wherein the method comprises the step of administering to the subject a lipid nanoparticle comprising a compound of Formula (A-c), DSPC, cholesterol, and PEG-1, and one or more therapeutic and/or prophylactic agents selected from a nucleotide, a polypeptide, and a nucleic acid (e.g., an RNA).

In some aspects, the disclosure provides a method of producing a polypeptide of interest in a cell (e.g., a mammalian cell). This method includes the step of contacting the cell with a loaded LNP or a pharmaceutical composition of the disclosure, wherein the loaded LNP or pharmaceutical composition comprises an mRNA, whereby the mRNA is capable of being translated in the cell to produce the polypeptide. In some embodiments, the cell is in a subject and the contacting comprises administering the cell to the subject. In some embodiments, the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, a PEG lipid, and an mRNA, whereby the mRNA is capable of being translated in the cell to produce the polypeptide.

In some embodiments, the disclosure provides a method of producing a polypeptide of interest in a cell, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and $PEG_{2k}$-DMG, and an mRNA. For example, in some embodiments, the disclosure provides a method of producing a polypeptide of interest in a cell, wherein the method comprises the step of administering to the subject a lipid nanoparticle comprising a compound of Table 1, DSPC, cholesterol, and $PEG_{2k}$-DMG, and an mRNA. For example, in some embodiments, the disclosure provides a method of producing a polypeptide of interest in a cell, wherein the method comprises the step of administering to the subject a lipid nanoparticle comprising a compound of Formula (A-c), DSPC, cholesterol, and PEG$_{2k}$-DMG, and an mRNA.

In some embodiments, the disclosure provides a method of producing a polypeptide of interest in a cell, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and PEG-1, and an mRNA. For example, in some embodiments, the disclosure provides a method of producing a polypeptide of interest in a cell, wherein the method comprises the step of administering to the subject a lipid nanoparticle comprising a compound of Formula (A-c), DSPC, cholesterol, and PEG-1, and an mRNA. For example, in some embodiments, the disclosure provides a method of producing a polypeptide of interest in a cell, wherein the method comprises the step of administering to the subject a lipid nanoparticle comprising a compound of Table 1, DSPC, cholesterol, and PEG-1, and an mRNA.

In some aspects, the disclosure provides a method of treating a disease or disorder in a mammal (e.g., a human) in need thereof. The method includes the step of administering to the mammal a therapeutically effective amount of loaded LNP or a pharmaceutical composition of the disclosure. In some embodiments, the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, a PEG lipid, and one or more therapeutic and/or prophylactic agents, whereby the therapeutic and/or prophylactic is delivered to the cell. In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases, autoimmune diseases, diabetes, neurodegenerative diseases, cardio- and reno-vascular diseases, and metabolic diseases.

In some embodiments, the disclosure provides a method of treating a disease or disorder in a subject, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and PEG$_{2k}$-DMG, and one or more therapeutic and/or prophylactic agents selected from a nucleotide, a polypeptide, and a nucleic acid (e.g., an RNA). For example, in some embodiments, the disclosure provides a method of treating a disease or disorder in a subject, wherein the method comprises the step of administering to the subject a lipid nanoparticle comprising a compound of Formula (A-c), DSPC, cholesterol, and PEG2k-DMG, and one or more therapeutic and/or prophylactic agents selected from a nucleotide, a polypeptide, and a nucleic acid (e.g., an RNA). For example, in some embodiments, the disclosure provides a method of treating a disease or disorder in a subject, wherein the method comprises the step of administering to the subject a lipid nanoparticle comprising a compound of Table 1, DSPC, cholesterol, and PEG$_{2k}$-DMG, and one or more therapeutic and/or prophylactic agents selected from a nucleotide, a polypeptide, and a nucleic acid (e.g., an RNA).

In some embodiments, the disclosure provides a method of treating a disease or disorder in a subject, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of treating a disease or disorder in a subject, wherein the method comprises the step of administering to the subject a lipid nanoparticle comprising a compound of Formula (A-c), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of treating a disease or disorder in a subject, wherein the method comprises the step of administering to the subject a lipid nanoparticle comprising a compound of Table 1, DSPC, cholesterol, and PEG-1, and one or more therapeutic and/or prophylactic agents selected from a nucleotide, a polypeptide, and a nucleic acid (e.g., an RNA).

In yet another aspect, the disclosure features a method of lowering immunogenicity comprising introducing loaded LNP or a pharmaceutical composition of the disclosure into cells, wherein the loaded LNP or a pharmaceutical composition reduces the induction of the cellular immune response of the cells to the loaded LNP or a pharmaceutical composition, as compared to the induction of the cellular immune response in cells induced by a reference composition. In some embodiments, the cell is in a subject and the contacting comprises administering the cell to the subject. In some embodiments, the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid, a structural lipid, a PEG lipid, and one or more therapeutic and/or prophylactic agents selected from a nucleotide, a polypeptide, and a nucleic acid (e.g., an RNA), wherein the lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c) reduces the induction of the cellular immune response of the cells to the lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), as compared to the induction of the cellular immune response in cells induced by a reference composition. For example, the cellular immune response is an innate immune response, an adaptive immune response, or both.

In some embodiments, the disclosure provides a method of lowering immunogenicity in a subject, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and PEG$_{2k}$-DMG, and one or more therapeutic and/or prophylactic agents selected from a nucleotide, a polypeptide, and a nucleic acid (e.g., an RNA). For example, in some embodiments, the disclosure provides a method of lowering immunogenicity in a subject, wherein the method comprises the step of administering to the subject a lipid nanoparticle comprising a compound of Formula (A-c), DSPC, cholesterol, and PEG$_{2k}$-DMG, and one or more therapeutic and/or prophylactic agents selected from a nucleotide, a polypeptide, and a nucleic acid (e.g., an RNA). For example, in some embodiments, the disclosure provides a method of lowering immunogenicity in a subject, wherein the method comprises the step of administering to the subject a lipid nanoparticle comprising a compound of Table 1, DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method of lowering immunogenicity in a subject, wherein the method comprises the step of administering to the subject a lipid nanoparticle comprising a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of lowering immunogenicity in a subject, wherein the method comprises the step of administering to the subject a lipid nanoparticle comprising a compound of Formula (A-c), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of lowering immunogenicity in a subject, wherein the method comprises the step of administering to the subject a lipid nanoparticle comprising a compound of Table 1, DSPC, cholesterol, and PEG-1, and one or more therapeutic and/or prophylactic agents selected from a nucleotide, a polypeptide, and a nucleic acid (e.g., an RNA).

The disclosure also includes methods of synthesizing a compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), and methods of making a lipid nanoparticle (e.g., an empty LNP or a loaded LNP) including a lipid component comprising the compound of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c).

Methods of Producing Polypeptides in Cells

The present disclosure provides methods of producing a polypeptide of interest in a mammalian cell. Methods of producing polypeptides involve contacting a cell with a lipid nanoparticle (e.g., an empty LNP or a loaded LNP) including an mRNA encoding the polypeptide of interest. Upon contacting the cell with the nanoparticle composition, the mRNA may be taken up and translated in the cell to produce the polypeptide of interest.

In general, the step of contacting a mammalian cell with a lipid nanoparticle (e.g., an empty LNP or a loaded LNP) including an mRNA encoding a polypeptide of interest may be performed in vivo, ex vivo, in culture, or in vitro. The amount of lipid nanoparticle (e.g., an empty LNP or a loaded LNP) contacted with a cell, and/or the amount of mRNA therein, may depend on the type of cell or tissue being contacted, the means of administration, the physiochemical characteristics of the lipid nanoparticle (e.g., an empty LNP or a loaded LNP) and the mRNA (e.g., size, charge, and chemical composition) therein, and other factors. In general, an effective amount of the lipid nanoparticle (e.g., an empty LNP or a loaded LNP) will allow for efficient polypeptide production in the cell. Metrics for efficiency may include polypeptide translation (indicated by polypeptide expression), level of mRNA degradation, and immune response indicators.

The step of contacting a lipid nanoparticle (e.g., an empty LNP or a loaded LNP) including an mRNA with a cell may involve or cause transfection. A phospholipid including in the lipid component of a lipid nanoparticle (e.g., an empty LNP or a loaded LNP) may facilitate transfection and/or increase transfection efficiency, for example, by interacting and/or fusing with a cellular or intracellular membrane. Transfection may allow for the translation of the mRNA within the cell.

In some embodiments, the lipid nanoparticles (e.g., empty LNPs or loaded LNPs) described herein may be used therapeutically. For example, an mRNA included in a lipid nanoparticle (e.g., an empty LNP or a loaded LNP) may encode a therapeutic polypeptide (e.g., in a translatable region) and produce the therapeutic polypeptide upon contacting and/or entry (e.g., transfection) into a cell. In other embodiments, an mRNA included in a lipid nanoparticle (e.g., an empty LNP or a loaded LNP) may encode a polypeptide that may improve or increase the immunity of a subject. For example, an mRNA may encode a granulocyte-colony stimulating factor or trastuzumab.

In certain embodiments, an mRNA included in a lipid nanoparticle (e.g., an empty LNP or a loaded LNP) may encode a recombinant polypeptide that may replace one or more polypeptides that may be substantially absent in a cell contacted with the nanoparticle composition. The one or more substantially absent polypeptides may be lacking due to a genetic mutation of the encoding gene or a regulatory pathway thereof. Alternatively, a recombinant polypeptide produced by translation of the mRNA may antagonize the activity of an endogenous protein present in, on the surface of, or secreted from the cell. An antagonistic recombinant polypeptide may be desirable to combat deleterious effects caused by activities of the endogenous protein, such as altered activities or localization caused by mutation. In another alternative, a recombinant polypeptide produced by translation of the mRNA may indirectly or directly antagonize the activity of a biological moiety present in, on the surface of, or secreted from the cell. Antagonized biological moieties may include, but are not limited to, lipids (e.g., cholesterol), lipoproteins (e.g., low density lipoprotein), nucleic acids, carbohydrates, and small molecule toxins. Recombinant polypeptides produced by translation of the mRNA may be engineered for localization within the cell, such as within a specific compartment such as the nucleus, or may be engineered for secretion from the cell or for translocation to the plasma membrane of the cell.

In some embodiments, contacting a cell with a lipid nanoparticle (e.g., an empty LNP or a loaded LNP) including an mRNA may reduce the innate immune response of a cell to an exogenous nucleic acid. A cell may be contacted with a first lipid nanoparticle (e.g., an empty LNP or a loaded LNP) including a first amount of a first exogenous mRNA including a translatable region and the level of the innate immune response of the cell to the first exogenous mRNA may be determined. Subsequently, the cell may be contacted with a second composition including a second amount of the first exogenous mRNA, the second amount being a lesser amount of the first exogenous mRNA compared to the first amount. Alternatively, the second composition may include a first amount of a second exogenous mRNA that is different from the first exogenous mRNA. The steps of contacting the cell with the first and second compositions may be repeated one or more times. Additionally, efficiency of polypeptide production (e.g., translation) in the cell may be optionally determined, and the cell may be re-contacted with the first and/or second composition repeatedly until a target protein production efficiency is achieved.

Methods of Delivering Therapeutic Agents to Cells and Organs

The present disclosure provides methods of delivering a therapeutic and/or prophylactic to a mammalian cell or organ. Delivery of a therapeutic and/or prophylactic to a cell involves administering a lipid nanoparticle (e.g., an empty LNP or a loaded LNP) including the therapeutic and/or prophylactic to a subject, where administration of the composition involves contacting the cell with the composition. For example, a protein, cytotoxic agent, radioactive ion, chemotherapeutic agent, or nucleic acid (such as an RNA, e.g., mRNA) may be delivered to a cell or organ. In the instance that a therapeutic and/or prophylactic is an mRNA, upon contacting a cell with the nanoparticle composition, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some embodiments, a lipid nanoparticle (e.g., an empty LNP or a loaded LNP) may target a particular type or class of cells (e.g., cells of a particular organ or system thereof). For example, a lipid nanoparticle (e.g., an empty LNP or a loaded LNP) including a therapeutic and/or prophylactic of interest may be specifically delivered to a mammalian liver, kidney, spleen, or lung. Specific delivery to a particular class of cells, an organ, or a system or group thereof implies that a higher proportion of lipid nanoparticles (e.g., loaded LNPs) including a therapeutic and/or prophylactic are delivered to the destination (e.g., tissue) of interest relative to other destinations. In some embodiments, specific delivery of a loaded LNP comprising an mRNA may result in a greater than 2 fold, 5 fold, 10 fold, 15 fold, or 20 fold increase in mRNA expression in cells of the targeted destination (e.g., tissue of interest, such as a liver) as compared to cells of another destination (e.g., the spleen). In some embodiments, the tissue of interest is selected from the group consisting of a liver, a kidney, a lung, a spleen, and tumor tissue (e.g., via intratumoral injection).

In some embodiments, specific delivery of an mRNA comprised in a loaded LNP of the disclosure (i.e., a lipid nanoparticle formulated with a compound of the disclosure) may result in a greater than 2 fold, 5 fold, 10 fold, 15 fold, or 20 fold increase in mRNA expression as compared to delivery of an mRNA comprised in an LNP formulated with another lipid (i.e., without any of the lipids of Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c)).

As another example of targeted or specific delivery, an mRNA that encodes a protein-binding partner (e.g., an antibody or functional fragment thereof, a scaffold protein, or a peptide) or a receptor on a cell surface may be included in a nanoparticle composition. An mRNA may additionally or instead be used to direct the synthesis and extracellular localization of lipids, carbohydrates, or other biological moieties. Alternatively, other therapeutic and/or prophylactics or elements (e.g., lipids or ligands) of a lipid nanoparticle (e.g., an empty LNP or a loaded LNP) may be selected based on their affinity for particular receptors (e.g., low density lipoprotein receptors) such that a lipid nanoparticle (e.g., an empty LNP or a loaded LNP) may more readily interact with a target cell population including the receptors. For example, ligands may include, but are not limited to, members of a specific binding pair, antibodies, monoclonal antibodies, Fv fragments, single chain Fv (scFv) fragments, Fab' fragments, F(ab')2 fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tribodies, or tetrabodies; and aptamers, receptors, and fusion proteins.

In some embodiments, a ligand may be a surface-bound antibody, which can permit tuning of cell targeting specificity. This is especially useful since highly specific antibodies can be raised against an epitope of interest for the desired targeting site. In some embodiments, multiple antibodies are expressed on the surface of a cell, and each antibody can have a different specificity for a desired target. Such approaches can increase the avidity and specificity of targeting interactions.

A ligand can be selected, e.g., by a person skilled in the biological arts, based on the desired localization or function of the cell.

Targeted cells may include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells.

In some embodiments, a lipid nanoparticle (e.g., an empty LNP or a loaded LNP) may target hepatocytes. Apolipoprotiens such as apolipoprotein E (apoE) have been shown to associate with neutral or near neutral lipid-containing lipid nanoparticles (e.g., empty LNPs or loaded LNPs) in the body, and are known to associate with receptors such as low-density lipoprotein receptors (LDLRs) found on the surface of hepatocytes. Thus, a lipid nanoparticle (e.g., an empty LNP or a loaded LNP) including a lipid component with a neutral or near neutral charge that is administered to a subject may acquire apoE in a subject's body and may subsequently deliver a therapeutic and/or prophylactic (e.g., an RNA) to hepatocytes including LDLRs in a targeted manner.

Methods of Treating Diseases and Disorders

Lipid nanoparticles (e.g., empty LNPs or loaded LNPs) may be useful for treating a disease, disorder, or condition. In particular, such compositions may be useful in treating a disease, disorder, or condition characterized by missing or aberrant protein or polypeptide activity. For example, a lipid nanoparticle (e.g., an empty LNP or a loaded LNP) comprising an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic included in a lipid nanoparticle (e.g., an empty LNP or a loaded LNP) may also be capable of altering the rate of transcription of a given species, thereby affecting gene expression.

Diseases, disorders, and/or conditions characterized by dysfunctional or aberrant protein or polypeptide activity for which a composition may be administered include, but are not limited to, rare diseases, infectious diseases (as both vaccines and therapeutics), cancer and proliferative diseases, genetic diseases, autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional. The present disclosure provides a method for treating such diseases, disorders, and/or conditions in a subject by administering a lipid nanoparticle (e.g., an empty LNP or a loaded LNP) including an RNA and a lipid component including a lipid according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), a phospholipid (optionally unsaturated), a PEG lipid, and a structural lipid, wherein the RNA may be an mRNA encoding a polypeptide that antagonizes or otherwise overcomes an aberrant protein activity present in the cell of the subject.

The disclosure provides methods involving administering lipid nanoparticles (e.g., empty LNPs or loaded LNPs) including one or more therapeutic and/or prophylactic agents and pharmaceutical compositions including the same. The terms therapeutic and prophylactic can be used interchangeably herein with respect to features and embodiments of the present disclosure. Therapeutic compositions, or imaging, diagnostic, or prophylactic compositions thereof, may be administered to a subject using any reasonable amount and any route of administration effective for preventing, treating, diagnosing, or imaging a disease, disorder, and/or condition and/or any other purpose. The specific amount administered to a given subject may vary depending on the species, age, and general condition of the subject; the purpose of the administration; the particular composition; the mode of administration; and the like. Compositions in accordance with the present disclosure may be formulated in dosage unit form for ease of administration and uniformity of dosage. It will be understood, however, that the total daily usage of a composition of the present disclosure will be decided by an attending physician within the scope of sound medical judgment. The specific therapeutically effective, prophylactically effective, or otherwise appropriate dose level (e.g., for imaging) for any particular patient will depend upon a variety of factors including the severity and identify of a disorder being treated, if any; the one or more therapeutic and/or prophylactics employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

A loaded LNP may be administered by any route. In some embodiments, compositions, including prophylactic, diagnostic, or imaging compositions including one or more loaded LNPs described herein, are administered by one or more of a variety of routes, including oral, intravenous, intramuscular, intra-arterial, subcutaneous, trans- or intradermal, interdermal, intraperitoneal, mucosal, nasal, intratumoral, intranasal; by inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, or by any other parenteral route of administration or by inhalation. However, the present disclosure encompasses the delivery or administration of compositions described herein by any appropriate route taking into consideration likely advances in the sciences of drug delivery. In general, the most appropriate route of administration will depend upon a variety of factors including the nature of the loaded LNP including one or more therapeutic and/or prophylactics (e.g., its stability in various bodily environments such as the bloodstream and gastrointestinal tract), the condition of the patient (e.g., whether the patient is able to tolerate particular routes of administration), etc.

In certain embodiments, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a therapeutic and/or prophylactic (e.g., an mRNA) in a given dose, where a dose of 1 mg/kg (mpk) provides 1 mg of a therapeutic and/or prophylactic per 1 kg of subject body weight. In some embodiments, a dose of about 0.001 mg/kg to about 10 mg/kg of a therapeutic and/or prophylactic of a loaded LNP may be administered. In other embodiments, a dose of about 0.005 mg/kg to about 2.5 mg/kg of a therapeutic and/or prophylactic may be administered. In certain embodiments, a dose of about 0.1 mg/kg to about 1 mg/kg may be administered. In other embodiments, a dose of about 0.05 mg/kg to about 0.25 mg/kg may be administered. A dose may be administered one or more times per day, in the same or a different amount, to obtain a desired level of mRNA expression and/or therapeutic, diagnostic, prophylactic, or imaging effect. The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition.

Lipid nanoparticles (e.g., empty LNPs or loaded LNPs) including one or more therapeutic and/or prophylactics may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. For example, one or more lipid nanoparticles (e.g., empty LNPs or loaded LNPs) including one or more different therapeutic and/or prophylactics may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some embodiments, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

A lipid nanoparticle (e.g., an empty LNP or a loaded LNP) may be used in combination with an agent to increase the effectiveness and/or therapeutic window of the composition. Such an agent may be, for example, an anti-inflammatory compound, a steroid (e.g., a corticosteroid), a statin, an estradiol, a BTK inhibitor, an SlPl agonist, a glucocorticoid receptor modulator (GRM), or an anti-histamine. In some embodiments, a lipid nanoparticle (e.g., an empty LNP or a loaded LNP) may be used in combination with dexamethasone, methotrexate, acetaminophen, an H1 receptor blocker, or an H2 receptor blocker. In some embodiments, a method of treating a subject in need thereof or of delivering a therapeutic and/or prophylactic to a subject (e.g., a mammal) may involve pre-treating the subject with one or more agents prior to administering a nanoparticle composition. For example, a subject may be pre-treated with a useful amount (e.g., 10 mg, 20 mg, 30 mg, 40 mg, 50 mg, 60 mg, 70 mg, 80 mg, 90 mg, 100 mg, or any other useful amount) of dexamethasone, methotrexate, acetaminophen, an H1 receptor blocker, or an H2 receptor blocker. Pre-treatment may occur 24 or fewer hours (e.g., 24 hours, 20 hours, 16 hours, 12 hours, 8 hours, 4 hours, 2 hours, 1 hour, 50 minutes, 40 minutes, 30 minutes, 20 minutes, or 10 minutes) before administration of the lipid nanoparticle (e.g., an empty LNP or a loaded LNP) and may occur one, two, or more times in, for example, increasing dosage amounts.

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all, of the group members are present in, employed in, or otherwise relevant to a given product or process. As used herein, the expressions "one or more of A, B, or C," "one or more A, B, or C," "one or more of A, B, and C," "one or more A, B, and C", "selected from A, B, and C," "selected from the group consisting of A, B, and C," and the like are used interchangeably and all refer to a selection from a group consisting of A, B, and/or C, i.e., one or more As, one or more Bs, one or more $C_8$, or any combination thereof, unless otherwise specified.

It is also noted that the term "comprising" is intended to be open and permits but does not require the inclusion of additional elements or steps. When the term "comprising" is used herein, the terms "consisting essentially of" and "consisting of" are thus also encompassed and disclosed. Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5th edition, John Wiley & Sons: New York, 2001; Greene, T. W., Wuts, P. G. M., *Protective Groups in Organic Synthesis*, 3rd edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

The compounds of this disclosure having any of the formulae described herein may be prepared according to the procedures illustrated in Schemes 1, 2, and 3 below, from commercially available starting materials or starting materials which can be prepared using literature procedures. The variables in the schemes (e.g., $R^1$, $R^2$, and $R^3$ etc. are as defined herein). One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis*, 3rd edition, John Wiley & Sons: New York, 1999.

Preferred protecting groups include, but are not limited to:
For a hydroxyl moiety: TBS, benzyl, THP, Ac.
For carboxylic acids: benzyl ester, methyl ester, ethyl ester, allyl ester.
For amines: Fmoc, Cbz, BOC, DMB, Ac, Bn, Tr, Ts, trifluoroacetyl, phthalimide, benzylideneamine.
For diols: Ac (×2) TBS (×2), or when taken together acetonides.
For thiols: Ac.
For benzimidazoles: SEM, benzyl, PMB, DMB.
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

Scheme 1

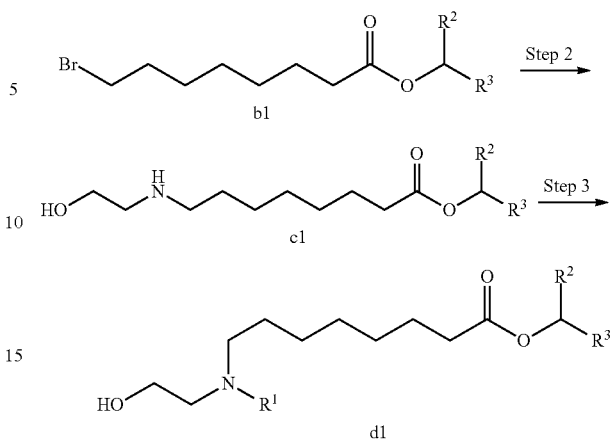

As illustrated in Scheme 1 above, 8-bromooctanoic acid reacts with an alcohol a1 (e.g., heptadecan-9-ol) to afford an ester b1 (e.g., heptadecan-9-yl 8-bromooctanoate). Step 1 can take place in an organic solvent (e.g., dichloromethane) in the presence of, e.g., N-(3-dimethylaminopropyl)-N'-ethylcarbodiimide hydrochloride, N,N-diisopropylethylamine and DMAP. Step 1 can take place at room temperature for 18 h. Next, ester b1 reacts with 2-aminoethan-1-ol to afford amine c1 (e.g., heptadecan-9-yl 8-((2-hydroxyethyl)amino)octanoate). Step 2 can take place in ethanol at, e.g., a temperature of about 60° C. Then amine c1 reacts with an bromoalkyl $R^1$—Br (e.g., 1-bromotetradecane) to afford compound d1 (e.g., heptadecan-9-yl 8-((2-hydroxyethyl)(tetradecyl)amino)octanoate). Step 3 can take place in ethanol in the presence of N,N-diisopropylethylamine.

Scheme 2

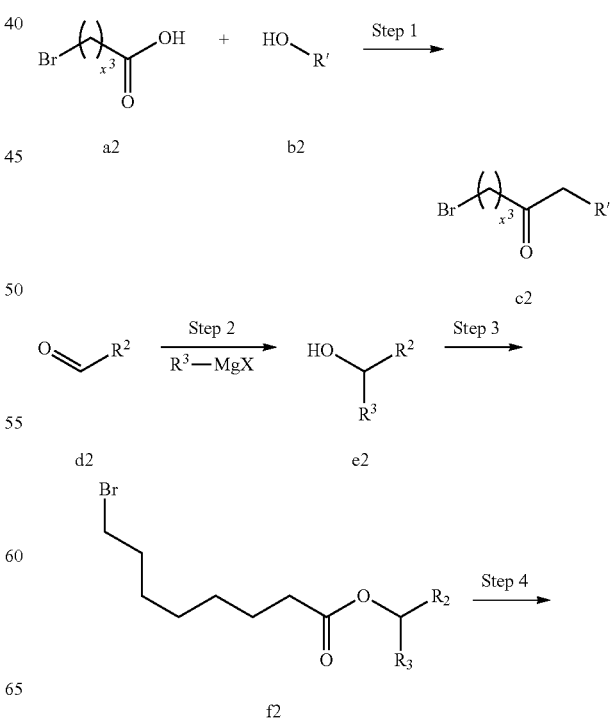

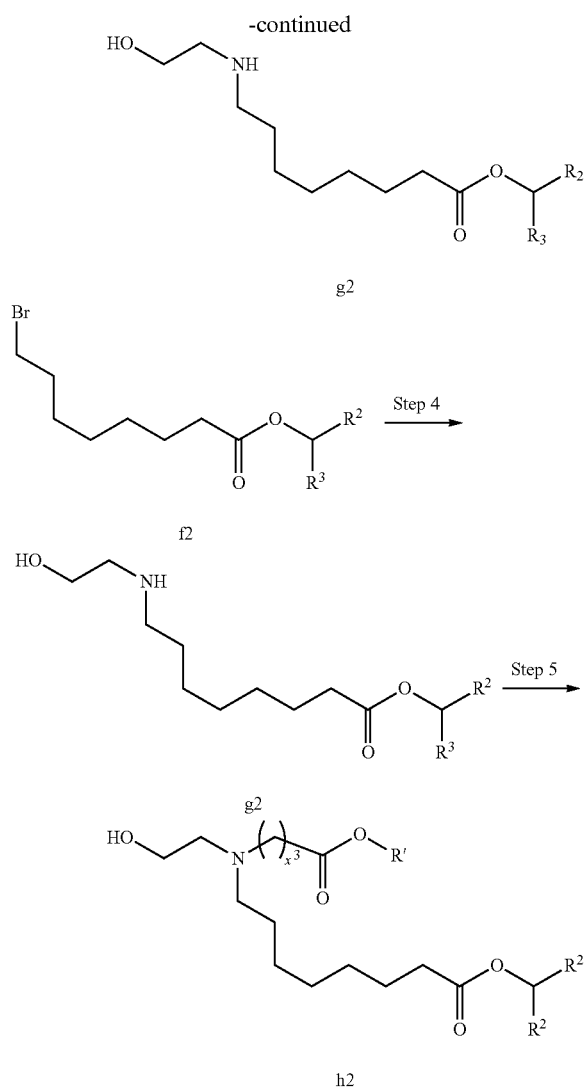

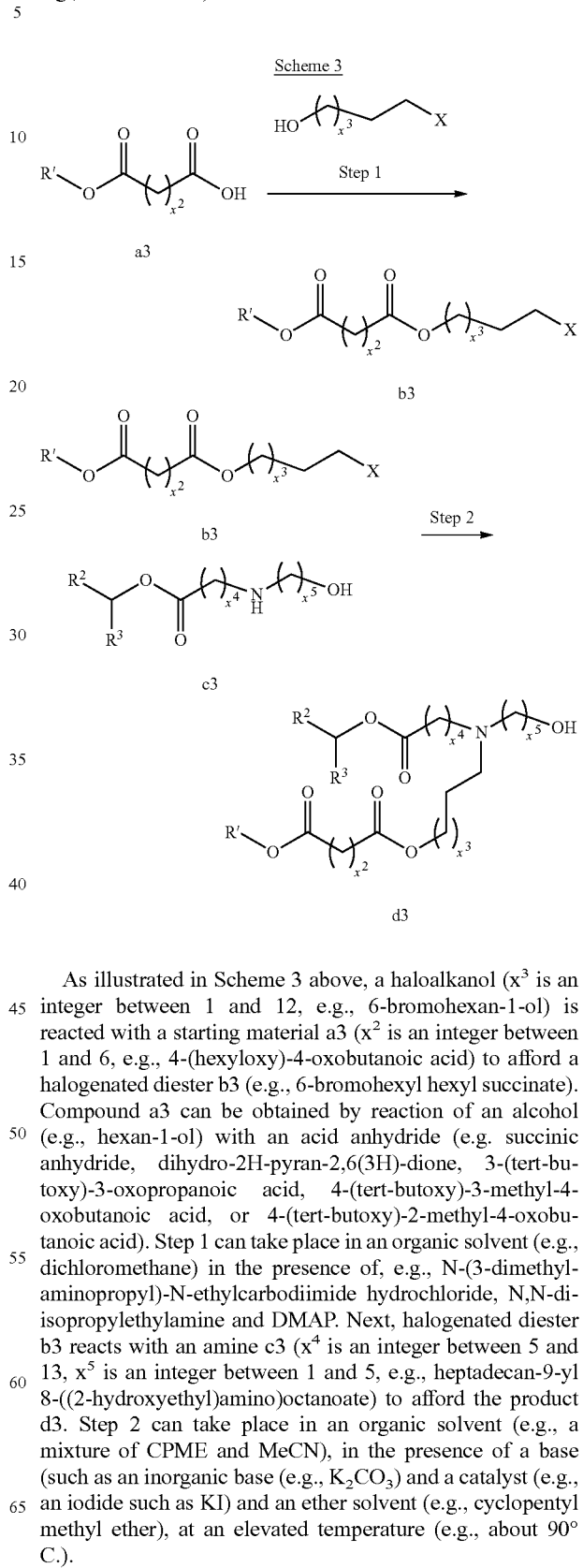

As illustrated in Scheme 2 above, an acid a2 ($x^3$ is an integer between 1 and 7; e.g., 8-bromooctanoic acid) reacts with an alcohol b2 (e.g., nonan-1-ol) to afford an ester c2 (e.g., nonyl-8-bromooctanoate). Step 1 can take place in an organic solvent (e.g., dichloromethane) in the presence of, e.g., N-(3-dimethylaminopropyl)-N-ethylcarbodiimide hydrochloride, N,N-diisopropylethylamine and DMAP. Alcohol e2 (e.g., heptadecan-9-ol) can be obtained from reacting aldehyde d2 (e.g., nonanal) with a Grignard reagent $R^3$—MgX (e.g., n-C8H17MgBr) via Step 2. Next, 8-bromooctanoic acid reacts with an alcohol e2 (e.g., heptadecan-9-ol) to afford an ester f2 (e.g., heptadecan-9-yl 8-bromooctanoate). Step 3 can take place in an organic solvent (e.g., dichloromethane) in the presence of, e.g., N-(3-dimethylaminopropyl)-N-ethylcarbodiimide hydrochloride, N,N-diisopropylethylamine and DMAP. Next, ester f2 reacts with 2-aminoethan-1-ol to afford amine g2 (e.g., heptadecan-9-yl 8-((2-hydroxyethyl)amino)octanoate). Step 4 can take place in ethanol in the presence of i-Pr2EtN. Then amine g2 reacts with ester c2 (e.g., nonyl-8-bromooctanoate) to afford compound h2 (e.g., heptadecan-9-yl 8-((2-hydroxyethyl)(8-(nonyloxy)-8-oxooctyl)amino)octanoate). Step 5 can take place in an organic solvent (e.g., a mixture of CPME and MeCN), in the presence of a base (such as an inorganic base (e.g., $K_2CO_3$) or non-nucleophilic organic base (e.g., i-Pr2EtN)) and a catalyst (e.g., an iodide such as KI or NaI) at, e.g., an elevated temperature (such as at about 70-90° C., e.g., about 80° C.).

As illustrated in Scheme 3 above, a haloalkanol ($x^3$ is an integer between 1 and 12, e.g., 6-bromohexan-1-ol) is reacted with a starting material a3 ($x^2$ is an integer between 1 and 6, e.g., 4-(hexyloxy)-4-oxobutanoic acid) to afford a halogenated diester b3 (e.g., 6-bromohexyl hexyl succinate). Compound a3 can be obtained by reaction of an alcohol (e.g., hexan-1-ol) with an acid anhydride (e.g. succinic anhydride, dihydro-2H-pyran-2,6(3H)-dione, 3-(tert-butoxy)-3-oxopropanoic acid, 4-(tert-butoxy)-3-methyl-4-oxobutanoic acid, or 4-(tert-butoxy)-2-methyl-4-oxobutanoic acid). Step 1 can take place in an organic solvent (e.g., dichloromethane) in the presence of, e.g., N-(3-dimethylaminopropyl)-N-ethylcarbodiimide hydrochloride, N,N-diisopropylethylamine and DMAP. Next, halogenated diester b3 reacts with an amine c3 ($x^4$ is an integer between 5 and 13, $x^5$ is an integer between 1 and 5, e.g., heptadecan-9-yl 8-((2-hydroxyethyl)amino)octanoate) to afford the product d3. Step 2 can take place in an organic solvent (e.g., a mixture of CPME and MeCN), in the presence of a base (such as an inorganic base (e.g., $K_2CO_3$) and a catalyst (e.g., an iodide such as KI) and an ether solvent (e.g., cyclopentyl methyl ether), at an elevated temperature (e.g., about 90° C.).

A person of ordinary skill in the art will recognize that in the above schemes the order of certain steps may be interchangeable.

In certain aspects, the disclosure also includes methods of synthesizing a compound of any of Formulae (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), and (B-c) and intermediate(s) for synthesizing the compound.

In some embodiments, the method of synthesizing a compound of the disclosure includes reacting a compound of Formula (X2):

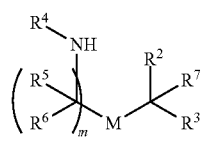

with $R^1$—Br to afford the compound of the disclosure, wherein each variables are as defined herein. For example, m is 5, 6, 7, 8, or 9, preferably 5, 7, or 9. For example, each of $R^5$, $R^6$, and $R^7$ is H. For example, M is —C(O)O— or —OC(O)—. For example, $R^4$ is unsubstituted $C_{1-3}$ alkyl, or —$(CH_2)_n$Q, in which n is 2, 3, or 4 and Q is OH, —NHC(S)N(R)$_2$, —NHC(O)N(R)$_2$, —N(R)C(O)R, or —N(R)S(O)$_2$ R. For example, the reaction of the compound of Formula (X2) with $R^1$—Br takes place in the presence of a base (such as an inorganic base (e.g., $K_2CO_3$) or non-nucleophilic organic base (e.g., i-Pr2EtN)). For example, the reaction takes place in the presence of an inorganic base (e.g., $K_2CO_3$) and a catalyst (e.g., an iodide such as KI or NaI). For example, the reaction takes place at an elevated temperature, e.g., about 50-100° C., 70-90° C., or about 80° C.).

The method may also include reacting a compound of Formula (X1):

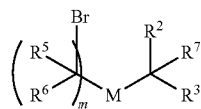

with $R^4NH_2$ to afford a compound of Formula (X2), wherein each variables are as defined herein.

In some embodiments, the intermediate(s) include those having any of Formulae (X1) and (X2):

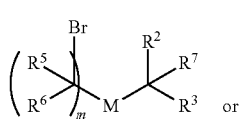 (X1)

or

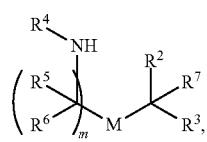 (X2)

wherein each variables are as defined herein. For example, the intermediate includes heptadecan-9-yl 8-bromooctanoate, and heptadecan-9-yl 8-((2-hydroxyethyl)amino)octanoate, and morphic forms thereof (e.g., a crystalline form).

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Example 1: Synthesis of Compounds of Table 1

A. General Considerations

All solvents and reagents used were obtained commercially and used as such unless noted otherwise. $^1$H NMR spectra were recorded in CDCl3, at 300 K using a Bruker Ultrashield 300 MHz instrument. Chemical shifts are reported as parts per million (ppm) relative to TMS (0.00) for $^1$H. Silica gel chromatographies were performed on ISCO CombiFlash Rf+ Lumen Instruments using ISCO RediSep Rf Gold Flash Cartridges (particle size: 20-40 microns). Reverse phase chromatographies were performed on ISCO CombiFlash Rf+ Lumen Instruments using RediSep Rf Gold C18 High Performance columns. All final compounds were determined to be greater than 85% pure via analysis by reverse phase UPLC-MS (retention times, RT, in minutes) using Waters Acquity UPLC instrument with DAD and ELSD and a ZORBAX Rapid Resolution High Definition (RRHD) SB—C18 LC column, 2.1 mm, 50 mm, 1.8 μm, and a gradient of 65 to 100% acetonitrile in water with 0.10% TFA over 5 minutes at 1.2 mL/min. Injection volume was 5 μL and the column temperature was 80° C. Detection was based on electrospray ionization (ESI) in positive mode using Waters SQD mass spectrometer (Milford, MA, USA) and evaporative light scattering detector.

LCMS method:
Instrument Information: HPLC/MS-Agilent 1100
Column: Agela Technologies Durashell C18 3.5 μm, 100 Å, 4.6×50 mm
Mobile Phase A: Water/0.1% Trifluoroacetic Acid
Mobile Phase B: Acetonitrile/0.10% Trifluoroacetic Acid
Flow Rate: 1 mL/min
Gradient: 70% B to 100% B in 5 minutes, hold 100% B for 10 minutes, 100% B to 70% B in minute, and then stop.
Column Temperature: Ambient
Detector: ELSD The procedures described below are useful in the synthesis of compounds of Table 1.

The following abbreviations are employed herein:
THF: Tetrahydrofuran
MeCN: Acetonitrile
LAH: Lithium Aluminum Hydride
DCM: Dichloromethane
DMAP: 4-Dimethylaminopyridine
LDA: Lithium Diisopropylamide
rt: Room Temperature
DME: 1,2-Dimethoxyethane
n-BuLi: n-Butyllithium
CPME: Cyclopentyl methyl ether
i-Pr2EtN: N,N-Diisopropylethylamine Representative Synthesis for Compounds 7, 12, and 13

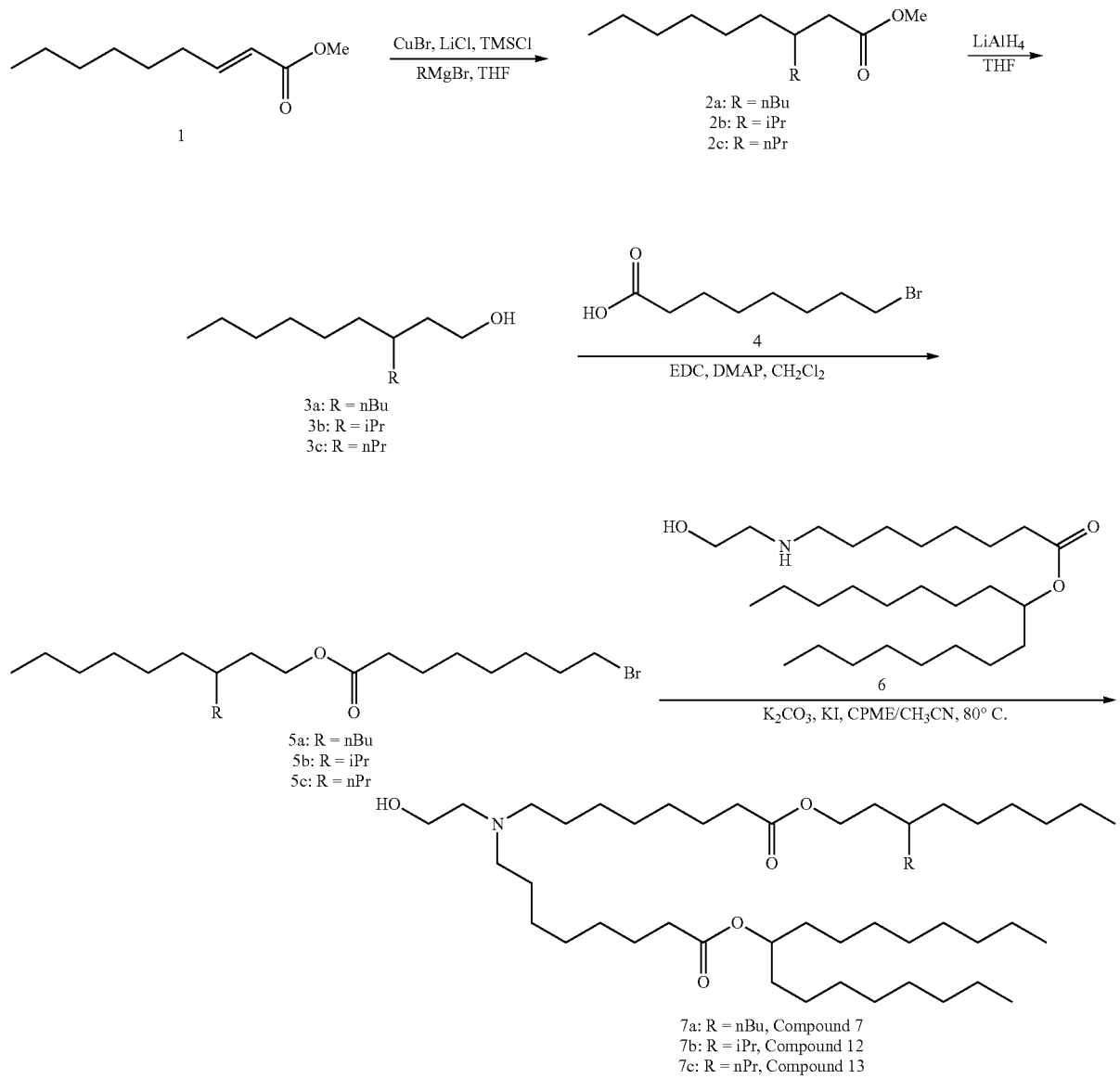

Representative Procedure A: 1,4-Addition of Grignard Reagent RMgX to Methyl (E)-non-2-enoate, 1

A1. Compound 2a: Methyl 3-butylnonanoate

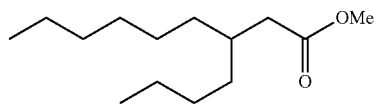

Chemical Formula: $C_{14}H_{28}O_2$
Molecular Weight: 228.4

To an oven-dried 100 mL round bottom flask was added copper(I) bromide (421.3 mg, 2.93 mmol) and lithium chloride (249 mg, 5.87 mmol), then dry THF (15 mL) was added and the mixture was stirred for 10 min during which time the solids were dissolved. The flask was put in an ice bath and methyl (E)-non-2-enoate 1 (5 g, 29.37 mmol) was added, followed by addition of TMSCl 4 mL, 32.31 mmol). The reaction was stirred for 15 min. A THF solution of butylmagnesium bromide (17.6 mL, 35.2 mmol, 2.0 M in THF) was added slowly and the reaction was stirred for 2 h. The reaction was quenched with saturated $NH_4Cl$ (10 mL) and extracted with diethyl ether (100 mL) and dried over anhydrous sodium sulfate. After removing the solvent, the crude was purified by flash chromatography ($SiO_2$:ethyl acetate/hexane 0-100%) and colorless oil product 2a was obtained (3 g, 45%). $^1H$ NMR (300 MHz, $CDCl_3$): δ ppm 3.64 (s, 3H); 2.21 (d, 2H, J=6.9 Hz); 1.85-1.81 (m, 1H); 1.23-1.20 (m, 16H); 0.86-0.84 (m, 6H).

A2. Compound 2b: Methyl 3-isopropylnonanoate

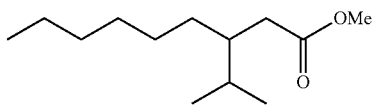

Chemical Formula: $C_{13}H_{26}O_2$
Molecular Weight: 214.3

Same as the procedure A1 but using isoproypylmagnesium bromide. Yield=2.4 g (38%). $^1$H NMR (300 MHz, CDCl$_3$): δ ppm 3.65 (s, 3H); 2.25 (dd, 1H, J=15.1, 6.1 Hz); 2.14 (dd, 1H, J=15.1, 7.1 Hz); 1.23-1.20 (m, 12H); 0.87-0.84 (m, 9H).

A3. Compound 2c: Methyl 3-propylnonanoate

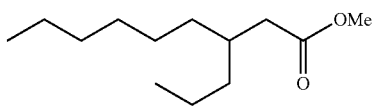

Chemical Formula: $C_{13}H_{26}O_2$
Molecular Weight: 214.3

Same as the procedure A1 but using n-proypylmagnesium bromide. Yield=2.2 g (35%). $^1$H NMR (300 MHz, CDCl$_3$): δ ppm 3.64 (s, 3H); 2.23 (d, 2H, J=6.8 Hz); 1.85-1.84 (m, 1H); 1.23-1.20 (m, 14H); 0.87-0.84 (m, 6H).

Representative Procedure B: LAH Reduction

B1. Compound 3a: 3-Butylnonan-1-ol

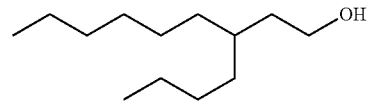

Chemical Formula: $C_{13}H_{28}O$
Molecular Weight: 200.4

A solution of the methyl 3-butylnonanoate, 2a (2.2 g, 9.63 mmol) in THF (10 mL) was added dropwise to a stirred suspension of LiAlH$_4$ (0.73 g, 19.27 mmol) in THF (10 mL) under N$_2$. The mixture was heated under reflux for 5 h. The reaction was cooled to room temperature. Under 0° C. ice-water bath, 0.7 mL of H$_2$O, 0.7 mL 15% NaOH, 2.1 mL of H$_2$O were added sequentially. The white precipitate was filtered, and the filtrate was concentrated. The crude product was purified by flash chromatography (SiO$_2$:ethyl acetate/hexane 0-100%) and colorless oil product 3a was obtained (980 mg, 51%). $^1$H NMR (300 MHz, CDCl$_3$): δ ppm 3.64 (t, 2H, J=6.8 Hz); 1.52 (q, 2H, J=7.1 Hz); 1.32-1.30 (m, 1H); 1.23-1.20 (m, 17H); 0.88-0.84 (m, 6H).

B2. Compound 3b: 3-Isopropylnonan-1-ol

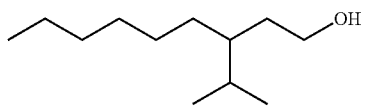

Chemical Formula: $C_{12}H_{26}O$
Molecular Weight: 186.3

Same as the procedure B1 but using Methyl 3-isopropylnonanoate, 2b. Yield=1.7 g (81%). $^1$H NMR (300 MHz, CDCl$_3$): δ ppm 3.64 (m, 2H); 1.55 (m, 2H); 1.43-1.41 (m, 1H); 1.23-1.20 (m, 12H); 0.88-0.84 (m, 9H).

B3. Compound 3c: 3-Propylnonan-1-ol

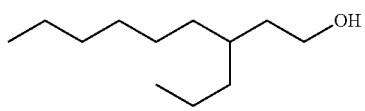

Chemical Formula: $C_{12}H_{26}O$
Molecular Weight: 186.3

Same as the procedure B1 but using Methyl 3-propylnonanoate, 2c. Yield=1.28 g (67%). $^1$H NMR (300 MHz, CDCl$_3$): δ ppm 3.64 (t, 2H, J=6.6 Hz); 1.52 (q, 2H, J=6.3 Hz); 1.23-1.20 (m, 16H); 0.88-0.84 (m, 6H).

Representative Procedure C for Esterification of 8-Bromooctanoic Acid, 4

C$_1$. Compound 5a: 3-Butylnonyl 8-bromooctanoate

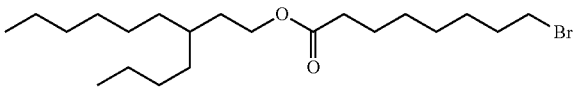

Chemical Formula: $C_{21}H_{41}BrO_2$
Molecular Weight: 405.5

To a solution of 3-Butylnonan-1-ol 3a (458 mg, 2.28 mmol), 8-bromooctanoic acid 4 (611.9 mg, 2.74 mmol) and DMAP (55.9 mg, 0.46 mmol) in dichloromethane (30 mL) at 0° C. was added EDCI (657.3 mg, 3.43 mmol) and the reaction mixture stirred at room temperature overnight. TLC showed the completed reaction. The reaction mixture was cooled to 0° C. and 1N hydrochloric acid (3 mL) was added slowly, then the mixture was extracted with diethyl ether (100 mL) and the layers were separated. The organic layer washed with saturated sodium bicarbonate (100 mL), water and brine. The organic layer was separated and concentrated. The crude was purified by flash chromatography (SiO$_2$: hexane/diethyl ether 0-100%) and colorless oil product 5a was obtained (680 mg. 73%). $^1$H NMR (300 MHz, CDCl$_3$): δ ppm 4.07 (t, 2H, J=6.8 Hz); 3.39 (t, 2H, J=6.8 Hz); 2.28 (t, 2H, J=7.6 Hz); 1.88-1.79 (m, 2H); 1.70-1.42 (m, 6H); 1.38-1.17 (m, 21H); 0.88-0.82 (m, 6H).

123

C₂. Compound 5b: 3-Isopropylnonyl 8-bromooctanoate

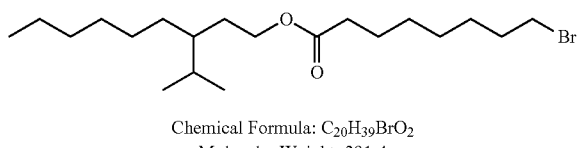

Chemical Formula: $C_{20}H_{39}BrO_2$
Molecular Weight: 391.4

Same as the procedure $C_1$ but using 3-Isopropylnonan-1-ol, 3b. Yield=297 mg (71%). $^1$H NMR (300 MHz, CDCl$_3$): δ ppm 4.05 (dd, 2H, J=14.3, 6.6 Hz); 3.39 (t, 2H, J=6.8 Hz); 2.28 (t, 2H, J=7.7 Hz); 1.86-1.81 (m, 2H); 1.70-1.42 (m, 6H); 1.38-1.17 (m, 16H); 0.84-0.82 (m, 9H).

124

C₃. Compound 5c: 3-Propylnonyl 8-bromooctanoate

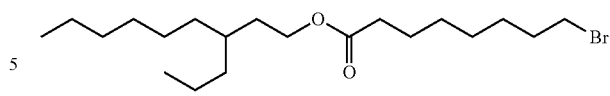

Chemical Formula: $C_{20}H_{39}BrO_2$
Molecular Weight: 391.4

Same as the procedure $C_1$ but using 3-Propylnonan-1-ol, 3c. Yield=430 mg (68%). $^1$H NMR (300 MHz, CDCl$_3$): δ ppm 3.96 (d, 2H, J=5.8 Hz); 3.38 (t, 2H, J=5.5 Hz); 2.27 (t, 2H, J=7.4 Hz); 1.88-1.79 (m, 2H); 1.70-1.42 (m, 6H); 1.38-1.17 (m, 19H); 0.88-0.82 (m, 6H).

Representative Procedure D: N-alkylation of Heptadecan-9-yl 8-((2-hydroxyethyl)amino)octanoate, 6

D1. Compound 7: 3-Butylnonyl 8-((8-(heptadecan-9-yloxy)-8-oxooctyl)(2-hydroxyethyl)amino)octanoate (86-g-nBu)

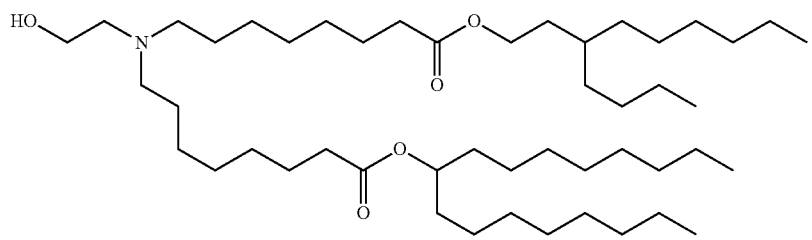

Chemical Formula: $C_{48}H_{95}NO_5$
Molecular Weight: 766.3

In a 500 mL round bottom flask connected with condenser, heptadecan-9-yl 8-((2-hydroxyethyl)amino)octanoate 6 (601 mg, 1.36 mmol), 3-butylnonyl 8-bromooctanoate 5a (606 mg, 1.49 mmol), potassium carbonate (676 mg, 4.9 mmol) and potassium iodide (248.4 mg, 1.49 mmol) were mixed in cyclopentylmethyl ether (30 mL) and acetonitrile (30 mL), and the reaction mixture was heated to 85° C. for 18 h. MS showed clean conversion, and the mixture was cooled to room temperature and diluted with hexanes. The mixture was filtered through pad of Celite. After washing with hexanes, the filtrate was concentrated to give brown oil which was purified by flash chromatography ($SiO_2$:hexane/diethyl ether 0-100%) to afford 7 as a colorless oil (588 mg. 56%). HPLC/ELSD: RT=7.07 min. MS (CI): m/z (MH+) 766.7 for $C_{48}H_{95}NO_5$. $^1$H NMR (300 MHz, $CDCl_3$) δ: ppm 4.85 (quint., 1H, J=6.1 Hz); 4.07 (t, 2H, J=6.9 Hz); 3.50 (t, 2H, J=5.5 Hz); 2.98 (bs, 1H); 2.55 (t, 2H, J=5.2 Hz); 2.41 (t, 4H, J=7.4 Hz); 2.26 (t, 4H, J=7.4 Hz); 1.65-1.48 (m, 19H); 1.26 (br. m, 48H); 0.88-0.84 (m, 12H).

D2. Compound 12: Heptadecan-9-yl 8-((2-hydroxyethyl)(8-((3-isopropylnonyl)oxy)-8-oxooctyl)amino)octanoate (86-g-iPr)

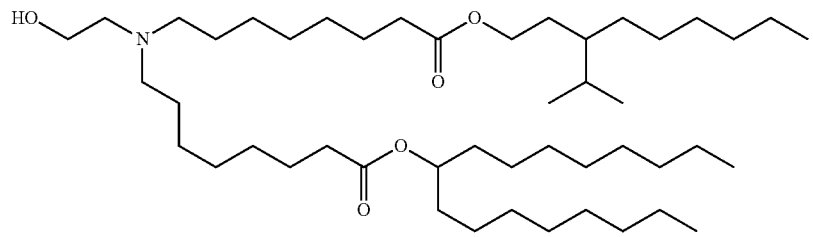

Chemical Formula: $C_{47}H_{93}NO_5$
Molecular Weight: 752.3

Same as the procedure D1 but using 3-Isopropylnonyl 8-bromooctanoate, 5b. Yield=258 mg (50%). HPLC/ELSD: RT=6.98 min. MS (CI): m/z (MH+) 752.6 for $C_{47}H_{93}NO_5$. $^1$H NMR (300 MHz, $CDCl_3$) δ: ppm 4.85 (quint., 1H, J=6.1 Hz); 4.07 (m, 2H); 3.50 (t, 2H, J=5.2 Hz); 3.01 (bs, 1H); 2.55 (t, 2H, J=5.2 Hz); 2.41 (t, 4H, J=7.4 Hz); 2.26 (dd, 4H, J=7.6, 2.7 Hz); 1.65-1.48 (m, 14H); 1.26 (br. m, 48H); 0.88-0.84 (m, 15H).

D3. Compound 13: Heptadecan-9-yl 8-((2-hydroxyethyl)(8-oxo-8-((3-propylnonyl)oxy)octyl)amino)octanoate (86-g-nPr)

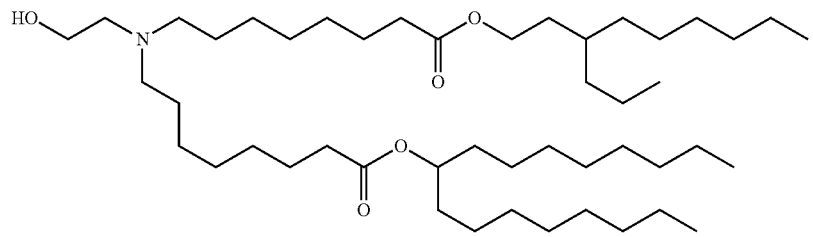

Chemical Formula: $C_{47}H_{93}NO_5$
Molecular Weight: 752.3

Same as the procedure D1 but using 3-Propylnonyl 8-bromooctanoat, 5c. Yield=510 mg (68%). HPLC/ELSD: RT=7.01 min. MS (CI): m/z (MH+) 752.6 for $C_{47}H_{93}NO_5$. $^1$H NMR (300 MHz, $CDCl_3$) δ: ppm 4.85 (quint., 1H, J=6.3 Hz); 4.07 (t, 2H, J=7.1 Hz); 3.50 (t, 2H, J=5.5 Hz); 2.98 (bs, 1H); 2.55 (t, 2H, J=5.2 Hz); 2.41 (t, 4H, J=7.4 Hz); 2.26 (t, 4H, J=7.4 Hz); 1.65-1.48 (m, 17H); 1.26 (br. m, 48H); 0.88-0.84 (m, 12H).
Synthetic Scheme for Preparation of Compound 8
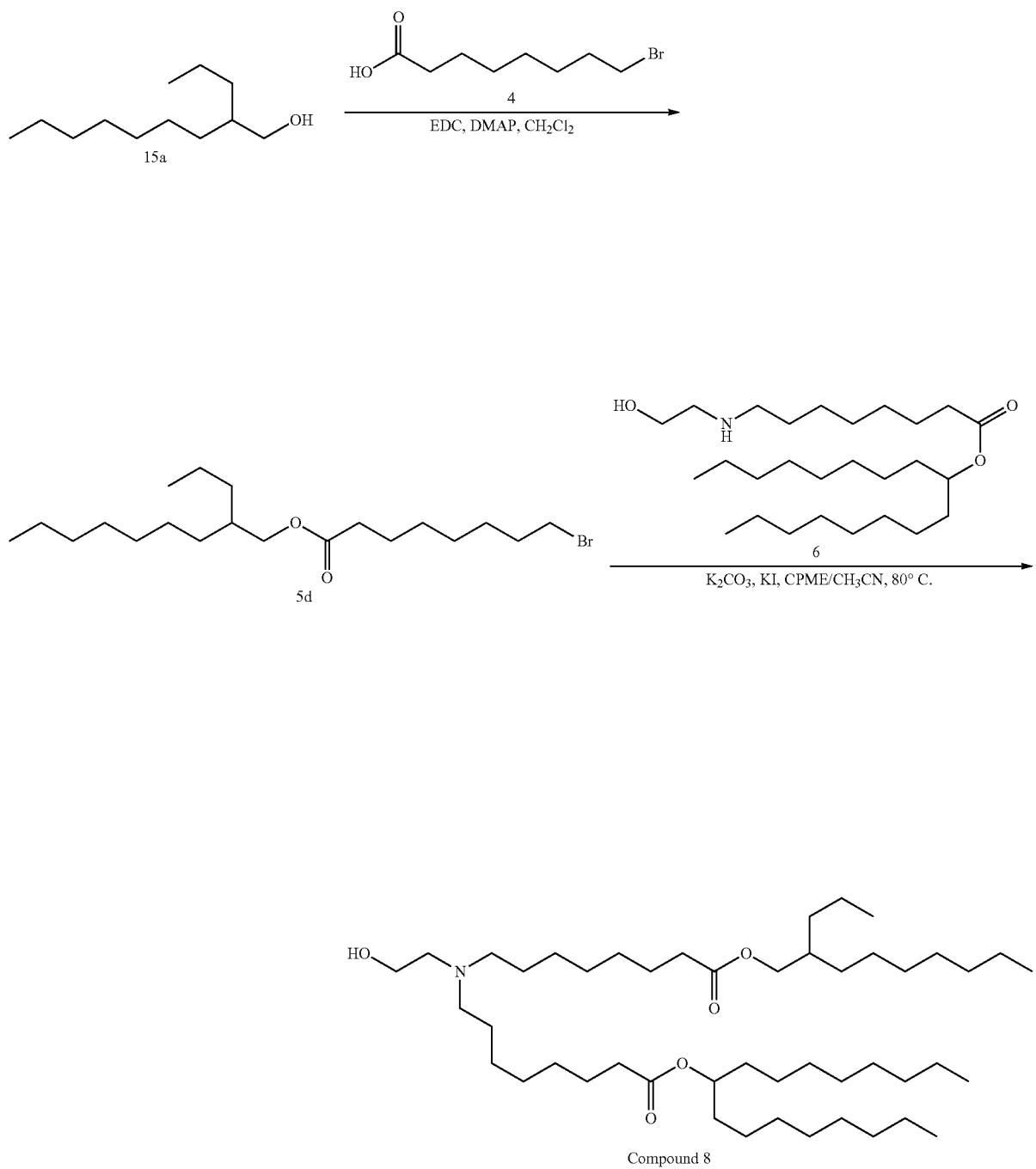

C4. Compound 5d: 2-Propylnonyl 8-bromooctanoate

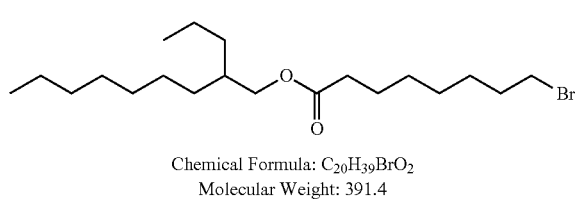 [SMILES: CCCCCCCC(CCC)COC(=O)CCCCCCCBr]

Chemical Formula: $C_{20}H_{39}BrO_2$
Molecular Weight: 391.4

Same as procedure C$_1$ but using 2-propylnonan-1-ol 15a. Yield=1.67 g (79%). $^1$H NMR (300 MHz, CDCl$_3$): δ ppm 3.96 (d, 2H, J=5.8 Hz); 3.38 (t, 2H, J=5.5 Hz); 2.27 (t, 2H, J=7.4 Hz); 1.88-1.79 (m, 2H); 1.70-1.42 (m, 6H); 1.38-1.17 (m, 19H); 0.88-0.82 (m, 6H).

D4. Compound 8: Heptadecan-9-yl 8-((2-hydroxyethyl)(8-oxo-8-((2-propylnonyl)oxy)octyl amino)octanoate (86-b-nPr)

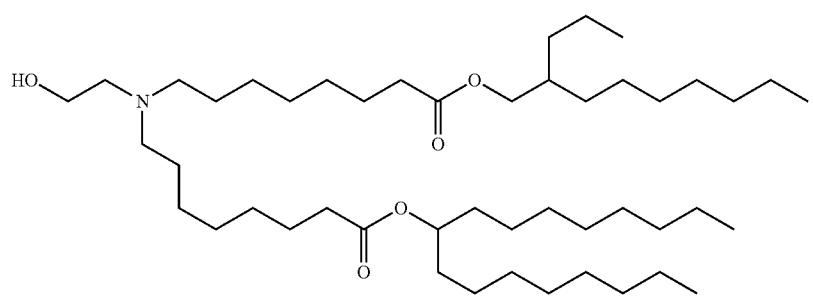

Chemical Formula: $C_{47}H_{93}NO_5$
Molecular Weight: 752.3

Same as procedure D1 but using 2-Propylnonyl 8-bromooctanoate, 5d. Yield=355 mg (68%). HPLC/ELSD: RT=7.0 min. MS (CI): m/z (MH$^+$) 752.6 for $C_{47}H_{93}NO_5$. $^1$H NMR (300 MHz, CDCl$_3$) δ: ppm 4.85 (quint., 1H, J=6.3 Hz); 3.95 (d, 2H, J=5.8 Hz); 3.50 (t, 2H, J=5.5 Hz); 3.02 (bs, 1H); 2.55 (t, 2H, J=5.5 Hz); 2.41 (t, 4H, J=7.7 Hz); 2.26 (dd, 4H, J=13.9, 6.6 Hz); 1.65-1.48 (m, 17H); 1.26 (br. m, 48H); 0.88-0.84 (m, 12H).

Synthesis of Intermediates

Intermediate AA: Ethyl 3-propylhex-2-enoate

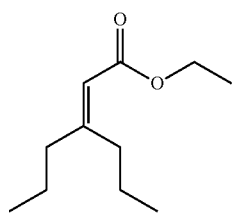

Chemical Formula: $C_{11}H_{20}O_2$
Molecular Weight: 184.28

Triethyl phosphonoacetate (11.3 mL, 56.9 mmol) was added dropwise over 20 minutes to a suspension of sodium hydride (2.28 g, 56.9 mmol) in THF (17 mL) and the mixture was stirred at room temperature until gas evolution ceased (approximately 30 min). The reaction mixture was chilled to 0° C. and 4-heptanone (6.12 mL, 43.8 mmol) was added in portions. The reaction was gradually warmed to room temperature and allowed to stir under reflux for 24 h. The reaction was cooled to room temperature prior to being quenched with saturated aqueous sodium bicarbonate. The aqueous phase was extracted with diethyl ether, and the organic extracts were washed with brine, dried (MgSO$_4$), and concentrated. The crude material was purified by silica gel chromatography (0-20% EtOAc:hexanes) to afford ethyl 3-propylhex-2-enoate (8.07 g, 43.8 mmol, 100%) as a clear oil and as a mixture of regioisomers. $^1$H NMR (300 MHz, CDCl$_3$) as a mixture of regioisomers δ: ppm 5.63 (s, 1H); 5.38-5.25 (m, 0.74H); 4.19-4.07 (m, 3.40H); 3.02 (s, 0.81H); 2.96 (s, 0.59H); 2.57 (ddd, 2H, J=6.0, 6.0, 3.0 Hz); 2.16-1.98 (m, 4.87H); 1.57-1.35 (m, 6.10H); 1.34-1.21 (m, 7.59H); 1.01-0.82 (m, 12.9H).

Intermediate AB: Ethyl 3-propylhexanoate

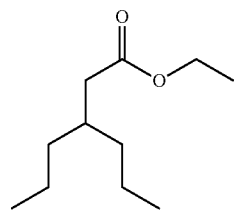

Chemical Formula: $C_{11}H_{22}O_2$
Molecular Weight: 186.30

A steel Parr reactor equipped with a stir bar was charged with ethyl 3-propylhex-2-enoate (8.07 g, 43.8 mmol) in ethanol (44 mL). Palladium hydroxide on carbon (922 mg, 6.57 mmol) was added and the vessel was sealed, evacuated, refilled with $H_2$ gas (3×), and the pressure was set to 200 psi. The reaction was stirred at 500 rpm, under 200 psi $H_2$ gas, at room temperature for 2 h. The vessel was then evacuated, refilled with $N_2$ gas, and opened. The crude reaction mixture was filtered through a Celite pad. The Celite pad was washed with EtOH and the crude material was concentrated to give ethyl 3-propylhexanoate (6.55 g, 35.2 mmol, 80%) as a clear oil. The compound was carried onto the next step without further purification. $^1$H NMR (300 MHz, $CDCl_3$) δ: ppm 4.12 (q, 2H, J=6.0 Hz); 2.22 (d, 2H, J=9.0 Hz); 1.95-1.81 (m, 1H); 1.38-1.18 (m, 11H); 0.89 (br. t, 6H, J=6.0 Hz).

Intermediate AC: 3-Propylhexan-1-ol

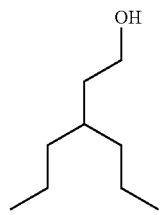

Chemical Formula: $C_9H_{20}O$
Molecular Weight: 144.26

To a mixture of lithium aluminum hydride (1.60 g, 42.2 mmol) in dry ether (42 mL) under $N_2$ at 0° C., was added dropwise ethyl 3-propylhexanoate (6.55 g, 35.2 mmol) in dry ether (28 mL). The mixture was stirred at room temperature for 2.5 h prior to being cooled to 0° C. Water (1 mL per g of $LiAlH_4$) was added to the solution dropwise, followed by the slow addition of 15% sodium hydroxide (1 mL per g of $LiAlH_4$) and water (3 mL per g of $LiAlH_4$). The solution was stirred for a few minutes at room temperature and filtered through a Celite pad. The Celite pad was washed with diethyl ether and the filtrate was concentrated. The crude material was purified by silica gel chromatography (0-40% EtOAc:hexanes) to afford 3-propylhexan-1-ol (4.82 g, 33.4 mmol, 95%) as a clear oil. $^1$H NMR (300 MHz, $CDCl_3$) δ: ppm 3.67 (t, 2H, J=6.0 Hz); 1.57-1.39 (m, 3H); 1.37-1.18 (m, 9H); 0.88 (t, 6H, J=6.0 Hz).

Intermediate AD: Ethyl 3-butylhept-2-enoate

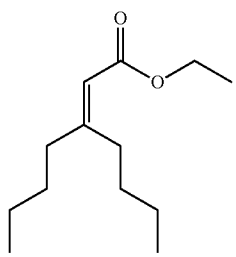

Chemical Formula: $C_{13}H_{24}O_2$
Molecular Weight: 212.33

Triethyl phosphonoacetate (9.07 mL, 45.7 mmol) was added dropwise over 20 minutes to a suspension of sodium hydride (1.83 g, 45.7 mmol) in THF (14 mL) and the mixture was stirred at room temperature until gas evolution ceased (approximately 30 min). The reaction mixture was chilled to 0° C. and 5-nonanone (6.05 mL, 35.2 mmol) was added in portions. The reaction was gradually warmed to room temperature and allowed to stir under reflux for 24 h. The reaction was cooled to room temperature prior to being quenched with saturated aqueous sodium bicarbonate. The aqueous phase was extracted with diethyl ether, and the organic extracts were washed with brine, dried ($MgSO_4$), and concentrated. The crude material was purified by silica gel chromatography (0-20% EtOAc:hexanes) to afford ethyl 3-butylhept-2-enoate (5.27 g, 24.8 mmol, 71%) as a clear oil. $^1$H NMR (300 MHz, $CDCl_3$) δ: ppm 5.62 (s, 1H); 4.14 (q, 2H, J=6.0 Hz); 2.59 (t, 2H, J=6.0 Hz); 2.14 (t, 2H, J=6.0 Hz); 1.50-1.23 (m, 11H); 0.99-0.82 (m, 6H).

Intermediate AE: Ethyl 3-butylheptanoate

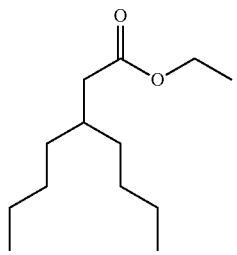

Chemical Formula: $C_{13}H_{26}O_2$
Molecular Weight: 214.35

A steel Parr reactor equipped with a stir bar was charged with ethyl 3-butylhept-2-enoate (10.5 g, 49.5 mmol) in ethanol (50 mL). Palladium hydroxide on carbon (1.04 g, 7.42 mmol) was added and the vessel was sealed, evacuated, refilled with $H_2$ gas (3×), and the pressure was set to 200 psi. The reaction was stirred at 500 rpm, under 200 psi $H_2$ gas, at room temperature for 2 h. The vessel was then evacuated, refilled with $N_2$ gas, and opened. The crude reaction mixture was filtered through a Celite pad. The Celite pad was washed with EtOH and the crude material was concentrated to give ethyl 3-butylheptanoate (9.69 g, 45.2 mmol, 91%) as a clear oil. The compound was carried onto the next step without further purification. $^1$H NMR (300 MHz, $CDCl_3$) δ: ppm 4.12 (q, 2H, J=9.0 Hz); 2.22 (d, 2H, J=6.0 Hz); 1.90-1.76 (m, 1H); 1.38-1.19 (m, 15H); 0.88 (br. t, 6H, J=6.0 Hz).

Intermediate AF: 3-Butylheptan-1-ol

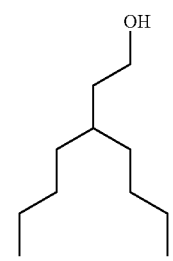

Chemical Formula: $C_{11}H_{24}O$
Molecular Weight: 172.31

To a mixture of lithium aluminum hydride (850 mg, 22.4 mmol) in dry ether (23 mL) under $N_2$ at 0° C., was added dropwise ethyl 3-butylheptanoate (4.00 g, 18.7 mmol) in dry ether (15 mL). The mixture was stirred at room temperature for 2.5 h prior to being cooled to 0° C. Water (1 mL per g of $LiAlH_4$) was added to the solution dropwise, followed by the slow addition of 15% sodium hydroxide (1 mL per g of $LiAlH_4$) and water (3 mL per g of $LiAlH_4$). The solution was stirred for a few minutes at room temperature and filtered through a Celite pad. The Celite pad was washed with diethyl ether and the filtrate was concentrated. The crude material was purified by silica gel chromatography (0-40% EtOAc:hexanes) to afford 3-butylheptan-1-ol (3.19 g, 18.5 mmol, 99%) as a clear oil. $^1$H NMR (300 MHz, $CDCl_3$) δ: ppm 3.66 (t, 2H, J=6.0 Hz); 1.53 (q, 2H, J=6.0 Hz); 1.46-1.36 (m, 1H); 1.35-1.21 (m, 12H); 1.18 (br. s, 1H); 0.89 (br. t, 6H, J=6.0 Hz).

Intermediate AG: Ethyl 3-pentyloct-2-enoate

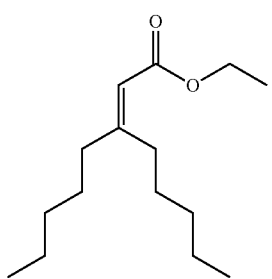

Chemical Formula: $C_{15}H_{28}O_2$
Molecular Weight: 240.39

Triethyl phosphonoacetate (10.6 mL, 53.4 mmol) was added dropwise over 20 minutes to a suspension of sodium hydride (2.13 g, 53.4 mmol) in THF (16 mL) and the mixture was stirred at room temperature until gas evolution ceased (approximately 30 min). The reaction mixture was chilled to 0° C. and 6-undecanone (8.42 mL, 41.1 mmol) was added in portions. The reaction was gradually warmed to room temperature and allowed to stir under reflux for 60 h. The reaction was cooled to room temperature prior to being quenched with saturated aqueous sodium bicarbonate. The aqueous phase was extracted with diethyl ether, and the organic extracts were washed with brine, dried ($MgSO_4$), and concentrated. The crude material was purified by silica gel chromatography (0-20% EtOAc:hexanes) to afford ethyl 3-pentyloct-2-enoate (8.76 g, 36.5 mmol, 89%) as a clear oil. $^1$H NMR (300 MHz, $CDCl_3$) δ: ppm 5.61 (s, 1H); 4.14 (q, 2H, J=6.0 Hz); 2.58 (ddd, 2H, J=9.0, 9.0, 6.0 Hz); 2.13 (ddd, 2H, J=6.0, 6.0, 3.0 Hz); 1.52-1.38 (m, 3H); 1.38-1.23 (m, 12H); 0.93-0.86 (m, 6H).

Intermediate AH: Ethyl 3-pentyloctanoate

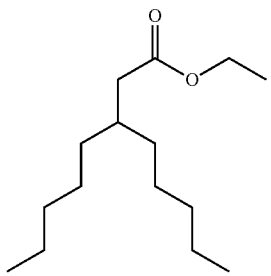

Chemical Formula: $C_{15}H_{30}O_2$
Molecular Weight: 242.40

A steel Parr reactor equipped with a stir bar was charged with ethyl 3-pentyloct-2-enoate (8.76 g, 36.5 mmol) in ethanol (37 mL). Palladium hydroxide on carbon (768 mg, 5.47 mmol) was added and the vessel was sealed, evacuated, refilled with $H_2$ gas (3×), and the pressure was set to 200 psi. The reaction was stirred at 500 rpm, under 200 psi $H_2$ gas, at room temperature for 2 h. The vessel was then evacuated, refilled with $N_2$ gas, and opened. The crude reaction mixture was filtered through a Celite pad. The Celite pad was washed with EtOH and the crude material was concentrated to give ethyl 3-pentyloctanoate (8.45 g, 34.9 mmol, 96%) as a clear oil. The compound was carried onto the next step without further purification. $^1$H NMR (300 MHz, $CDCl_3$) δ: ppm 4.12 (q, 2H, J=6.0 Hz); 2.22 (d, 2H, J=6.0 Hz); 1.92-1.77 (br. m, 1H); 1.37-1.19 (m, 19H); 0.88 (t, 6H, J=6.0 Hz).

Intermediate AI: 3-Pentyloctan-1-ol

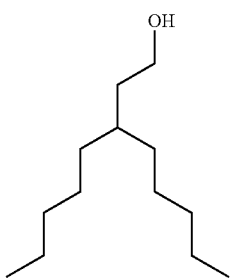

Chemical Formula: $C_{13}H_{28}O$
Molecular Weight: 200.37

To a mixture of lithium aluminum hydride (1.59 g, 41.8 mmol) in dry ether (42 mL) under $N_2$ at 0° C., was added dropwise ethyl 3-pentyloctanoate (8.45 g, 34.9 mmol) in dry ether (28 mL). The mixture was stirred at room temperature for 2.5 h prior to being cooled to 0° C. Water (1 mL per g of LiAlH$_4$) was added to the solution dropwise, followed by the slow addition of 15% sodium hydroxide (1 mL per g of LiAlH$_4$) and water (3 mL per g of LiAlH$_4$). The solution was stirred for a few minutes at room temperature and filtered through a Celite pad. The Celite pad was washed with diethyl ether and the filtrate was concentrated. The crude material was purified by silica gel chromatography (0-40% EtOAc:hexanes) to afford 3-pentyloctan-1-ol (6.98 g, 34.9 mmol, 100%) as a clear oil. $^1$H NMR (300 MHz, CDCl$_3$) δ: ppm 3.66 (t, 2H, J=6.0 Hz); 1.53 (q, 2H, J=6.0 Hz); 1.47-1.37 (br. s, 1H); 1.36-1.15 (m, 17H); 0.88 (t, 6H, J=6.0 Hz).

Intermediate AJ: 3-Pentyloctanal

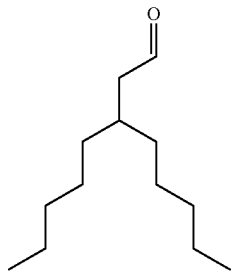

Chemical Formula: C$_{13}$H$_{26}$O
Molecular Weight: 198.35

To a stirred suspension of pyridinium chlorochromate (9.02 g, 41.8 mmol) and silica gel (9.02 g, 1 g/g of pyridinium chlorochromate) in dichloromethane (90 mL) under a N$_2$ atmosphere was added 3-pentyloctan-1-ol (6.98 g, 34.9 mmol). The suspension was stirred at room temperature for 1 h. The reaction was then filtered through a Celite pad, the Celite pad was washed with dichloromethane, and the filtrate was concentrated. The crude material was purified by silica gel chromatography (0-20% EtOAc:hexanes) to afford 3-pentyloctanal (4.66 g, 23.5 mmol, 67%) as a clear oil. $^1$H NMR (300 MHz, CDCl$_3$) δ: ppm 9.76 (t, 1H, J=3.0 Hz); 2.33 (dd, 2H, J=6.0, 3.0 Hz); 2.01-1.86 (br. m, 1H); 1.40-1.19 (m, 16H); 0.88 (t, 6H, J=6.0 Hz).

Intermediate AK: 6-Allylundecane

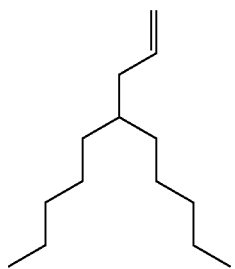

Chemical Formula: C$_{14}$H$_{28}$
Molecular Weight: 196.38

To a suspension of methyltriphenylphosphonium bromide (4.68 g, 13.1 mmol) in dry ether (190 mL) under a N$_2$ was added potassium tert-butoxide (1.47 g, 13.1 mmol) in one portion. The mixture was stirred at room temperature for 15 minutes, prior to the dropwise addition of 3-pentyloctanal (2.00 g, 10.1 mmol) in dry ether (26 mL) over 15 min. The resulting mixture was allowed to stir for 90 min at room temperature. The reaction mixture was diluted with ice water, the layers were separated, and the organic layer was extracted with ether. The combined organics were dried (MgSO$_4$), filtered, and concentrated. The crude material was purified by silica gel chromatography (0-10% EtOAc: hexanes) to afford 6-allylundecane (1.65 g, 8.38 mmol, 83%) as a clear oil. $^1$H NMR (300 MHz, CDCl$_3$) δ: ppm 5.77 (dddd, 1H, J=15.0, 12.0, 9.0, 9.0 Hz); 5.03-4.94 (m, 2H); 2.02 (ddd, 2H, J=9.0, 6.0, 6.0 Hz); 1.43-1.16 (m, 17H); 0.88 (d, 6H, J=6.0 Hz).

Intermediate AL: 4-Pentylnonan-1-ol

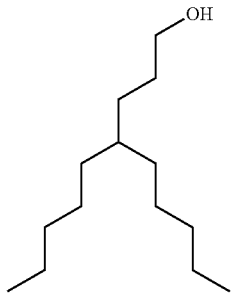

Chemical Formula: C$_{14}$H$_{30}$O
Molecular Weight: 214.39

To a stirred solution of sodium borohydride (131 mg, 3.46 mmol) in dry diglyme (3.6 mL) under a N$_2$ atmosphere was added a solution of 6-allylundecane (2.26 g, 11.5 mmol) in dry diglyme (2.3 mL). Next, a solution of boron trifluoride etherate (569 µL, 4.61 mmol) in 1.2 mL of dry diglyme was added over 15 min at room temperature. The resulting mixture was stirred for 1 hour prior to the dropwise addition of water (1.2 mL). When gas evolution ceased, 2.3 mL of 3M NaOH was added at room temperature, followed by the dropwise addition of 2.3 mL of 30% H$_2$O$_2$ at 40° C. After 1 hour of stirring at 40° C., the reaction was poured into 10 mL of water. The reaction vessel was washed with additional water. The combined water solutions were extracted with ether (2×). Combined ethereal extracts were washed with water (×5). Ethereal extracts were dried (MgSO$_4$), filtered, and concentrated. The crude residue was purified by silica gel chromatography (0-40% EtOAc:hexanes) to afford 4-pentylnonan-1-ol (1.88 g, 8.77 mmol, 76%) as a clear oil. $^1$H NMR (300 MHz, CDCl$_3$) δ: ppm 3.62 (t, 2H, J=6.0 Hz); 1.60-1.48 (m, 2H); 1.37-1.19 (m, 20H); 0.88 (t, 6H, J=6.0 Hz).

Intermediate AM: 3-Propylhexyl 8-bromooctanoate

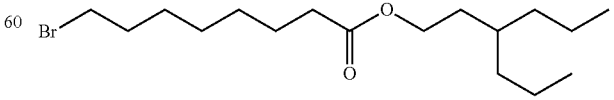

Chemical Formula: C$_{17}$H$_{33}$BrO$_2$
Molecular Weight: 349.35

To a solution of 3-propylhexan-1-ol (4.82 g, 33.4 mmol), 8-bromooctanoic acid (8.94 g, 40.1 mmol), and DMAP (816 mg, 6.68 mmol) in methylene chloride (58 mL) at 0° C. was added EDCI (9.60 g, 50.1 mmol) and the reaction mixture stirred at room temperature overnight. The reaction mixture was then cooled to 0° C. and a solution of 10% hydrochloric acid (180 mL) was added slowly over 20 minutes. The layers were separated, and the organic layer was concentrated in vacuum to give a crude oil. The oil was dissolved in hexane (180 mL) and washed with a mixture of acetonitrile (180 mL) and 5% sodium bicarbonate (180 mL). The hexane layer was separated, dried (MgSO$_4$), and filtered. The solvent was removed under vacuum to give 3-propylhexyl 8-bromooctanoate (10.9 g, 31.2 mmol, 93%) as a clear oil. The compound was carried onto the next step without further purification. $^1$H NMR (300 MHz, CDCl$_3$) δ: ppm 4.08 (t, 2H, J=6.0 Hz); 3.40 (t, 2H, J=6.0 Hz); 2.28 (t, 2H, J=6.0 Hz); 1.85 (pent., 2H, J=6.0 Hz); 1.68-1.51 (m, 4H); 1.49-1.18 (m, 15H); 0.88 (t, 6H, J=6.0 Hz).

Intermediate AN: 3-Butylheptyl 8-bromooctanoate

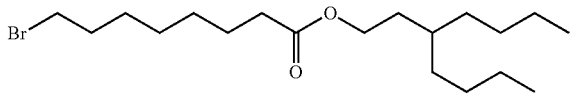

Chemical Formula: C$_{19}$H$_{37}$BrO$_2$
Molecular Weight: 377.41

To a solution of 3-butylheptan-1-ol (3.19 g, 18.5 mmol), 8-bromooctanoic acid (4.96 g, 22.2 mmol), and DMAP (453 mg, 3.71 mmol) in methylene chloride (32 mL) at 0° C. was added EDCI (5.33 g, 27.8 mmol) and the reaction mixture stirred at room temperature overnight. The reaction mixture was then cooled to 0° C. and a solution of 10% hydrochloric acid (150 mL) was added slowly over 20 minutes. The layers were separated, and the organic layer was concentrated in vacuum to give a crude oil. The oil was dissolved in hexane (150 mL) and washed with a mixture of acetonitrile (150 mL) and 5% sodium bicarbonate (150 mL). The hexane layer was separated, dried (MgSO$_4$), and filtered. The solvent was removed under vacuum to give 3-butylheptyl 8-bromooctanoate (6.90 g, 18.3 mmol, 99%) as a clear oil. The compound was carried onto the next step without further purification. $^1$H NMR (300 MHz, CDCl$_3$) δ: ppm 4.08 (t, 2H, J=6.0 Hz); 3.40 (t, 2H, J=6.0 Hz); 2.29 (t, 2H, J=6.0 Hz); 1.85 (pent., 2H, J=6.0 Hz); 1.69-1.52 (m, 4H); 1.49-1.20 (m, 19H); 0.89 (br. t, 6H, J=6.0 Hz).

Intermediate AO: 3-Pentyloctyl 8-bromooctanoate

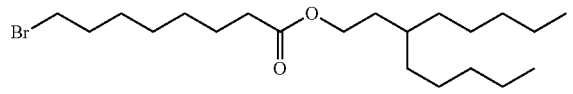

Chemical Formula: C$_{21}$H$_{41}$BrO$_2$
Molecular Weight: 405.46

To a solution of 3-pentyloctan-1-ol (2.00 g, 9.98 mmol), 8-bromooctanoic acid (2.67 g, 12.0 mmol), and DMAP (244 mg, 2.00 mmol) in methylene chloride (18 mL) at 0° C. was added EDCI (2.87 g, 15.0 mmol) and the reaction mixture stirred at room temperature overnight. The reaction mixture was then cooled to 0° C. and a solution of 10% hydrochloric acid (70 mL) was added slowly over 20 minutes. The layers were separated, and the organic layer was concentrated in vacuum to give a crude oil. The oil was dissolved in hexane (70 mL) and washed with a mixture of acetonitrile (70 mL) and 5% sodium bicarbonate (70 mL). The hexane layer was separated, dried (MgSO$_4$), and filtered. The solvent was removed under vacuum to give 3-pentyloctyl 8-bromooctanoate (3.94 g, 9.72 mmol, 97%) as a clear oil. The compound was carried onto the next step without further purification. $^1$H NMR (300 MHz, CDCl$_3$) δ: ppm 4.08 (t, 2H, J=6.0 Hz); 3.40 (t, 2H, J=6.0 Hz); 3.29 (t, 2H, J=6.0 Hz); 1.85 (pent., 2H, J=6.0 Hz); 1.68-1.52 (m, 4H); 1.49-1.19 (m, 23H); 0.88 (t, 6H, J=6.0 Hz).

Intermediate AP: 4-Pentylnonyl-8-bromooctanoate

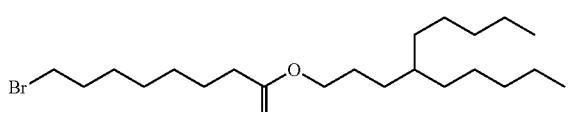

Chemical Formula: C$_{22}$H$_{43}$BrO$_2$
Molecular Weight: 419.49

To a solution of 4-pentylnonan-1-ol (1.88 g, 8.77 mmol), 8-bromooctanoic acid (2.35 g, 10.5 mmol), and DMAP (214 mg, 1.75 mmol) in methylene chloride (15 mL) at 0° C. was added EDCI (2.52 g, 13.2 mmol) and the reaction mixture stirred at room temperature overnight. The reaction mixture was then cooled to 0° C. and a solution of 10% hydrochloric acid (60 mL) was added slowly over 20 minutes. The layers were separated, and the organic layer was concentrated in vacuum to give a crude oil. The oil was dissolved in hexane (60 mL) and washed with a mixture of acetonitrile (60 mL) and 5% sodium bicarbonate (60 mL). The hexane layer was separated, dried (MgSO$_4$), and filtered. The solvent was removed under vacuum to give 4-pentylnonyl-8-bromooctanoate (3.68 g, 8.77 mmol, 100%) as a clear oil. The compound was carried onto the next step without further purification. $^1$H NMR (300 MHz, CDCl$_3$) δ: ppm 4.04 (t, 2H, J=6.0 Hz); 3.40 (t, 2H, J=6.0 Hz); 2.29 (t, 2H, J=6.0 Hz); 1.85 (pent., 2H, J=6.0 Hz); 1.70-1.52 (m, 4H); 1.50-1.18 (m, 25H); 0.88 (t, 6H, J=6.0 Hz).

Intermediate AQ: Pentadecan-8-yl 8-bromooctanoate

Chemical Formula: C$_{23}$H$_{45}$BrO$_2$
Molecular Weight: 433.52

To a solution of 8-bromooctanoic acid (1.98 g, 8.87 mmol) in dichloromethane (30 mL) were added 1-ethyl-3-(3-dimethylaminopropyl)carbodiimide hydrochloride (2.13 g, 11.1 mmol), 4-(dimethylamino)pyridine (0.217 g, 1.77 mmol), and pentadecan-8-ol (2.03 g, 8.87 mmol). The reaction was allowed to stir at room temperature for 18 hours. The reaction mixture was cooled to 0° C. and a solution of 10% hydrochloric acid was added slowly. The organic layer was separated and evaporated under vacuum. The residue was dissolved in hexanes and washed with a 1:1 mixture of acetonitrile and saturated $NaHCO_3$(aq.). The hexane layer was separated, died over $MgSO_4$, then filtered and evaporated under vacuum. The residue was purified by silica gel chromatography (0-10% ethyl acetate in hexanes) to obtain a mixture of ~13.2:1 pentadecan-8-yl 8-bromooctanoate and pentadecan-8-yl 8-chlorooctanoate (3.19 g, 83.1%) as a colorless liquid. $^1$H NMR (300 MHz, $CDCl_3$) δ: ppm 4.89 (p, 1H); 3.55 (t, 0.14H); 3.42 (t, 1.86H); 2.31 (t, 2H); 1.88 (p, 2H); 1.72-1.59 (m, 2H); 1.59-1.42 (m, 6H); 1.42-1.18 (m, 24H); 0.90 (t, 6H).

Intermediate AR: Tridecan-7-yl 8-bromooctanoate

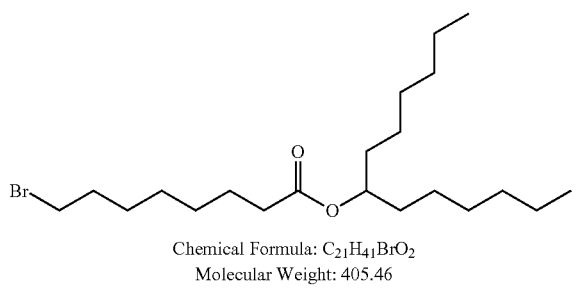 [SMILES: CCCCCCC(CCCCCC)OC(=O)CCCCCCCBr]

Chemical Formula: $C_{21}H_{41}BrO_2$
Molecular Weight: 405.46

To a solution of 8-bromooctanoic acid (1.96 g, 8.76 mmol) in dichloromethane (30 mL) were added 1-ethyl-3-(3-dimethylaminopropyl)carbodiimide hydrochloride (2.10 g, 10.9 mmol), 4-(dimethylamino)pyridine (0.234 g, 1.92 mmol), and tridecan-7-ol (1.75 g, 8.73 mmol). The reaction was allowed to stir at room temperature for 18 hours. The reaction was diluted with dichloromethane and extracted with saturated $NaHCO_3$(aq.). The organic layer was separated and washed with brine, died over $MgSO_4$, then filtered and evaporated under vacuum. The residue was purified by silica gel chromatography (0-10% ethyl acetate in hexanes) to obtain a mixture of ~12.3:1 tridecan-7-yl 8-bromooctanoate and tridecan-7-yl 8-chlorooctanoate (2.10 g, 59.4%) as a colorless liquid. $^1$H NMR (300 MHz, $CDCl_3$) δ: ppm 4.89 (p, 1H); 3.55 (t, 0.15H); 3.42 (t, 1.85H); 2.31 (t, 2H); 1.88 (p, 2H); 1.72-1.60 (m, 2H); 1.60-1.42 (m, 6H); 1.42-1.19 (m, 20H); 0.90 (t, 6H).

Intermediate AS: Undecan-6-yl 8-bromooctanoate

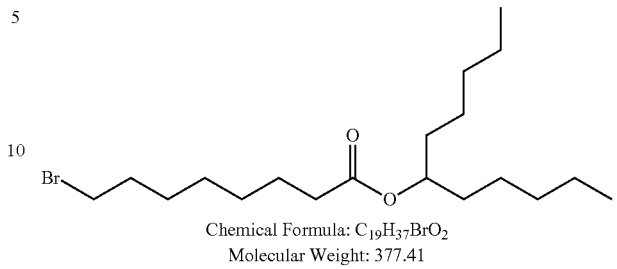

Chemical Formula: $C_{19}H_{37}BrO_2$
Molecular Weight: 377.41

To a solution of 8-bromooctanoic acid (4.00 g, 17.9 mmol) in dichloromethane (60 mL) were added 1-ethyl-3-(3-dimethylaminopropyl)carbodiimide hydrochloride (4.31 g, 22.5 mmol), 4-(dimethylamino)pyridine (0.438 g, 3.58 mmol), and 6-undecanol (3.09 g, 17.9 mmol). The reaction was allowed to stir at room temperature for 18 hours The reaction mixture was cooled to 0° C. and a solution of 10% hydrochloric acid was added slowly. The organic layer was separated and evaporated under vacuum. The residue was dissolved in hexanes and washed with a 1:1 mixture of acetonitrile and saturated $NaHCO_3$(aq.). The hexane layer was separated, died over $MgSO_4$, then filtered and evaporated under vacuum. The residue was purified by silica gel chromatography (0-10% ethyl acetate in hexanes) to obtain a mixture of ~19:1 undecan-6-yl 8-bromooctanoate and undecan-6-yl 8-chlorooctanoate (4.33 g, 64.01%) as a colorless liquid. $^1$H NMR (300 MHz, $CDCl_3$) δ: ppm 4.89 (p, 1H); 3.55 (t, 0.10H); 3.42 (t, 1.90H); 2.31 (t, 2H); 1.88 (p, 2H); 1.72-1.59 (m, 2H); 1.59-1.42 (m, 6H); 1.42-1.18 (m, 16H); 0.90 (t, 6H).

Intermediate AT: Nonan-5-yl 8-bromooctanoate

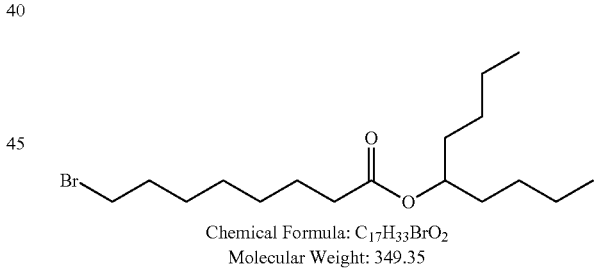

Chemical Formula: $C_{17}H_{33}BrO_2$
Molecular Weight: 349.35

To a solution of 8-bromooctanoic acid (4.00 g, 17.9 mmol) in dichloromethane (60 mL) were added 1-ethyl-3-(3-dimethylaminopropyl)carbodiimide hydrochloride (4.31 g, 22.5 mmol), 4-(dimethylamino)pyridine (0.438 g, 3.59 mmol), and 5-nonanol (2.59 g, 17.9 mmol). The reaction was allowed to stir at room temperature for 18 hours. The reaction mixture was cooled to 0° C. and a solution of 10% hydrochloric acid was added slowly. The organic layer was separated and evaporated under vacuum. The residue was dissolved in hexanes and washed with a 1:1 mixture of acetonitrile and saturated $NaHCO_3$(aq.). The hexane layer was separated, died over $MgSO_4$, then filtered and evaporated under vacuum. The residue was purified by silica gel chromatography (0-10% ethyl acetate in hexanes) to obtain a mixture of ~7:1 nonan-5-yl 8-bromooctanoate and nonan-5-yl 8-chlorooctanoate (5.23 g, 83.5%) as a colorless liquid.

$^1$H NMR (300 MHz, CDCl$_3$) δ: ppm 4.90 (p, 1H); 3.55 (t, 0.25H); 3.42 (t, 1.75H); 2.31 (t, 2H); 1.88 (p, 2H); 1.72-1.59 (m, 2H); 1.59-1.19 (m, 18H); 0.91 (t, 6H).

Intermediate AU: 3-Propylhexyl 8-((3-((tert-butoxycarbonyl)amino)propyl)amino)octanoate

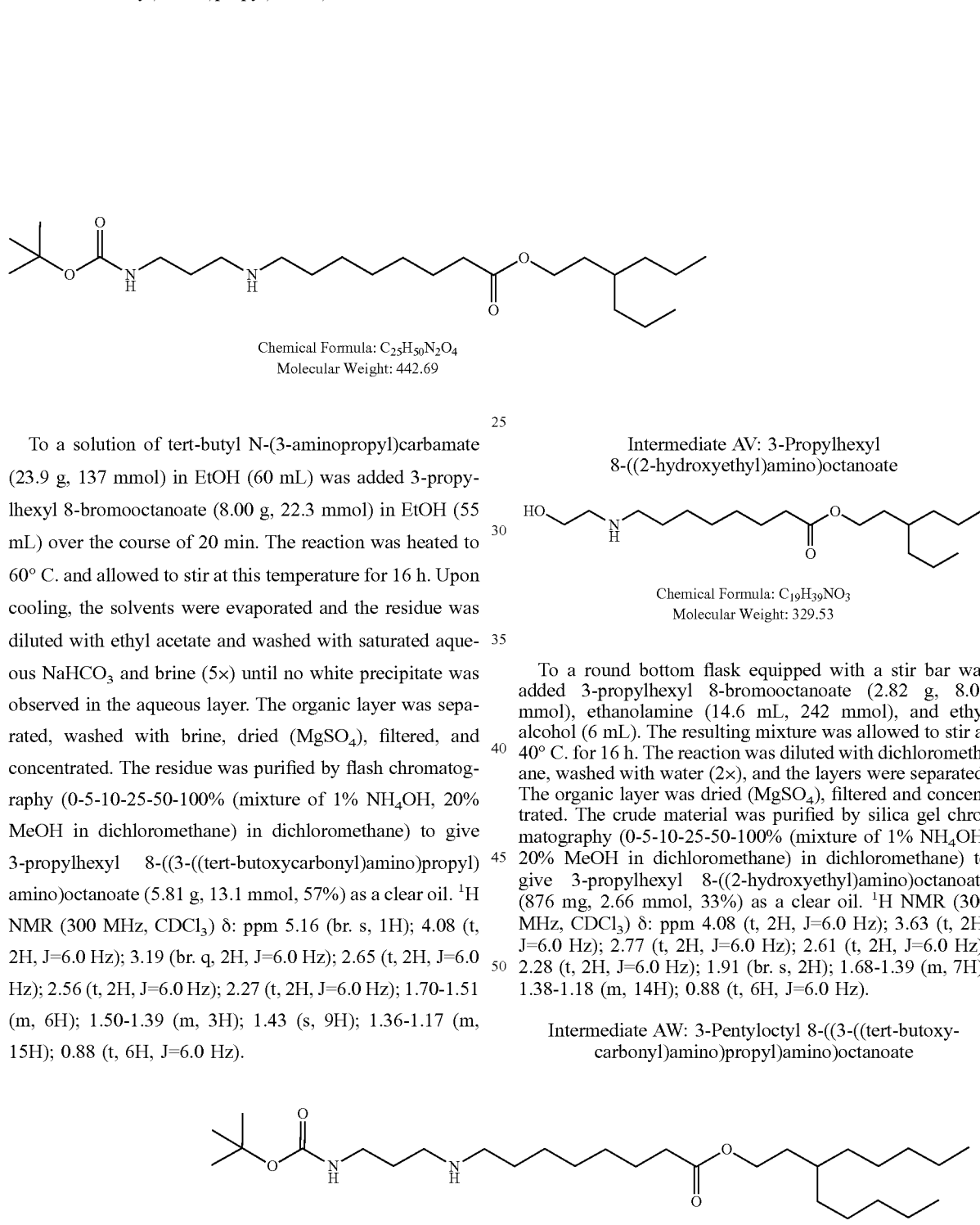

Chemical Formula: C$_{25}$H$_{50}$N$_2$O$_4$
Molecular Weight: 442.69

To a solution of tert-butyl N-(3-aminopropyl)carbamate (23.9 g, 137 mmol) in EtOH (60 mL) was added 3-propylhexyl 8-bromooctanoate (8.00 g, 22.3 mmol) in EtOH (55 mL) over the course of 20 min. The reaction was heated to 60° C. and allowed to stir at this temperature for 16 h. Upon cooling, the solvents were evaporated and the residue was diluted with ethyl acetate and washed with saturated aqueous NaHCO$_3$ and brine (5×) until no white precipitate was observed in the aqueous layer. The organic layer was separated, washed with brine, dried (MgSO$_4$), filtered, and concentrated. The residue was purified by flash chromatography (0-5-10-25-50-100% (mixture of 1% NH$_4$OH, 20% MeOH in dichloromethane) in dichloromethane) to give 3-propylhexyl 8-((3-((tert-butoxycarbonyl)amino)propyl)amino)octanoate (5.81 g, 13.1 mmol, 57%) as a clear oil. $^1$H NMR (300 MHz, CDCl$_3$) δ: ppm 5.16 (br. s, 1H); 4.08 (t, 2H, J=6.0 Hz); 3.19 (br. q, 2H, J=6.0 Hz); 2.65 (t, 2H, J=6.0 Hz); 2.56 (t, 2H, J=6.0 Hz); 2.27 (t, 2H, J=6.0 Hz); 1.70-1.51 (m, 6H); 1.50-1.39 (m, 3H); 1.43 (s, 9H); 1.36-1.17 (m, 15H); 0.88 (t, 6H, J=6.0 Hz).

Intermediate AV: 3-Propylhexyl 8-((2-hydroxyethyl)amino)octanoate

Chemical Formula: C$_{19}$H$_{39}$NO$_3$
Molecular Weight: 329.53

To a round bottom flask equipped with a stir bar was added 3-propylhexyl 8-bromooctanoate (2.82 g, 8.06 mmol), ethanolamine (14.6 mL, 242 mmol), and ethyl alcohol (6 mL). The resulting mixture was allowed to stir at 40° C. for 16 h. The reaction was diluted with dichloromethane, washed with water (2×), and the layers were separated. The organic layer was dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give 3-propylhexyl 8-((2-hydroxyethyl)amino)octanoate (876 mg, 2.66 mmol, 33%) as a clear oil. $^1$H NMR (300 MHz, CDCl$_3$) δ: ppm 4.08 (t, 2H, J=6.0 Hz); 3.63 (t, 2H, J=6.0 Hz); 2.77 (t, 2H, J=6.0 Hz); 2.61 (t, 2H, J=6.0 Hz); 2.28 (t, 2H, J=6.0 Hz); 1.91 (br. s, 2H); 1.68-1.39 (m, 7H); 1.38-1.18 (m, 14H); 0.88 (t, 6H, J=6.0 Hz).

Intermediate AW: 3-Pentyloctyl 8-((3-((tert-butoxycarbonyl)amino)propyl)amino)octanoate Chemical Formula: C$_{29}$H$_{58}$N$_2$O$_4$
Molecular Weight: 498.79

To a solution of tert-butyl N-(3-aminopropyl)carbamate (15.5 g, 88.8 mmol) in EtOH (38 mL) was added 3-pentyloctyl 8-bromooctanoate (6.00 g, 14.8 mmol) in EtOH (36 mL) over the course of 20 min. The reaction was heated to 60° C. and allowed to stir at this temperature for 16 h. Upon cooling, the solvents were evaporated and the residue was diluted with ethyl acetate and washed with saturated aqueous $NaHCO_3$ and brine (5×) until no white precipitate was observed in the aqueous layer. The organic layer was separated, washed with brine, dried ($MgSO_4$), filtered, and concentrated. The residue was purified by flash chromatography (0-5-10-25-50-100% (mixture of 1% $NH_4OH$, 20% MeOH in dichloromethane) in dichloromethane) to give 3-pentyloctyl 8-((3-((tert-butoxycarbonyl)amino)propyl)amino)octanoate (4.23 g, 8.49 mmol, 57%) as a clear oil. $^1$H NMR (300 MHz, $CDCl_3$) δ: ppm 5.17 (br. s, 1H); 4.07 (t, 2H, J=6.0 Hz); 3.19 (br. q, 2H, J=6.0 Hz); 2.66 (t, 2H, J=6.0 Hz); 2.56 (t, 2H, J=6.0 Hz); 2.28 (t, 2H, J=6.0 Hz); 1.70-1.52 (m, 6H); 1.51-1.39 (m, 3H); 1.44 (s, 9H); 1.36-1.19 (m, 22H); 0.88 (t, 6H, J=6.0 Hz).

Intermediate AX: 4-Pentylnonyl 8-((2-hydroxyethyl)amino)octanoate

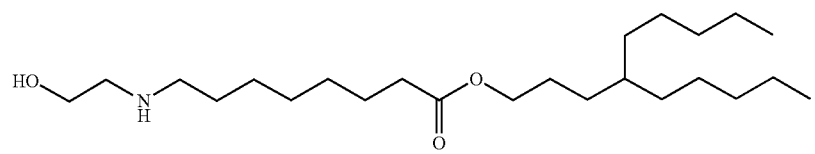

Chemical Formula $C_{24}H_{49}NO_3$
Molecular Weight: 399.66

To a round bottom flask equipped with a stir bar was added 4-pentylnonyl 8-bromooctanoate (600 mg, 1.43 mmol), ethanolamine (2.59 mL, 42.9 mmol), and ethyl alcohol (1 mL). The resulting mixture was allowed to stir at 40° C. for 16 h. The reaction was diluted with dichloromethane, washed with water (2×), and the layers were separated. The organic layer was dried ($MgSO_4$), filtered and concentrated. The crude material was purified by silica gel chromatography (0-5-10-25-50-100% (mixture of 1% $NH_4OH$, 20% MeOH in dichloromethane) in dichloromethane) to give 4-pentylnonyl 8-((2-hydroxyethyl)amino)octanoate (306 mg, 0.77 mmol, 54%) as a clear oil. UPLC/ELSD: RT=1.66 min. MS (ES): m/z (MH$^+$) 400.31 for $C_{24}H_{49}NO_3$. $^1$H NMR (300 MHz, $CDCl_3$) δ: ppm 3.97 (t, 2H, J=6.0 Hz); 3.57 (br. t, 2H, J=6.0 Hz); 2.81 (br. s, 2H), 2.67 (br. t, 2H, J=6.0 Hz); 2.53 (t, 2H, J=6.0 Hz); 2.22 (t, 2H, J=6.0 Hz); 1.61-1.35 (m, 6H); 1.32-1.10 (m, 25H); 0.81 (t, 6H, J=6.0 Hz).

Intermediate AY: 3-Pentyloctyl 8-((3-hydroxypropyl)amino)octanoate

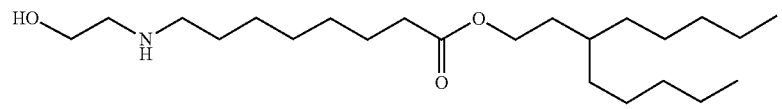

Chemical Formula: $C_{24}H_{49}NO_3$
Molecular Weight: 399.66

To a round bottom flask equipped with a stir bar was added 3-pentyloctyl 8-bromooctanoate (1.00 g, 2.47 mmol), propanolamine (5.66 mL, 74.0 mmol), and ethyl alcohol (2 mL). The resulting mixture was allowed to stir at 40° C. for 16 h. The reaction was diluted with dichloromethane, washed with water (2×), and the layers were separated. The organic layer was dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give 3-pentyloctyl 8-((3-hydroxypropyl)amino)octanoate (374 mg, 0.94 mmol, 38%) as a clear oil. UPLC/ELSD: RT=1.64 min. MS (ES): m/z (MH$^+$) 400.18 for C$_{24}$H$_{49}$NO$_3$.

Intermediate AZ: Heptadecan-9-yl 8-((3-hydroxypropyl)amino)octanoate

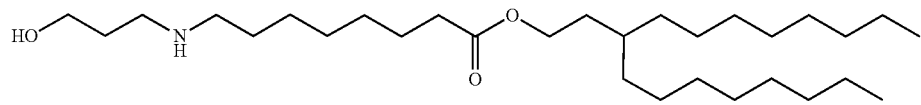

Chemical Formula: C$_{28}$H$_{57}$NO$_3$
Molecular Weight: 455.77

To a round bottom flask equipped with a stir bar was added heptadecane-9-yl 8-bromooctanoate (1.00 g, 2.17 mmol), propanolamine (4.97 mL, 65.0 mmol), and ethyl alcohol (2 mL). The resulting mixture was allowed to stir at 40° C. for 16 h. The reaction was diluted with dichloromethane, washed with water (2×), and the layers were separated. The organic layer was dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give heptadecan-9-yl 8-((3-hydroxypropyl)amino)octanoate (723 mg, 1.59 mmol, 73%) as a clear oil. UPLC/ELSD: RT=2.06 min. MS (ES): m/z (MH$^+$) 456.17 for C$_{28}$H$_{57}$NO$_3$.

Intermediate BA: Heptadecan-9-yl 8-((4-hydroxybutyl)amino)octanoate

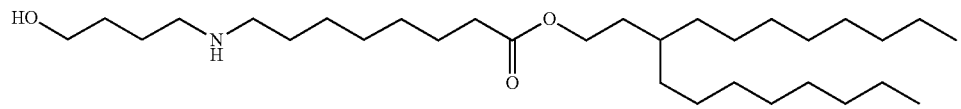

Chemical Formula: C$_{29}$H$_{59}$NO$_3$
Molecular Weight: 469.80

To a round bottom flask equipped with a stir bar was added heptadecane-9-yl 8-bromooctanoate (1.00 g, 2.17 mmol), 4-aminobutan-1-ol (5.99 mL, 65.0 mmol), and ethyl alcohol (2 mL). The resulting mixture was allowed to stir at 40° C. for 16 h. The reaction was diluted with dichloromethane, washed with water (2×), and the layers were separated. The organic layer was dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give heptadecan-9-yl 8-((4-hydroxybutyl)amino)octanoate (773 mg, 1.65 mmol, 76%) as a clear oil. UPLC/ELSD: RT=2.02 min. MS (ES): m/z (MH$^+$) 470.23 for C$_{29}$H$_{59}$NO$_3$.

Intermediate BB: 3-Pentyloctyl 8-((4-hydroxybutyl)amino)octanoate

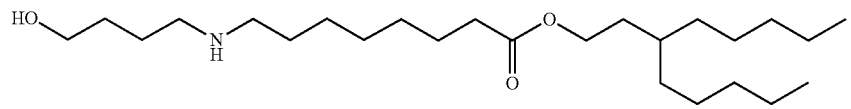

Chemical Formula: C$_{25}$H$_{51}$NO$_3$
Molecular Weight: 413.69

To a round bottom flask equipped with a stir bar was added 3-pentyloctyl 8-bromooctanoate (1.00 g, 2.47 mmol), 4-aminobutan-1-ol (6.82 mL, 74.0 mmol), and ethyl alcohol (2 mL). The resulting mixture was allowed to stir at 40° C. for 16 h. The reaction was diluted with dichloromethane, washed with water (2×), and the layers were separated. The organic layer was dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give 3-pentyloctyl 8-((4-hydroxybutyl)amino)octanoate (501 mg, 1.21 mmol, 49%) as a clear oil. UPLC/ELSD: RT=1.67 min. MS (ES): m/z (MH$^+$) 414.24 for C$_{25}$H$_{51}$NO$_3$.

Intermediate BC: 3-Pentyloctyl 8-((3-((tert-butoxycarbonyl)amino)propyl)(8-oxo-8-((3-propylhexyl)oxy)octyl)amino)octanoate

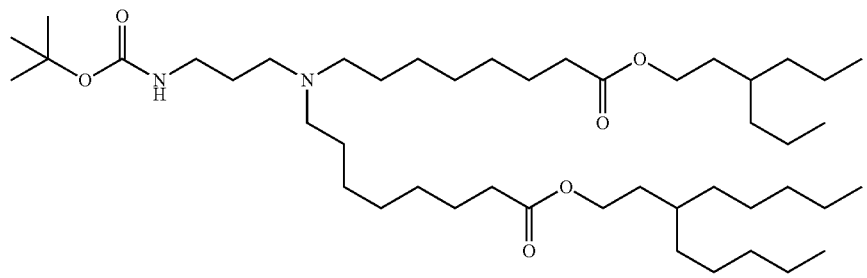

Chemical Formula: C$_{46}$H$_{90}$N$_2$O$_6$
Molecular Weight: 767.23

To a solution of 3-propylhexyl 8-bromooctanoate (735 mg, 2.11 mmol) and 3-pentyloctyl 8-((3-(((tert-butoxycarbonyl)amino)propyl)amino)octanoate (1.00 g, 2.01 mmol) in cyclopentyl methyl ether (9 mL) and actonitrile (9 mL) was added potassium carbonate (1.66 g, 12.0 mmol) and iodopotassium (366 mg, 2.21 mmol). The reaction was allowed to stir at 80° C. for 16 h. Upon cooling, the volatiles were evaporated under vacuum. The residue was diluted with dichloromethane and washed with water. The organic layer was separated, washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give 3-pentyloctyl 8-((3-((tert-butoxycarbonyl)amino)propyl)(8-oxo-8-((3-propylhexyl)oxy)octyl)amino)octanoate (698 mg, 0.91 mmol, 45%) as a golden oil. UPLC/ELSD: RT=2.82 min. MS (ES): m/z (MH$^+$) 767.59 for C$_{46}$H$_{90}$N$_2$O$_6$.

Intermediate BD: 3-Butylheptyl 8-((3-((tert-butoxycarbonyl)amino)propyl)(8-oxo-8-((3-propylhexyl)oxy)octyl)amino)octanoate

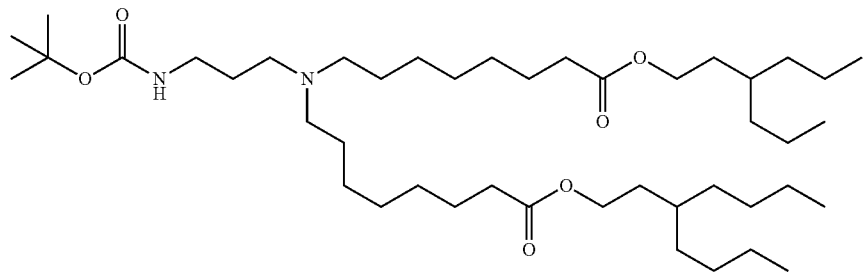

Chemical Formula: C$_{44}$H$_{86}$N$_2$O$_6$
Molecular Weight: 739.18

To a solution of 3-butylheptyl 8-bromooctanoate (895 mg, 2.37 mmol) and 3-propylhexyl 8-((3-(((tert-butoxycarbonyl)amino)propyl)amino)octanoate (1.00 g, 2.26 mmol) in cyclopentyl methyl ether (10 mL) and actonitrile (10 mL) was added potassium carbonate (1.87 g, 13.6 mmol) and iodopotassium (412 mg, 2.49 mmol). The reaction was allowed to stir at 80° C. for 16 h. Upon cooling, the volatiles were evaporated under vacuum. The residue was diluted with dichloromethane and washed with water. The organic layer was separated, washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give 3-butylheptyl 8-((3-((tert-butoxycarbonyl)amino)propyl)(8-oxo-8-((3-propylhexyl)oxy)octyl)amino)octanoate (972 mg, 1.32 mmol, 58%) as a golden oil. UPLC/ELSD: RT=2.69 min. MS (ES): m/z (MH$^+$) 739.46 for C$_{44}$H$_{86}$N$_2$O$_6$.

Intermediate BE: Bis(3-propylhexyl) 8,8'-((3-((tert-butoxycarbonyl)amino)propyl)azanediyl)dioctanoate

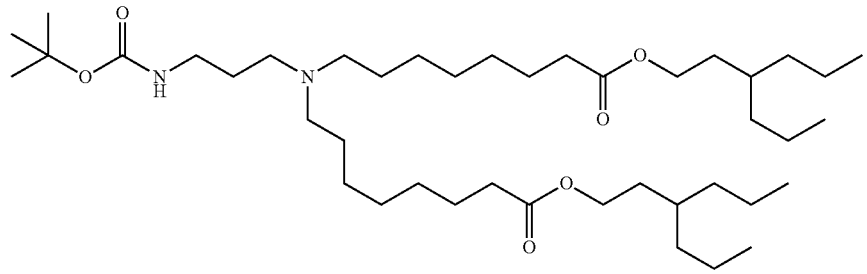

Chemical Formula: C$_{42}$H$_{82}$N$_2$O$_6$
Molecular Weight: 711.13

To a solution of 3-propylhexyl 8-bromooctanoate (829 mg, 2.37 mmol) and 3-propylhexyl 8-((3-((tert-butoxycarbonyl)amino)propyl)amino)octanoate (1.00 g, 2.26 mmol) in cyclopentyl methyl ether (10 mL) and actonitrile (10 mL) was added potassium carbonate (1.87 g, 13.6 mmol) and iodopotassium (412 mg, 2.49 mmol). The reaction was allowed to stir at 80° C. for 16 h. Upon cooling, the volatiles were evaporated under vacuum. The residue was diluted with dichloromethane and washed with water. The organic layer was separated, washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give bis(3-propylhexyl) 8,8'-((3-((tert-butoxycarbonyl)amino)propyl)azanediyl)dioctanoate (730 mg, 1.03 mmol, 45%) as a clear viscous oil. UPLC/ELSD: RT=2.58 min. MS (ES): m/z (MH$^+$) 711.59 for C$_{42}$H$_{82}$N$_2$O$_6$.

Intermediate BF: 3-Butylheptyl 8-((3-((tert-butoxycarbonyl)amino)propyl)(8-oxo-8-((3-pentyloctyl)oxy)octyl)amino)octanoate Chemical Formula: C$_{48}$H$_{94}$N$_2$O$_6$
Molecular Weight: 795.29

To a solution of 3-butylheptyl 8-bromooctanoate (794 mg, 2.11 mmol) and 3-pentyloctyl 8-((3-((tert-butoxycarbonyl)amino)propyl)amino)octanoate (1.00 g, 2.01 mmol) in cyclopentyl methyl ether (9 mL) and actonitrile (9 mL) was added potassium carbonate (1.66 g, 12.0 mmol) and iodopotassium (366 mg, 2.21 mmol). The reaction was allowed to stir at 80° C. for 16 h. Upon cooling, the volatiles were evaporated under vacuum. The residue was diluted with dichloromethane and washed with water. The organic layer was separated, washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give 3-butylheptyl 8-((3-((tert-butoxycarbonyl)amino)propyl)(8-oxo-8-((3-pentyloctyl)oxy)octyl)amino)octanoate (896 mg, 1.13 mmol, 56%) as a clear oil. UPLC/ELSD: RT=2.95 min. MS (ES): m/z (MH$^+$) 795.59 for C$_{48}$H$_{94}$N$_2$O$_6$.

Intermediate BG: 3-Pentyloctyl 8-((3-((tert-butoxycarbonyl)amino)propyl)(8-oxo-8-(undecan-6-yloxy)octyl)amino)octanoate

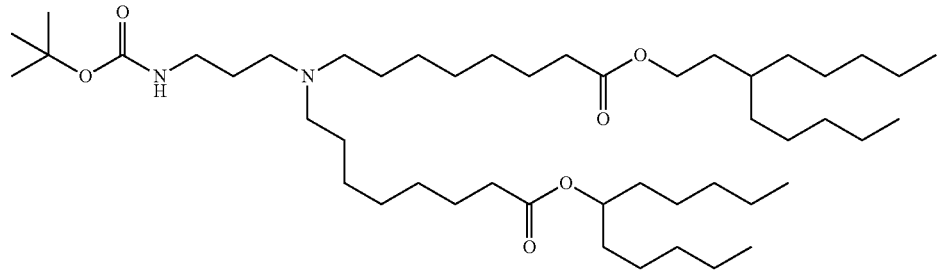

Chemical Formula: C$_{48}$H$_{94}$N$_2$O$_6$
Molecular Weight: 795.288

UPLC/ELSD: RT=2.93 min. MS (ESI): m/z calcd for $C_{45}H_{95}N_2O_6^+$ (M+H) 795.288; found, 795.71. 1H NMR (300 MHz, CDCl$_3$) δ: ppm 5.66 (br. s, 1H); 4.88 (p, 1H); 4.09 (t, 2H); 3.18 (br. d, 2H); 2.50 (br. d, 2H); 2.32 (br. d, 3H); 2.29 (t, 4H); 1.65-1.46 (m, 28H); 1.27 (m, 44H); 0.90 (t, 12H).

Intermediate BH: Nonan-5-yl 8-((3-((tert-butoxycarbonyl)amino)propyl)(8-oxo-8-((3-pentyloctyl)oxy)octyl)amino)octanoate

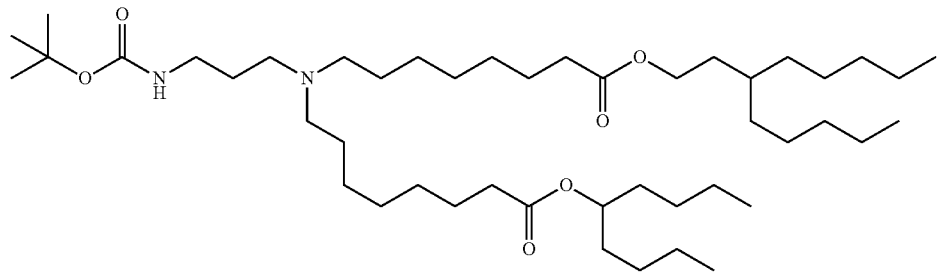

Chemical Formula: $C_{46}H_{90}N_2O_6$
Molecular Weight: 767.23

To a solution of nonan-5-yl 8-bromooctanoate (882 mg, 2.53 mmol) and 3-pentyloctyl 8-((3-((tert-butoxycarbonyl)amino)propyl)amino)octanoate (1.20 g, 2.41 mmol) in cyclopentyl methyl ether (11 mL) and actonitrile (11 mL) was added potassium carbonate (2.00 g, 14.4 mmol) and iodopotassium (439 mg, 2.65 mmol). The reaction was allowed to stir at 80° C. for 16 h. Upon cooling, the volatiles were evaporated under vacuum. The residue was diluted with dichloromethane and washed with water. The organic layer was separated, washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give nonan-5-yl 8-((3-((tert-butoxycarbonyl)amino)propyl)(8-oxo-8-((3-pentyloctyl)oxy)octyl)amino)octanoate (1.06 g, 1.39 mmol, 58%) as a golden oil. $^1$H NMR (300 MHz, CDCl$_3$) δ: ppm 5.65 (br. s, 1H); 4.87 (pent., 2H, J=6.0 Hz); 4.08 (t, 2H, J=6.0 Hz); 3.18 (br. q, 2H, J=6.0 Hz); 2.44 (br. s, 2H); 2.35 (br. s, 2H); 2.28 (t, 4H, J=6.0 Hz); 1.71-1.17 (m, 53H); 1.43 (s, 9H); 0.88 (t, 12H, J=6.0 Hz).

Intermediate BI: Pentadecan-8-yl 8-((3-((tert-butoxycarbonyl)amino)propyl)(8-oxo-8-((3-propylhexyl)oxy)octyl)amino)octanoate

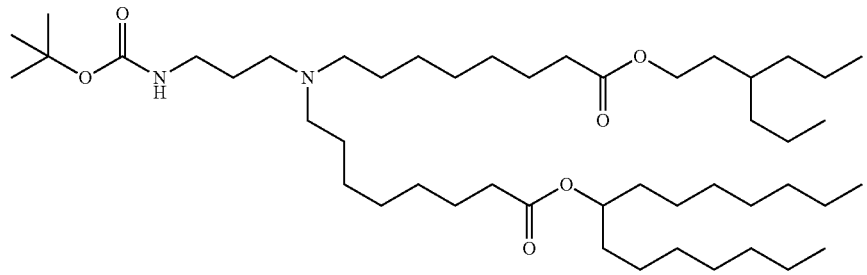

Chemical Formula: $C_{48}H_{94}N_2O_6$
Molecular Weight: 795.288

UPLC/ELSD: RT=2.68 min. MS (ESI): m/z calcd for $C_{48}H_{95}N_2O_6^+$(M+H) 795.288; found, 795.71. 1H NMR (300 MHz, CDCl$_3$) δ: ppm 5.66 (br. s, 1H); 4.89 (p, 1H); 4.10 (t, 2H); 3.19 (br. d, 2H); 2.56-2.35 (br. d, 5H); 2.30 (t, 5H); 1.66-1.39 (m, 66H); 0.90 (t, 12H).

Intermediate BJ: 3-Propylhexyl 8-((3-((tert-butoxycarbonyl)amino)propyl)(8-oxo-8-(tridecan-7-yloxy)octyl)amino)octanoate

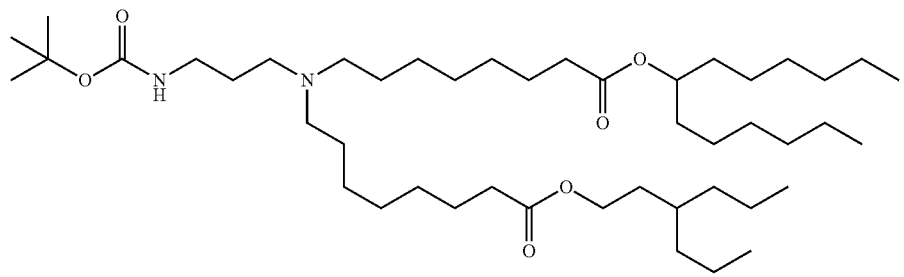

Chemical Formula: $C_{46}H_{90}N_2O_6$
Molecular Weight: 767.23

To a solution of 3-propylhexyl 8-({3-[(tert-butoxycarbonyl)amino]propyl}amino)octanoate (1.38 g, 3.11 mmol) in Acetonitrile (9 mL) were added potassium iodide (0.588 g, 3.54 mmol), potassium carbonate (1.73 g, 12.5 mmol), and a solution of tridecan-7-yl 8-bromooctanoate (1.26 g, 3.11 mmol) in CMPE (9 mL). The reaction was allowed to stir at 77° C. for 18 hours. The reaction was cooled to room temperature and filtered, then the filtrate was evaporated under vacuum. The residue was purified by silica gel chromatography [0-70% (mixture of 1% NH$_4$OH, 20% MeOH in dichloromethane) in dichloromethane] to obtain 3-propylhexyl 8-({3-[(tert-butoxycarbonyl)amino]propyl}[8-oxo-8-(tridecan-7-yloxy)octyl]amino)octanoate (1.32 g, 55.1%) as a yellow tinted oil. UPLC/ELSD: RT=2.70 min found, 767.34. $^1$H NMR (300 MHz, CDCl$_3$) δ: ppm 5.67 (br. s, 1H); 4.89 (p, 1H); 4.10 (t, 2H); 3.20 (q, 2H); 2.61-2.43 (m, 2H); 2.43-2.35 (m, 4H); 2.30 (dt, 4H); 1.71-1.49 (m, 14H); 1.49-1.40 (m, 12H); 1.40-1.19 (m, 36H); 1.01-0.83 (m, 12H).

Intermediate BK: 3-Propylhexyl 8-((3-((tert-butoxycarbonyl)amino)propyl)(8-oxo-8-(undecan-6-yloxy)octyl)amino)octanoate

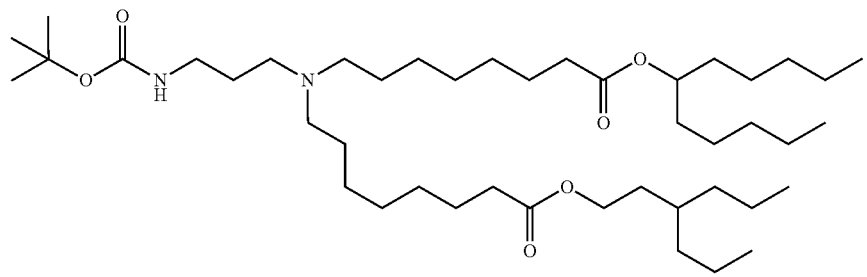

Chemical Formula: $C_{44}H_{86}N_2O_6$
Molecular Weight: 739.18

To a solution of 3-propylhexyl 8-({3-[(tert-butoxycarbonyl)amino]propyl}amino)octanoate (1.50 g, 3.39 mmol) in Acetonitrile (10 mL) were added potassium iodide (0.619 g, 3.73 mmol), potassium carbonate (1.87 g, 13.6 mmol), and a solution of undecan-6-yl 8-bromooctanoate (1.28 g, 3.39 mmol) in CPME (10 mL). The reaction was allowed to stir at 77° C. for 18 hours. The reaction was cooled to room temperature and filtered, then the filtrate was evaporated under vacuum. The residue was purified by silica gel chromatography [0-70% (mixture of 1% NH$_4$OH, 20% MeOH in dichloromethane) in dichloromethane] to obtain 3-propylhexyl 8-({3-[(tert-butoxycarbonyl)amino]propyl}[8-oxo-8-(undecan-6-yloxy)octyl]amino)octanoate (1.53 g, 61.2%) as a yellow tinted oil. UPLC/ELSD: RT=2.56 min found, 739.46. $^1$H NMR (300 MHz, CDCl$_3$) δ: ppm 5.66 (br. s, 1H); 4.89 (p, 1H); 4.10 (t, 2H); 3.20 (q, 2H); 2.60-2.44 (m, 2H); 2.44-2.35 (m, 4H); 2.30 (t, 4H); 1.74-1.49 (m, 14H); 1.49-1.39 (m, 12H); 1.39-1.19 (m, 32H); 0.91 (t, 12H).

Intermediate BL: Nonan-5-yl 8-((3-((tert-butoxycarbonyl)amino)propyl)(8-oxo-8-((3-propylhexyl)oxy)octyl)amino)octanoate

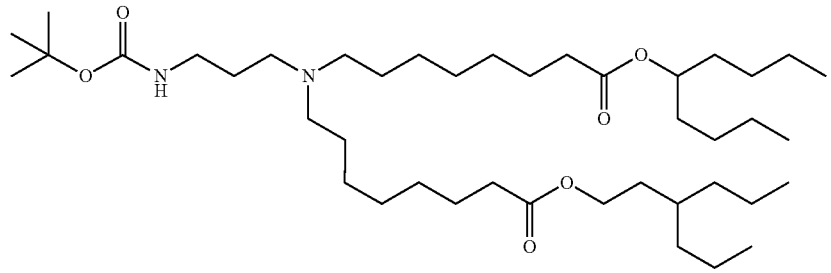

Chemical Formula: C$_{42}$H$_{82}$N$_2$O$_6$
Molecular Weight: 711.13

To a solution of 3-propylhexyl 8-({3-[(tert-butoxycarbonyl)amino]propyl}amino)octanoate (1.50 g, 3.39 mmol) in acetonitrile (10 mL) were added potassium iodide (0.619 g, 3.73 mmol), potassium carbonate (1.87 g, 13.6 mmol), and a solution of nonan-5-yl 8-bromooctanoate (1.18 g, 3.39 mmol) in CMPE (10 mL). The reaction was allowed to stir at 77° C. for 18 hours. The reaction was cooled to room temperature and filtered, then the filtrate was evaporated under vacuum. The residue was purified by silica gel chromatography [0-70% (mixture of 1 NH$_4$OH, 20% MeOH in dichloromethane) in dichloromethane] to obtain nonan-5-yl 8-({3-[(tert-butoxycarbonyl)amino]propyl}({8-oxo-8-[(3-propylhexyl)oxy]octyl})amino)octanoate (0.483 g, 20.1%) as a yellow tinted oil. UPLC/ELSD: RT=2.45 min found, 711.46. $^1$H NMR (300 MHz, CDCl$_3$) δ: ppm 5.66 (br. s, 1H); 4.89 (p, 1H); 4.11 (t, 2H); 3.28-3.11 (m, 2H); 2.60-2.44 (m, 2H); 2.44-2.35 (m, 4H); 2.30 (t, 4H); 1.74-1.49 (m, 14H); 1.49-1.39 (m, 12H); 1.39-1.20 (m, 28H); 0.91 (t, 12H).

Intermediate BM: 3-Pentyloctyl 8-((3-aminopropyl)(8-oxo-8-((3-propylhexyl)oxy)octyl)amino)octanoate

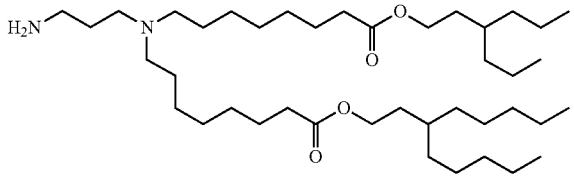

Chemical Formula: C$_{41}$H$_{82}$N$_2$O$_4$
Molecular Weight: 667.12

To a solution of 3-pentyloctyl 8-((3-((tert-butoxycarbonyl)amino)propyl)(8-oxo-8-((3-propylhexyl)oxy)octyl)amino)octanoate (698 mg, 0.91 mmol) in methylene chloride (18 mL) was added trifluoroacetic acid (1.39 mL, 18.2 mmol). The reaction was allowed to stir at room temperature for 4 h. The reaction was quenched with saturated aqueous NaHCO$_3$ and extracted with dichloromethane. The organic layer was separated, washed with brine, dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give 3-pentyloctyl 8-((3-aminopropyl)(8-oxo-8-((3-propylhexyl)oxy)octyl)amino)octanoate (378 mg, 0.57 mmol, 62%) as a clear oil. UPLC/ELSD: RT=2.26 min. MS (ES): m/z (MH$^+$) 667.56 for C$_{41}$H$_{82}$N$_2$O$_4$.

Intermediate BN: 3-Butylheptyl 8-((3-aminopropyl)(8-oxo-8-((3-propylhexyl)oxy)octyl)amino)octanoate

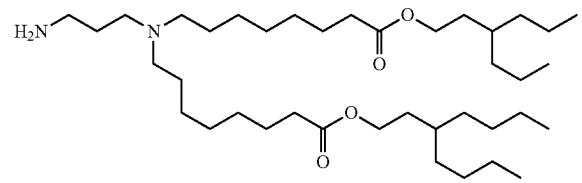

Chemical Formula: C$_{39}$H$_{78}$N$_2$O$_4$
Molecular Weight: 639.06

To a solution of 3-butylheptyl 8-((3-((tert-butoxycarbonyl)amino)propyl)(8-oxo-8-((3-propylhexyl)oxy)octyl)amino)octanoate (972 mg, 1.32 mmol) in methylene chloride (27 mL) was added trifluoroacetic acid (2.01 mL, 26.3 mmol). The reaction was allowed to stir at room temperature for 4 h. The reaction was quenched with saturated aqueous NaHCO$_3$ and extracted with dichloromethane. The organic layer was separated, washed with brine, dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give 3-butylheptyl 8-((3-aminopropyl)(8-oxo-8-((3-propylhexyl)oxy)octyl)amino)octanoate (503 mg, 0.79 mmol, 60%) as a clear oil. UPLC/ELSD: RT=2.13 min. MS (ES): m/z (MH$^+$) 639.31 for C$_{39}$H$_{78}$N$_2$O$_4$.

Intermediate BO: Bis(3-propylhexyl) 8,8'-((3-aminopropyl)azanediyl)dioctanoate

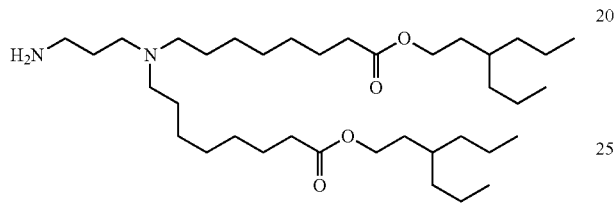

Chemical Formula: C$_{37}$H$_{74}$N$_2$O$_4$
Molecular Weight: 611.01

To a solution of bis(3-propylhexyl) 8,8'-((3-((tert-butoxycarbonyl)amino)propyl)azanediyl)dioctanoate (730 mg, 1.03 mmol) in methylene chloride (21 mL) was added trifluoroacetic acid (1.57 mL, 20.5 mmol). The reaction was allowed to stir at room temperature for 4 h. The reaction was quenched with saturated aqueous NaHCO$_3$ and extracted with dichloromethane. The organic layer was separated, washed with brine, dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give bis(3-propylhexyl) 8,8'-((3-aminopropyl)azanediyl)dioctanoate (499 mg, 0.82 mmol, 80%) as a clear oil. UPLC/ELSD: RT=1.93 min. MS (ES): m/z (MH$^+$) 611.44 for C$_{37}$H$_{74}$N$_2$O$_4$.

Intermediate BP: 3-Butylheptyl 8-((3-aminopropyl)(8-oxo-8-((3-pentyloctyl)oxy)octyl)amino)octanoate

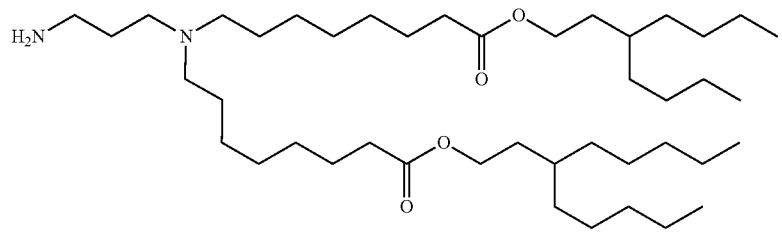

Chemical Formula: C$_{43}$H$_{86}$N$_2$O$_4$
Molecular Weight: 695.17

To a solution of 3-butylheptyl 8-((3-((tert-butoxycarbonyl)amino)propyl)(8-oxo-8-((3-pentyloctyl)oxy)octyl)amino)octanoate (896 mg, 1.13 mmol) in methylene chloride (23 mL) was added trifluoroacetic acid (1.72 mL, 22.5 mmol). The reaction was allowed to stir at room temperature for 4 h. The reaction was quenched with saturated aqueous NaHCO₃ and extracted with dichloromethane. The organic layer was separated, washed with brine, dried (MgSO₄), filtered and concentrated. The crude material was purified by silica gel chromatography (0-5-10-25-50-100% (mixture of 1% NH₄OH, 20% MeOH in dichloromethane) in dichloromethane) to give 3-butylheptyl 8-((3-aminopropyl)(8-oxo-8-((3-pentyloctyl)oxy)octyl)amino)octanoate (632 mg, 0.91 mmol, 81%) as a clear oil. UPLC/ELSD: RT=2.47 min. MS (ES): m/z (MH⁺) 695.68 for $C_{43}H_{86}N_2O_4$.

Intermediate BQ: 3-Pentyloctyl 8-((4-aminobutyl)(8-oxo-8-(undecan-6-yloxy)octyl)amino)octanoate

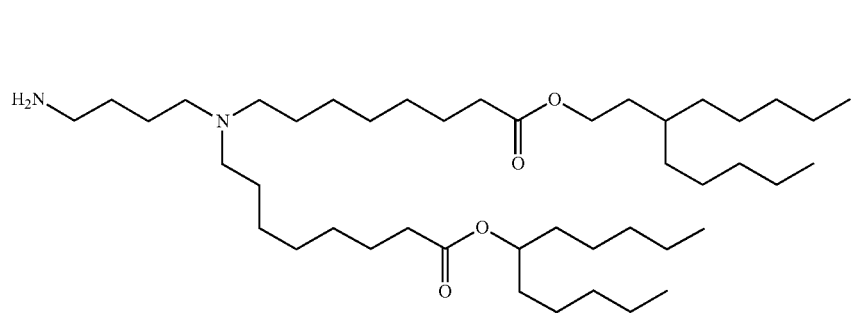

Chemical Formula: $C_{44}H_{88}N_2O_6$
Molecular Weight: 709.198

UPLC/ELSD: RT=2.49 min. MS (ESI): m/z calcd for $C_{44}H_{59}N_2O_6^+$ (M+H) 709.198; found, 695.43. ¹H NMR (300 MHz, CDCl₃) δ: ppm 4.88 (p, 1H); 4.09 (t, 2H); 2.74 (t, 2H); 2.47 (t, 2H); 2.39 (t, 4H); 2.29 (t, 4H); 1.69-1.38 (m, 25H); 1.29 (br. m, 38H); 0.90 (t, 12H).

Intermediate BR: Nonan-5-yl 8-((3-aminopropyl)(8-oxo-8-((3-pentyloctyl)oxy)octyl)amino)octanoate

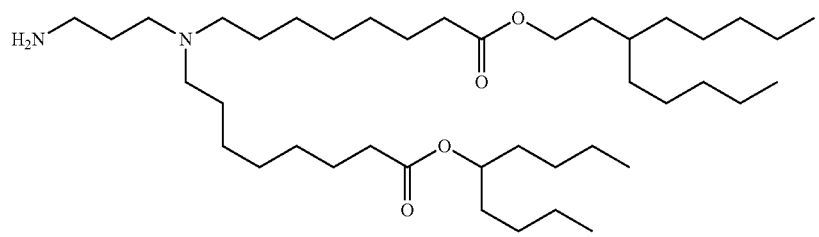

Chemical Formula: $C_{41}H_{82}N_2O_4$
Molecular Weight: 667.12

To a solution of nonan-5-yl 8-((3-((tert-butoxycarbonyl)amino)propyl)(8-oxo-8-((3-pentyloctyl)oxy)octyl)amino)octanoate (1.06 g, 1.39 mmol) in methylene chloride (28 mL) was added trifluoroacetic acid (2.12 mL, 27.7 mmol). The reaction was allowed to stir at room temperature for 4 h. The reaction was quenched with saturated aqueous NaHCO$_3$ and extracted with dichloromethane. The organic layer was separated, washed with brine, dried (MgSO$_4$), filtered and concentrated. The crude material was purified by silica gel chromatography (0-5-10-25-50-100% (mixture of 1% NH$_4$OH, 20% MeOH in dichloromethane) in dichloromethane) to give nonan-5-yl 8-((3-aminopropyl)(8-oxo-8-((3-pentyloctyl)oxy)octyl)amino)octanoate (718 mg, 1.08 mmol, 78%) as a clear oil. UPLC/ELSD: RT=2.31 min. MS (ES): m/z (MH$^+$) 667.43 for C$_{41}$H$_{82}$N$_2$O$_4$.

Intermediate BS: 3-Pentyloctyl 8-((3-aminopropyl)(8-oxo-8-(undecan-6-yloxy)octyl)amino)octanoate

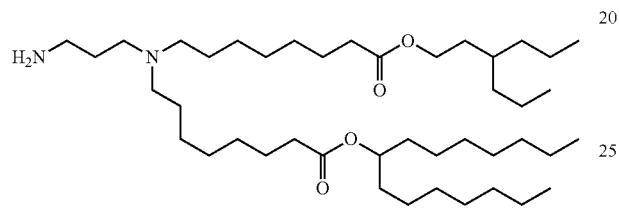

Chemical Formula: C$_{43}$H$_{86}$N$_3$O$_6$
Molecular Weight: 695.171

UPLC/ELSD: RT=2.34 min. MS (ESI): m/z calcd for C$_{43}$H$_{57}$N$_3$O$_6$$^+$(M+H) 695.171; found, 695.430. 1H NMR (300 MHz, CDCl$_3$) δ: ppm 4.88 (p, 1H); 4.10 (t, 2H); 4.10 (t, 2H); 2.92 (t, 2H); 2.61 (t, 2H); 2.46 (t, 4H); 2.30 (t, 4H); 1.73-1.41 (m, 18H); 1.28 (br. m, 40H); 0.90 (t, 12H).

Intermediate BT: 3-Propylhexyl 8-((3-aminopropyl)(8-oxo-8-(tridecan-7-yloxy)octyl)amino)octanoate

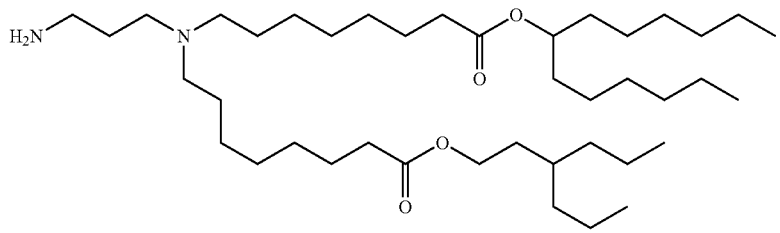

Chemical Formula: C$_{41}$H$_{82}$N$_2$O$_4$
Molecular Weight: 667.12

To a solution of 3-propylhexyl 8-({3-[(tert-butoxycarbonyl)amino]propyl}[8-oxo-8-(tridecan-7-yloxy)octyl]amino)octanoate (1.32 g, 1.72 mmol) in dichloromethane (33 mL) was added trifluoroacetic acid (6.63 mL, 34.3 mmol). The reaction was allowed to stir at room temperature for 4 hours. Saturated NaHCO$_3$(aq.) was added and the reaction was diluted with dichloromethane. The organic layer was separated and washed twice more with saturated NaHCO$_3$(aq.) then brine. The organic layer was died over MgSO$_4$, then filtered and evaporated under vacuum. The residue was purified by silica gel chromatography [0-70% (mixture of 1% NH$_4$OH, 20% MeOH in dichloromethane) in dichloromethane] to obtain 3-propylhexyl 8-[(3-aminopropyl)[8-oxo-8-(tridecan-7-yloxy)octyl]amino]octanoate (0.774 g, 67.6%) as a yellow tinted oil. UPLC/ELSD: RT=2.03 min found, 667.31. $^1$H NMR (300 MHz, CDCl$_3$) δ: ppm 4.88 (p, 1H); 4.10 (t, 2H); 2.79 (t, 2H); 2.51 (t, 2H); 2.42 (t, 4H); 2.30 (t, 4H); 1.79-1.39 (m, 17H); 1.39-1.18 (m, 36H); 0.90 (t, 12H).

Intermediate BU: 3-Propylhexyl 8-((3-aminopropyl)(8-oxo-8-(undecan-6-yloxy)octyl)amino)octanoate

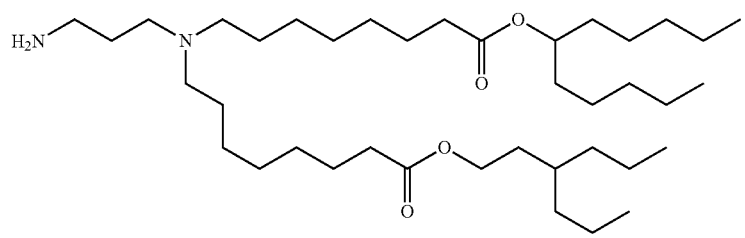

Chemical Formula: C$_{39}$H$_{78}$N$_2$O$_4$
Molecular Weight: 639.06

To a solution of 3-propylhexyl 8-({3-[(tert-butoxycarbonyl)amino]propyl}[8-oxo-8-(undecan-6-yloxy)octyl]amino)octanoate (1.53 g, 2.07 mmol) in dichloromethane (40 mL) was added trifluoroacetic acid (3.05 mL, 39.9 mmol). The reaction was allowed to stir at room temperature for 4 hours. Saturated NaHCO$_3$(aq.) was added and the reaction was diluted with dichloromethane. The organic layer was separated and washed twice more with saturated NaHCO$_3$(aq.) then brine. The organic layer was died over MgSO$_4$, then filtered and evaporated under vacuum. The residue was purified by silica gel chromatography [0-70% (mixture of 1% NH$_4$OH, 20% MeOH in dichloromethane) in dichloromethane] to obtain 3-propylhexyl 8-[(3-aminopropyl)[8-oxo-8-(undecan-6-yloxy)octyl]amino]octanoate (0.682 g, 51.5%) as a yellow tinted oil. UPLC/ELSD: RT=1.85 min found, 639.19. $^1$H NMR (300 MHz, CDCl$_3$) δ: ppm 4.89 (p, 1H); 4.10 (t, 2H); 2.82 (t, 2H); 2.53 (t, 2H); 2.44 (t, 4H); 2.30 (t, 4H); 1.75-1.40 (m, 17H); 1.40-1.18 (m, 32H); 0.91 (t, 12H).

Intermediate BV: Nonan-5-yl 8-((3-aminopropyl)(8-oxo-8-((3-propylhexyl)oxy)octyl)amino)octanoate

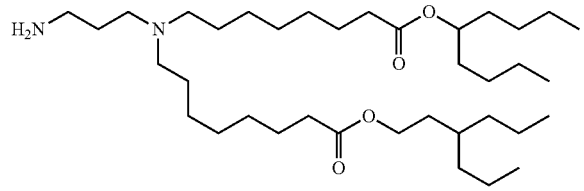

Chemical Formula: C$_{37}$H$_{74}$N$_2$O$_4$
Molecular Weight: 611.01

To a solution of nonan-5-yl 8-({3-[(tert-butoxycarbonyl)amino]propyl}({8-oxo-8-[(3-propylhexyl)oxy]octyl})amino)octanoate (0.483 g, 0.679 mmol) in dichloromethane (13 mL) was added trifluoroacetic acid (1.00 mL, 13.1 mmol). The reaction was allowed to stir at room temperature for 4 hours. Saturated NaHCO$_3$(aq.) was added and the reaction was diluted with dichloromethane. The organic layer was separated and washed twice more with saturated NaHCO$_3$(aq.) then brine. The organic layer was died over MgSO$_4$, then filtered and evaporated under vacuum. The residue was purified by silica gel chromatography [0-70% (mixture of 1% NH$_4$OH, 20% MeOH in dichloromethane) in dichloromethane] to obtain nonan-5-yl 8-[(3-aminopropyl)({8-oxo-8-[(3-propylhexyl)oxy]octyl})amino]octanoate (0.202 g, 48.7%) as a yellow tinted oil. UPLC/ELSD: RT=1.85 min found, 611.44. $^1$H NMR (300 MHz, CDCl$_3$) δ: ppm 4.89 (p, 1H); 4.10 (t, 2H); 2.80 (t, 2H); 2.52 (t, 2H); 2.42 (t, 4H); 2.30 (t, 4H); 1.74-1.39 (m, 17H); 1.39-1.20 (m, 28H); 0.91 (t, 12H).

Synthesis of Final Compounds

AA. Compound 3: Heptadecan-9-yl 8-((2-hydroxyethyl)(6-((((3-pentyloctyl)oxy)carbonyl)oxy)hexyl)amino)octanoate

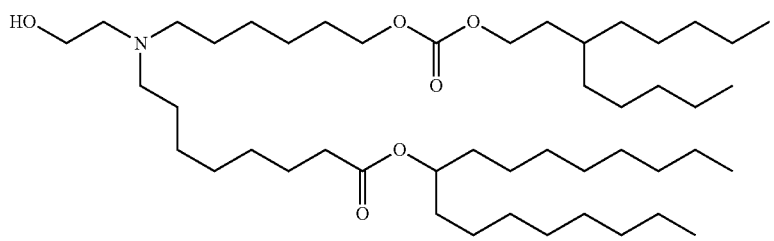

Chemical Formula: C$_{47}$H$_{93}$NO$_6$
Molecular Weight: 768.26

UPLC/ELSD: RT=3.04 min. MS (ES): m/z (MH⁺) 769.313 for $C_{47}H_{93}NO_6$. ¹H NMR (300 MHz, CDCl₃) δ: ppm 4.89 (p, 1H); 4.14 (m, 4H); 3.54 (bm, 2H); 2.66-2.37 (m, 6H); 2.30 (m, 2H); 1.77-1.17 (m, 66H); 0.91 (m, 12H).

AB. Compound 4: Heptadecan-9-yl 8-((6-((((3-hexylnonyl)oxy)carbonyl)oxy)hexyl)(3-((2-(methylamino)-3,4-dioxocyclobut-1-en-1-yl)amino)propyl)amino)octanoate Ethyl 3-hexylnon-2-enoate

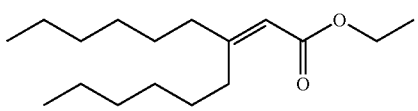

Chemical Formula: $C_{17}H_{32}O_2$
Molecular Weight: 268.44

Triethyl phosphonoacetate (26.33 g, 117.4 mmol) was added dropwise over 20 minutes to a suspension of sodium hydride (4.697 g, 117.4 mmol) in THF (294 mL) and the mixture was stirred at room temperature until gas evolution ceased (approximately 30 min). The reaction mixture was chilled to 0° C. and 7-tridecanone (10 g, 58.7 mmol) was added. The reaction was gradually warmed to room temperature, then heated to reflux and stirred overnight. The reaction was quenched with saturated aqueous sodium bicarbonate. The aqueous phase was extracted with diethyl ether, and the organic extracts were washed with brine, dried with MgSO₄, and concentrated. The crude material was purified by silica gel chromatography (0-20% EtOAc:hexanes) to afford ethyl 3-hexylnon-2-enoate (6.7 g, 27.9 mmol, 47.5%) as a clear oil. ¹H NMR (300 MHz, CDCl₃) δ: ppm 5.63 (s, 1H); 4.15 (q, 2H); 2.61 (t, 2H); 2.15 (t, 2H); 1.53-1.20 (m, 19H); 0.91 (m, 6H).

Ethyl 3-hexylnonanoate

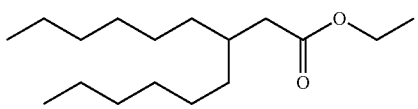

Chemical Formula: $C_{17}H_{34}O_2$
Molecular Weight: 270.46

To a flask containing a slurry of Pearlmans catalyst (0.73 g, 5.2 mmol) in ethanol (20 mL) under N₂ was added a solution of ethyl 3-hexylnon-2-enoate (6.975 g, 25.9 mmol) in ethanol (5 mL). The reaction was stirred under H₂ (balloon) for 16 h. The reaction was filtered through a plug of Celite and the filtrate was evaporated under vacuum to afford ethyl 3-hexylnonanoate (6.7 g, 24.7 mmol, 95%). The residue was taken to the next step without further purification.

¹H NMR (300 MHz, CDCl₃) δ: ppm 4.16 (q, 2H); 2.23 (d, 2H); 1.86 (bs, 1H); 1.28 (m, 23H); 0.90 (m, 6H).

3-Hexylnonan-1-ol

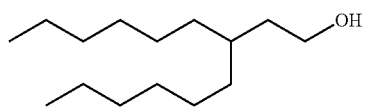

Chemical Formula: $C_{15}H_{32}O$
Molecular Weight: 228.42

To a solution of lithium aluminium hydride (49.5 mL of 1M solution in THF, 49.5 mmol) in THF was added a solution of ethyl 3-hexylnonanoate (6.7 g, 24.7 mmol) in THF (20 mL). The reaction was stirred at room temperature for 16 h. The reaction was quenched with a saturated solution of sodium sulfate decahydrate. The white solids were removed by filtration through a plug of Celite and the filtrate was evaporated under vacuum. The residue was purified by flash chromatography (ISCO) by 0-100% ethyl acetate in hexanes to obtain 3-hexylnonan-1-ol (5.62 g, 24.6 mmol, 99%).

¹H NMR (300 MHz, CDCl₃) δ: ppm 3.69 (t, 2H); 1.61-1.19 (m, 24H); 0.91 (m, 6H).

6-Bromohexyl 3-hexylnonyl carbonate

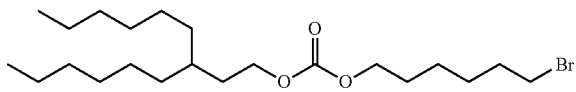

Chemical Formula: $C_{22}H_{43}BrO_3$
Molecular Weight: 435.49

3-Hexylnonan-1-ol (1.24 g, 5.4 mmol) was added dropwise to a solution of 6-bromohexyl 4-nitrophenyl carbonate (1.88 g, 5.43 mmol) in DCM (15 mL) in a round bottom flask charged with a magnetic stir bar at room temperature under N₂. The reaction was kept under N₂ and pyridine (0.55 mL, 6.8 mmol) was added dropwise over 10 min. followed by 4-dimethylaminopyridine (0.133 g, 1.1 mmol) in one portion. The reaction was allowed to stir at room temperature for 16 h then diluted with water and DCM. The organic layer was separated, and the aqueous layer was washed with DCM. The combined organics were washed with brine, dried with Na₂SO₄. and evaporated under vac. The residue was purified by silica gel chromatography (0-100% ethyl acetate in hexanes) to give 6-bromohexyl 3-hexylnonyl carbonate (1.3 g, 3.0 mmol, 55%).

Heptadecan-9-yl 8-((3-((tert-butoxycarbonyl)amino)propyl)amino)octanoate

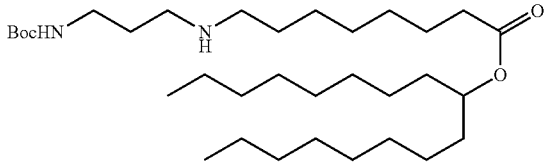

Chemical Formula: $C_{33}H_{66}N_2O_4$
Molecular Weight: 554.90

A solution of heptadecan-9-yl 8-bromooctanoate (69.2 g, 0.15 mole) and tert-butyl (3-aminopropyl)carbamate (130.6 g, 0.75 mole) in 500 mL ethanol was heated to 65° C. overnight. The reaction mixture was concentrated, and the crude was purified by flash column chromatography (SiO$_2$: methanol/dichloromethane 0-20%) to get heptadecan-9-yl 8-((3-((tert-butoxycarbonyl)amino)propyl)amino)octanoate (62 g, 74%) as light yellow oil. MS (CI): m/z (MH$^+$) 555.5 for C$_{33}$H$_{66}$N$_2$O$_4$. $^1$H NMR (300 MHz, CDCl$_3$): δ ppm 5.15 (bs, 1H); 4.85 (quint., 1H, J=6.0 Hz); 3.17 (m, 2H); 2.65 (t, 2H, J=6.6 Hz); 2.56 (t, 2H, J=6.8 Hz); 2.26 (t, 2H, J=7.6 Hz); 1.68-1.56 (m, 6H); 1.46 (m, 5H); 1.43 (s, 9H); 1.24 (m, 30H); 0.86 (t, 6H, J=6.6 Hz).

Heptadecan-9-yl 8-((3-((tert-butoxycarbonyl)amino)propyl)(6-((((3-hexylnonyl)oxy)carbonyl)oxy)hexyl)amino)octanoate

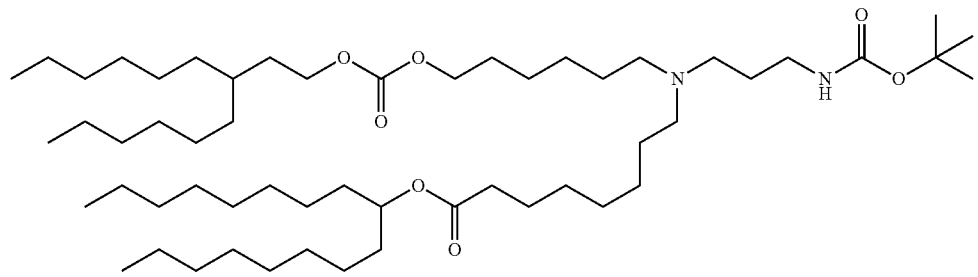

Chemical Formula: C$_{55}$H$_{108}$N$_2$O$_7$
Molecular Weight: 909.48

To a solution of 6-bromohexyl 3-hexylnonyl carbonate (0.5 g, 1.15 mmol) and heptadecan-9-yl 8-((3-((tert-butoxycarbonyl)amino)propyl)amino)octanoate (0.637 g, 1.15 mmol) in 6 mL of a 1:1 mixture of cyclopropyl methyl ether and acetonitrile was added potassium carbonate (0.635 g, 4.59 mmol) and potassium iodide (0.21 g, 1.26 mmol). The reaction was allowed to stir at 77° C. for 16 h. The reaction was cooled, filtered and the volatiles were evaporated under vacuum. The residue was purified by silica gel chromatography (0-100% (a solution of 20% MeOH, 80% DCM, 1% NH$_4$OH) in DCM) to give heptadecan-9-yl 8-((3-((tert-butoxycarbonyl)amino)propyl)(6-((((3-hexylnonyl)oxy)carbonyl)oxy)hexyl)amino)octanoate (0.32 g, 0.35 mmol, 31%).

Heptadecan-9-yl 8-((6-((((3-hexylnonyl)oxy)carbonyl)oxy)hexyl)(3-((2-(methylamino)-3,4-dioxocyclobut-1-en-1-yl)amino)propyl)amino)octanoate

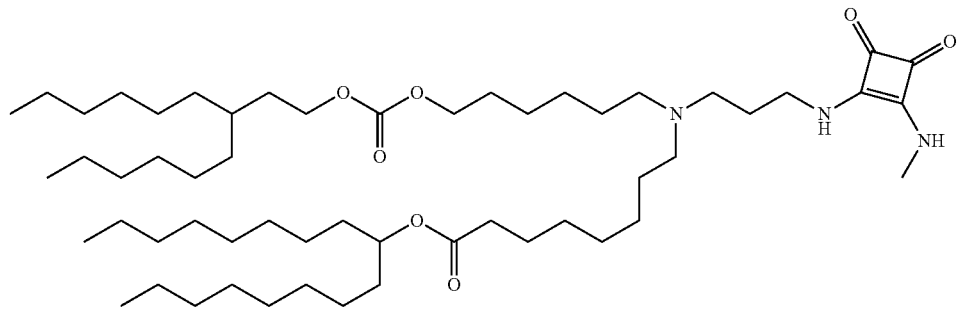

Chemical Formula: C$_{55}$H$_{103}$N$_3$O$_7$
Molecular Weight: 918.44

Compound 4 was prepared analogously to compound 14 using heptadecan-9-yl 8-((3-((tert-butoxycarbonyl)amino)propyl)(6-((((3-hexylnonyl)oxy)carbonyl)oxy)hexyl)amino)octanoate instead of undecan-3-yl 8-((3-(((tert-butoxycarbonyl)amino)propyl)(6-((2-octyldecyl)oxy)-6-oxohexyl)amino)octanoate. UPLC/ELSD: RT=3.13 min. MS (ES): m/z (MH$^+$) 919.429 for $C_{55}H_{103}N_3O_7$. $^1$H NMR (300 MHz, CDCl$_3$) δ: ppm 4.87 (p, 1H); 4.17 (m, 4H); 3.68 (bm, 2H); 3.30 (m, 3H); 2.65-2.41 (m, 6H); 2.31 (m, 2H); 1.87-1.19 (m, 73H); 0.90 (m, 12H).

AC. Compound 5: Heptadecan-9-yl 8-((6-((((3-hexylnonyl)oxy)carbonyl)oxy)hexyl)(2-hydroxyethyl)amino)octanoate

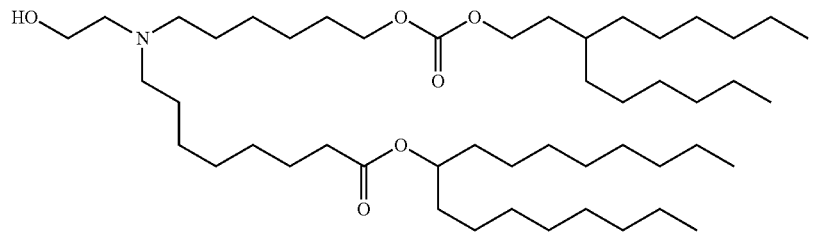

Chemical Formula: $C_{49}H_{97}NO_6$
Molecular Weight: 796.32

UPLC/ELSD: RT=3.16 min. MS (ES): m/z (MH$^+$) 797.683 for $C_{49}H_{97}NO_6$. $^1$H NMR (300 MHz, CDCl$_3$) δ: ppm 4.89 (p, 1H); 4.14 (m, 4H); 3.54 (bm, 2H); 2.68-2.38 (m, 6H); 2.30 (m, 2H); 1.77-1.17 (m, 70H), 0.90 (m, 12H).

AD. Compound 6: Heptadecan-9-yl 8-((3-((2-(methylamino)-3,4-dioxocyclobut-1-en-1-yl)amino)propyl)(6-((((3-pentyloctyl)oxy)carbonyl)oxy)hexyl)amino)octanoate

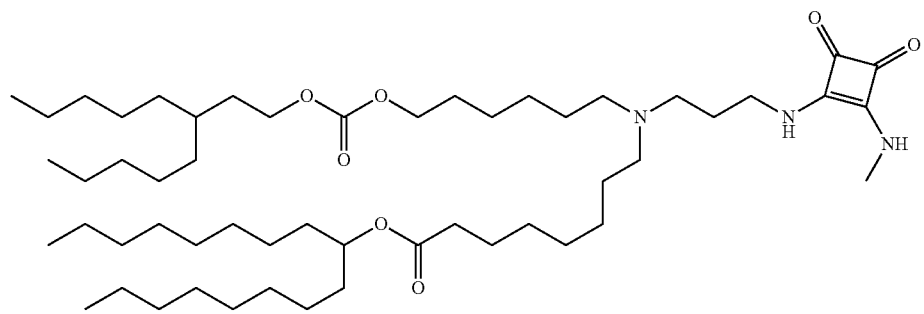

Chemical Formula: $C_{53}H_{99}N_3O_7$
Molecular Weight: 890.39

Compound 6 was prepared analogously to compound 4 using 6-undecanone instead of 7-tridecanone. UPLC/ELSD: RT=3.04 min. MS (ES): m/z (MH$^+$) 891.552 for $C_{53}H_{99}N_3O_7$. $^1$H NMR (300 MHz, CDCl$_3$) δ: ppm 4.87 (p, 1H); 4.17 (m, 4H); 3.67 (bm, 2H); 3.28 (m, 3H); 2.68-2.38 (m, 6H); 2.31 (m, 2H); 1.86-1.18 (m, 69H); 0.90 (m, 12H).

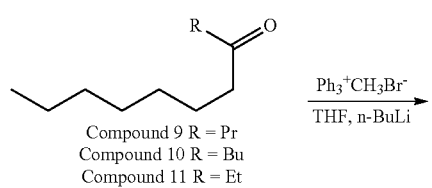

Compound 9 R = Pr
Compound 10 R = Bu
Compound 11 R = Et

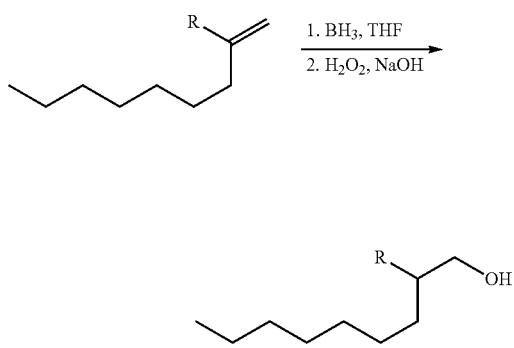

AE. Compound 9: Heptadecan-9-yl 8-((3-((2-(methylamino)-3,4-dioxocyclobut-1-en-1-yl)amino)propyl)(8-oxo-8-((2-propylnonyl)oxy)octyl)amino)octanoate Heptadecan-9-yl 8-((3-(((benzyloxy)carbonyl)amino)propyl)amino) octanoate

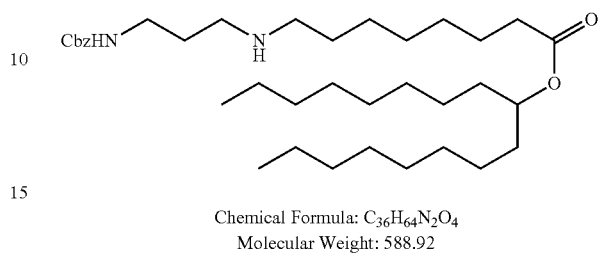

Chemical Formula: $C_{36}H_{64}N_2O_4$
Molecular Weight: 588.92

To a solution of heptadecan-9-yl 8-bromooctanoate (50 g, 204 mmol) and benzyl (3-aminopropyl)carbamate (35 g, 76 mmol) in 500 mL ethanol was added sodium bicarbonate (57 g, 0.68 mole) in one portion at room temperature, the mixture heated to 65° C. and stirred for two days. The reaction mixture was cooled to room temperature and the solid was filtered away through a pad of Celite. The filtrate was concentrated and purified by column chromatography (dichloromethane/methanol 9:1) to give heptadecan-9-yl 8-((3-(((benzyloxy)carbonyl)amino)propyl)amino) octanoate (29.2 g, 66%) as a light yellow oil. $^1$H NMR (300 MHz, CDCl$_3$): δ 0.84 (m, 6H); 1.10-1.57 (m, 42H); 2.24 (t, 2H, J=6.7 Hz); 2.49 (m, 2H); 2.56 (m, 2H); 3.04 (m, 2H); 4.76 (m, 1H); 4.99 (s, 2H); 7.29-7.35 (m, 5H).

tert-Butyl 8-((3-(((benzyloxy)carbonyl)amino)propyl)(8-(heptadecan-9-yloxy)-8-oxooctyl)amino)octanoate

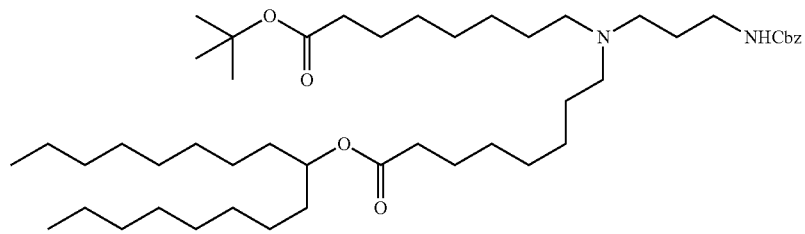

Chemical Formula: $C_{48}H_{86}N_2O_6$
Molecular Weight: 787.22

To a solution of heptadecan-9-yl 8-((3-(((benzyloxy)carbonyl)amino)propyl)amino) octanoate (14.6 g, 24.9 mmol) in 500 mL cyclopentylmethyl ether/acetonitrile (1:1, v/v) at room temperature was added tert-butyl 8-bromooctanoate (Oakwood Chemical, Estill, SC; 7.62 g, 387 mL, 27.3 mmol), followed by potassium carbonate (13.7 g, 99.6 mmol) and potassium iodide (5 g, 30 mmol). The reaction mixture was stirred at room temperature for 30 min and then at 85° C. overnight. The reaction mixture was cooled to room temperature and the solids were removed through a pad of Celite. The filtrate was concentrated and purified by column chromatography (hexane/ethyl acetate, 9:1 to 1:1) to give tert-butyl 8-((3-(((benzyloxy)carbonyl)amino)propyl) (8-(heptadecan-9-yloxy)-8-oxooctyl)amino)octanoate (14.3 g, 73%) as a colorless oil.

$^1$H NMR (300 MHz, CDCl$_3$): δ 0.84 (m, 6H); 1.10-1.64 (m, 59H); 2.17-2.32 (m, 8H); 2.42 (m, 2H); 3.26 (m, 2H); 4.84 (m, 1H); 5.07 (s, 2H); 6.20 (m, 1H); 7.29-7.35 (m, 5H).

tert-Butyl 8-((3-aminopropyl)(8-(heptadecan-9-yloxy)-8-oxooctyl)amino) octanoate

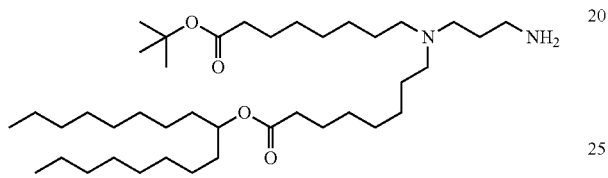

Chemical Formula: C$_{40}$H$_{80}$N$_2$O$_4$
Molecular Weight: 653.09

To a solution of tert-butyl 8-((3-(((benzyloxy)carbonyl)amino)propyl)(8-(heptadecan-9-yloxy)-8-oxooctyl)amino) octanoate (28.6 g, 36.3 mmol) in 500 mL ethanol was added palladium on carbon (3 g, 10% wet, matrix activated). The reaction mixture was stirred under a hydrogen balloon overnight. MS showed no more starting material, and the mixture was filtered through a pad of Celite. The filtrate was concentrated to give tert-butyl 8-((3-aminopropyl)(8-(heptadecan-9-yloxy)-8-oxooctyl)amino) octanoate (23.4 g, quant.) as a brown oil, which was used in the next step without further purification.

$^1$H NMR (300 MHz, CDCl$_3$): δ 0.84 (m, 6H); 1.22-1.71 (m, 61H); 2.18 (t, 2H, J=6.7 Hz); 2.25 (t, 2H, J=6.7 Hz); 2.32 (m, 4H); 2.39 (t, 2H, J=6.8 Hz); 2.70 (t, 2H, J=6.7 Hz); 4.86 (m, 1H).

tert-Butyl 8-((8-(heptadecan-9-yloxy)-8-oxooctyl)(3-((2-(methylamino)-3,4-dioxocyclobut-1-en-1-yl)amino)propyl)amino)octanoate

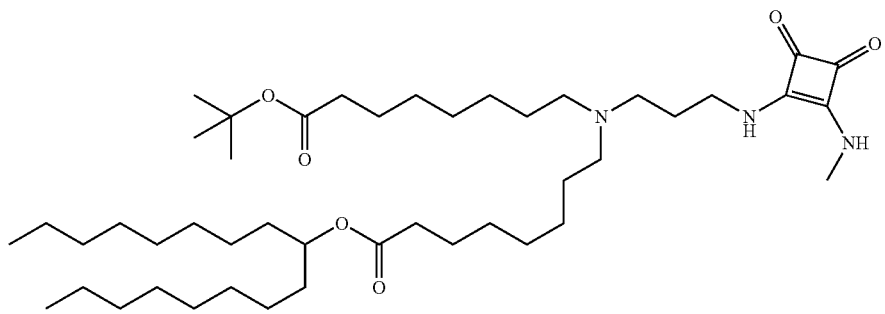

Chemical Formula: C$_{45}$H$_{83}$N$_3$O$_6$
Molecular Weight: 762.17

To a solution of tert-butyl 8-((3-aminopropyl)(8-(heptadecan-9-yloxy)-8-oxooctyl)amino) octanoate (23.47 g, 36 mmol) in 500 mL diethyl ether at 0° C., was added 3,4-dimethoxy cyclobut-3-ene-1,2-dione (5.63 g, 40 mmol) and the reaction mixture stirred at room temperature for 4 hours. Methylamine solution (2 Min methanol, 23.4 mL, 46.8 mmol) was added, and the reaction mixture stirred at room temperature overnight. The reaction mixture was concentrated, and the residue was triturated with 100 mL tetrahydrofuran. The solid was removed through a pad of Celite. The filtrate was concentrated and purified by column chromatography with dichloromethane to dichloromethane/methanol/NH$_4$OH (9:1:0.1) to give tert-butyl 8-((8-(heptadecan-9-yloxy)-8-oxooctyl)(3-((2-(methylamino)-3,4-dioxocyclobut-1-en-1-yl)amino)propyl)amino)octanoate (23 g, 86%) as a white wax.

HPLC/UV (254 nm, Method-B): RT=6.73 min. MS (CI): m/z (MH$^+$) 762.5 for C$_{45}$H$_{83}$N$_3$O$_6$. $^1$H NMR (300 MHz, CDCl$_3$): δ 0.84 (m, 6H); 1.22-1.64 (m, 57H); 1.78 (m, 2H); 2.18 (t, 2H, J=6.7 Hz); 2.26 (t, 2H, J=6.7 Hz); 8-((8-(Heptadecan-9-yloxy)-8-oxooctyl)(3-((2-(methylamino)-3,4-dioxocyclobut-1-en-1-yl)amino)propyl)amino)octanoic acid

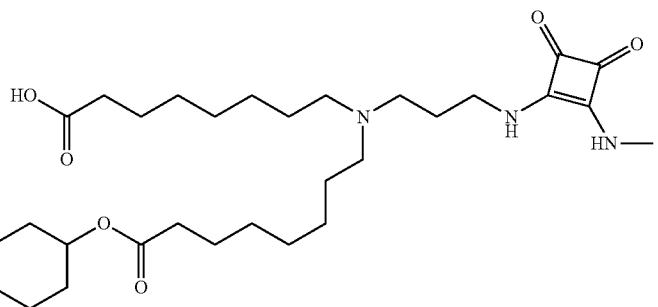

Chemical Formula: C$_{41}$H$_{75}$N$_3$O$_6$
Molecular Weight: 706.07

To a solution of tert-butyl 8-((8-(heptadecan-9-yloxy)-8-oxooctyl)(3-((2-(methylamino)-3,4-dioxocyclobut-1-en-1-yl)amino)propyl)amino)octanoate (450 mg, 0.59 mmol) in DCM (9.7 mL) was added trifluoroacetic acid (2.4 mL, 32.0 mmol) at 0° C. The resulting mixture was allowed to stir at room temperature for 4 h. The reaction mixture was then concentrated in vacuo and the crude residue was purified by silica gel chromatography (0-5-10-25-50-100% (mixture of 1% NH$_4$OH, 20% MeOH in dichloromethane) in dichloromethane) to give 8-((8-(heptadecan-9-yloxy)-8-oxooctyl)(3-((2-(methylamino)-3,4-dioxocyclobut-1-en-1-yl)amino)propyl)amino)octanoic acid (389 mg, 0.55 mmol, 93%) as a golden oil. UPLC/ELSD: RT=2.12 min. MS (ES): m/z (MH$^+$) 706.41 for C$_{41}$H$_{75}$N$_3$O$_6$. $^1$H NMR (300 MHz, CDCl$_3$) δ: ppm 11.42 (br. s, 1H); 9.29 (br. s, 1H); 8.64 (br. s, 1H); 4.83 (pent., 1H, J=6 Hz); 3.71 (br. t, 2H, J=6 Hz); 3.27 (br. s, 3H); 3.14 (br. t, 2H, J=6 Hz); 2.94 (br. t, 4H, J=6 Hz); 2.31-2.14 (m, 4H); 2.04 (br. s, 2H); 1.77-1.10 (m, 48H); 0.85 (t, 6H, J=6 Hz).

4-Methyleneundecane

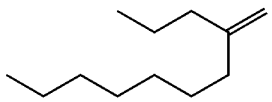

Chemical Formula: C$_{12}$H$_{24}$
Molecular Weight: 168.32

To a suspension of methyltriphenylphosphonium bromide (11 g, 31 mmol) in tetrahydrofuran at −78° C., was added n-BuLi solution (2.5 M in hexane, 16.8 mL, 40 mmol) dropwise. The reaction mixture was slowly warmed up to 0° C. for 3 hours until all the solid was dissolved. A solution of undecan-4-one (5 g, 29.5 mmol) in tetrahydrofuran was added, and then the reaction mixture was heated to reflux overnight. After the reaction mixture was cooled to room temperature, the solvent was removed under vacuum. The residue was purified by silica gel chromatography (pentane) to give 4-methyleneundecane (4.9 g, 99%) as colorless oil.

$^1$H NMR (300 MHz, CDCl$_3$): δ 0.87 (m, 6H); 1.22-1.36 (m, 12H); 1.97 (m, 4H); 4.68 (s, 2H).

2-Propylnonan-1-ol

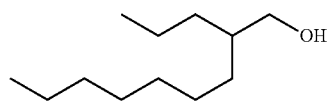

Chemical Formula: $C_{12}H_{26}O$
Molecular Weight: 186.34

To a solution of 4-methyleneundecane (4.9 g, 29.2 mmol) in tetrahydrofuran was added borane-tetrahydrofuran complex (1 M in THF, 36 mL) dropwise at 0° C. The reaction mixture was stirred at room temperature for 3 hours until TLC indicated no more starting material, and aqueous 4 M NaOH (40 mL) was added. After stirring for 10 min, 30% hydrogen peroxide (10 mL) was added and stirred for 4 hours. The reaction mixture was quenched by aqueous sodium bisulfite solution and extracted with ethyl acetate (50 mL×3). The combined organic layer was dried ($Na_2SO_4$), concentrated and purified by silica gel chromatography (hexane/ethyl acetate) to give 2-propylnonan-1-ol (4.2 g, 77%) as a colorless oil. $^1$H NMR (300 MHz, $CDCl_3$): δ 0.87 (m, 6H); 1.22-1.36 (m, 17H); 3.52 (d, 2H, J=5.5 Hz).

Heptadecan-9-yl 8-((3-((2-(methylamino)-3,4-dioxocyclobut-1-en-1-yl)amino)propyl)(8-oxo-8-((2-propylnonyl)oxy)octyl)amino)octanoate

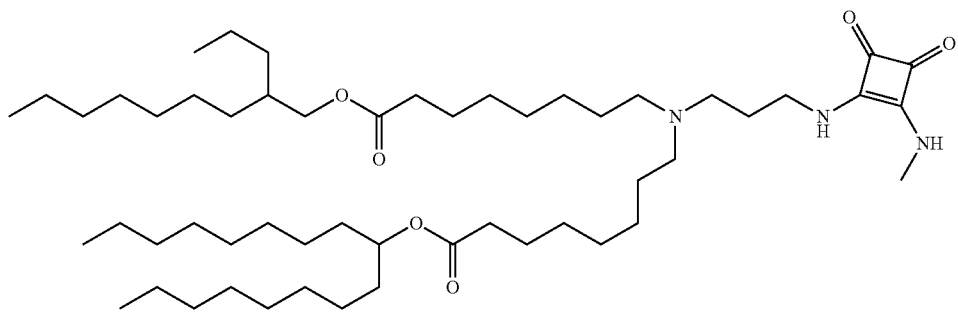

Chemical Formula: $C_{53}H_{99}N_3O_6$
Molecular Weight: 874.39

To a solution of 8-((8-(heptadecan-9-yloxy)-8-oxooctyl)(3-((2-(methylamino)-3,4-dioxocyclobut-1-en-1-yl)amino)propyl)amino)octanoic acid (830 mg, 1.17 mmol) in dichloromethane was added 2-propylnonan-1-ol (500 mg, 2.7 mmol), EDCI (1.3 g, 6.75 mmol) and 4-dimethylaminopyridine (33 mg, 0.27 mmol), and the mixture was stirred at room temperature overnight. The reaction was quenched with water and the organic layer was separated. The aqueous layer was extracted with dichloromethane (50 mL×3). The combined organics were dried ($Na_2SO_4$), concentrated and purified by silica gel chromatography)dichloromethane/methanol/$NH_4OH$ (9:1:0.1)) to give heptadecan-9-yl 8-((3-((2-(methylamino)-3,4-dioxocyclobut-1-en-1-yl)amino)propyl)(8-oxo-8-((2-propylnonyl)oxy)octyl)amino)octanoate (405 mg, 57%) as light yellow wax.

HPLC/UV (254 nm, Method-A): RT=7.04 min. MS (CI): m/z (MH$^+$) 874.7 for $C_{53}H_{99}N_3O_6$. $^1$H NMR (300 MHz, $CDCl_3$): δ 0.86 (m, 12H); 1.22-1.49 (m, 60H); 1.60 (m, 6H); 1.75 (m, 2H); 2.27 (m, 4H); 2.43 (m, 4H); 2.59 (m, 2H); 3.25 (d, 3H, J=4.9 Hz); 3.63 (m, 2H); 3.96 (d, 2H, J=5.7 Hz); 4.84 (m, 1H).

AF. Compound 10: 2-Butylnonyl 8-((8-(heptadecan-9-yloxy)-8-oxooctyl)(3-((2-(methyl amino)-3,4-dioxocyclobut-1-en-1-yl)amino)propyl)amino)octanoate 5-Methylenedodecane

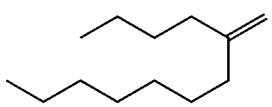

Chemical Formula: $C_{13}H_{26}$
Molecular Weight: 182.35

Same as procedure as for compound 9 but using dodecan-5-one instead of undecan-4-one.

$^1$H NMR (300 MHz, CDCl$_3$): δ 0.87 (m, 6H); 1.22-1.36 (m, 14H); 1.99 (m, 4H); 4.68 (s, 2H).

2-Butylnonan-1-ol

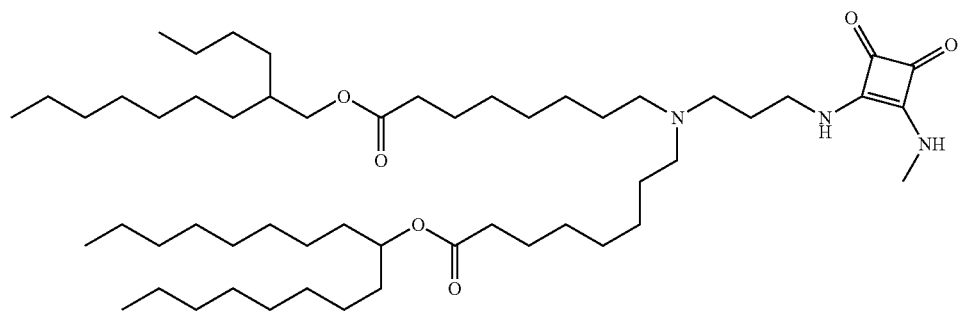

Chemical Formula: C$_{13}$H$_{28}$O
Molecular Weight: 200.37

Same as procedure as for compound 9 but using 5-methylenedodecane instead of 4-methyleneundecane.

$^1$H NMR (300 MHz, CDCl$_3$): δ 0.87 (m, 6H); 1.22-1.36 (m, 19H); 3.52 (d, 2H, J=5.5 Hz).

2-Butylnonyl 8-((8-(heptadecan-9-yloxy)-8-oxooctyl)(3-((2-(methyl amino)-3,4-dioxocyclobut-1-en-1-yl)amino)propyl)amino)octanoate

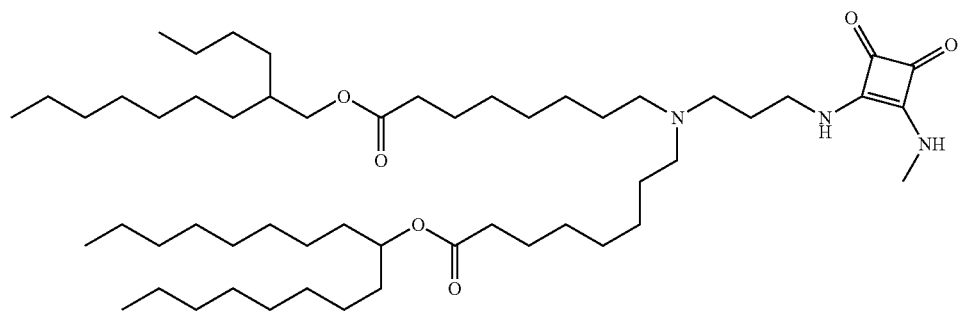

Chemical Formula: C$_{54}$H$_{101}$N$_3$O$_6$
Molecular Weight: 888.42

Same as procedure as for compound 9 but using 2-butylnonan-1-ol instead of 2-propylnonan-1-ol. Light yellow wax.

HPLC/UV (254 nm, Method-A): RT=6.98 min. MS (CI): m/z (MH$^+$) 888.7 for C$_{54}$H$_{101}$N$_3$O$_6$. $^1$H NMR (300 MHz, CDCl$_3$): δ 0.86 (m, 12H); 1.22-1.49 (m, 62H); 1.60 (m, 6H); 1.78 (m, 2H); 2.27 (m, 4H); 2.43 (m, 4H); 2.58 (m, 2H); 3.25 (d, 3H, J=4.8 Hz); 3.64 (m, 2H); 3.96 (d, 2H, J=5.8 Hz); 4.84 (m, 1H).

AG. Compound 11: 2-Ethylnonyl 8-((8-(heptadecan-9-yloxy)-8-oxooctyl)(3-((2-(methyl amino)-3,4-dioxocyclobut-1-en-1-yl)amino)propyl)amino)octanoate 3-Methylenedecane

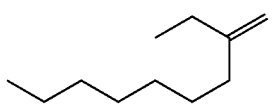

Chemical Formula: C$_{11}$H$_{22}$
Molecular Weight: 154.30

Same as procedure as for compound 9 but using decan-3-one instead of undecan-4-one. $^1$H NMR (300 MHz, CDCl$_3$): δ 0.87 (m, 6H); 1.22-1.36 (m, 10H); 1.99 (m, 4H); 4.68 (s, 2H).

2-Ethylnonan-1-ol

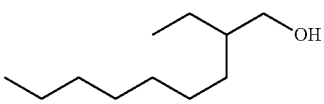

Chemical Formula: C$_{11}$H$_{24}$O
Molecular Weight: 172.31

Same as procedure as for compound 9 but using 3-methylenedecane instead of 4-methyleneundecane.

$^1$H NMR (300 MHz, CDCl$_3$): δ 0.87 (m, 6H); 1.22-1.36 (m, 15H); 3.52 (d, 2H, J=5.5 Hz).

2-Ethylnonyl 8-((8-(heptadecan-9-yloxy)-8-oxooctyl)(3-((2-(methyl amino)-3,4-dioxocyclobut-1-en-1-yl)amino)propyl)amino)octanoate

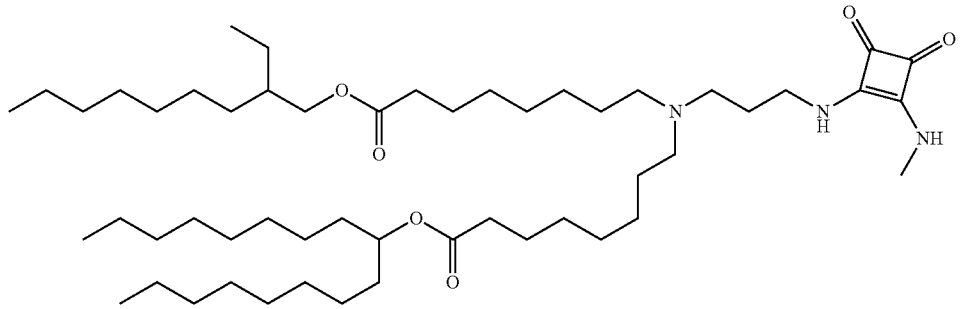

Chemical Formula: C$_{52}$H$_{97}$N$_3$O$_6$
Molecular Weight: 860.36

Same as procedure as for compound 9 but using 2-ethylnonan-1-ol instead of 2-propylnonan-1-ol. Light yellow wax.

HPLC/UV (254 nm, Method-A): RT=6.99 min. MS (CI): m/z (MH$^+$) 860.7 for C$_{52}$H$_{97}$N$_3$O$_6$. $^1$H NMR (300 MHz, CDCl$_3$): δ 0.86 (m, 12H); 1.22-1.49 (m, 58H); 1.60 (m, 5H); 1.78 (m, 2H); 2.26 (m, 4H); 2.43 (m, 4H); 2.58 (m, 2H); 3.25 (d, 3H, J=4.6 Hz); 3.64 (m, 2H); 3.96 (d, 2H, J=5.7 Hz); 4.84 (m, 1H); 7.43 (br, 2H).

AH. Compound 14: Undecan-3-yl 8-((3-((2-(methylamino)-3,4-dioxocyclobut-1-en-1-yl)amino)propyl)(6-((2-octyldecyl)oxy)-6-oxohexyl)amino)octanoate 2-Octyldecanoic acid

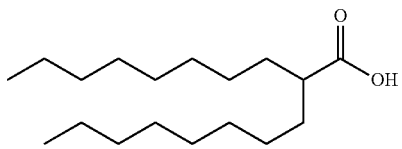

Chemical Formula: C$_{18}$H$_{36}$O$_2$
Molecular Weight: 284.48

A solution of diisopropylamine (2.92 mL, 20.8 mmol) in THF (10 mL) was cooled to −78° C. and a solution of n-BuLi (7.5 mL, 18.9 mmol, 2.5 M in hexanes) was added. The reaction was allowed to warm to 0° C. To a solution of decanoic acid (2.96 g, 17.2 mmol) and NaH (754 mg, 18.9 mmol, 60% w/w) in THF (20 mL) at 0° C. was added the solution of LDA and the mixture was allowed to stir at room temperature for 30 min. After this time 1-iodooctane (5 g, 20.8 mmol) was added and the reaction mixture was heated at 45° C. for 6 h. The reaction was quenched with 1N HCl (10 mL). The organic layer was dried over MgSO$_4$, filtered and evaporated under vacuum. The residue was purified by silica gel chromatography (0-20% ethyl acetate in hexanes) to yield 2-octyldecanoic acid (1.9 g, 6.6 mmol).

$^1$H NMR (300 MHz, CDCl$_3$) δ: ppm 2.38 (br. m, 1H); 1.74-1.03 (br. m, 28H); 0.91 (m, 6H).

2-Octyldecanol

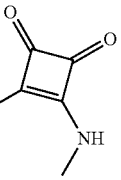

Chemical Formula: C$_{18}$H$_{38}$O$_2$
Molecular Weight: 270.50

A solution of 2-octyldecanoic acid (746 mg, 2.6 mmol) in dry THF (12 mL) was added to a stirred solution of LAH (5.2 mL, 5.2 mmol, 1M solution in THF) in dry THF (6 mL) under nitrogen at 0° C. The reaction was allowed to warm to room temperature and stirred at room temperature for 12 h. A solution of saturated Na$_2$SO$_4$*10H$_2$O solution (10 mL) was added. The solids were filtered through a plug of Celite. The filtrate was evaporated under vacuum and the residue was purified by silica gel chromatography (0-20% ethyl acetate in hexanes) to yield 2-octyldecan-1-ol (635 mg, 2.3 mmol).

$^1$H NMR (300 MHz, CDCl$_3$) δ: ppm 3.55 (d, 2H); 1.57-1.18 (m, 30H); 0.91 (m, 6H).

2-Octyldecyl 6-bromohexanoate

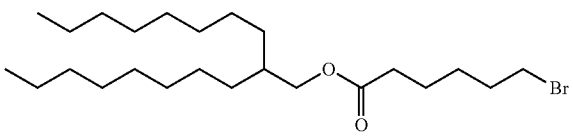

Chemical Formula: C$_{24}$H$_{47}$BrO$_2$
Molecular Weight: 447.54

To a solution of 6-bromohexanoic acid (606 mg, 3.1 mmol) and 2-octyldecanol (840 mg, 3.1 mmol) in dichloromethane (3.1 mL) was added N-(3-dimethylaminopropyl)-N'-ethylcarbodiimide hydrochloride (655 mg, 3.4 mmol), N,N-diisopropylethylamine (1.2 mL, 6.8 mmol) and DMAP (76 mg, 0.62 mmol). The reaction was allowed to stir at room temperature for 16 h. The reaction was diluted with dichloromethane and washed with saturated sodium bicarbonate. The organic layer was separated and washed with brine, and dried over MgSO$_4$. The organic layer was filtered and evaporated in vacuo. The residue was purified by silica gel chromatography (0-100% ethyl acetate in hexanes) to obtain 2-octyldecyl 6-bromohexanoate (849 mg, 1.9 mmol, 61%).

$^1$H NMR (300 MHz, CDCl$_3$) δ: ppm 4.01 (d, 2H); 3.56 (t, 0.24); 3.43 (t, 1.76); 2.35 (t, 2H); 1.99-1.43 (m, 8H); 1.29 (m, 27H); 0.91 (m, 6H).

Undecan-3-yl 8-bromooctanoate

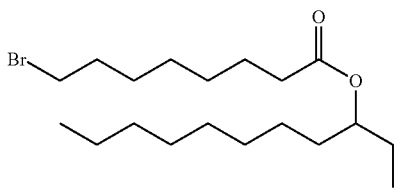

Chemical Formula: C$_{19}$H$_{37}$BrO$_2$
Molecular Weight: 377.41

To a solution of 3-undecanol (4.14 g, 24 mmol), 8-bromooctanoic acid (8.01 g, 36 mmol) and DMAP (0.58 g, 4.8 mmol) in dichloromethane (50 mL) at 0° C. was added EDCI (6.9 g, 36 mmol) and the reaction mixture stirred at room temperature overnight. TLC showed the reaction completed. The reaction mixture was cooled to 0° C. and a solution of hydrochloric acid (10 mL conc. HCl, 90 mL water, 7.5 g sodium chloride) was added very slowly over 20 minutes. Then acetonitrile (100 mL) and hexane (100 mL) were added, the layers separated and the organic layer dried and removed in vacuum to give an oil. The oil was dissolved in hexane (100 mL) and washed with a mixture of acetonitrile (100 mL) and 5% sodium bicarbonate (100 mL). The hexane layer was separated and filtered through Celite, which was then washed with hexane. The solvent was removed under vacuum to give undecan-3-yl 8-bromooctanoate (8.76 g, 97%) as colorless oil. Contains approximately 13% of the corresponding chloride.

$^1$H NMR (300 MHz, CDCl$_3$): δ ppm 4.82-4.76 (m, 1H); 3.39 (t, 2H, J=6.7 Hz); 2.44 (t, 0.3H, J=7.4 Hz, for CH$_2$Cl); 2.28 (t, 2H, J=7.5 Hz, for CH$_2$Br); 1.88-1.79 (m, 2H); 1.70-1.42 (m, 6H); 1.38-1.17 (m, 18H);

Undecan-3-yl 8-({3-[(tert-butoxycarbonyl)amino]propyl}amino)octanoate

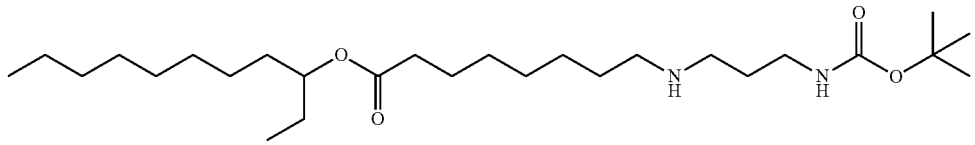

Chemical Formula: C$_{27}$H$_{54}$N$_2$O$_4$
Molecular Weight: 470.74

Prepared from tert-butyl N-(3-aminopropyl)carbamate analogously to compound 34 using undecan-3-yl 8-bromooctanoate instead of 4-pentylnonyl-8-bromooctanoate to give undecan-3-yl 8-({3-[(tert-butoxycarbonyl)amino]propyl}amino)octanoate.

Undecan-3-yl 8-((3-(((tert-butoxyoxycarbonyl)amino)propyl)(6-((2-octyldecyl)oxy)-6-oxohexyl)amino)octanoate

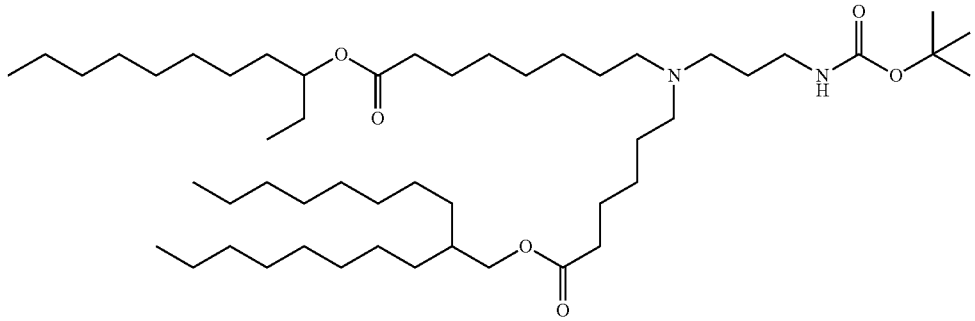

Chemical Formula: C$_{51}$H$_{100}$N$_2$O$_6$
Molecular Weight: 837.37

To a solution of 2-octyldecyl 6-bromohexanoate (0.4 g, 0.894 mmol) and undecan-3-yl 8-({3-[(tert-butoxycarbonyl)amino]propyl}amino)octanoate (0.501 g, 0.894 mmol) in 40 mL of a 1:1 mixture of cyclopropyl methyl ether and acetonitrile were added potassium carbonate (0.741 g, 5.363 mmol) and potassium iodide (0.163 g, 0.983 mmol). The reaction was heated to 77° C. and stirred for 16 hours. The mixture was cooled to room temp., filtered, and the filtrate evaporated under vacuum. The residue was purified by silica gel chromatography (0-100% (solution of 20% MeOH, 80% DCM, 1% NH$_4$OH) in DCM) to give undecan-3-yl 8-((3-(((tert-butoxycarbonyl)amino)propyl)(6-((2-octyldecyl)oxy)-6-oxohexyl)amino)octanoate (323 mg, 0.39 mmol, 43%).

UPLC/ELSD: RT=3.15 min. MS (ES): m/z (MH$^+$) 837.525 for C$_{51}$H$_{100}$N$_2$O$_6$. $^1$H NMR (300 MHz, CDCl$_3$) δ: ppm 5.64 (bm, 1H), 4.83 (p, 1H); 3.98 (d, 2H); 3.19 (bm, 2H); 2.55-2.23 (m, 10H); 1.75-1.18 (m, 72H); 0.90 (m, 12H).

Undecan-3-yl 8-((3-aminopropyl)(6-((2-octyldecyl)oxy)-6-oxohexyl)amino)octanoate

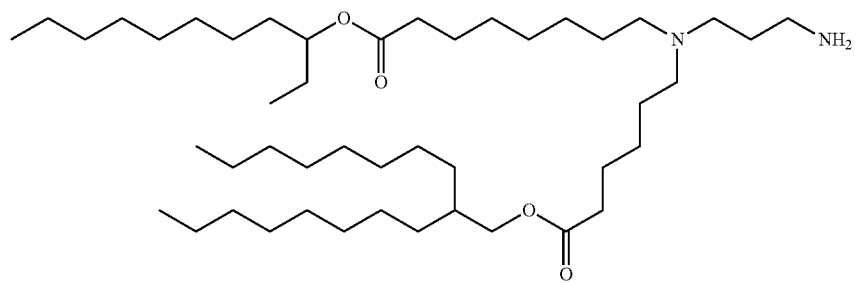

Chemical Formula: C$_{46}$H$_{92}$N$_2$O$_4$
Molecular Weight: 737.25

To a solution of undecan-3-yl 8-({3-[(tert-butoxycarbonyl)amino]propyl}({6-[(2-octyldecyl)oxy]-6-oxohexyl})amino)octanoate (0.277 g, 0.331 mmol) in DCM (10 mL) was added trifluoroacetic acid (0.506 mL, 6.62 mmol). The reaction was allowed to stir at RT for 4 h. The reaction was diluted with DCM and slowly quenched with a saturated aqueous sodium bicarbonate solution. The organic layer was separated, washed with brine, dried with $Na_2SO_4$, filtered and evaporated under vacuum to give undecan-3-yl 8-((3-aminopropyl)(6-((2-octyldecyl)oxy)-6-oxohexyl)amino)octanoate (0.24 g, 0.33 mmol, quant.) which was taken to the next step without further purification.

UPLC/ELSD: RT=2.79 min. MS (ES): m/z (MH$^+$) 737.613 for $C_{46}H_{92}N_2O_4$.

3-Methoxy-4-(methylamino)cyclobut-ene-1,2-dione

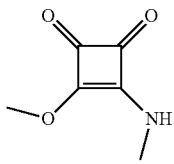

Chemical Formula: $C_6H_7NO_3$
Molecular Weight: 141.13

To a solution of 3,4-dimethoxy-3-cyclobutene-1,2-dione (1 g, 7 mmol) in 100 mL diethyl ether was added a 2M methylamine solution in THF (3.8 mL, 7.6 mmol) and a ppt. formed almost immediately. The mixture was stirred at room temperature for 24 hours, then filtered, the filter solids washed with diethyl ether and air-dried. The filter solids were dissolved in hot EtOAc, filtered, the filtrate allowed to cool to room temp., then cooled to 0° C. to give a ppt. This was isolated via filtration, washed with cold EtOAc, air-dried, then dried under vacuum to give 3-methoxy-4-(methylamino)cyclobut-3-ene-1,2-dione (0.70 g, 5 mmol, 73%) as a white solid.

$^1$H NMR (300 MHz, DMSO-d$_6$) δ: ppm 8.50 (br. d, 1H, J=69 Hz); 4.27 (s, 3H); 3.02 (sdd, 3H, J=42 Hz, 4.5 Hz).

Undecan-3-yl 8-((3-((2-(methylamino)-3,4-dioxocyclobut-1-en-1-yl)amino)propyl)(6-((2-octyldecyl)oxy)-6-oxohexyl)amino)octanoate

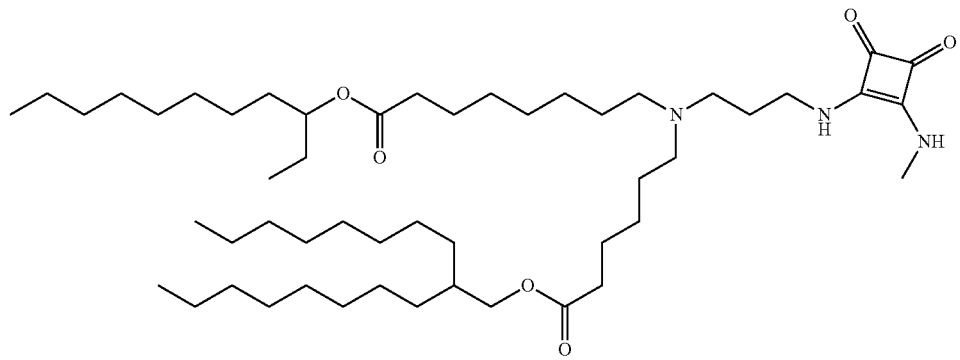

Chemical Formula: $C_{51}H_{95}N_3O_6$
Molecular Weight: 846.34

3-Methoxy-4-(methylamino)cyclobut-3-ene-1,2-dione (69 mg, 0.49 mmol) was reacted as in Compound 34 using undecan-3-yl 8-((3-aminopropyl)(6-((2-octyldecyl)oxy)-6-oxohexyl)amino)octanoate instead of bis(4-pentylnonyl)-8,8'-((3-aminopropyl)azanediyl)dioctanoate to give undecan-3-yl 8-((3-((2-(methylamino)-3,4-dioxocyclobut-1-en-1-yl)amino)propyl)(6-((2-octyldecyl)oxy)-6-oxohexyl)amino)octanoate (80 mg, 0.09 mmol, 29%).

UPLC/ELSD: RT=2.99 min. MS (ES): m/z (MH$^+$) 847.392 for $C_{51}H_{95}N_3O_6$. $^1$H NMR (300 MHz, CDCl$_3$) δ: ppm 4.82 (p, 1H); 3.97 (m, 2H); 3.69 (m, 2H); 3.29 (m, 3H); −2.62-2.25 (m, 10H); 1.85-1.17 (m, 64H); 0.91 (m, 12H).

AI. Compound 15: Undecan-3-yl 8-((6-((2-hexyldecyl)oxy)-6-oxohexyl)(3-((2-(methylamino)-3,4-dioxocyclobut-1-en-1-yl)amino)propyl)amino)octanoate

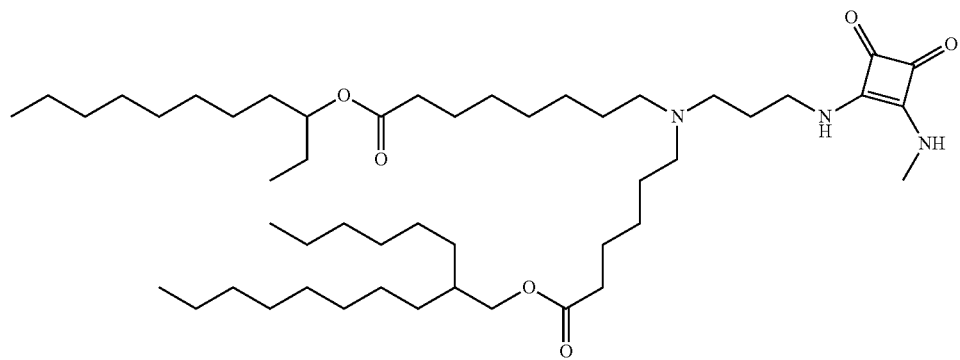

Chemical Formula: $C_{49}H_{91}N_3O_6$
Molecular Weight: 818.28

Compound 15 was prepared analogously to compound 14 starting from decanoic acid and using 1-iodohexane instead of 1-iodooctane.

UPLC/ELSD: RT=2.86 min. MS (ES): m/z (MH$^+$) 819.269 for $C_{49}H_{91}N_3O_6$. $^1$H NMR (300 MHz, CDCl$_3$) δ: ppm 4.78 (m, 1H); 3.95 (m, 2H); 3.63 (m, 2H); 3.28 (m, 3H); 2.59-2.20 (m, 13H); 1.83-1.16 (m, 58H); 0.87 (m, 12H).

AJ. Compound 16: Heptadecan-9-yl 8-((3-((2-(methylamino)-3,4-dioxocyclobut-1-en-1-yl)amino)propyl)(8-oxo-8-((2-pentylnonyl)oxy)octyl)amino)octanoate

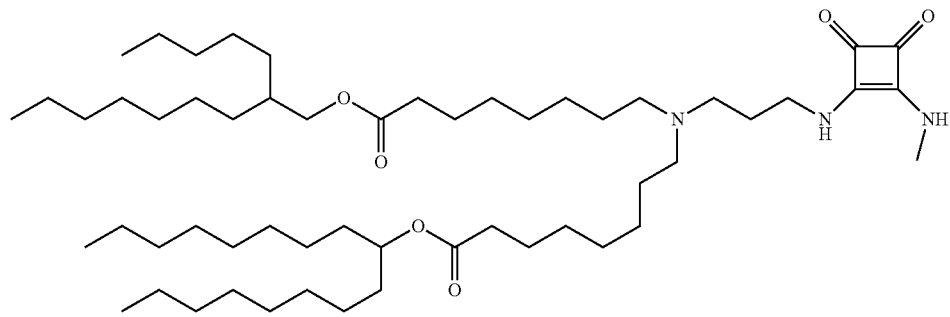

Chemical Formula: $C_{55}H_{103}N_3O_6$
Molecular Weight: 902.44

To a solution of 8-{[8-(heptadecan-9-yloxy)-8-oxooctyl](3-{[2-(methylamino)-3,4-dioxocyclobut-1-en-1-yl]amino}propyl)amino}octanoic acid (400 mg, 0.56 mmol) and 2-pentylnonan-1-ol (364 mg, 1.7 mmol) in 5.6 mL dry DCM was added 4-(dimethylamino)pyridine (35.0 mg, 0.28 mmol) and dicyclohexyl carbodiimide (369 mg, 1.7 mmol). The solution was stirred at room temperature for 18 hours, after which no starting alcohol remained by LC/MS. The mixture was diluted with a DCM and washed twice with aqueous saturated sodium bicarbonate solution, dried (MgSO$_4$), filtered and conc. The residue was purified by silica gel chromatography (0-50% (mixture of 1% NH$_4$OH, 20% MeOH in dichloromethane) in dichloromethane) to give heptadecan-9-yl 8-((3-((2-(methylamino)-3,4-dioxocyclobut-1-en-1-yl)amino)propyl)(8-oxo-8-((2-pentylnonyl)oxy)octyl)amino)octanoate (154 mg, 0.17 mmol, 30%) as a white waxy solid.

UPLC/ELSD: RT=3.04 min. MS (ES): m/z (MH$^+$) 903.8 for C$_{55}$H$_{103}$N$_3$O$_6$. $^1$H NMR (300 MHz, CDCl$_3$) δ: ppm 5.32 (s, 1H); 4.87 (quint., 1H, J=6 Hz); 4.00 (d, 2H, J=6 Hz); 3.68 (br. s, 2H); 3.29 (d, 3H, J=6 Hz); 2.65 (br. s, 2H); 2.51 (br. m, 4H); 2.33 (m, 5H); 1.81 (br. m, 3H); 1.64 (br. m, 6H); 1.52 (br. m, 9H); 1.28 (br. s, 61H); 0.88 (br. t, 13H, J=7.5 Hz).

AK. Compound 17: Heptadecan-9-yl 8-({8-[(3-isopropylnonyl)oxy]-8-oxooctyl}(3-{[2-(methylamino)-3,4-dioxocyclobut-1-en-1-yl]amino}propyl)amino)octanoate

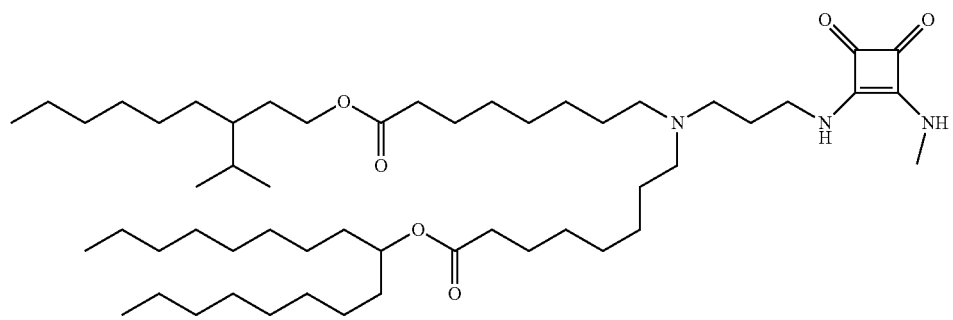

Chemical Formula: C$_{53}$H$_{99}$N$_3$O$_6$
Molecular Weight: 847.39

To a solution of 8-{[8-(heptadecan-9-yloxy)-8-oxooctyl](3-{[2-(methylamino)-3,4-dioxocyclobut-1-en-1-yl]amino}propyl)amino}octanoic acid (400 mg, 0.57 mmol) and 3-isopropylnonan-1-ol (317 mg, 1.7 mmol) in 5.6 mL dry DCM was added 4-(dimethylamino)pyridine (35.0 mg, 0.28 mmol) and dicyclohexylcarbodiimide (369 mg, 1.7 mmol). The solution was stirred at room temperature for 18 hours, after which no starting alcohol remained by LC/MS. The mixture was diluted with a DCM and washed twice with aqueous saturated sodium bicarbonate solution, dried (MgSO$_4$), filtered and conc. The residue was purified by silica gel chromatography (0-50% (mixture of 1% NH$_4$OH, 20% MeOH in dichloromethane) in dichloromethane) to give heptadecan-9-yl 8-({8-[(3-isopropylnonyl)oxy]-8-oxooctyl}(3-{[2-(methylamino)-3,4-dioxocyclobut-1-en-1-yl]amino}propyl)amino)octanoate (202 mg, 0.23 mmol, 41%) as a white waxy solid.

UPLC/ELSD: RT=2.92 min. MS (ES): m/z (MH$^+$) 875.5 for C$_{53}$H$_{99}$N$_3$O$_6$. $^1$H NMR (300 MHz, CDCl$_3$) δ: ppm 5.32 (s, 1H); 4.87 (quint., 1H, J=6 Hz); 4.08 (m, 2H, J=7 Hz); 3.67 (br. s, 2H); 3.30 (d, 3H, J=5 Hz); 2.64 (br. s, 2H); 2.51 (br. m, 4H); 2.31 (m, 5H); 1.81 (br. m, 3H); 1.64 (br. m, 6H); 1.52 (br. m, 9H); 1.28 (br. s, 46H); 0.90 (br. m, 15H).

AL. Compound 18: Heptadecan-9-yl 8-[(3-{[2-(methylamino)-3,4-dioxocyclobut-1-en-1-yl]amino}propyl)({8-oxo-8-[(3-propylnonyl)oxy]octyl})amino]octanoate

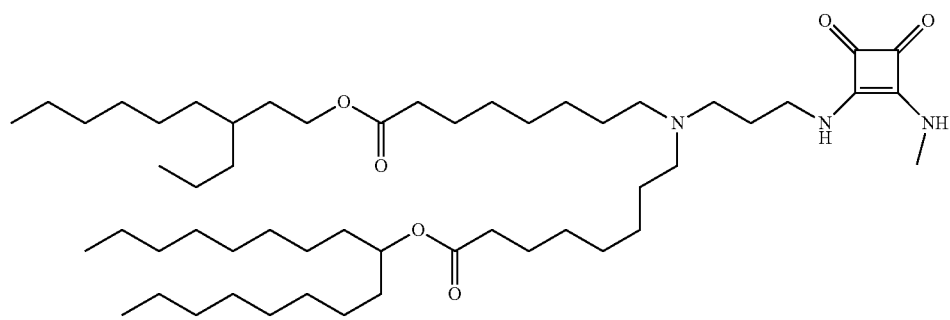

Chemical Formula: $C_{53}H_{99}N_3O_6$
Molecular Weight: 874.39

To a solution of 8-{[8-(heptadecan-9-yloxy)-8-oxooctyl](3-{[2-(methylamino)-3,4-dioxocyclobut-1-en-1-yl]amino}propyl)amino}octanoic acid (400 mg, 0.57 mmol) and 3-propylnonan-1-ol (317 mg, 1.7 mmol) in 5.6 mL dry DCM was added 4-(dimethylamino)pyridine (35.0 mg, 0.28 mmol) and dicyclohexylcarbodiimide (369 mg, 1.7 mmol). The solution was stirred at room temperature for 18 hours, after which no starting alcohol remained by LC/MS. The mixture was diluted with a DCM and washed twice with aqueous saturated sodium bicarbonate solution, dried (MgSO$_4$), filtered and conc. The residue was purified by silica gel chromatography (0-50% (mixture of 1% NH$_4$OH, 20% MeOH in dichloromethane) in dichloromethane) to give heptadecan-9-yl 8-[(3-{[2-(methylamino)-3,4-dioxocyclobut-1-en-1-yl]amino}propyl)({8-oxo-8-[(3-propylnonyl)oxy]octyl})amino]octanoate (206 mg, 0.24 mmol, 42%) as a white waxy solid.

UPLC/ELSD: RT=2.93 min. MS (ES): m/z (MH$^+$) 875.5 for $C_{53}H_{99}N_3O_6$. $^1$H NMR (300 MHz, CDCl$_3$) δ: ppm 5.32 (s, 2H); 4.87 (quint., 1H, J=5 Hz); 4.10 (t, 2H, J=8 Hz); 3.68 (br. s, 2H); 3.30 (d, 3H, J=5 Hz); 2.67 (br. s, 2H); 2.53 (br. m, 4H); 2.31 (t, 5H, J=7 Hz); 1.83 (br. m, 3H); 1.62 (br. m, 7H); 1.51 (br. m, 10H); 1.28 (br. s, 52H); 0.90 (br. m, 13H).

AM. Compound 19: Heptadecan-9-yl 8-({8-[(2-isopropylnonyl)oxy]-8-oxooctyl}(3-{[2-(methylamino)-3,4-dioxocyclobut-1-en-1-yl]amino}propyl)amino)octanoate

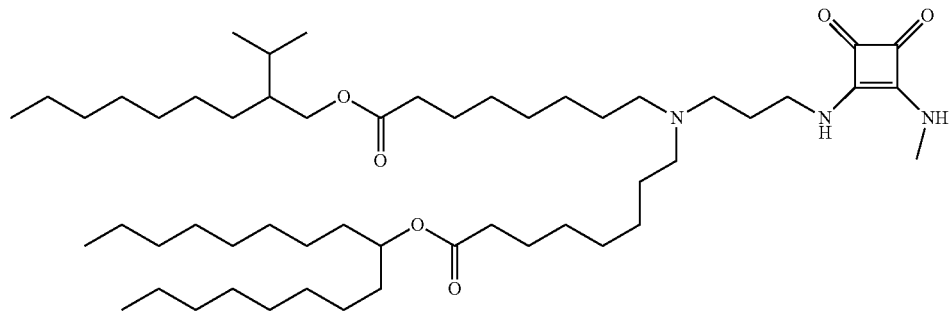

Chemical Formula: $C_{53}H_{99}N_3O_6$
Molecular Weight: 874.39

To a solution of 8-{[8-(heptadecan-9-yloxy)-8-oxooctyl](3-{[2-(methylamino)-3,4-dioxocyclobut-1-en-1-yl]amino}propyl)amino}octanoic acid (400 mg, 0.57 mmol) and 3-propylnonan-1-ol (317 mg, 1.7 mmol) in 5.6 mL dry DCM was added 4-(dimethylamino)pyridine (35.0 mg, 0.28 mmol) and dicyclohexylcarbodiimide (369 mg, 1.7 mmol). The solution was stirred at room temperature for 18 hours, after which no starting alcohol remained by LC/MS. The mixture was diluted with a DCM and washed twice with aqueous saturated sodium bicarbonate solution, dried (MgSO$_4$), filtered and conc. The residue was purified by silica gel chromatography (0-50% (mixture of 1% NH$_4$OH, 20% MeOH in dichloromethane) in dichloromethane) to give heptadecan-9-yl 8-({8-[(2-isopropylnonyl)oxy]-8-oxooctyl}(3-{[2-(methylamino)-3,4-dioxocyclobut-1-en-1-yl]amino}propyl)amino)octanoate (163 mg, 0.19 mmol, 33%) as a white waxy solid.

UPLC/ELSD: RT=2.95 min. MS (ES): m/z (MH$^+$) 875.5 for C$_{53}$H$_{99}$N$_3$O$_6$. $^1$H NMR (300 MHz, CDCl$_3$) δ: ppm 5.23 (s, 1H); 4.87 (quint., 1H, J=6 Hz); 3.94 (m, 2H, J=5 Hz); 3.60 (br. s, 2H); 3.20 (d, 3H, J=6 Hz); 2.94 (s, 1H); 2.57 (br. s, 2H); 2.43 (br. m, 4H); 2.23 (br. m, 5H); 1.73 (br. m, 4H); 1.55 (br. m, 4H); 1.41 (br. m, 9H); 1.19 (br. s, 45H); 0.81 (br. m, 14H).

AN. Compound 20: 3-Butylnonyl 8-{[8-(heptadecan-9-yloxy)-8-oxooctyl](3-{[2-(methylamino)-3,4-dioxocyclobut-1-en-1-yl]amino}propyl)amino}octanoate

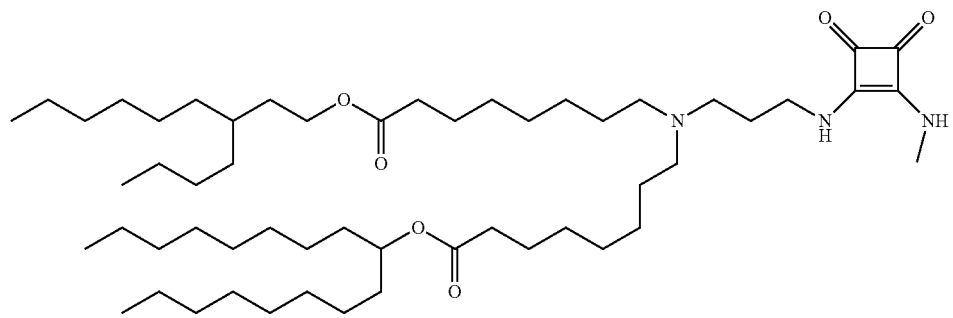

Chemical Formula: C$_{54}$H$_{101}$N$_3$O$_6$
Molecular Weight: 888.42

To a solution of 8-{[8-(heptadecan-9-yloxy)-8-oxooctyl](3-{[2-(methylamino)-3,4-dioxocyclobut-1-en-1-yl]amino}propyl)amino}octanoic acid (400 mg, 0.57 mmol) and 3-butylnonan-1-ol (341 mg, 1.7 mmol) in 5.6 mL dry DCM was added 4-(dimethylamino)pyridine (35.0 mg, 0.28 mmol) and dicyclohexylcarbodiimide (369 mg, 1.7 mmol). The solution was stirred at room temperature for 18 hours, after which no starting alcohol remained by LC/MS. The mixture was diluted with a DCM and washed twice with aqueous saturated sodium bicarbonate solution, dried (MgSO$_4$), filtered and conc. The residue was purified by silica gel chromatography (0-50% (mixture of 1% NH$_4$OH, 20% MeOH in dichloromethane) in dichloromethane) to give 3-butylnonyl 8-{[8-(heptadecan-9-yloxy)-8-oxooctyl](3-{[2-(methylamino)-3,4-dioxocyclobut-1-en-1-yl]amino}propyl)amino}octanoate (116 mg, 0.13 mmol, 23%) as a white waxy solid. UPLC/ELSD: RT=3.01 min. MS (ES): m/z (MH$^+$) 888.7 for C$_{54}$H$_{101}$N$_3$O$_6$. $^1$H NMR (300 MHz, CDCl$_3$) δ: ppm 5.23 (s, 1H); 4.78 (quint., 1H, J=6 Hz); 4.01 (m, 2H, J=5 Hz); 3.58 (br. s, 2H); 3.20 (d, 3H, J=6 Hz); 2.50 (br. s, 2H); 2.37 (br. m, 4H); 2.22 (br. t, 4H); 1.69 (br. m, 5H); 1.55 (br. m, 6H); 1.43 (br. m, 5H); 1.35 (br. m, 5H); 1.19 (br. s, 50H); 0.81 (br. m, 12H).

AO. Compound 21: Heptadecan-9-yl 8-((8-((3-hexylnonyl)oxy)-8-oxooctyl)(2-hydroxyethyl)amino)octanoate

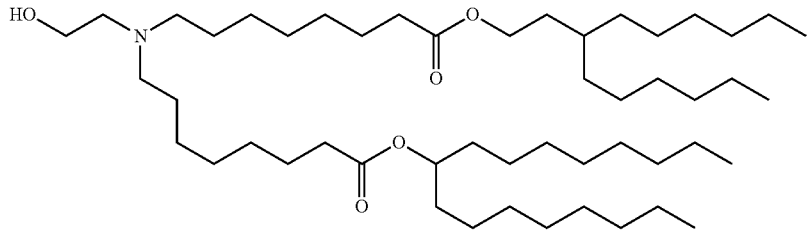

Chemical Formula: C$_{50}$H$_{99}$NO$_5$
Molecular Weight: 794.34

UPLC/ELSD: RT=3.20 min. MS (ES): m/z (MH$^+$) 795.093 for C$_{50}$H$_{99}$NO$_5$. $^1$H NMR (300 MHz, CDCl$_3$) δ: ppm 4.89 (p, 1H); 4.10 (t, 2H); 3.56 (m, 2H); 2.67-2.41 (m, 6H); 2.30 (m, 4H), 1.74-1.17 (m, 72H); 0.90 (m, 12H).

AP. Compound 22: 3-Butylheptyl 8-((8-(heptadecan-9-yloxy)-8-oxooctyl)(2-hydroxyethyl)amino)octanoate Step 1: Heptadecan-9-yl 8-((2-hydroxyethyl)amino)octanoate

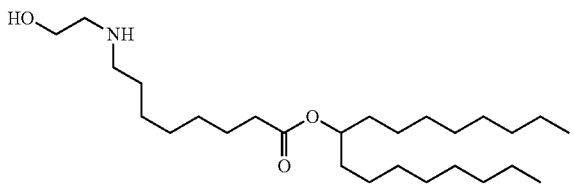 [SMILES: CCCCCCCCC(CCCCCCCC)OC(=O)CCCCCCCNCCO]

A solution of heptadecan-9-yl 8-bromooctanoate (10 g, 21.67 mmol) and ethanolamine (39.70 g, 649.96 mmol) in EtOH (5 mL) was heated to 65° C. for 16 h. The reaction was cooled to rt and dissolved in ethyl acetate and extracted with water (4×). The organic layer was separated, washed with brine, dried with Na$_2$SO$_4$, filtered and evaporated under vacuum. The residue was purified by flash chromatography (ISCO) by 0-100% (a solution of 20% MeOH, 80% DCM, 1% NH$_4$OH) in DCM to obtain heptadecan-9-yl 8-((2-hydroxyethyl)amino)octanoate (7.85 g, 82%).

UPLC/ELSD: RT=2.06 min. MS (ES): m/z (MH$^+$) 442.689 for C$_{27}$H$_{55}$NO$_3$. $^1$H NMR (300 MHz, CDCl$_3$) δ: ppm 4.89 (p, 1H); 3.66 (t, 2H); 2.79 (t, 2H); 2.63 (m, 2H); 2.30 (t, 2H); 1.77-1.20 (m, 40H); 0.90 (m, 6H).

Step 2: Compound 22: 3-Butylheptyl 8-((8-(heptadecan-9-yloxy)-8-oxooctyl)(2-hydroxyethyl)amino)octanoate

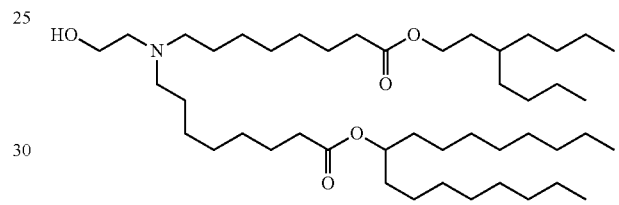

To a solution of 3-butylheptyl 8-bromooctanoate (6.15 g, 16.31 mmol) and heptadecan-9-yl 8-((2-hydroxyethyl)amino)octanoate (6.86 g, 15.53 mmol) in a mixture of CPME (15 mL) and acetonitrile (6 mL) was added potassium carbonate (8.59 g, 62.12 mmol) and potassium iodide (2.84 g, 17.08 mmol). The reaction was allowed to stir at 77° C. for 16 h. The reaction was cooled and filtered, and the volatiles were evaporated under vacuum. The residue was purified by flash chromatography (ISCO) by 0-100% (a solution of 20% MeOH, 80% DCM, 1% NH$_4$OH) in DCM to obtain 3-butylheptyl 8-((8-(heptadecan-9-yloxy)-8-oxooctyl)(2-hydroxyethyl)amino)octanoate (4.53 g, 37.8%).

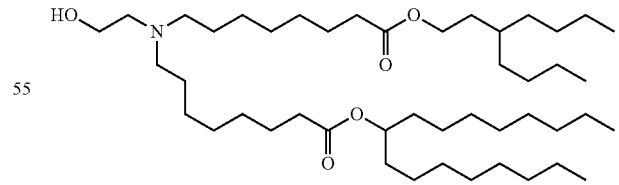

Chemical Formula: C$_{46}$H$_{91}$NO$_5$
Molecular Weight: 738.24

UPLC/ELSD: RT=3.04 min. MS (ES): m/z (MH$^+$) 739.464 for C$_{46}$H$_{91}$NO$_5$. $^1$H NMR (300 MHz, CDCl$_3$) δ: ppm 4.89 (p, 1H); 4.11 (m, 2H), 3.57 (bm, 2H); 2.73-2.39 (m, 6H); 2.30 (m, 4H); 1.72-1.17 (m, 64H); 0.92 (m, 12H).

AQ. Compound 23: Bis(3-hexylnonyl) 8,8'-((2-hydroxyethyl)azanediyl)dioctanoate

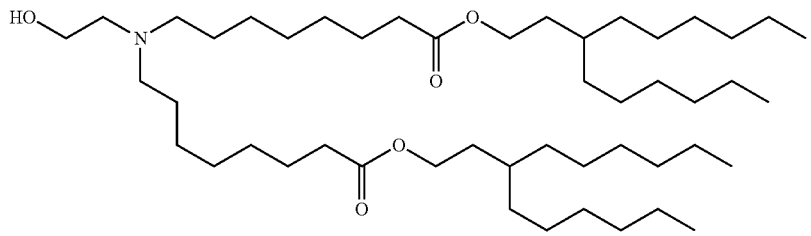

Chemical Formula: C$_{48}$H$_{95}$NO$_5$
Molecular Weight: 766.29

UPLC/ELSD: RT=3.11 min. MS (ES): m/z (MH$^+$) 767.710 for C$_{48}$H$_{95}$NO$_5$. $^1$H NMR (300 MHz, CDCl$_3$) δ: ppm 4.10 (m, 4H); 3.55 (bm, 2H); 2.65-2.37 (m, 6H); 2.31 (m, 4H); 1.72-1.16 (m, 67H); 0.91 (m, 12H).

AR. Compound 24: Heptadecan-9-yl 8-((2-hydroxyethyl)(8-oxo-8-((3-pentyloctyl)oxy)octyl) amino) octanoate

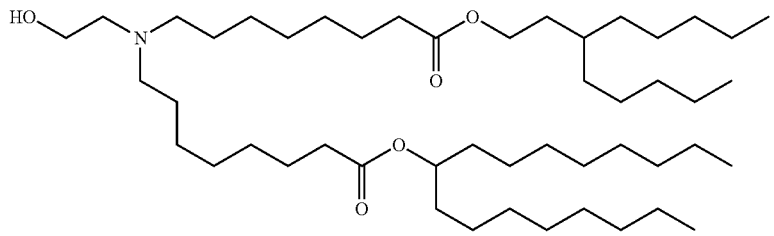

Chemical Formula: C$_{48}$H$_{95}$NO$_5$
Molecular Weight: 766.29

UPLC/ELSD: RT=3.13 min. MS (ES): m/z (MH$^+$) 767.586 for C$_{48}$H$_{95}$NO$_5$. $^1$H NMR (300 MHz, CDCl$_3$) δ: ppm 4.89 (p, 1H); 4.10 (t, 2H); 3.56 (bm, 2H), 2.68-2.40 (m, 6H); 2.30 (m, 4H); 1.74-1.18 (m, 68H); 0.91 (m, 12H).

AS. Compound 25: Bis(3-pentyloctyl) 8,8'-((2-hydroxyethyl)azanediyl)dioctanoate

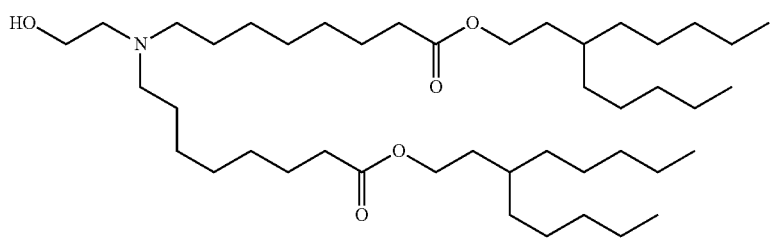

Chemical Formula: C$_{44}$H$_{87}$NO$_5$
Molecular Weight: 710.18

UPLC/ELSD: RT=2.86 min. MS (ES): m/z (MH⁺) 711.341 for $C_{44}H_{87}NO_5$. $^1$H NMR (300 MHz, CDCl$_3$) δ: ppm 4.10 (t, 4H); 3.55 (m, 2H); 2.65-2.38 (m, 6H), 2.31 (m, 4H); 1.73-1.16 (m, 59); 0.91 (m, 12H).

AT. Compound 26: Heptadecan-9-yl 8-((8-((3-hexylnonyl)oxy)-8-oxooctyl)(3-((2-(methylamino)-3,4-dioxocyclobut-1-en-1-yl)amino)propyl)amino)octanoate Ethyl 3-hexylnon-2-enoate

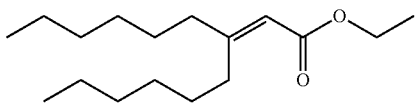

Chemical Formula: $C_{17}H_{32}O_2$
Molecular Weight: 268.44

Triethyl phosphonoacetate (26.33 g, 117.4 mmol) was added dropwise over 20 minutes to a suspension of sodium hydride (4.697 g, 117.4 mmol) in THF (294 mL) and the mixture was stirred at room temperature until gas evolution ceased (approximately 30 min). The reaction mixture was chilled to 0° C. and 7-tridecanone (10 g, 58.7 mmol) was added. The reaction was gradually warmed to room temperature, then heated to reflux and stirred overnight. The reaction was quenched with saturated aqueous sodium bicarbonate. The aqueous phase was extracted with diethyl ether, and the organic extracts were washed with brine, dried with MgSO$_4$, and concentrated. The crude material was purified by silica gel chromatography (0-20% EtOAc:hexanes) to afford ethyl 3-hexylnon-2-enoate (6.7 g, 27.9 mmol, 47.5%) as a clear oil.

$^1$H NMR (300 MHz, CDCl$_3$) δ: ppm 5.63 (s, 1H); 4.15 (q, 2H); 2.61 (t, 2H); 2.15 (t, 2H); 1.53-1.20 (m, 19H); 0.91 (m, 6H).

Ethyl 3-hexylnonanoate

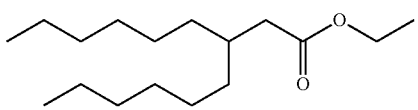

Chemical Formula: $C_{17}H_{34}O_2$
Molecular Weight: 270.46

To a flask containing a slurry of Pearlmans catalyst (0.73 g, 5.2 mmol) in ethanol (20 mL) under N$_2$ was added a solution of ethyl 3-hexylnon-2-enoate (6.975 g, 25.9 mmol) in ethanol (5 mL). The reaction was stirred under H$_2$ (balloon) for 16 h. The reaction was filtered through a plug of Celite and the filtrate was evaporated under vacuum to afford ethyl 3-hexylnonanoate (6.7 g, 24.7 mmol, 95%). The residue was taken to the next step without further purification.

$^1$H NMR (300 MHz, CDCl$_3$) δ: ppm 4.16 (q, 2H); 2.23 (d, 2H); 1.86 (bs, 1H); 1.28 (m, 23H); 0.90 (m, 6H).

3-Hexylnonan-1-ol

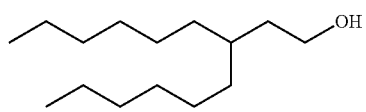

Chemical Formula: $C_{15}H_{32}O$
Molecular Weight: 228.42

To a solution of lithium aluminum hydride (49.5 mL of 1M solution in THF, 49.5 mmol) in THF was added a solution of ethyl 3-hexylnonanoate (6.7 g, 24.7 mmol) in THF (20 mL). The reaction was stirred at room temperature for 16 h. The reaction was quenched with a saturated solution of sodium sulfate decahydrate. The white solids were removed by filtration through a plug of Celite and the filtrate was evaporated under vacuum. The residue was purified by flash chromatography (ISCO) by 0-100% ethyl acetate in hexanes to obtain 3-hexylnonan-1-ol (5.62 g, 24.6 mmol).

Heptadecan-9-yl 8-((8-((3-hexylnonyl)oxy)-8-oxooctyl)(3-((2-(methylamino)-3,4-dioxocyclobut-1-en-1-yl)amino)propyl)amino)octanoate

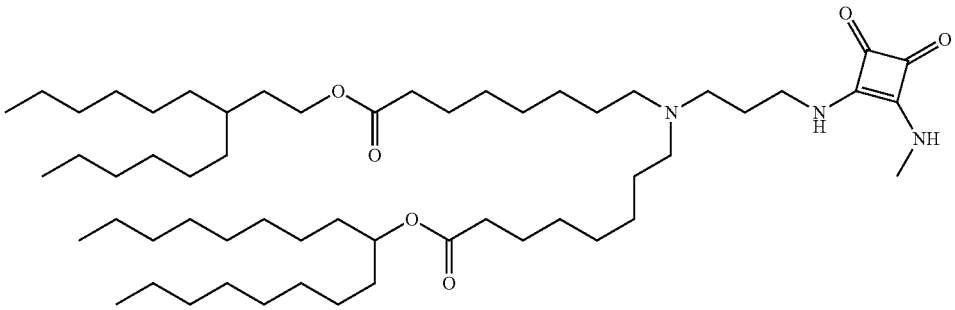

Chemical Formula: $C_{56}H_{105}N_3O_6$
Moelcular Weight: 916.47

Heptadecan-9-yl 8-((8-((3-hexylnonyl)oxy)-8-oxooctyl)(3-((2-(methylamino)-3,4-dioxocyclobut-1-en-1-yl)amino)propyl)amino)octanoate was prepared analogously to compound 9 using 3-hexylnonan-1-ol instead of 2-propylnonan-1-ol.

UPLC/ELSD: RT=3.17 min. MS (ES): m/z (MH+) 917.085 for $C_{58}H_{105}N_3O_6$. $^1$H NMR (300 MHz, CDCl$_3$) δ: ppm 4.88 (p, 1H); 4.10 (t, 2H); 3.68 (bm, 2H); 3.28 (m; 3H); 2.75-2.44 (m, 6H); 2.31 (m, 4H); 1.82 (m, 3H); 1.72-1.18 (m, 71H); 0.90 (m, 12H).

AU. Compound 27: 3-Butylheptyl 8-((8-(heptadecan-9-yloxy)-8-oxooctyl)(3-((2-(methylamino)-3,4-dioxocyclobut-1-en-1-yl)amino)propyl)amino)octanoate Step 1: Heptadecan-9-yl 8-((3-((tert-butoxycarbonyl)amino)propyl)amino)octanoate

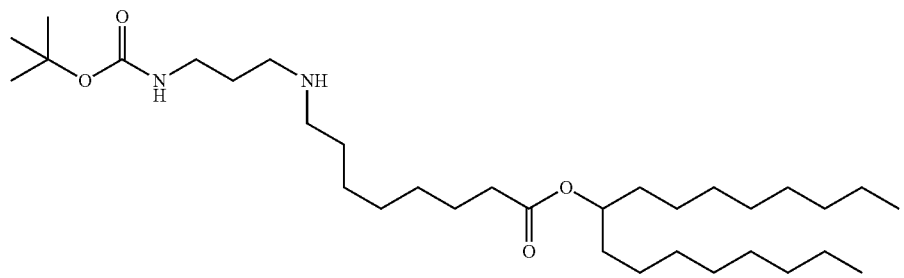 [SMILES: CCCCCCCCC(CCCCCCCC)OC(=O)CCCCCCCNCCCNC(=O)OC(C)(C)C]

A solution of tert-butyl N-(3-aminopropyl)carbamate (34.35 g, 197.15 mmol) in EtOH (200 mL) was heated to 65° C. and a solution of heptadecan-9-yl 8-bromooctanoate (26 g, 56.33 mmol) in EtOH (90 mL) was added over 3 h. The reaction was heated at 65° C. for 3 h. The reaction was cooled to <50° C. and EtOH was evaporated under vacuum and azeotroped with heptane (4×). To a solution of crude product in 2-MeTHF (150 mL) 5% K$_2$CO$_3$ (150 mL) was added and the resulting mixture was stirred for 10 minutes. The two layers were allowed to form. The aqueous layer was removed and the 2-MeTHF layer was washed with 100 mL water (×3). The organic layer was separated, washed with brine, dried with Na$_2$SO$_4$, filtered and evaporated under vacuum. The residue was purified by flash chromatography (ISCO) by 0-100% (a solution of 20% MeOH, 80% DCM, 1% NH$_4$OH) in DCM to obtain heptadecan-9-yl 8-((3-((tert-butoxycarbonyl)amino)propyl)amino)octanoate (20 g, 63.9%). UPLC/ELSD: RT=2.34 min. MS (ES): m/z (MH+) 555.319 for $C_{33}H_{66}N_2O_4$. $^1$H NMR (300 MHz, CDCl$_3$) δ: ppm 5.18 (bs, 1H); 4.89 (p, 1H); 3.22 (m, 2H); 2.64 (t, 2H); 2.59 (t, 2H); 2.30 (t, 2H); 1.73-1.21 (m, 50H); 0.90 (m, 6H).

Step 2: 3-Butylheptyl 8-((3-((tert-butoxycarbonyl)amino)propyl)(8-(heptadecan-9-yloxy)-8-oxooctyl)amino)octanoate

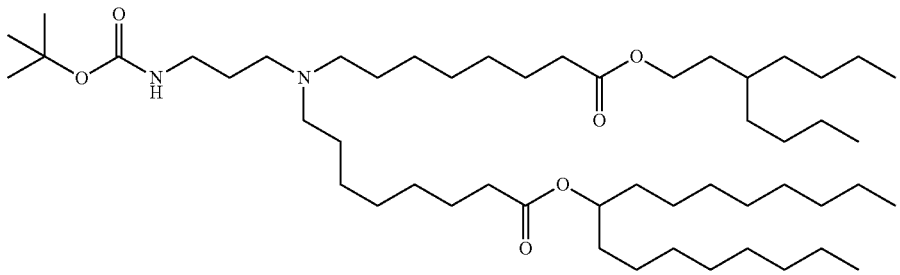 [SMILES: CCCCCCCCC(CCCCCCCC)OC(=O)CCCCCCCN(CCCCCCCC(=O)OCCC(CCCC)CCCC)CCCNC(=O)OC(C)(C)C]

To a solution of heptadecan-9-yl 8-({3-[(tert-butoxycarbonyl)amino]propyl}amino)octanoate (11.76 g, 21.19 mmol) and 3-butylheptyl 8-bromooctanoate (9.2 g, 24.37 mmol) in propionitrile (52 mL) was added Potassium carbonate (4.39 g, 31.79 mmol) and Potassium iodide (0.53 g, 3.18 mmol). The reaction was heated at 80° C. for 16 h. The reaction was cooled and filtered, and the volatiles were evaporated under vacuum. The residue was purified by flash chromatography (ISCO) by 0-100% (a solution of 20% MeOH, 80% DCM, 1% NH$_4$OH) in DCM to obtain 3-butylheptyl 8-((3-((tert-butoxycarbonyl)amino)propyl)(8-(heptadecan-9-yloxy)-8-oxooctyl)amino)octanoate (9.68 g, 53.6%). UPLC/ELSD: RT=3.07 min. MS (ES): m/z (MH$^+$) 851.216 for $C_{52}H_{102}N_2O_6$. $^1$H NMR (300 MHz, CDCl$_3$) δ: ppm 5.68 (bs, 1H); 4.90 (p, 1H); 4.11 (t, 2H); 3.20 (m, 2H); 2.52-2.24 (m, 10H); 1.76-1.20 (m, 74H); 0.90 (m, 12H).

Step 3: 3-Butylheptyl 8-((3-aminopropyl)(8-(heptadecan-9-yloxy)-8-oxooctyl)amino)octanoate

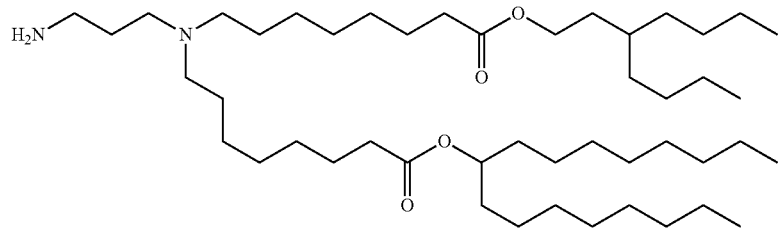 [SMILES: CCCCCCCCC(CCCCCCCC)OC(=O)CCCCCCCN(CCCN)CCCCCCCC(=O)OCCC(CCCC)CCCC]

To a solution of 3-butylheptyl 8-({3-[(tert-butoxycarbonyl)amino]propyl} [8-(heptadecan-9-yloxy)-8-oxooctyl] amino)octanoate (7 g, 8.22 mmol) in DCM (25 mL) was added trifluoroacetic acid (9.4 mL, 123.32 mmol). The reaction was allowed to stir at rt for 2 h. The reaction was evaporated under vacuum. The residue was dissolved in mixture of methyl THF/heptane (1:9) and extracted with sat. sodium bicarbonate (3×). The organic layer was separated, washed with brine, dried with Na$_2$SO$_4$, filtered and evaporated under vacuum to obtain 3-Butylheptyl 8-((3-aminopropyl)(8-(heptadecan-9-yloxy)-8-oxooctyl)amino)octanoate. This was taken as a crude to the next step without further purification. UPLC/ELSD: RT=2.63 min. MS (ES): m/z (MH$^+$) 751.305 for $C_{47}H_{94}N_2O_4$.

Step 4: Compound 27: 3-Butylheptyl 8-((8-(heptadecan-9-yloxy)-8-oxooctyl)(3-((2-(methylamino)-3,4-dioxocyclobut-1-en-1-yl)amino)propyl)amino)octanoate

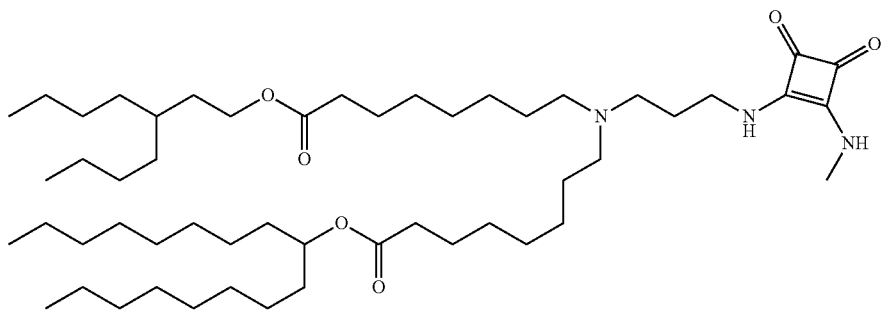

Chemical Formula: $C_{52}H_{97}N_3O_6$
Moelcular Weight: 860.36

To a solution of 3-butylheptyl 8-[(3-aminopropyl)[8-(heptadecan-9-yloxy)-8-oxooctyl]amino]octanoate (7 g, 9.32 mmol) in methyl THF (31 mL) was added 3-methoxy-4-(methylamino)cyclobut-3-ene-1,2-dione (1.71 g, 12.11 mmol), and a aqueous solution of 10% Sodium bicarbonate (8.6 mL, 10.25 mmol). The reaction was allowed to stir at 50° C. for 2.5 h. The reaction was cooled to rt and diluted with heptane and extracted with water. The organic layer was separated, washed with brine, dried with $Na_2SO_4$, filtered and evaporated under vacuum. The residue was purified by flash chromatography (ISCO) by 0-100% (a solution of 20% MeOH, 80% DCM, 1% $NH_4OH$) in DCM to obtain 3-Butylheptyl 8-((8-(heptadecan-9-yloxy)-8-oxooctyl)(3-((2-(methylamino)-3,4-dioxocyclobut-1-en-1-yl)amino)propyl)amino)octanoate (5.4 g, 63%). UPLC/ELSD: RT=2.98 min. MS (ES): m z (MH$^+$) 861.714 for $C_{52}H_{97}N_3O_6$. $^1$H NMR (300 MHz, $CDCl_3$) δ: ppm 4.89 (p, 1H); 4.10 (t, 2H); 3.75 (m, 2H); 3.39-3.20 (m, 5H); 3.08 (m, 4H); 2.31 (m, 4H); 2.12 (bm, 2H); 1.81-1.20 (m, 65H); 0.90 (m, 12H).

AV. Compound 28: Bis(3-hexylnonyl) 8,8'-((3-((2-(methylamino)-3,4-dioxocyclobut-1-en-1-yl)amino)propyl)azanediyl)dioctanoate

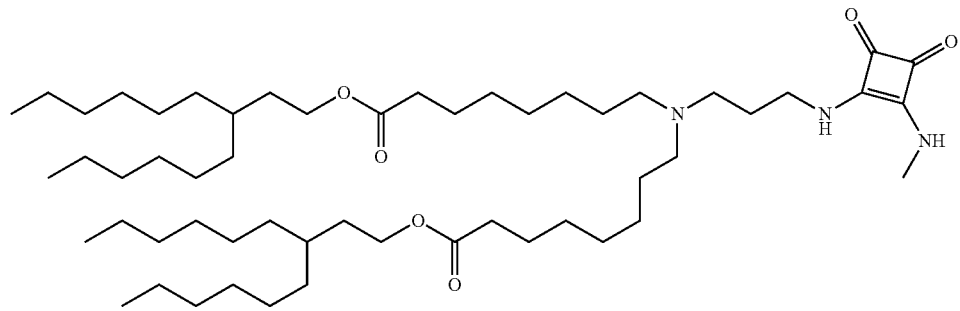

Chemical Formula: $C_{54}H_{101}N_3O_6$
Moelcular Weight: 888.42

Compound 28 was prepared analogously to compound 34 starting from 3-hexylnonyl-8-bromooctanoate instead of 4-pentylnonyl-8-bromooctanoate.
UPLC/ELSD: RT=3.08 min. MS (ES): m/z (MH$^+$) 889.332 for $C_{54}H_{101}N_3O_6$. $^1$H NMR (300 MHz, $CDCl_3$) δ: ppm 4.10 (m, 4H); 3.67 (bm, 2H); 3.28 (m, 3H); 2.57 (m, 2H); 2.44 (m, 4H); 2.31 (m, 4H); 1.77 (m, 2H); 1.62 (m, 8H); 1.52-1.19 (m, 58H); 0.90 (m, 12H).

AW. Compound 29: Heptadecan-9-yl 8-((3-((2-(methylamino)-3,4-dioxocyclobut-1-en-1-yl)amino)propyl)(8-oxo-8-((3-pentyloctyl)oxy)octyl)amino)octanoate

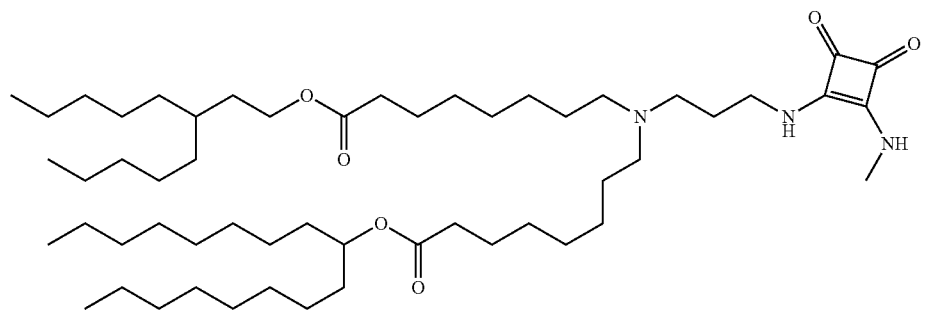

Chemical Formula: $C_{54}H_{101}N_3O_6$
Molecular Weight: 888.42

Compound 29 was prepared analogously to compound 9 starting from 6-undecanone instead of 7-tridecanone.
UPLC/ELSD: RT=3.12 min. MS (ES): m/z (MH$^+$) 889.332 for $C_{54}H_{101}N_3O_6$. $^1$H NMR (300 MHz, CDCl$_3$) δ: ppm 4.87 (p, 1H); 4.10 (t, 2H); 3.67 (bm, 2H); 3.29 (m, 3H); 2.67-2.41 (m, 6H); 2.31 (m, 4H); 1.85-1.18 (m, 71H), 0.90 (m, 12H).

AX. Compound 30: Bis(3-pentyloctyl) 8,8'-((3-((2-(methylamino)-3,4-dioxocyclobut-1-en-1-yl)amino)propyl)azanediyl)dioctanoate Step 1: Bis(3-pentyloctyl) 8,8'-((3-((tert-butoxycarbonyl)amino)propyl) azanediyl)dioctanoate

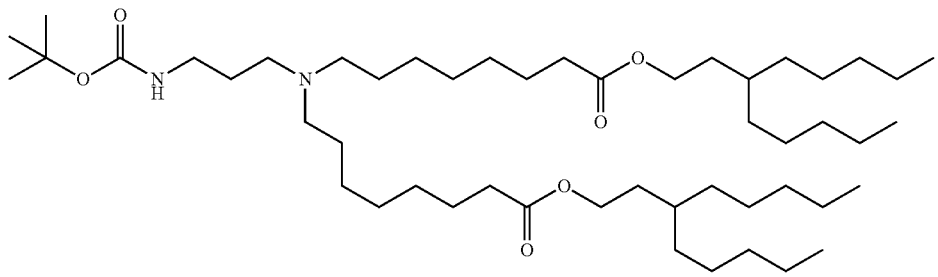

Chemical Formula: $C_{50}H_{98}H_2O_6$
Molecular Weight: 823.34

To a solution of 3-pentyloctyl 8-bromooctanoate (5.61 g, 13.8 mmol) and 3-pentyloctyl 8-((3-((tert-butoxycarbonyl)amino)propyl)amino)octanoate (6.00 g, 12.0 mmol) in propionitrile (30 mL) was added potassium carbonate (2.49 g, 18.0 mmol) and iodopotassium (300 mg, 1.80 mmol). The reaction was allowed to stir at 80° C. for 16 h. Upon cooling to room temperature, the reaction mixture was filtered via vacuum filtration. The residue in the vessel and the filter cake on the funnel was washed twice with propionitrile. The filtrate was then concentrated in vacuo at 40° C. The crude residue was purified by silica gel chromatography (0-5-10-20-25-30-35-40-50-80-100% (mixture of 1% NH$_4$OH, 20% MeOH in dichloromethane) in dichloromethane) to give bis(3-pentyloctyl) 8,8'-((3-((tert-butoxycarbonyl)amino) propyl) azanediyl)dioctanoate (7.37 g, 8.95 mmol, 74%) as a light yellow transparent oil. $^1$H NMR (300 MHz, CDCl$_3$) δ: ppm 5.66 (br. s, 1H); 4.08 (t, 4H, J=6.0 Hz); 3.17 (br. q, 2H, J=6.0 Hz); 2.43 (t, 2H, J=6.0 Hz); 2.34 (br. t, 4H, J=6.0 Hz); 2.28 (t, 4H, J=9.0 Hz); 1.67-1.52 (m, 10H); 1.48-1.37 (m, 14H); 1.35-1.17 (m, 45H); 0.88 (t, 12H, J=6.0 Hz).

Step 2: Bis(3-pentyloctyl) 8,8'-((3-aminopropyl)azanediyl)dioctanoate

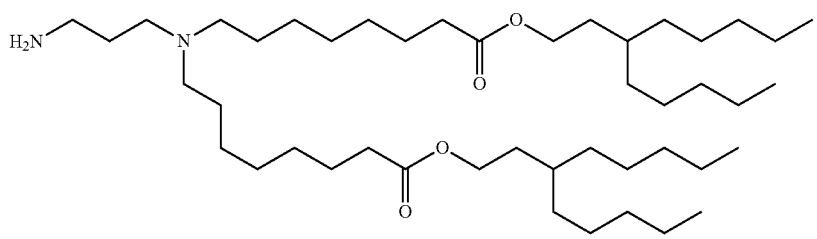

Chemical Formula: $C_{45}H_{90}N_2O_4$
Molecular Weight: 723.23

To a round bottom flask equipped with a stir bar was added bis(3-pentyloctyl) 8,8'-((3-((tert-butoxycarbonyl)amino)propyl) azanediyl)dioctanoate (3.00 g, 3.64 mmol). The oil was dissolved in cyclopentyl methyl ether (8 mL) and stirred for 5 minutes. 3M HCl in cyclopentyl methyl ether (6.07 mL, 18.2 mmol) was added dropwise. After addition was complete, the reaction was heated to 40° C. for 1 hour and reaction completion was monitored by TLC/LCMS analysis. The reaction was cooled to room temperature, and then chilled to 0° C. 10% $K_2CO_3$ solution was then added dropwise to the reaction mixture. After addition was complete, the aqueous/cyclopentyl methyl ether emulsion was diluted with EtOAc and the resulting mixture stirred for 10 minutes. The solution was transferred to a separation funnel and the layers were separated. The organic layer was dried ($MgSO_4$), filtered, and concentrated. The residue was redissolved in heptane and washed twice with MeCN. The heptane layer was dried ($MgSO_4$), filtered, and concentrated to afford crude bis(3-pentyloctyl) 8,8'-((3-aminopropyl)azanediyl)dioctanoate (2.43 g, 3.36 mmol, 92%) as an off-white oil. The crude material was carried onto the next step without further purification. $^1$H NMR (300 MHz, $CDCl_3$) δ: ppm 4.08 (t, 4H, J=6.0 Hz); 2.98 (t, 2H, J=6.0 Hz); 2.71 (t, 2H, J=6.0 Hz); 2.54 (br. t, 4H, J=6.0 Hz); 2.28 (t, 6H, J=6.0 Hz); 1.76 (br. pentet, 2H, J=2.0 Hz); 1.66-1.52 (m, 9H); 1.52-1.43 (m, 4H); 1.37-1.18 (m, 45H); 0.88 (t, 12H, J=6.0 Hz).

Step 3: Compound 30: Bis(3-pentyloctyl) 8,8'-((3-((2-(methylamino)-3,4-dioxocyclobut-1-en-1-yl)amino)propyl)azanediyl)dioctanoate

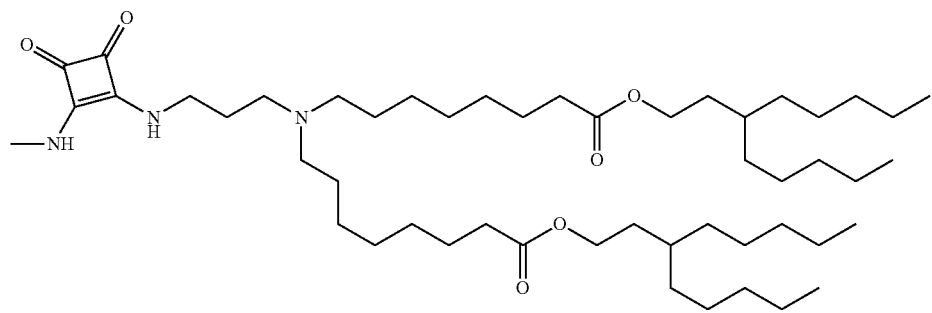

Chemical Formula: $C_{50}H_{93}N_3O_6$
Molecular Weight: 832.31

To a round bottom flask equipped with a stir bar was added bis(3-pentyloctyl) 8,8'-((3-aminopropyl)azanediyl)dioctanoate (2.43 g, 3.36 mmol), 3-methoxy-4-(methylamino)cyclobut-3-ene-1,2-dione (616 mg, 4.36 mmol) and 2-Methyl THF (10 mL). 10% $K_2CO_3$ solution (10 mL) was added and the resulting biphasic mixture was heated to 45° C. and stirred vigorously for 3 hours. Reaction completion was monitored by TLC/LCMS analysis. Upon completion the mixture was allowed to cool to room temperature. The reaction was diluted with water, layers were separated, and the aqueous layer was extracted twice with heptane. The organics were combined, washed with water (3×), brine, and with a 1:1 acetonitrile/water mixture. The combined organics were then dried ($Na_2SO_4$), filtered, and concentrated. The crude residue was azeotroped and concentrated with DCM and MeOH three times to yield a pale yellow crude waxy oil. The crude residue was purified by silica gel chromatography (0-100% (mixture of 1% $NH_4OH$, 20% MeOH in dichloromethane) in dichloromethane) to give bis(3-pentyloctyl) 8,8'-((3-((2-(methylamino)-3,4-dioxocyclobut-1-en-1-yl)amino)propyl)azanediyl)dioctanoate (2.11 g, 2.54 mmol, 76%) as a white waxy solid. UPLC/ELSD: RT=2.79 min. MS (ES): m/z (MH$^+$) 832.34 for $C_{50}H_{93}N_3O_6$. $^1$H NMR (300 MHz, $CDCl_3$) δ: ppm 7.83 (br. s, 1H); 7.61 (br. s, 1H); 4.03 (t, 4H, J=9.0 Hz); 3.64 (br. s, 2H); 3.28 (br. d, 3H, J=6.0 Hz); 2.46 (t, 2H, J=9.0 Hz); 2.33 (br. t, 4H, J=6.0 Hz); 2.33 (t, 4H, J=9.0 Hz); 1.74 (br. pentet, 2H, J=6.0 Hz); 1.62-1.47 (m, 8H); 1.41-1.12 (m, 50H); 0.83 (t, 12H, J=9.0 Hz).

AY. Compound 31: Heptadecan-9-yl 8-((2-hydroxy-ethyl)(8-oxo-8-((4-pentylnonyl)oxy)octyl)amino)octanoate

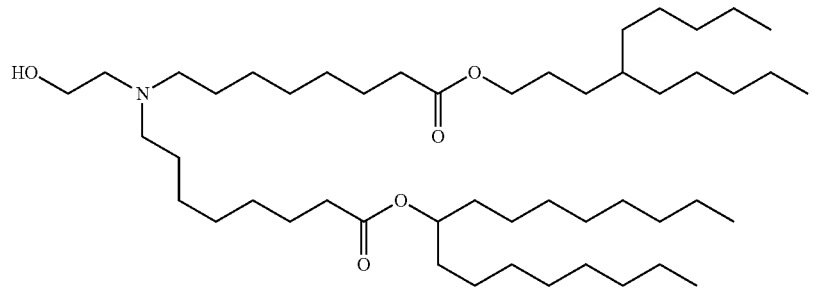

Chemical Formula: $C_{49}H_{97}NO_5$
Molecular Weight: 780.32

To a solution of 4-pentylnonyl-8-bromooctanoate (499 mg, 1.19 mmol) and heptadecan-9-yl 8-((2-hydroxyethyl)amino)octanoate (500 mg, 1.13 mmol) in cyclopentyl methyl ether (5 mL) and acetonitrile (5 mL) was added potassium carbonate (939 mg, 6.79 mmol) and potassium iodide (207 mg, 1.25 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give heptadecan-9-yl 8-((2-hydroxyethyl)(8-oxo-8-((4-pentylnonyl)oxy)octyl)amino)octanoate (242 mg, 0.31 mmol, 27%) as a clear viscous oil. UPLC/ELSD: RT=3.18 min. MS (ES): m/z (MH$^+$) 780.66 for $C_{49}H_{97}NO_5$. $^1$H NMR (300 MHz, $CDCl_3$) δ: ppm 4.83 (pent., 1H, J=6.0 Hz); 4.00 (t, 2H, J=6.0 Hz); 3.64 (br. s, 1H), 3.53 (t, 2H, J=6.0 Hz); 2.59 (t, 2H, J=3.0 Hz); 2.46 (br. t, 4H, J=6.0 Hz); 2.30-2.18 (m, 4H); 1.65-1.37 (m, 15H); 1.36-1.11 (m, 55H); 0.91-0.78 (m, 12H).

AZ. Compound 32: Heptadecan-9-yl 8-((3-((2-(methylamino)-3,4-dioxocyclobut-1-en-1-yl)amino)propyl)(8-oxo-8-((4-pentylnonyl)oxy)octyl)amino)octanoate

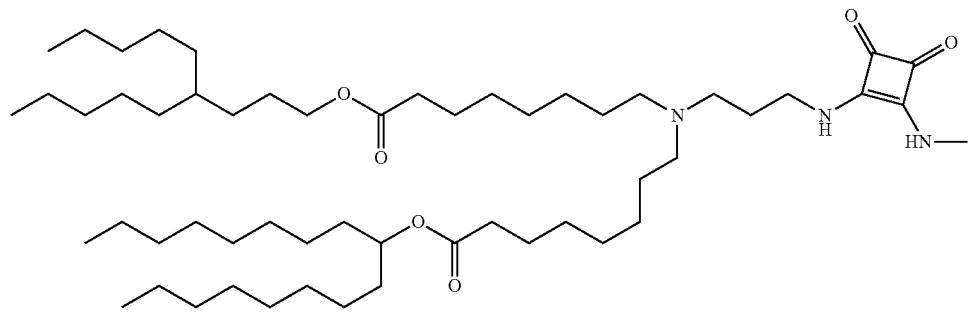

Chemical Formula: $C_{55}H_{103}N_3O_6$
Molecular Weight: 902.44

To a solution of 8-((8-(heptadecan-9-yloxy)-8-oxooctyl)(3-((2-(methylamino)-3,4-dioxocyclobut-1-en-1-yl)amino)propyl)amino)octanoic acid (706 mg, 1.00 mmol), 4-pentylnonan-1-ol (322 mg, 1.50 mmol), and DMAP (37.0 mg, 0.30 mmol) in dichloromethane (5 mL) at room temperature was added N,N'-dicyclohexylcarbodiimide (309 mg, 1.50 mmol). The resulting mixture was allowed to stir at room temperature for 16 h. The reaction was then diluted with additional dichloromethane and washed with saturated aqueous sodium bicarbonate. The organic layer washed with 1M HCl, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give heptadecan-9-yl 8-((3-((2-(methylamino)-3,4-dioxocyclobut-1-en-1-yl)amino)propyl)(8-oxo-8-((4-pentylnonyl)oxy)octyl)amino)octanoate (186 mg, 0.21 mmol, 21%) as a beige oil. UPLC/ELSD: RT=3.15 min. MS (ES): m/z ($MH^+$) 902.65 for $C_{55}H_{103}N_3O_6$. $^1H$ NMR (300 MHz, $CDCl_3$) δ: ppm 8.78 (br. s, 1H); 8.18 (br. s, 1H); 4.83 (pent., 2H, J=6 Hz); 4.01 (t, 2H, J=6 Hz); 3.68 (br. d, 2H, J=6 Hz); 3.28 (d, 3H, J=6 Hz); 3.15 (br. s, 2H); 2.95 (br. s, 4H); 2.32-2.20 (m, 4H); 2.12-1.97 (br. m, 2H); 1.73-1.41 (m, 14H); 1.40-1.11 (m, 54H); 0.93-0.78 (m, 12H).

BA. Compound 33: Bis(4-pentylnonyl)-8,8'-((2-hydroxyethyl)azanediyl)dioctanoate Bis(4-pentylnonyl)-8,8'-((2-hydroxyethyl)azanediyl)dioctanoate (Compound 33)

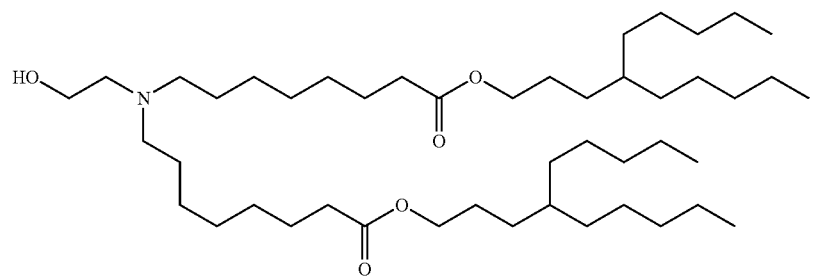

Chemical Formula: $C_{46}H_{91}NO_5$
Molecular Weight: 738.24

To a solution of 4-pentylnonyl-8-bromooctanoate (337 mg, 0.80 mmol) and 4-pentylnonyl-8-((2-hydroxyethyl)amino)octanoate (306 mg, 0.77 mmol) in cyclopentyl methyl ether (4 mL) and acetonitrile (4 mL) was added potassium carbonate (635 mg, 4.59 mmol) and potassium iodide (140 mg, 0.84 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give bis(4-pentylnonyl)-8,8'-((2-hydroxyethyl)azanediyl)dioctanoate (224 mg, 0.30 mmol, 40%) as a clear oil. UPLC/ELSD: RT=3.05 min. MS (ES): m/z ($MH^+$) 738.48 for $C_{46}H_{91}NO_5$. $^1H$ NMR (300 MHz, $CDCl_3$) δ: ppm 4.02 (t, 4H, J=6.0 Hz); 3.51 (t, 2H, J=6.0 Hz); 3.25 (br. s, 1H); 2.56 (t, 2H, J=6.0 Hz); 2.43 (br. t, 4H, J=6.0 Hz); 2.27 (t, 4H, J=6.0 Hz); 1.67-1.50 (m, 8H); 1.48-1.36 (m, 5H); 1.36-1.12 (m, 50H); 0.93-0.80 (m, 12H).

BB. Compound 34: Bis(4-pentylnonyl)-8,8'-((3-((2-(methylamino)-3,4-dioxocyclobut-1-en-1-yl)amino)propyl)azanediyl)dioctanoate 4-Pentylnonyl-8-((3-((tert-butoxycarbonyl)amino)propyl)amino)octanoate

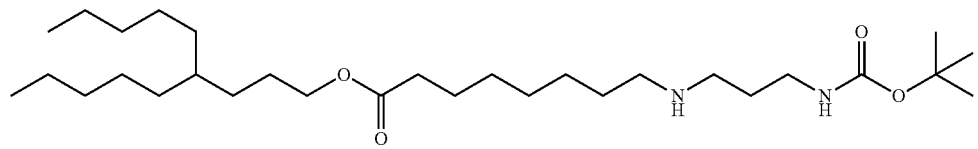

Chemical Formula: $C_{30}H_{60}N_2O_4$
Molecular Weight: 512.82

To a solution of tert-butyl N-(3-aminopropyl)carbamate (2.99 g, 17.2 mmol) in ethanol (8 mL) was added a solution of 4-pentylnonyl-8-bromooctanoate (1.2 g, 2.86 mmol) in ethanol (7 mL) at room temperature over the course of 20 min. The reaction was heated to 60° C., and allowed to stir at this temperature for 16 h. The reaction mixture was then cooled to room temperature, and the solvents were evaporated. The resulting residue was diluted with ethyl acetate and washed with saturated aqueous sodium bicarbonate and brine (5×) until no white precipitate was observed in the aqueous layer. The organic layer was separated, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give 4-pentylnonyl-8-((3-((tert-butoxycarbonyl)amino)propyl)amino)octanoate (802 mg, 1.56 mmol, 55%) as a clear oil. UPLC/ELSD: RT=2.11 min. MS (ES): m/z ($MH^+$) 513.26 for $C_{30}H_{60}N_2O_4$.

Bis(4-pentylnonyl)-8,8'-((3-((tert-butoxycarbonyl)amino)propyl) azanediyl)dioctanoate

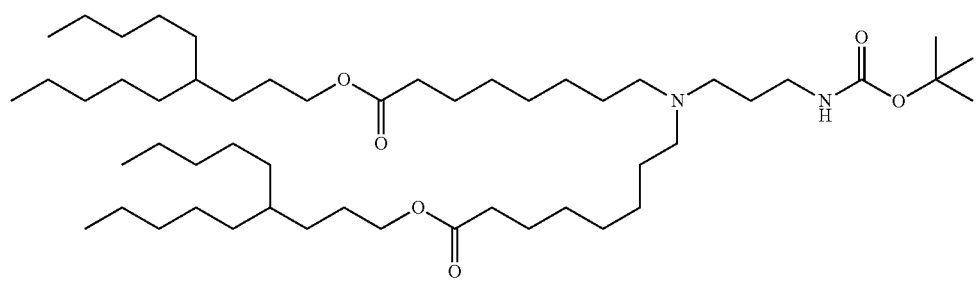

Chemical Formula: $C_{52}H_{102}N_2O_6$
Molecular Weight: 851.40

To a solution of 4-pentylnonyl-8-bromooctanoate (667 mg, 1.59 mmol) and 4-pentylnonyl-8-((3-((tert-butoxycarbonyl)amino)propyl)amino)octanoate (777 mg, 1.52 mmol) in cyclopentyl methyl ether (7 mL) and acetonitrile (7 mL) was added potassium carbonate (1.26 g, 9.09 mmol) and potassium iodide (277 mg, 1.67 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give bis(4-pentylnonyl)-8,8'-((3-((tert-butoxycarbonyl)amino)propyl) azanediyl)dioctanoate (742 mg, 0.87 mmol, 57%) as a clear oil.

UPLC/ELSD: RT=3.11 min. MS (ES): m/z (MH$^+$) 851.59 for C$_{52}$H$_{102}$N$_2$O$_6$.

Bis(4-pentylnonyl)-8,8'-((3-aminopropyl)azanediyl)dioctanoate

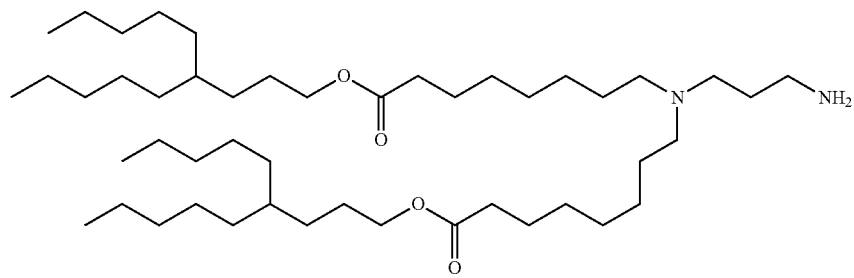

Chemical Formula: C$_{47}$H$_{94}$N$_2$O$_4$
Molecular Weight: 751.28

To a solution of bis(4-pentylnonyl)-8,8'-((3-((tert-butoxycarbonyl)amino)propyl) azanediyl)dioctanoate (742 mg, 0.87 mmol) in dichloromethane (17 mL) was added trifluoroacetic acid (1.33 mL, 17.4 mmol). The resulting mixture was allowed to stir at room temperature for 4 h prior to being quenched with saturated sodium bicarbonate. The aqueous layer was extracted with dichloromethane. The combined organics were washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give bis(4-pentylnonyl)-8,8'-((3-aminopropyl)azanediyl)dioctanoate (414 mg, 0.55 mmol, 63%) as a clear oil.

UPLC/ELSD: RT=2.58 min. MS (ES): m/z (MH$^+$) 751.68 for C$_{47}$H$_{94}$N$_2$O$_4$.

Bis(4-pentylnonyl)-8,8'-((3-((2-(methylamino)-3,4-dioxocyclobut-1-en-1-yl)amino)propyl)azanediyl)dioctanoate

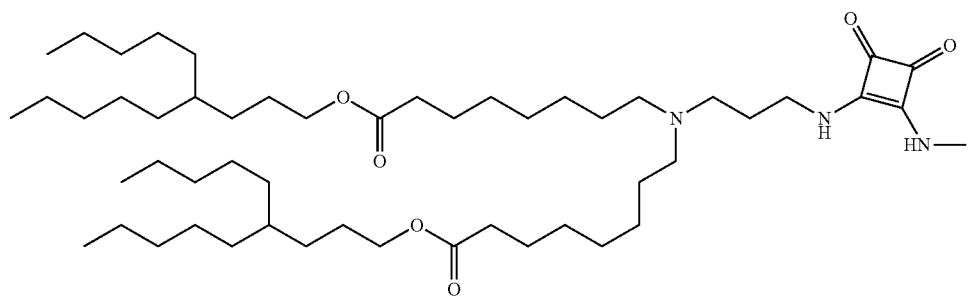

Chemical Formula: C$_{52}$H$_{97}$N$_3$O$_6$
Molecular Weight: 860.36

To a solution of bis(4-pentylnonyl)-8,8'-((3-aminopropyl)azanediyl)dioctanoate (414 mg, 0.55 mmol) in tetrahydrofuran (4 mL) and water (750 μL) was added 3-methoxy-4-(methylamino)cyclobut-3-ene-1,2-dione (117 mg, 0.83 mmol). The reaction was allowed to stir at 67° C. for 20 h. After 20 h, the reaction was cooled to room temperature and diluted with diethyl ether. The organics were washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give bis(4-pentylnonyl)-8,8'-((3-((2-(methylamino)-3,4-dioxocyclobut-1-en-1-yl)amino)propyl)azanediyl)dioctanoate (179 mg, 0.21 mmol, 38%) as an off-white waxy solid.

UPLC/ELSD: RT=2.97 min. MS (ES): m/z (MH$^+$) 860.59 for C$_{52}$H$_{97}$N$_3$O$_6$. $^1$H NMR (300 MHz, CDCl$_3$) δ: ppm 7.29 (br. s, 1H); 4.03 (t, 4H, J=6 Hz); 3.64 (br. s, 2H); 3.27 (d, 3H, J=3 Hz); 2.54 (br. t, 2H, J=6 Hz); 2.41 (br. t, 4H, J=6 Hz); 2.29 (t, 4H, J=9 Hz); 1.81-1.69 (m, 2H); 1.68-1.51 (m, 8H); 1.48-1.13 (m, 55H); 0.94-0.80 (m, 12H).

BC. Compound 35: 2-(4-Ethylcyclohexyl)ethyl 8-((8-(heptadecan-9-yloxy)-8-oxooctyl)(2-hydroxyethyl)amino)octanoate

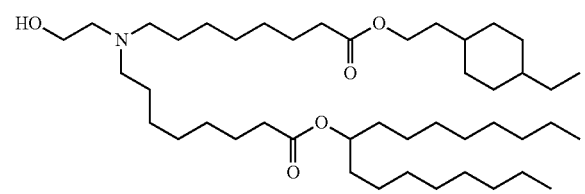

Chemical Formula: C$_{45}$H$_{87}$NO$_5$
Molecular Weight: 722.19

UPLC/ELSD: RT=2.92 min. MS (ES): m/z (MH$^+$) 723.059 for C$_{45}$H$_{87}$NO$_5$. $^1$H NMR (300 MHz, CDCl$_3$) δ: ppm 4.89 (p, 1H); 4.12 (m, 2H); 3.57 (bm, 2H); 2.73-2.22 (m, 10H); 1.82-1.15 (m, 61H), 0.90 (m, 11H).

BD. Compound 37: 2-(3-Ethylcyclopentyl)ethyl 8-((8-(heptadecan-9-yloxy)-8-oxooctyl)(2-hydroxyethyl)amino)octanoate

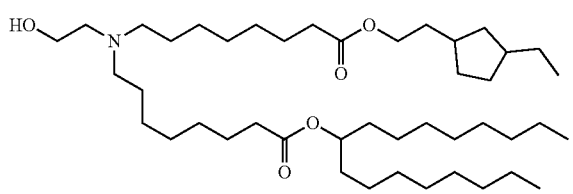

Chemical Formula: C$_{44}$H$_{85}$NO$_5$
Molecular Weight: 708.17

UPLC/ELSD: RT=2.89 min. MS (ES): m/z (MH$^+$) 709.614 for C$_{44}$H$_{85}$NO$_5$. $^1$H NMR (300 MHz, CDCl$_3$) δ: ppm 4.89 (p, 1H); 4.09 (m, 2H); 3.56 (m, 2H); 2.66-2.40 (m, 6H); 2.30 (m, 4H); 2.06-1.05 (m, 60H), 0.90 (m, 10H).

BE. Compound 39: Heptadecan-9-yl 8-((3-((2-(methylamino)-3,4-dioxocyclobut-1-en-1-yl)amino)propyl)(8-oxo-8-(2-(4-propylcyclohexyl)ethoxy)octyl)amino)octanoate

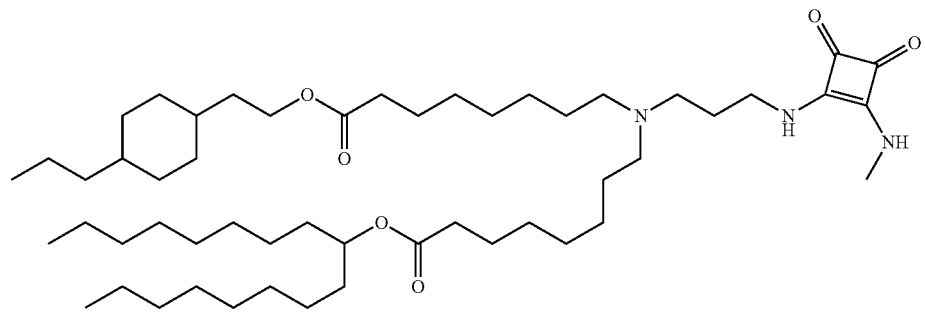

Chemical Formula: C$_{52}$H$_{95}$N$_3$O$_6$
Molecular Weight: 858.35

Compound 39 was prepared analogously to compound 26 starting from 4-propylcyclohexanone instead of 7-tridecanone.

UPLC/ELSD: RT=2.97 min. MS (ES): m/z (MH$^+$) 859.727 for $C_{52}H_{95}N_3O_6$. $^1$H NMR (300 MHz, CDCl$_3$) δ: ppm 4.87 (p, 1H); 4.12 (t, 2H); 3.68 (bm, 2H); 3.28 (m, 3H); 2.66-2.40 (m, 6H); 2.32 (m, 4H); 1.84-1.12 (m, 65H); 0.90 (m, 12H).

BF. Compound 40: 2-(3-Ethylcyclopentyl)ethyl 8-((8-(heptadecan-9-yloxy)-8-oxooctyl)(3-((2-(methylamino)-3,4-dioxocyclobut-1-en-1-yl)amino)propyl)amino)octanoate

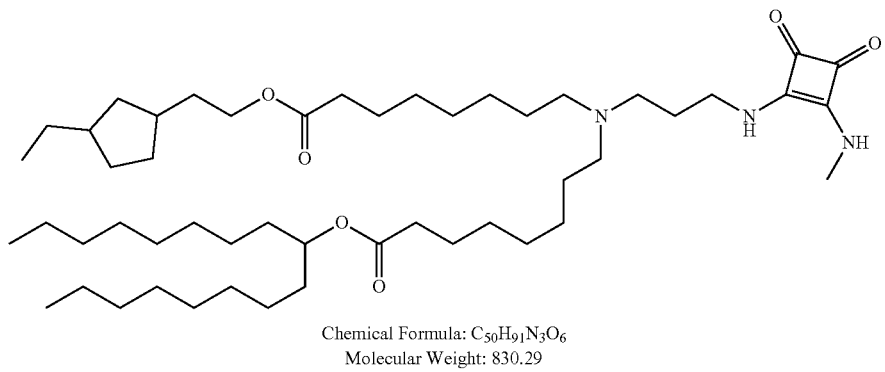 [SMILES: CCCCCCCCC(CCCCCCCC)OC(=O)CCCCCCCN(CCCCCCCC(=O)OCCC1CCC(CC)C1)CCCNc1c(NC)c(=O)c1=O]

Chemical Formula: $C_{50}H_{91}N_3O_6$
Molecular Weight: 830.29

Compound 40 was prepared analogously to compound 26 starting from 3-ethylcyclopentanone instead of 7-tridecanone.

UPLC/ELSD: RT=2.84 min. MS (ES): m/z (MH$^+$) 831.604 for $C_{50}H_{91}N_3O_6$. $^1$H NMR (300 MHz, CDCl$_3$) δ: ppm 5.79 (p, 1H); 4.87 (t, 2H); 4.08 (bm, 2H); 3.66 (m, 3H); 3.50 (m, 2H); 3.28 (m, 3H); 2.57 (m, 2H); 2.44 (m, 4H); 2.31 (m, 4H); 2.03-1.08 (m, 63H); 0.89 (m, 8H); 0.71 (m, 1H).

BG. Compound 42: Bis(3-pentyloctyl) 8,8'-((3-hydroxypropyl)azanediyl)dioctanoate

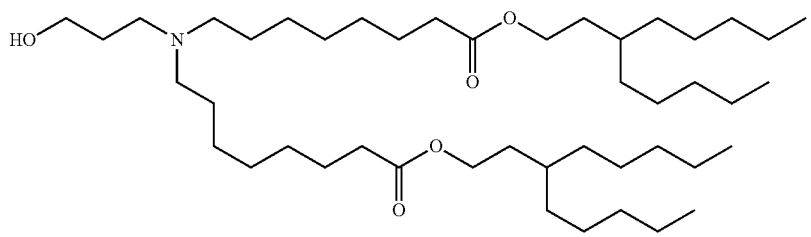

Chemical Formula: $C_{45}H_{89}NO_5$
Molecular Weight: 724.21

To a solution of 3-pentyloctyl 8-bromooctanoate (398 mg, 0.98 mmol) and 3-pentyloctyl 8-((3-hydroxypropyl)amino) octanoate (374 mg, 0.94 mmol) in cyclopentyl methyl ether (5 mL) and acetonitrile (5 mL) was added potassium carbonate (776 mg, 5.62 mmol) and potassium iodide (171 mg, 1.03 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give bis(3-pentyloctyl) 8,8'-((3-hydroxypropyl) azanediyl)dioctanoate (296 mg, 0.41 mmol, 44%) as a clear viscous oil. UPLC/ELSD: RT=2.94 min. MS (ES): m z (MH$^+$) 724.42 for $C_{45}H_{89}NO_5$. $^1$H NMR (300 MHz, CDCl$_3$) δ: ppm 5.69 (br. s, 1H); 4.08 (t, 4H, J=6.0 Hz); 3.79 (br. t, 2H, J=6.0 Hz); 2.63 (br. t, 2H, J=6.0 Hz); 2.39 (br. dd, 4H, J=9.0, 9.0 Hz); 2.28 (t, 4H, J=6.0 Hz); 1.72-1.52 (m, 10H); 1.51-1.20 (m, 50H); 0.88 (t, 12H, J=6.0 Hz).

BH. Compound 44: Bis(3-pentyloctyl) 8,8'-((4-hydroxybutyl)azanediyl)dioctanoate

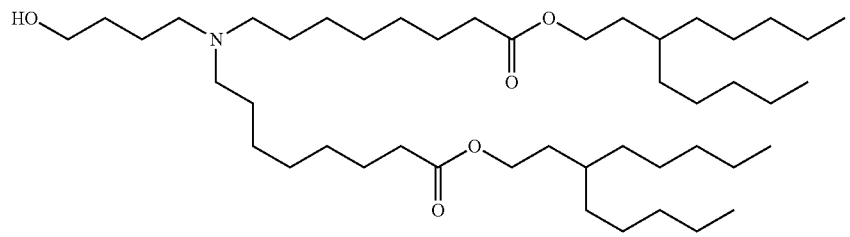

Chemical Formula: $C_{46}H_{91}NO_5$
Molecular Weight: 738.24

To a solution of 3-pentyloctyl 8-bromooctanoate (516 mg, 1.27 mmol) and 3-pentyloctyl 8-((4-hydroxybutyl)amino)octanoate (501 mg, 1.21 mmol) in cyclopentyl methyl ether (6 mL) and acetonitrile (6 mL) was added potassium carbonate (1.00 g, 7.27 mmol) and potassium iodide (221 mg, 1.33 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give bis(3-pentyloctyl) 8,8'-((4-hydroxybutyl)azanediyl)dioctanoate (515 mg, 0.70 mmol, 58%) as a clear viscous oil. UPLC/ELSD: RT=2.93 min. MS (ES): m/z (MH$^+$) 738.35 for $C_{46}H_{91}NO_5$. $^1$H NMR (300 MHz, CDCl$_3$) δ: ppm 6.56 (br. s, 1H); 4.08 (t, 4H, J=6.0 Hz); 3.54 (br. t, 2H, J=6.0 Hz); 2.42 (br. t, 6H, J=6.0 Hz); 2.28 (t, 4H, J=6.0 Hz); 1.71-1.52 (m, 12H); 1.52-1.19 (m, 50H); 0.88 (t, 12H, J=6.0 Hz).

BI. Compound 49: 3-Butylheptyl 8-((8-(heptadecan-9-yloxy)-8-oxooctyl)(3-hydroxypropyl)amino)octanoate

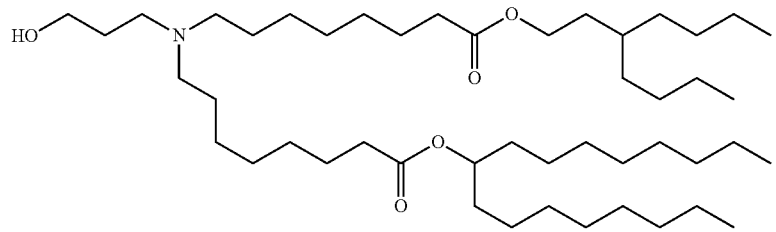

Chemical Formula: $C_{47}H_{93}NO_5$
Molecular Weight: 752.26

To a solution of 3-butylheptyl 8-bromooctanoate (629 mg, 1.67 mmol) and heptadecan-9-yl 8-((3-hydroxypropyl)amino)octanoate (723 mg, 1.59 mmol) in cyclopentyl methyl ether (7 mL) and acetonitrile (7 mL) was added potassium carbonate (1.32 g, 9.52 mmol) and potassium iodide (290 mg, 1.75 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give 3-butylheptyl 8-((8-(heptadecan-9-yloxy)-8-oxooctyl)(3-hydroxypropyl)amino)octanoate (503 mg, 0.67 mmol, 42%) as a clear viscous oil. UPLC/ELSD: RT=3.04 min. MS (ES): m/z ($MH^+$) 752.42 for $C_{47}H_{93}NO_5$. $^1$H NMR (300 MHz, $CDCl_3$) δ: ppm 5.68 (br. s, 1H); 4.86 (pent., 1H, J=6.0 Hz); 4.08 (t, 2H, J=6.0 Hz); 3.79 (br. t, 2H, J=6.0 Hz); 2.63 (br. t, 2H, J=6.0 Hz); 2.39 (br. t, 4H, J=6.0 Hz); 2.28 (dt, 4H, J=6.0, 3.0 Hz); 1.73-1.17 (m, 65H); 0.96-0.82 (m, 12H).

BJ. Compound 50: 3-Butylheptyl 8-((8-(heptadecan-9-yloxy)-8-oxooctyl)(4-hydroxybutyl)amino)octanoate

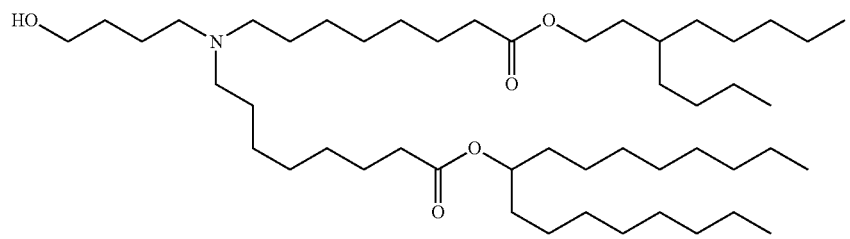

Chemical Formula: $C_{48}H_{95}NO_5$
Molecular Weight: 766.29

To a solution of 3-butylheptyl 8-bromooctanoate (652 mg, 1.65 mmol) and heptadecan-9-yl 8-((4-hydroxybutyl)amino)octanoate (773 mg, 1.65 mmol) in cyclopentyl methyl ether (8 mL) and acetonitrile (8 mL) was added potassium carbonate (1.36 g, 9.87 mmol) and potassium iodide (300 mg, 1.81 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give 3-butylheptyl 8-((8-(heptadecan-9-yloxy)-8-oxooctyl)(4-hydroxybutyl)amino)octanoate (829 mg, 1.08 mmol, 66%) as a clear viscous oil. UPLC/ELSD: RT=3.05 min. MS (ES): m/z ($MH^+$) 766.48 for $C_{48}H_{95}NO_5$. $^1$H NMR (300 MHz, $CDCl_3$) δ: ppm 6.58 (br. s, 1H); 4.86 (pent., 1H, J=6.0 Hz); 4.08 (t, 2H, J=6.0 Hz); 3.55 (br. t, 2H, J=6.0 Hz); 2.44 (br. t, 6H, J=6.0 Hz); 2.27 (dt, 4H, J=6.0, 3.0 Hz); 1.70-1.41 (m, 19H); 1.36-1.18 (m, 48H); 0.94-0.81 (m, 12H).

BK. Compound 51: 3-Pentyloctyl 8-((3-((2-(methylamino)-3,4-dioxocyclobut-1-en-1-yl)amino)propyl)(8-oxo-8-((3-propylhexyl)oxy)octyl)amino)octanoate

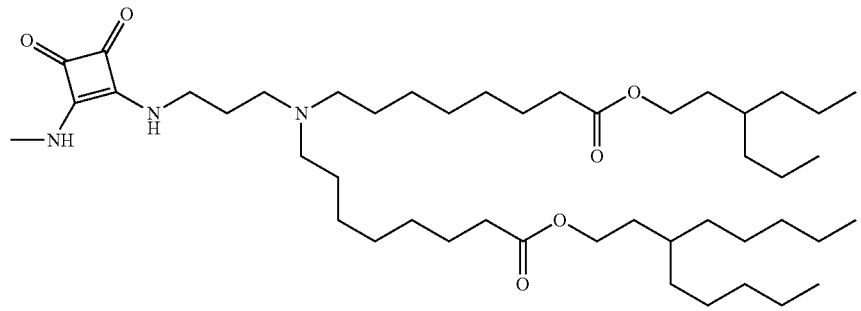

Chemical Formula: $C_{46}H_{85}N_3O_6$
Molecular Weight: 776.20

To a solution of 3-pentyloctyl 8-((3-aminopropyl)(8-oxo-8-((3-propylhexyl)oxy)octyl)amino)octanoate (378 mg, 0.57 mmol) in ethanol (5 mL) was added 3-methoxy-4-(methylamino)cyclobut-3-ene-1,2-dione (120 mg, 0.85 mmol). The reaction was allowed to stir at 67° C. for 20 h. After 20 h, the reaction was cooled to room temperature and diluted with diethyl ether. The organics were washed with brine, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give 3-pentyloctyl 8-((3-((2-(methylamino)-3,4-dioxocyclobut-1-en-1-yl)amino) propyl)(8-oxo-8-((3-propylhexyl)oxy)octyl)amino) octanoate (198 mg, 0.26 mmol, 45%) as light-yellow amorphous solid. UPLC/ELSD: RT=2.54 min. MS (ES): m/z (MH$^+$) 776.22 for $C_{46}H_{85}N_3O_6$. $^1$H NMR (300 MHz, CDCl$_3$) δ: ppm 7.25 (br. s, 1H); 4.07 (t, 4H, J=6.0 Hz); 3.65 (br. s, 2H); 3.27 (d, 3H, J=6.0 Hz); 2.54 (br. t, 2H, J=6.0 Hz); 2.41 (br. t, 4H, J=6.0 Hz); 2.29 (t, 4H, J=6.0 Hz); 1.74 (br. pent., 2H, J=6.0 Hz); 1.67-1.52 (m, 8H); 1.49-1.18 (m, 43H); 0.88 (t, 12H, J=6.0 Hz).

BL. Compound 52: 3-Butylheptyl 8-((3-((2-(methylamino)-3,4-dioxocyclobut-1-en-1-yl)amino)propyl)(8-oxo-8-((3-propylhexyl)oxy)octyl)amino)octanoate

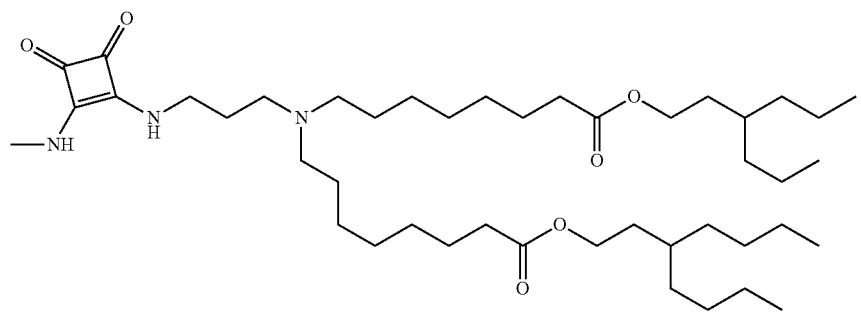

Chemical Formula: $C_{44}H_{81}N_3O_6$
Molecular Weight: 748.15

To a solution of 3-butylheptyl 8-((3-aminopropyl)(8-oxo-8-((3-propylhexyl)oxy)octyl)amino)octanoate (503 mg, 0.79 mmol) in ethanol (7 mL) was added 3-methoxy-4-(methylamino)cyclobut-3-ene-1,2-dione (167 mg, 1.18 mmol). The reaction was allowed to stir at 67° C. for 20 h. After 20 h, the reaction was cooled to room temperature and diluted with diethyl ether. The organics were washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give 3-butylheptyl 8-((3-((2-(methylamino)-3,4-dioxocyclobut-1-en-1-yl)amino)propyl)(8-oxo-8-((3-propylhexyl)oxy)octyl)amino)octanoate (228 mg, 0.31 mmol, 39%) as light-yellow amorphous solid. UPLC/ELSD: RT=2.43 min. MS (ES): m/z (MH$^+$) 748.47 for C$_{44}$H$_{51}$N$_3$O$_6$. $^1$H NMR (300 MHz, CDCl$_3$) δ: ppm 7.51 (br. s, 1H); 7.19 (br. s, 1H); 4.06 (t, 4H, J=6.0 Hz); 3.65 (br. s, 2H); 3.28 (d, 3H, J=6.0 Hz); 2.51 (br. t, 2H, J=6.0 Hz); 2.39 (br. t, 4H, J=6.0 Hz); 2.27 (t, 4H, J=6.0 Hz); 1.75 (br. pent., 2H, J=6.0 Hz); 1.67-1.51 (m, 8H); 1.47-1.16 (m, 38H); 0.92-0.82 (m, 12H).

BM. Compound 53: Bis(3-propylhexyl) 8,8'-((3-((2-(methylamino)-3,4-dioxocyclobut-1-en-1-yl)amino)propyl)azanediyl)dioctanoate

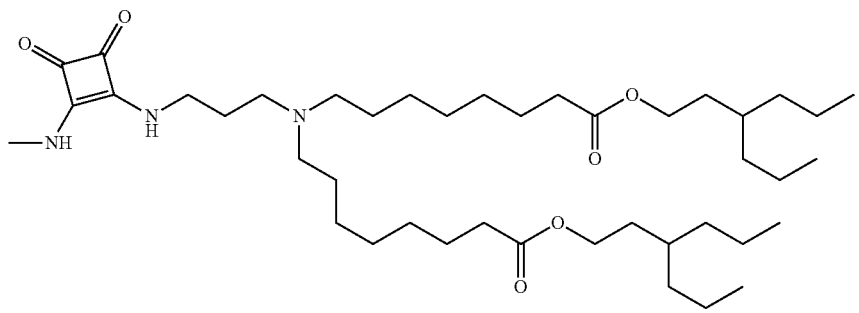

Chemical Formula: C$_{42}$H$_{77}$N$_3$O$_6$
Molecular Weight: 720.09

To a solution of bis(3-propylhexyl) 8,8'-((3-aminopropyl)azanediyl)dioctanoate (499 mg, 0.82 mmol) in ethanol (8 mL) was added 3-methoxy-4-(methylamino)cyclobut-3-ene-1,2-dione (173 mg, 1.23 mmol). The reaction was allowed to stir at 67° C. for 20 h. After 20 h, the reaction was cooled to room temperature and diluted with diethyl ether. The organics were washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give bis(3-propylhexyl) 8,8'-((3-((2-(methylamino)-3,4-dioxocyclobut-1-en-1-yl)amino)propyl)azanediyl)dioctanoate (199 mg, 0.28 mmol, 34%) as an off-white waxy solid. UPLC/ELSD: RT=2.25 min. MS (ES): m/z (MH$^+$) 720.47 for C$_{42}$H$_{77}$N$_3$O$_6$. $^1$H NMR (300 MHz, CDCl$_3$) δ: ppm 7.56 (br. s, 1H); 7.25 (br. s, 1H); 4.06 (t, 4H, J=6.0 Hz); 3.65 (br. s, 2H); 3.28 (d, 3H, J=6.0 Hz); 2.50 (br. t, 2H, J=6.0 Hz); 2.38 (br. t, 4H, J=6.0 Hz); 2.27 (t, 4H, J=6.0 Hz); 1.75 (br. pent., 2H, J=6.0 Hz); 1.65-1.50 (m, 8H); 1.47-1.16 (m, 34H); 0.86 (t, 12H, J=6.0 Hz).

BN. Compound 54: 3-Butylheptyl 8-((3-((2-(methylamino)-3,4-dioxocyclobut-1-en-1-yl)amino)propyl)(8-oxo-8-((3-pentyloctyl)oxy)octyl)amino)octanoate

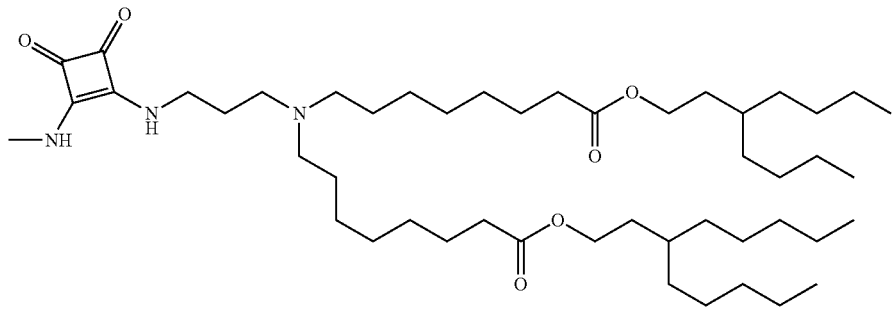

Chemical Formula: $C_{48}H_{89}N_3O_6$
Molecular Weight: 804.26

To a solution of 3-butylheptyl 8-((3-aminopropyl)(8-oxo-8-((3-pentyloctyl)oxy)octyl)amino)octanoate (632 mg, 0.91 mmol) in ethanol (8 mL) was added 3-methoxy-4-(methylamino)cyclobut-3-ene-1,2-dione (192 mg, 1.36 mmol). The reaction was allowed to stir at 67° C. for 20 h. After 20 h, the reaction was cooled to room temperature and diluted with diethyl ether. The organics were washed with brine, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give 3-butylheptyl 8-((3-((2-(methylamino)-3,4-dioxocyclobut-1-en-1-yl)amino)propyl)(8-oxo-8-((3-pentyloctyl)oxy)octyl)amino)octanoate (240 mg, 0.30 mmol, 33%) as an off-white waxy solid. UPLC/ELSD: RT=2.67 min. MS (ES): m/z (MH$^+$) 804.22 for $C_{48}H_{89}N_3O_6$. $^1$H NMR (300 MHz, $CDCl_3$) δ: ppm 7.38 (br. s, 1H); 7.03 (br. s, 1H); 4.07 (t, 4H, J=6.0 Hz); 3.65 (br. s, 2H, J=6.0 Hz); 3.27 (d, 3H, J=6.0 Hz); 2.52 (br. t, 2H, J=6.0 Hz); 2.40 (br. t, 4H, J=6.0 Hz); 2.28 (t, 4H, J=6.0 Hz); 1.75 (br. pent., 2H, J=6.0 Hz); 1.67-1.51 (m, 8H); 1.47-1.17 (m, 46H); 0.93-0.82 (m, 12H).

BO. Compound 55: Bis(3-butylheptyl) 8,8'-((3-((2-(methylamino)-3,4-dioxocyclobut-1-en-1-yl)amino)propyl)azanediyl)dioctanoate Chemical Formula: $C_{46}H_{85}N_3O_6$
Exact Mass: 775.64
Molecular Weight: 776.20

UPLC/ELSD: RT=2.52 min. MS (ES): m/z (MH$^+$) 776.462 for $C_{46}H_{85}N_3O_6$. $^1$H NMR (300 MHz, CDCl$_3$) δ: ppm 4.10 (m, 4H); 3.67 (bm, 2H); 3.29 (m, 3H); 2.58 (m, 2H); 2.43 (m, 4H); 2.32 (t, 4H); 1.84-1.16 (m, 54H); 0.91 (m, 12H).

BP. Compound 57: 3-Pentyloctyl 8-((3-((2-(methyl-amino)-3,4-dioxocyclobut-1-en-1-yl)amino)propyl)(8-oxo-8-(undecan-6-yloxy)octyl)amino)octanoate

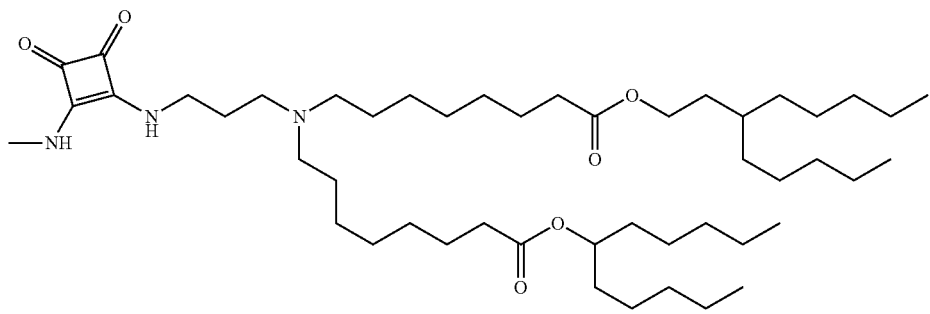

Chemical Formula: $C_{48}H_{89}N_3O_6$
Molecular Weight: 804.255

To a solution of undecan-6-yl 8-[(3-aminopropyl)[8-oxo-8-(undecan-6-yloxy)octyl]amino]octanoate (0.870 g, 1.304 mmol, 1 equiv.) in THF (6.5 mL) and water (1.1 mL) added 3-methoxy-4-(methylamino)cyclobut-3-ene-1,2-dione (0.321 g, 2.274 mmol, 1.744 equiv.). The reaction was allowed to stir at 67° C. for 16 h. The reaction was cooled to room temperature, dried, and filtered. The organics were removed under vacuum. The residue was purified by silica gel chromatography [0-30% (mixture of 1% NH$_4$OH, 20% MeOH in dichloromethane) in dichloromethane] to obtain 3-pentyloctyl 8-[(3-{[2-(methylamino)-3,4-dioxocyclobut-1-en-1-yl]amino}propyl)[8-oxo-8-(undecan-6-yloxy)octyl]amino]octanoate (0.126 g, 12%). UPLC/ELSD: RT=2.68 min. MS (ESI): m/z calcd for $C_{45}H_{90}N_3O_6^+$(M+H) 804.255; found, 804.47. $^1$H NMR (300 MHz, CDCl$_3$) δ: ppm 4.88 (p, 1H); 4.10 (t, 2H); 3.67 (br. s, 2H); 3.30 (d, 3H); 2.59 (br. t, 2H); 2.41 (br. t, 4H); 2.31 (t, 4H); 1.78-1.28 (m, 58H); 0.90 (t, 12H).

BQ. Compound 58: Nonan-5-yl 8-((3-((2-(methyl-amino)-3,4-dioxocyclobut-1-en-1-yl)amino)propyl)(8-oxo-8-((3-pentyloctyl)oxy)octyl)amino)octanoate

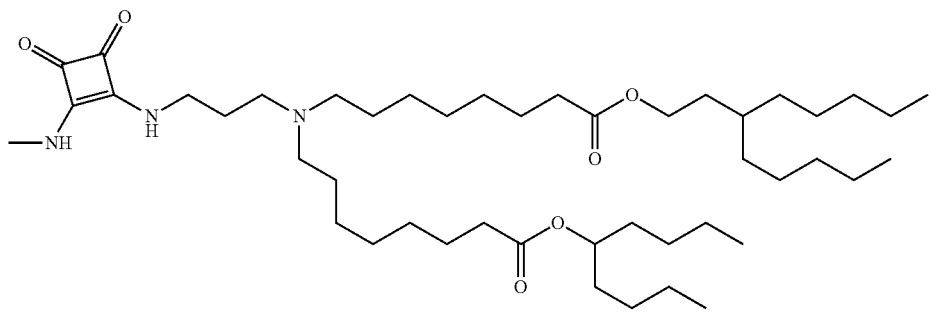

Chemical Formula: $C_{46}H_{85}N_3O_6$
Molecular Weight: 776.20

To a solution of nonan-5-yl 8-((3-aminopropyl)(8-oxo-8-((3-pentyloctyl)oxy)octyl)amino)octanoate (718 mg, 1.08 mmol) in ethanol (10 mL) was added 3-methoxy-4-(methylamino)cyclobut-3-ene-1,2-dione (228 mg, 1.61 mmol). The reaction was allowed to stir at 67° C. for 20 h. After 20 h, the reaction was cooled to room temperature and diluted with diethyl ether. The organics were washed with brine, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give nonan-5-yl 8-((3-((2-(methylamino)-3,4-dioxocyclobut-1-en-1-yl)amino)propyl)(8-oxo-8-((3-pentyloctyl)oxy)octyl)amino)octanoate (215 mg, 0.28 mmol, 26%) as an off-white waxy solid. UPLC/ELSD: RT=2.55 min. MS (ES): m/z (MH$^+$) 776.34 for C$_{46}$H$_{85}$N$_3$O$_6$. $^1$H NMR (300 MHz, CDCl$_3$) δ: ppm 7.22 (br. s, 1H); 6.80 (br. s, 1H); 4.86 (pent., 1H, J=6.0 Hz); 4.07 (t, 2H, J=6.0 Hz); 3.65 (br. s, 2H); 3.27 (d, 3H, J=6.0 Hz); 2.54 (br. t, 2H, J=6.0 Hz); 2.41 (br. t, 4H, J=6.0 Hz); 2.29 (t, 4H, J=6.0 Hz); 1.74 (br. pent., 2H, J=6.0 Hz); 1.67-1.47 (m, 10H); 1.45-1.19 (m, 41H); 0.88 (t, 12H, J=6.0 Hz).

BR. Compound 60: 3-Butylheptyl 8-((3-((2-(methylamino)-3,4-dioxocyclobut-1-en-1-yl)amino)propyl)(8-oxo-8-(tridecan-7-yloxy)octyl)amino)octanoate

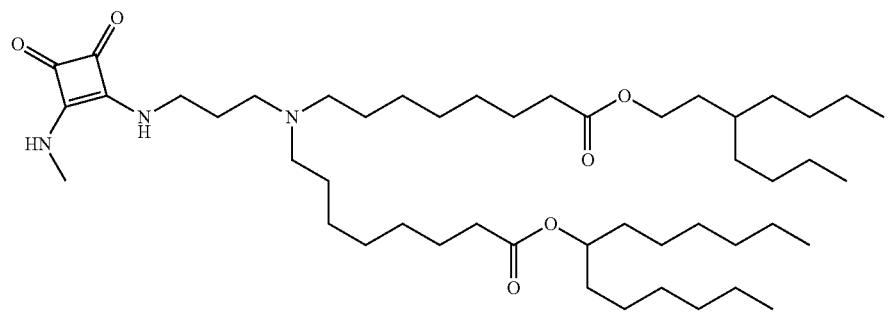

Chemical Formula: C$_{48}$H$_{89}$N$_3$O$_6$
Exact Mass: 803.68
Molecular Weight: 804.26

UPLC/ELSD: RT=2.74 min. MS (ES): m/z (MH$^+$) 804.220 for $C_{48}H_{89}N_3O_6$. $^1$H NMR (300 MHz, CDCl$_3$) δ: ppm 4.88 (p, 1H); 4.10 (t, 2H); 3.70 (bm, 2H); 3.30 (m, 3H); 2.90-2.57 (m, 5H); 2.31 (m, 4H); 1.90 (bm, 2H); 1.74-1.19 (m, 56H); 0.91 (m, 12H).

BS. Compound 61: 3-Butylheptyl 8-((3-((2-(methylamino)-3,4-dioxocyclobut-1-en-1-yl)amino)propyl)(8-oxo-8-(undecan-6-yloxy)octyl)amino)octanoate

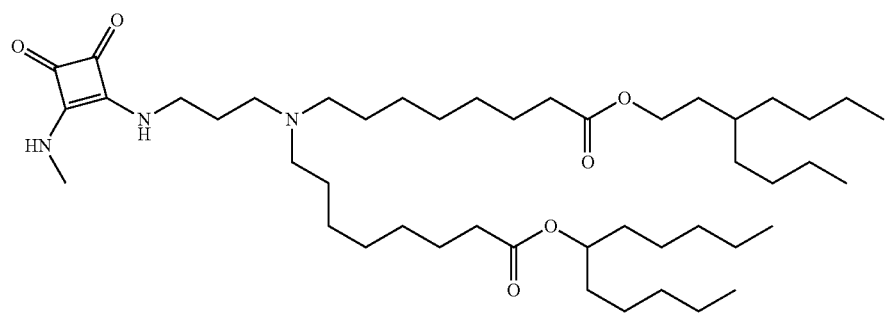

Chemical Formula: $C_{46}H_{85}N_3O_6$
Exact Mass: 775.64
Molecular Weight: 776.20

UPLC/ELSD: RT=2.56 min. MS (ES): m/z (MH$^+$) 776.344 for $C_{46}H_{85}N_3O_6$. $^1$H NMR (300 MHz, CDCl$_3$) δ: ppm 4.88 (p, 1H); 4.10 (t, 2H); 3.72 (bm, 2H); 3.33 (m, 3H); 3.15-2.72 (m, 5H); 2.31 (m, 4H); 2.01 (bm, 2H); 1.77-1.18 (m, 52H); 0.91 (m, 12H).

BT. Compound 62: 3-Butylheptyl 8-((3-((2-(methylamino)-3,4-dioxocyclobut-1-en-1-yl)amino)propyl)(8-(nonan-5-yloxy)-8-oxooctyl)amino)octanoate

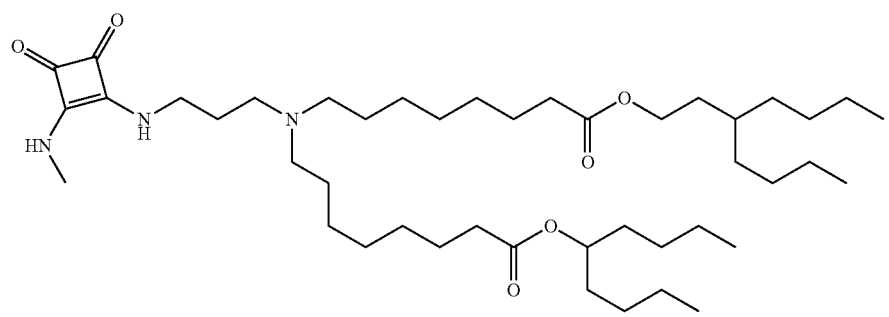

Chemical Formula: $C_{44}H_{81}N_3O_6$
Exact Mass: 747.61
Molecular Weight: 748.15

UPLC/ELSD: RT=2.36 min. MS (ES): m/z (MH⁺) 748.344 for C$_{44}$H$_{81}$N$_3$O$_6$. ¹H NMR (300 MHz, CDCl$_3$) δ: ppm 4.88 (p, 1H); 4.10 (t, 2H); 3.68 (bm, 2H); 3.30 (m, 3H); 2.74-2.43 (m, 6H); 2.31 (m, 4H); 1.82 (bm, 2H); 1.73-1.16 (m, 47H); 0.91 (m, 12H).

BU. Compound 63: Pentadecan-8-yl 8-((3-((2-(methylamino)-3,4-dioxocyclobut-1-en-1-yl)amino)propyl)(8-oxo-8-((3-propylhexyl)oxy)octyl)amino)octanoate

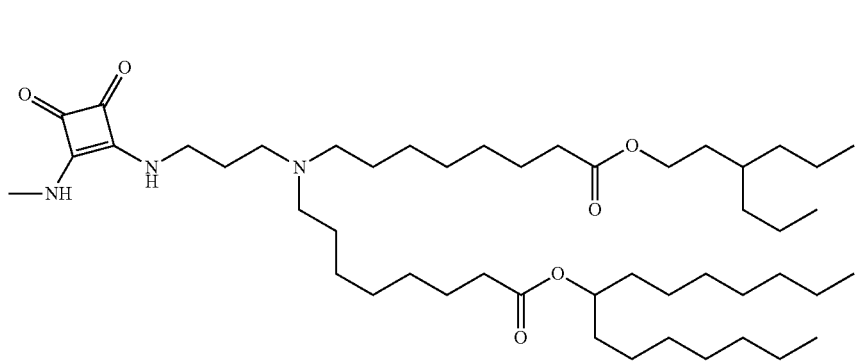

Chemical Formula: C$_{48}$H$_{89}$N$_3$O$_6$
Molecular Weight: 804.255

To a solution of pentadecan-8-yl 8-[(3-aminopropyl)({8-oxo-8-[(3-propylhexyl)oxy]octyl})amino]octanoate (3.779 g, 5.436 mmol, 1 equiv.) in THF (10 mL) and added 3-methoxy-4-(methylamino)cyclobut-3-ene-1,2-dione (1.151 g, 8.154 mmol, 1.5 equiv.) in water (0.4 mL). The reaction was allowed to stir at 67° C. for 16 h under reflux. The reaction was cooled to room temperature, dried, and filtered. The organics were removed under vacuum. The residue was purified by silica gel chromatography [0-30% (mixture of 1% NH$_4$OH, 20% MeOH in dichloromethane) in dichloromethane] to obtain pentadecan-8-yl 8-[(3-{[2-(methylamino)-3,4-dioxocyclobut-1-en-1-yl]amino}propyl)({8-oxo-8-[(3-propylhexyl)oxy]octyl})amino]octanoate (0.252 g, 6%). UPLC/ELSD: RT=2.75 min. MS (ESI): m/z calcd for C$_{45}$H$_{90}$N$_3$O$_6$⁺(M+H) 804.255; found, 804.34. ¹H NMR (300 MHz, CDCl$_3$) δ: ppm 9.05 (br. s, 1H); 8.37 (br. s, 1H); 4.88 (p, 1H); 4.10 (t, 2H); 3.73 (br. d, 2H); 3.34 (d, 3H); 3.26 (m, 2H); 3.07 (br. t, 4H); 2.30 (t, 4H); 2.11 (br. t, 2H); 1.71-1.28 (m, 61H); 0.90 (t, 12H).

BV. Compound 64: 3-Propylhexyl 8-((3-((2-(methylamino)-3,4-dioxocyclobut-1-en-1-yl)amino)propyl)(8-oxo-8-(tridecan-7-yloxy)octyl)amino)octanoate

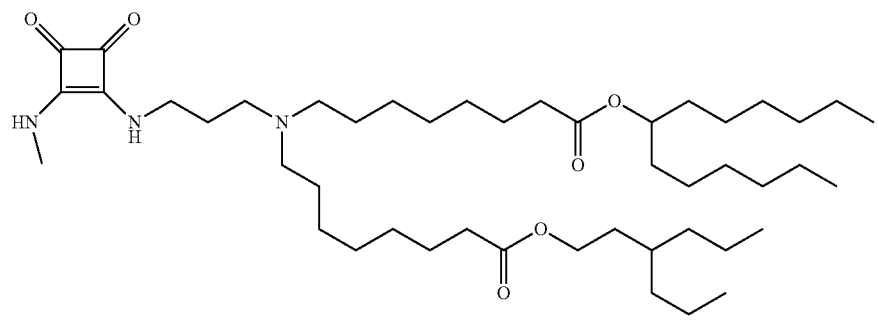

Chemical Formula: C$_{46}$H$_{85}$N$_3$O$_6$
Molecular Weight: 766.20

To a solution of 3-propylhexyl 8-[(3-aminopropyl)[8-oxo-8-(tridecan-7-yloxy)octyl]amino]octanoate (0.774 g, 1.16 mmol) in tetrahydrofuran (5.8 mL) and water (1.0 mL) was added 3-methoxy-4-(methylamino)cyclobut-3-ene-1,2-dione (0.246 g, 1.74 mmol). The reaction was allowed to stir at 67° C. for 18 hours. The reaction was cooled to room temperature and diluted with dichloromethane (40 mL), then washed with saturated NaHCO$_3$(aq.). The organic layer was separated and washed twice more with saturated NaHCO$_3$ (aq.). The organic layer was died over MgSO$_4$, then filtered and evaporated under vacuum. The residue was purified by silica gel chromatography [0-70% (mixture of 1% NH$_4$OH, 20% MeOH in dichloromethane) in dichloromethane] to 3-propylhexyl 8-[(3-{[2-(methylamino)-3,4-dioxocyclobut-1-en-1-yl]amino}propyl)[8-oxo-8-(tridecan-7-yloxy)octyl]amino]octanoate (0.317 g, 0.375 mmol, Yield 32.3%) as a waxy yellow tinted solid. UPLC/ELSD: RT=2.48 min found, 776.34. $^1$H NMR (300 MHz, CDCl$_3$) δ: ppm 4.88 (p, 1H); 4.10 (t, 2H); 3.78-3.55 (m, 2H); 3.29 (d, 3H); 2.56 (t, 2H); 2.43 (t, 4H); 2.31 (t, 4H); 1.85-1.70 (m, 2H); 1.70-1.48 (m, 11H); 1.48-1.39 (m, 4H); 1.39-1.17 (m, 36H); 0.90 (t, 12H).

BW. Compound 65: 3-Propylhexyl 8-((3-((2-(methylamino)-3,4-dioxocyclobut-1-en-1-yl)amino)propyl)(8-oxo-8-(undecan-6-yloxy)octyl)amino)octanoate

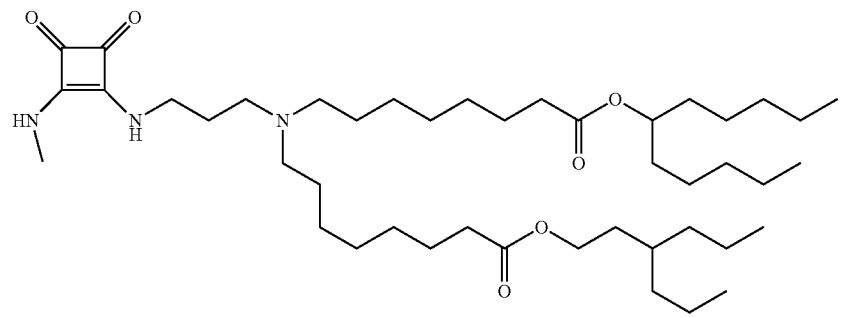

Chemical Formula: C$_{44}$H$_{81}$N$_3$O$_6$
Molecular Weight: 748.15

To a solution of 3-propylhexyl 8-[(3-aminopropyl)[8-oxo-8-(undecan-6-yloxy)octyl]amino]octanoate (0.682 g, 1.07 mmol) in tetrahydrofuran (5.4 mL) and water (0.9 mL) was added 3-methoxy-4-(methylamino)cyclobut-3-ene-1,2-dione (0.226 g, 1.60 mmol). The reaction was allowed to stir at 67° C. for 18 hours. The reaction was cooled to room temperature and diluted with dichloromethane (40 mL), then washed with saturated NaHCO$_3$(aq.). The organic layer was separated and washed twice more with saturated NaHCO$_3$ (aq.). The organic layer was died over MgSO$_4$, then filtered and evaporated under vacuum. The residue was purified by silica gel chromatography [0-70% (mixture of 10% NH$_4$OH, 20% MeOH in dichloromethane) in dichloromethane] to obtain 3-propylhexyl 8-[(3-{[2-(methylamino)-3,4-dioxocyclobut-1-en-1-yl]amino}propyl)[8-oxo-8-(undecan-6-yloxy)octyl]amino]octanoate (0.377 g, 44.8%) as a waxy yellow/white tinted solid. UPLC/ELSD: RT=2.42 min found, 748.47. $^1$H NMR (300 MHz, CDCl$_3$) δ: ppm 4.88 (p, 1H); 4.10 (t, 2H); 3.76-3.57 (m, 2H); 3.29 (d, 3H); 2.56 (t, 2H); 2.43 (t, 4H); 2.31 (t, 4H); 1.84-1.71 (m, 2H); 1.71-1.48 (m, 11H); 1.48-1.40 (m, 4H); 1.40-1.17 (m, 32H); 0.91 (t, 12H).

BX. Compound 66: Nonan-5-yl 8-((3-((2-(methylamino)-3,4-dioxocyclobut-1-en-1-yl)amino)propyl)(8-oxo-8-((3-propylhexyl)oxy)octyl)amino)octanoate

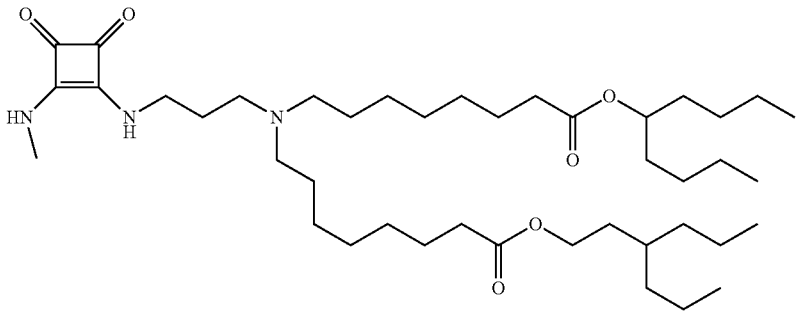

Chemical Formula: $C_{42}H_{77}N_3O_6$
Molecular Weight: 720.09

To a solution of nonan-5-yl 8-[(3-aminopropyl)({8-oxo-8-[(3-propylhexyl)oxy]octyl})amino]octanoate (0.20 g, 0.33 mmol) in tetrahydrofuran (1.7 mL) and water (0.3 mL) was added 3-methoxy-4-(methylamino)cyclobut-3-ene-1,2-dione (0.070 g, 0.49 mmol). The reaction was allowed to stir at 67° C. for 18 hours. The reaction was cooled to room temperature and diluted with dichloromethane (40 mL), then washed with saturated $NaHCO_3$(aq.). The organic layer was separated and washed twice more with saturated $NaHCO_3$ (aq.). The organic layer was died over $MgSO_4$, then filtered and evaporated under vacuum. The residue was purified by silica gel chromatography [0-70% (mixture of 10% $NH_4OH$, 20% MeOH in dichloromethane) in dichloromethane] to obtain nonan-5-yl 8-[(3-{[2-(methylamino)-3,4-dioxocyclobut-1-en-1-yl]amino}propyl)({8-oxo-8-[(3-propylhexyl)oxy]octyl})amino]octanoate (0.131 g, 51.9%) as a yellow tinted waxy solid. UPLC/ELSD: RT=2.24 min found, 720.22. $^1$H NMR (300 MHz, $CDCl_3$) δ: ppm 4.88 (p, 1H); 4.10 (t, 2H); 3.77-3.55 (m, 2H); 3.29 (d, 3H); 2.56 (t, 2H); 2.43 (t, 4H); 2.31 (t, 4H); 1.89-1.70 (m, 3H); 1.70-1.50 (m, 10H); 1.50-1.39 (m, 4H); 1.39-1.17 (m, 28H); 0.91 (t, 12H).

BY. Compound 67: 3-Pentyloctyl 8-((2-hydroxyethyl)(8-oxo-8-((3-propylhexyl)oxy)octyl)amino)octanoate

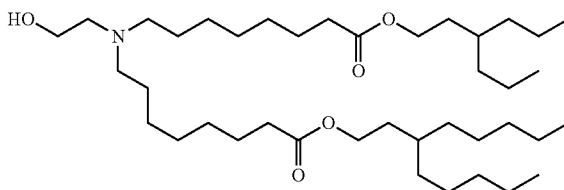

Chemical Formula: $C_{40}H_{79}NO_5$
Molecular Weight: 654.07

To a solution of 3-pentyloctyl 8-bromooctanoate (517 mg, 1.28 mmol) and 3-propylhexyl 8-((2-hydroxyethyl)amino)octanoate (400 mg, 1.21 mmol) in cyclopentyl methyl ether (6 mL) and acetonitrile (6 mL) was added potassium carbonate (1.01 g, 7.28 mmol) and potassium iodide (222 mg, 1.36 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried ($MgSO_4$), filtered, and concentrated. The crude residue was purified by silica gel chromatography (0-5-10-25-50-100% (mixture of 1% $NH_4OH$, 20% MeOH in dichloromethane) in dichloromethane) to give 3-pentyloctyl 8-((2-hydroxyethyl)(8-oxo-8-((3-propylhexyl)oxy)octyl)amino)octanoate (310 mg, 0.47 mmol, 39%) as a clear viscous oil. UPLC/ELSD: RT=2.58 min. MS (ES): m/z ($MH^+$) 654.23 for $C_{40}H_{79}NO_5$. $^1$H NMR (300 MHz, $CDCl_3$) δ: ppm 4.08 (t, 4H, J=6.0 Hz); 3.54 (br. t, 2H, J=6.0 Hz); 2.59 (br. t, 2H, J=6.0 Hz); 2.46 (br. t, 4H, J=6.0 Hz); 2.28 (t, 4H, J=6.0 Hz); 1.68-1.52 (m, 8H); 1.50-1.37 (m, 6H); 1.35-1.19 (m, 37H); 0.88 (t, 12H, J=6.0 Hz).

BZ. Compound 68: 3-Propylhexyl 8-((2-hydroxyethyl)(8-oxo-8-(undecan-6-yloxy)octyl)amino)octanoate

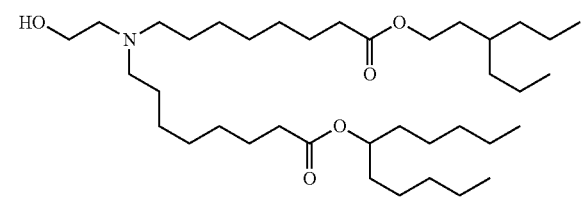

Chemical Formula: $C_{38}H_{75}NO_5$
Molecular Weight: 626.02

To a solution of undecan-6-yl 8-bromooctanoate (481 mg, 1.28 mmol) and 3-propylhexyl 8-((2-hydroxyethyl)amino)octanoate (400 mg, 1.21 mmol) in cyclopentyl methyl ether (6 mL) and acetonitrile (6 mL) was added potassium carbonate (1.01 g, 7.28 mmol) and potassium iodide (222 mg, 1.36 mmol). The resulting reaction mixture was allowed to stir at 80° C. for 16 h. The reaction mixture was then cooled to room temperature, and the volatiles were evaporated under vacuum. The resulting residue was diluted with dichloromethane and washed with water and brine. The organic layer was separated, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give 3-propylhexyl 8-((2-hydroxyethyl)(8-oxo-8-(undecan-6-yloxy)octyl)amino)octanoate (461 mg, 0.74 mmol, 61%) as a clear viscous oil. UPLC/ELSD: RT=2.43 min. MS (ES): m/z (MH$^+$) 626.24 for C$_{28}$H$_{75}$NO$_5$. $^1$H NMR (300 MHz, CDCl$_3$) δ: ppm 4.87 (pent., 1H, J=6.0 Hz); 4.08 (t, 2H, J=6.0 Hz); 3.52 (t, 2H, J=6.0 Hz); 2.57 (t, 2H, J=6.0 Hz); 2.44 (br. t, 4H, J=6.0 Hz); 2.28 (t, 4H, J=6.0 Hz); 1.67-1.38 (m, 16H); 1.37-1.18 (m, 32H); 0.88 (dt, 12H, J=6.0, 3.0 Hz).

CA. Compound 69: Bis(3-butylheptyl) 8,8'-((2-hydroxyethyl)azanediyl)dioctanoate

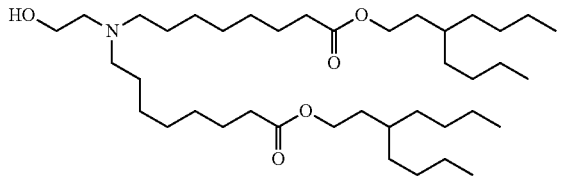

Chemical Formula: C$_{40}$H$_{79}$NO$_5$
Exact Mass: 653.60
Molecular Weight: 654.07

UPLC/ELSD: RT=2.66 min. MS (ES): m/z (MH$^+$) 654.34 for C$_{40}$H$_{79}$NO$_5$. $^1$H NMR (300 MHz, CDCl$_3$) δ: ppm 4.11 (t, 4H); 3.56 (bm, 2H); 2.69-2.39 (bm, 6H), 2.31 (t, 4H); 1.73-1.17 (m, 50H); 0.92 (m, 12H).

CB. Compound 70: 3-butylheptyl 8-((2-hydroxyethyl)(8-oxo-8-((3-pentyloctyl)oxy)octyl)amino)octanoate

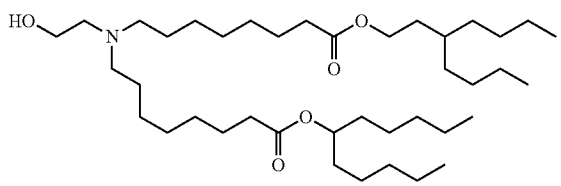

Chemical Formula: C$_{40}$H$_{79}$NO$_5$
Exact Mass: 653.60
Molecular Weight: 654.07

UPLC/ELSD: RT=2.63 min. MS (ES): m/z (MH$^+$) 654.357 for C$_{40}$H$_{79}$NO$_5$. $^1$H NMR (300 MHz, CDCl$_3$) δ: ppm 4.89 (p, 1H); 4.11 (t, 2H); 3.54 (m, 2H); 3.03 (bs, 1H); 2.59 (m, 2H); 2.45 (m, 4H); 2.30 (m, 4H); 1.74-1.18 (m, 51H); 0.91 (m, 12H).

CC. Compound 71: 3-Propylhexyl 8-((2-hydroxyethyl)(8-oxo-8-(tridecan-7-yloxy)octyl)amino)octanoate

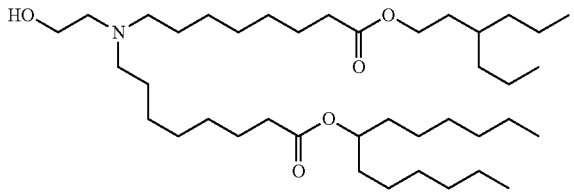

Chemical Formula: C$_{40}$H$_{79}$NO$_5$
Molecular Weight: 654.07

To a solution of tridecan-7-yl 8-bromooctanoate (517 mg, 1.28 mmol) and 3-propylhexyl 8-((2-hydroxyethyl)amino) octanoate (400 mg, 1.21 mmol) in cyclopentyl methyl ether (6 mL) and acetonitrile (6 mL) was added potassium carbonate (1.01 g, 7.28 mmol) and potassium iodide (222 mg, 1.36 mmol). The resulting reaction mixture was allowed to stir at 80° C. for 16 h. The reaction mixture was then cooled to rt, and the volatiles were evaporated under vacuum. The resulting residue was diluted with dichloromethane and washed with water and brine. The organic layer was separated, dried (MgSO$_4$), filtered, and concentrated. The crude residue was purified by silica gel chromatography (0-5-10-25-50-100% (mixture of 1% NH$_4$OH, 20% MeOH in dichloromethane) in dichloromethane) to give 3-propylhexyl 8-((2-hydroxyethyl)(8-oxo-8-(tridecan-7-yloxy)octyl) amino)octanoate (377 mg, 0.58 mmol, 47%) as a clear viscous oil. UPLC/ELSD: RT=2.60 min. MS (ES): m/z (MH$^+$) 654.23 for C$_{40}$H$_{79}$NO$_5$. $^1$H NMR (300 MHz, CDCl$_3$) δ: ppm 4.87 (pent., 1H, J=6.0 Hz); 4.08 (t, 2H, J=6.0 Hz); 3.53 (br. t, 2H, J=6.0 Hz); 2.58 (br. t, 2H, J=6.0 Hz); 2.45 (br. t, 4H, J=6.0 Hz); 2.28 (dt, 4H, J=9.0, 3.0 Hz); 1.69-1.39 (m, 16H); 1.38-1.18 (m, 36H); 0.94-0.81 (m, 12H).

Example 2: Sample Formulations

Lipid nanoparticles (e.g., empty LNPs or loaded LNPs) including a therapeutic and/or prophylactic can be optimized according to the selection of a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), the selection of additional lipids, the amount of each lipid in the lipid component, and the wt:wt ratio of the lipid component to the therapeutic and/or prophylactic.

Lipid nanoparticles (e.g., empty LNPs or loaded LNPs) including DSPC as a phospholipid, cholesterol as a structural lipid, PEG-1 as a PEG lipid, and a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c) were prepared. Tables 2a and 2b summarize the characteristics of the formulations.

As shown in Tables 2a and 2b, the choice of compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c) dramatically affects the size (e.g., diameter), polydispersity index ("PDI"), and encapsulation efficiency ("% EE") of the compositions.

TABLE 2a

Characteristics of nanoparticles comprising compounds of the disclosure.

| Compound | CAD Purity | Size (nm) | % EE | PDI |
|---|---|---|---|---|
| 51 | 90.4 | 58.3 | 95.9 | 0.12 |
| 52 | 90.0 | 70.5 | 84.9 | 0.16 |
| 53 | 83.7 | 106.7 | 84.2 | 0.28 |
| 54 | 87.8 | 64.3 | 98.3 | 0.10 |
| 55 | 97.1 | 77.0 | 88.9 | 0.25 |
| 57 | 83.6 | 69.4 | 90.1 | 0.12 |
| 58 | 92.5 | 63.9 | 90.1 | 0.12 |

TABLE 2b

Characteristics of nanoparticles comprising compounds of the disclosure.

| Compound | CAD Purity | Size (nm) | % EE | PDI |
|---|---|---|---|---|
| 60 | 77.5 | 60.4 | 98.8 | 0.14 |
| 61 | 95.5 | 63.5 | 98.1 | 0.09 |
| 62 | 98.2 | 91.0 | 83.0 | 0.17 |
| 63 | 84.8 | 56.2 | 98.1 | 0.15 |
| 64 | 91.7 | 73.6 | 89.2 | 0.13 |
| 65 | 95.0 | 83.1 | 88.6 | 0.17 |
| 66 | 94.3 | 145.3 | 81.7 | 0.25 |

Examples 3-7: Expression, Clearance, and Tolerability of Sample Formulations

The lipids of the disclosure were developed to promote potent delivery of therapeutic agents to cells, while maintaining a short half-life (i.e., a low metabolic stability) in tissue and thus reduced lipid accumulation in the tissue upon repeat dosing. High accumulation of a lipid in a tissue could trigger toxic effects, and is thus undesirable. On the other hand, a lipid which is metabolized quickly in a tissue may not deliver enough of a therapeutic agent, such as, e.g., an mRNA, to cells to be effective. The aim of the studies outlined below is the identification of amino lipids with optimal metabolic stability which also yield high potency lipid nanoparticles (LNPs).

Example 3: Expression of hEPO Induced by Sample Formulations in Mice and Residual Lipid Levels in the Liver To assess potency of expression and metabolic stability of lipids of the disclosure the hepatocyte protein expression (hEPO) following administration of a nanoparticle of the disclosure (e.g., a loaded LNP) to mice was measured.

Lipid nanoparticles (LNPs) including DSPC as a phospholipid, cholesterol as a structural lipid, PEG-1 as a PEG lipid, a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), and an mRNA encoding hEPO were intravenously administered to CD-1 mice. The concentration of hEPO in serum was tested at 6 h after injection. The particles tested had a PDI of between about 0.1-0.4, an encapsulation efficiency of between about 82-99%, and a particle diameter of about 56-145 nm. All of the tested LNPs demonstrated effective delivery of mRNA to hepatocytes with varying amounts of lipid remaining in the livers of the mice after 24 h.

TABLE 3

Expression of hEPO induced by administration of LNPs comprising lipids of the disclosure in mice and residual lipid levels in the liver.

| Ionizable Lipid Compound No. | Mean 6 hr hEPO Concentration (mIU/mL) | hEPO AUC | Parent Lipid Remaining (nmol/g liver tissue) at 24 h | Approx. Percent Total Dose of Parent Lipid Remaining at 24 h |
|---|---|---|---|---|
| 7 | 1355957 | 2.13E+07 | 0.3 ± 0.2 | 0.2% |
| 14 | 2952339 | 4.53E+07 | 56 ± 6 | 58% |
| 15 | 2933644 | 4.31E+07 | 51 ± 4 | 53% |
| 16 | 1461176 | 2.18E+07 | 77 ± 3 | 79% |
| 17 | 1777875 | 2.61E+07 | 35 ± 5 | 36% |
| 18 | 2158772 | 3.17E+07 | 40 ± 7 | 41% |
| 19 | 2089101 | 3.11E+07 | 73 ± 6 | 75% |
| 20 | 1414856 | 2.13E+07 | 65 ± 5 | 67% |
| 27 | 1316011 | 2.10E+07 | 27 ± 4 | 28% |
| 29 | 808734 | 1.23E+07 | 66 ± 16 | 68% |
| 26 | 496951 | 7.52E+06 | 141 ± 15 | >95%[b] |
| 30 | 1592050 | 2.40E+07 | 25 ± 4 | 26% |
| 28 | 938332 | 1.44E+07 | 58 ± 7 | 60% |
| 40 | 303957 | 4.64E+06 | 3 ± 0.3 | 3% |
| 39 | 129750 | 1.94E+06 | 4 ± 1 | 4% |
| 22 | 1264530 | 2.03E+07 | <0.1 | <0.1% |
| 24 | 1160499 | 1.93E+07 | 3 ± 1 | 2% |
| 21 | 458772 | 7.29E+06 | 13 ± 2 | 9% |
| 25 | 591942 | 1.07E+07 | 0.1 ± 0.04 | <0.1% |
| 23 | 847586 | 1.40E+07 | 24 ± 3 | 18% |
| 37 | 85052 | 1.25E+06 | <0.1 | <0.1% |
| 35 | 106485 | 1.72E+06 | <0.1 | <0.1% |
| 31 | 517841 | 7.72E+06 | 2 ± 0.6 | <0.1% |
| 33 | 389395 | 5.89E+06 | 0.5 ± 0.3 | <0.1% |
| 32 | 111656 | 1.63E+06 | 69 ± 17 | 71% |
| 34 | 205437 | 3.01E+06 | 12 ± 2 | 12% |
| 51 | 1556494 | 1.31E+07 | 4 ± 0.6 | 4% |
| 52 | 564670 | 3.82E+06 | <1 | <1% |
| 53 | 130324 | 6.63E+03 | <1 | <1% |
| 54 | 647775 | 1.97E+07 | 12 ± 1 | 12% |
| 55 | 1332073 | 1.99E+07 | 3 ± 0.6 | 3% |
| 57 | 1238977 | 1.60E+07 | 12 ± 1 | 13% |
| 58 | 1347883 | 2.33E+07 | 15 ± 2 | 15% |
| 60 | 1031398 | 1.42E+07 | 8.5 ± 0.6 | 9 ± 0.8% |
| 61 | 1020791 | 1.44E+07 | 5.1 ± 0.8 | 6 ± 0.3% |
| 62 | 475498 | 6.51E+06 | 1.8 ± 0.6 | 2 ± 0.9% |
| 63 | 692334 | 9.66E+06 | 8.9 ± 2.8 | 9 ± 3% |
| 64 | 1760015 | 2.43E+07 | 4.9 ± 0.9 | 6 ± 0.8% |
| 65 | 734054 | 1.02E+07 | 0.9 ± 0.3 | 0.9 ± 0.06% |
| 66 | 17801 | 2.10E+05 | 0.1 ± 0.03 | <1% |
| 42 | 1428145 | | | |
| 44 | 1273871 | | | |
| 49 | 2385524 | | | |
| 50 | 2617164 | | | |
| 67 | 969620 | | | |
| 68 | 488014 | | | |
| 69 | 1572094 | | | |
| 70 | 1479577 | | | |
| 71 | 1921281 | | | |

[a]The percent of total dose calculation assumes a 25 g mouse with a 1.5 g liver
[b]>95% equals very slow metabolism of the lipid Example 4: Expression of Luciferase Induced by Sample Formulations in Mice and Rats To further assess potency of expression and metabolic stability of lipids of the disclosure, expression of luciferase following administration of a nanoparticle of the disclosure comprising an mRNA containing luciferase (e.g., a loaded LNP) to rodents was measured.

Lipid nanoparticles (LNPs) including DSPC as a phospholipid, cholesterol as a structural lipid, PEG-1 as a PEG lipid, a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), and an mRNA encoding luciferase were intravenously administered to CD-1 mice and Sprague Dawley rats. The level of expression was tested via bioluminescence in the liver ex vivo at 6 h after injection. The particles tested had a PDI of between about 0.09-0.25 and an encapsulation efficiency of between about 89-98%. All of the tested LNPs demonstrated effective delivery of mRNA to the liver and mRNA expression in hepatocytes with varying amounts of lipid remaining in the liver tissue of the rats after 24 h.

TABLE 4a

Expression of NPI-Luciferase induced by administration of LNPs comprising lipids of the disclosure in mice and rats.

| Ionizable Lipid Compound No. | Mean 6 h ex vivo Liver NPI-Luciferase Total Flux (photons/second) | Approx. Percent Total Dose of Parent Lipid Remaining at 24 h | Test Animal |
|---|---|---|---|
| 27 | 357720000 | | mouse |
| 30 | 299800000 | | mouse |
| 22 | 300960000 | | mouse |
| 24 | 240400000 | | mouse |
| 18 | 372800000 | | mouse |
| 25 | 336800000 | | mouse |
| 14 | 465200000 | | mouse |
| 27 | 1215666667 | 28% | rat |
| 30 | 963633333.3 | 25% | rat |
| 22 | 2227666667 | <0.1% | rat |
| 24 | 2020000000 | 2% | rat |
| 18 | 1473333333 | 41% | rat |
| 25 | 4068000000 | <0.1% | rat |
| 14 | 1567000000 | 58% | rat |

TABLE 4b

Expression of luciferase induced by administration of LNPs comprising lipids of the disclosure in mice and residual lipid levels in the liver.

| Compound No. | Total Whole Body Flux @ 6 h (p/s) | % Lipid Remaining @ 24 h |
|---|---|---|
| 7 | 6.09E+10 | <1 |
| 8 | 3.82E+10 | <1 |
| 12 | 2.39E+10 | <1 |
| 13 | 3.77E+10 | <1 |
| 9 | 1.82E+10 | 68 ± 10 |
| 10 | 4.6E+09 | 67 ± 7 |
| 11 | 1.04E+10 | 23 ± 6 |

Example 5: Tolerability in Rats

To assess tolerability of the lipids of the disclosure, expression of a reporter antibody construct induced by sample formulations was assessed in rats.

Lipid nanoparticles (LNPs) including DSPC as a phospholipid, cholesterol as a structural lipid, PEG-1 as a PEG lipid, a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), and an mRNA encoding a reporter antibody construct were intravenously administered to Sprague Dawley rats. The level of reporter antibody construct was tested via an Enzyme-linked Immunosorbent Assay (ELISA) at 6 h after injection. For the formulations tested, high levels of the reporter antibody were measured with minimal signs of liver toxicity.

TABLE 5

Expression of reporter antibody construct induced by administration of LNPs comprising lipids of the disclosure in rats.

| Ionizable Lipid Compound No. | Mean 24 h Reporter Antibody Construct Concentration (ng/mL) |
|---|---|
| 27 | 833698 |
| 22 | 1113642 |
| 25 | 948617 |

Example 6: Expression of hEPO Induced by Sample Formulations in Rats

To further assess potency of expression and metabolic stability of lipids of the disclosure the hepatocyte protein expression (hEPO) following administration of a nanoparticle of the disclosure (e.g., a loaded LNP) to rats was measured.

Lipid nanoparticles (LNPs) including DSPC as a phospholipid, cholesterol as a structural lipid, PEG-1 as a PEG lipid, a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), and an mRNA encoding hEPO were intravenously administered to Sprague Dawley rats. The concentration of hEPO in serum was tested at 6 h after injection. All of the tested LNPs demonstrated effective delivery of mRNA to hepatocytes with varying amounts of lipid remaining in the livers of the rats after 6 h.

TABLE 6

Expression of hEPO induced by administration of LNPs comprising lipids of the disclosure in rats.

| Ionizable Lipid Compound No. | Mean 6 hr hEPO Concentration (mIU/mL) |
|---|---|
| 64 | 161146 |
| 30 | 688780 |
| 54 | 476742 |
| 27 | 664431 |
| 61 | 362569 |
| 55 | 161760 |

Example 7: Expression of Luciferase Induced by Sample Formulations in Non-Human Primates To the assess potency of expression and metabolic stability of lipids of the disclosure in different species, the expression of an mRNA following administration of a nanoparticle of the disclosure containing the mRNA (e.g., a loaded LNP) to non-human primates was measured.

Lipid nanoparticles (LNPs) including DSPC as a phospholipid, cholesterol as a structural lipid, PEG-1 as a PEG lipid, a compound according to Formula (1-1), (2-1), (I-a), (A), (B), (A-1), (A-2), (A-3), (IA), (IB), (B-1), (B-2), (B-3), (A-a), (A-a1), (A-a2), (A-a3), (A-b), (A-b1), (A-b2), (A-b3), (A-c), or (B-c), and an mRNA encoding luciferase were intravenously administered to cynomolgus monkeys. The level of luciferase in livers ex vivo was measured via ELISA at 6 h after injection. All of the tested LNPs demonstrated effective delivery of mRNA to hepatocytes of non-human primates.

TABLE 7

Expression of luciferase induced by administration of LNPs comprising lipids of the disclosure in non-human primates.

| Ionizable Lipid Compound No. | Mean 6 h NPI-Luciferase Concentration (ng/g) |
|---|---|
| 27 | 878 |
| 30 | 782 |
| 54 | 693 |
| 22 | 1322 |

ENUMERATED EMBODIMENTS

Embodiment 1. A Compound of Formula (1-A):

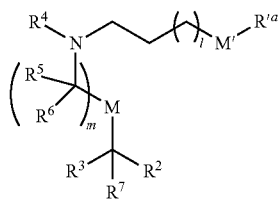

(1-A)

or its N-oxide, or a salt or isomer thereof,
wherein $R^{\prime a}$ is $R^{\prime branched}$ or $R^{\prime cyclic}$; wherein $R^{\prime branched}$ is:

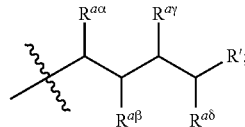

$R^{\prime cyclic}$ is:

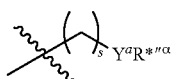

$R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are independently selected from the group consisting of H, $C_{1-14}$ alkyl, $C_{2-14}$ alkenyl, —R*YR*", —YR*", and —R*OR*", or $R^2$ and $R^3$, together with the atom to which they are attached, form a heterocycle or carbocycle;

$R^4$ is selected from the group consisting of hydrogen, a $C_{3-6}$ carbocycle, —$(CH_2)_nQ$, —$(CH_2)_n$CHQR, —$(CH_2)_oC(R^{12})_2(CH_2)_{n-o}Q$, —CHQR, —$CQ(R)_2$, —C(O)NQR and unsubstituted $C_{1-6}$ alkyl, where Q is selected from the group consisting of a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —N(R)S(O)$_2$R, —N(R)C(O)N(R)$_2$, —N(R)C(S)N(R)$_2$, —N(R) $R^8$, —N(R)S(O)$_2R^8$, —O(CH$_2$)$_n$OR, —N(R)C(=NR$^9$)N(R)$_2$, —N(R)C(=CHR$^9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$^9$)N(R)$_2$, —N(OR)C(=CHR$^9$)N(R)$_2$, —C(=NR$^9$)N(R)$_2$, —C(=NR$^9$)R, —C(O)N(R)OR, —(CH$_2$)$_n$N(R)$_2$, —C(R)N(R)$_2$C(O)OR, NC(R)=R$^{11}$, N(C=NR$^{15}$)R$^{11}$, NRC(C(O)NR$^{14}$R$^{14'}$)$_2$, —NRC(O)(CH$_2$)$_p$C(O)NR$^{14}$R$^{14'}$, and

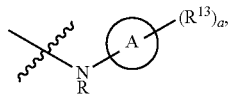

wherein A is $C_{6-10}$ aryl or a heterocycle; and
each o is independently selected from the group consisting of 1, 2, 3, and 4; p is 0, 1, 2, 3, or 4; a is 1, 2, 3, or 4; and each n is independently selected from the group consisting of 1, 2, 3, 4, and 5; or
$R^4$ is

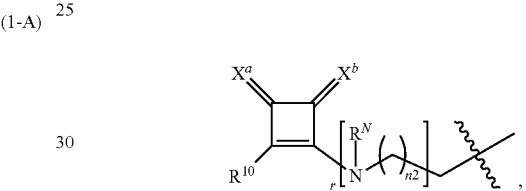

wherein
$X^a$ and $X^b$ are each independently O or S;
$R^{10}$ is selected from the group consisting of H, halo, —OH, R, —N(R)$_2$, —CN, —N$_3$, —C(O)OH, —C(O)OR, —OC(O)R, —OR, —SR, —S(O)R, —S(O)OR, —S(O)$_2$OR, —NO$_2$, —S(O)$_2$N(R)$_2$, —N(R)S(O)$_2$R, —NH(CH$_2$)$_{t1}$N(R)$_2$, —NH(CH$_2$)$_{p1}$O(CH$_2$)$_{q1}$N(R)$_2$, —NH(CH$_2$)$_{s1}$OR, —N((CH$_2$)$_{s1}$OR)$_2$, —N(R)-carbocycle, —N(R)-heterocycle, —N(R)-aryl, —N(R)-heteroaryl, —N(R)(CH$_2$)$_{t1}$-carbocycle, —N(R)(CH$_2$)$_{t1}$-heterocycle, —N(R)(CH$_2$)$_{t1}$-aryl, —N(R)(CH$_2$)$_{t1}$-heteroaryl, a carbocycle, a heterocycle, aryl and heteroaryl;
n2 is selected from the group consisting of 1, 2, 3, 4, 5, 6, 7, 8, 9, and 10;
r is 0 or 1;
$t^1$ is selected from the group consisting of 1, 2, 3, 4, and 5;
$p^1$ is selected from the group consisting of 1, 2, 3, 4, and 5;
$q^1$ is selected from the group consisting of 1, 2, 3, 4, and 5; and
$s^1$ is selected from the group consisting of 1, 2, 3, 4, and 5;
each $R^5$ is independently selected from the group consisting of OH, $C_{1-3}$ alkyl, $C_{2-3}$ alkenyl, and H;
each $R^6$ is independently selected from the group consisting of OH, $C_{1-3}$ alkyl, $C_{2-3}$ alkenyl, and H;
M and M' are independently selected from the group consisting of —OC(O)O—, —C(O)O—, —OC(O)—, —OC(O)-M"-C(O)O—, —OC(O)—NR$^M$—C(O)O—, —O-M"-O—, —C(O)N(R$^M$)—, —N(R$^M$)C(O)—, —OC(O)N(R$^M$)—, —N(R$^M$)C(O)O—, —NR$^M$C(O)NR$^M$—, —O—N=C(R$^M$), —C(O)—, —C(S)—, —C(S)S—, —SC(S)—, —CH(OH)—, —P(O)(OR$^M$)O—, —S(O)$_2$—, —S—

S—, —SO—, —OS—, S(R^M)_2O—, —O—S(R^M)_2—, —S(O)O—, —OS(O)—, an aryl group, and a heteroaryl group, in which M" is a bond, —(CH_2)_zC(O)—, $C_{1-13}$ alkyl, $C_{2-13}$ alkenyl, —B(R)—, —Si(R)_2—, —S(R**)_2—, or —S(O)—, wherein z is 1, 2, 3, or 4;

$R^7$ is selected from the group consisting of $C_{1-3}$ alkyl, $C_{2-3}$ alkenyl, and H;

$R^8$ is selected from the group consisting of $C_{3-6}$ carbocycle and heterocycle;

$R^9$ is selected from the group consisting of H, CN, NO_2, $C_{1-6}$ alkyl, —OR, —S(O)_2R, —S(O)_2N(R)_2, $C_{2-6}$ alkenyl, $C_{3-6}$ carbocycle and heterocycle;

$R^{11}$ is selected from the group consisting of $C_{3-6}$ carbocycle and heterocycle, wherein the $C_{3-6}$ carbocycle and heterocycle are each optionally substituted with one or more $R^{13}$;

$R^{12}$ is selected from the group consisting of H, OH, $C_{1-3}$ alkyl, and $C_{2-3}$ alkenyl;

each $R^{13}$ is independently selected from the group consisting of OH, oxo, halo, $C_{1-6}$ alkyl, $C_{1-6}$ alkoxyl, $C_{2-6}$ alkenyl, $C_{1-6}$ alkylamino, di-($C_{1-6}$ alkyl)amino, NH_2, C(O)NH_2, CN, and NO_2;

each $R^{14}$ is independently selected from the group consisting of H, OH, $C_{1-6}$ alkyl, and $C_{2-3}$ alkenyl;

each $R^{14'}$ is independently selected from the group consisting of H, OH, $C_{1-6}$ alkyl, and $C_{2-3}$ alkenyl;

$R^{15}$ is independently selected from the group consisting of H, OH, $C_{1-6}$ alkyl, and $C_{2-3}$ alkenyl;

each R is independently selected from the group consisting of $C_{1-6}$ alkyl, $C_{1-3}$ alkyl-aryl, $C_{2-3}$ alkenyl, and H;

each R' is independently selected from the group consisting of $C_{1-18}$ alkyl, $C_{2-18}$ alkenyl, —R*YR*''', —YR*''', $(CH_2)_q$ OR*, and H;

each $R^M$ is independently selected from the group consisting of H, $C_{1-6}$ alkyl and $C_{2-6}$ alkenyl;

each R*''' is selected from the group consisting of $C_{1-15}$ alkyl and $C_{2-15}$ alkenyl;

R*''a is selected from the group consisting of $C_{1-15}$ alkyl and $C_{2-15}$ alkenyl;

each R* is independently selected from the group consisting of $C_{1-12}$ alkyl and $C_{2-12}$ alkenyl;

each R** is independently selected from the group consisting of H, OH, $C_{1-12}$ alkyl, $C_{2-12}$ alkenyl, $(CH_2)_q$OR*, and $(CH_2)_q$OH;

each Y is independently a $C_{3-6}$ carbocycle;

$Y^a$ is a $C_{3-6}$ carbocycle;

each X is independently selected from the group consisting of F, Cl, Br, and I;

each q is independently selected from the group consisting of 1, 2, and 3;

l is selected from the group consisting of 1, 2, 3, 4, and 5;

s is selected from the group consisting of 0, 1, 2, 3, 4, 5, and 6; and m is selected from the group consisting of 5, 6, 7, 8, 9, 10, 11, 12, and 13.

Embodiment 2. A compound of Formula (1-B):

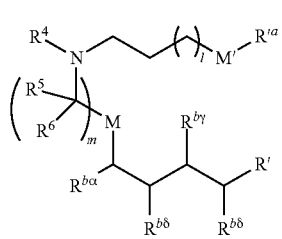

(1-B)

or its N-oxide, or a salt or isomer thereof, wherein $R^{ia}$ is $R^{ibranched}$ or $R^{icyclic}$; wherein $R^{ibranched}$ is:

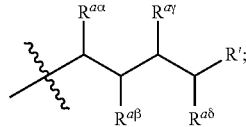

$R^{icyclic}$ is:

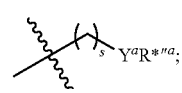

$R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^{b\alpha}$, $R^{b\beta}$, $R^{b\gamma}$, and $R^{b\delta}$ are each independently selected from the group consisting of H, $C_{2-30}$ alkyl, and $C_{5-20}$ alkenyl;

$R^4$ is selected from the group consisting of hydrogen, a $C_{3-6}$ carbocycle, —(CH_2)_nQ, —(CH_2)_nCHQR, —(CH_2)_oC(R^{12})_2(CH_2)_{n-o}Q, —CHQR, —CQ(R)_2, —C(O)NQR and unsubstituted $C_{1-6}$ alkyl, where Q is selected from the group consisting of a carbocycle, heterocycle, —OR, —O(CH_2)_nN(R)_2, —C(O)OR, —OC(O)R, —CX_3, —CX_2H, —CXH_2, —CN, —N(R)_2, —C(O)N(R)_2, —N(R)C(O)R, —N(R)S(O)_2 R, —N(R)C(O)N(R)_2, —N(R)C(S)N(R)_2, —N(R) $R^8$, —N(R)S(O)_2R^8, —O(CH_2)_nOR, —N(R)C(=NR^9)N(R)_2, —N(R)C(=CHR^9)N(R)_2, —OC(O)N(R)_2, —N(R)C(O)OR, —N(OR)C(O)R, —N(OR)S(O)_2R, —N(OR)C(O)OR, —N(OR)C(O)N(R)_2, —N(OR)C(S)N(R)_2, —N(OR)C(=NR^9)N(R)_2, —N(OR)C(=CHR^9)N(R)_2, —C(=NR^9)N(R)_2, —C(=NR^9)R, —C(O)N(R)OR, —(CH_2)_nN(R)_2, —C(R)N(R)_2C(O)OR, NC(R)=R^{11}, N(C=NR^{15})R^{11}, NRC(C(O)N^{14}R^{14'})_2, —NRC(O)(CH_2)_pC(O)NR^{14}R^{14'}, and

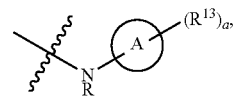

wherein A is $C_{6-10}$ aryl or a heterocycle; and each o is independently selected from the group consisting of 1, 2, 3, and 4; p is 0, 1, 2, 3, or 4; a is 1, 2, 3, or 4; and each n is independently selected from the group consisting of 1, 2, 3, 4, and 5; or $R^4$ is

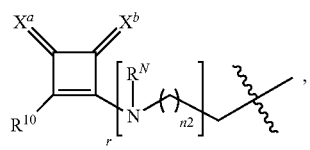

wherein $X^a$ and $X^b$ are each independently O or S;

$R^{10}$ is selected from the group consisting of H, halo, —OH, R, —N(R)$_2$, —CN, —N$_3$, —C(O)OH, —C(O)OR, —OC(O)R, —OR, —SR, —S(O)R, —S(O)OR, —S(O)$_2$OR, —NO$_2$, —S(O)$_2$N(R)$_2$, —N(R)S(O)$_2$R, —NH(CH$_2$)$_{r1}$N(R)$_2$, —NH(CH$_2$)$_{p1}$O(CH$_2$)$_{q1}$N(R)$_2$, —NH(CH$_2$)$_{s1}$OR, —N((CH$_2$)$_{s1}$OR)$_2$, —N(R)-carbocycle, —N(R)-heterocycle, —N(R)-aryl, —N(R)-heteroaryl, —N(R)(CH$_2$)$_{r1}$-carbocycle, —N(R)(CH$_2$)$_{r1}$-heterocycle, —N(R)(CH$_2$)$_{r1}$-aryl, —N(R)(CH$_2$)$_{r1}$-heteroaryl, a carbocycle, a heterocycle, aryl and heteroaryl;

n2 is selected from the group consisting of 1, 2, 3, 4, 5, 6, 7, 8, 9, and 10;

r is 0 or 1;

$t^1$ is selected from the group consisting of 1, 2, 3, 4, and 5;

$p^1$ is selected from the group consisting of 1, 2, 3, 4, and 5;

$q^1$ is selected from the group consisting of 1, 2, 3, 4, and 5; and $s^1$ is selected from the group consisting of 1, 2, 3, 4, and 5;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are independently selected from the group consisting of —OC(O)O—, —C(O)O—, —OC(O)—, —OC(O)-M"-C(O)O—, —OC(O)—NR$^M$—C(O)O—, —O-M"-O—, —C(O)N(R$^M$)—, —N(R$^M$)C(O)—, —OC(O)N(R$^M$)—, —N(R$^M$)C(O)O—, —NR$^M$C(O)NR$^M$—, —O—N=C(R$^M$)—C(O)—, —C(S)—, —C(S)S—, —SC(S)—, —CH(OH)—, —P(O)(OR$^M$)O—, —S(O)$_2$—, —S—S—, —SO—, —OS—, S(R$^M$)$_2$O—, —O—S(R$^M$)$_2$—, —S(O)O—, —OS(O)—, an aryl group, and a heteroaryl group, in which M" is a bond, —(CH$_2$)$_z$C(O)—, $C_{1-13}$ alkyl, $C_{2-13}$ alkenyl, —B(R)—, —Si(R)$_2$—, —S(R**)$_2$—, or —S(O)—, wherein z is 1, 2, 3, or 4;

$R^7$ is selected from the group consisting of $C_{1-3}$ alkyl, $C_{2-3}$ alkenyl, and H;

$R^8$ is selected from the group consisting of $C_{3-6}$ carbocycle and heterocycle;

$R^9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

$R^{11}$ is selected from the group consisting of $C_{3-6}$ carbocycle and heterocycle, wherein the $C_{3-6}$ carbocycle and heterocycle are each optionally substituted with one or more $R^{13}$;

$R^{12}$ is selected from the group consisting of H, OH, $C_{1-3}$ alkyl, and $C_{2-3}$ alkenyl;

each $R^{13}$ is independently selected from the group consisting of OH, oxo, halo, $C_{1-6}$ alkyl, $C_{1-6}$ alkoxyl, $C_{2-6}$ alkenyl, $C_{1-6}$ alkylamino, di-($C_{1-6}$ alkyl)amino, NH$_2$, C(O)NH$_2$, CN, and NO$_2$;

each $R^{14}$ is independently selected from the group consisting of H, OH, $C_{1-6}$ alkyl, and $C_{2-3}$ alkenyl;

each $R^{14'}$ is independently selected from the group consisting of H, OH, $C_{1-6}$ alkyl, and $C_{2-3}$ alkenyl;

$R^{15}$ is independently selected from the group consisting of H, OH, $C_{1-6}$ alkyl, and $C_{2-3}$ alkenyl;

each R is independently selected from the group consisting of $C_{1-6}$ alkyl, $C_{1-3}$ alkyl-aryl, $C_{2-3}$ alkenyl, and H;

each R' is independently selected from the group consisting of $C_{1-18}$ alkyl, $C_{2-18}$ alkenyl, —R*YR*''', —YR*''', (CH$_2$)$_q$OR*, and H;

each $R^M$ is independently selected from the group consisting of H, $C_{1-6}$ alkyl and $C_{2-6}$ alkenyl;

each R*''' is selected from the group consisting of $C_{1-15}$ alkyl and $C_{2-15}$ alkenyl;

R*''$^a$ is selected from the group consisting of $C_{1-15}$ alkyl and $C_{2-15}$ alkenyl;

each R* is independently selected from the group consisting of $C_{1-12}$ alkyl and $C_{2-12}$ alkenyl;

each R** is independently selected from the group consisting of H, OH, $C_{1-12}$ alkyl, $C_{2-12}$ alkenyl, (CH$_2$)$_q$OR*, and (CH$_2$)$_q$OH;

each Y is independently a $C_{3-6}$ carbocycle;

$Y^a$ is a $C_{3-6}$ carbocycle;

each X is independently selected from the group consisting of F, Cl, Br, and I;

each q is independently selected from the group consisting of 1, 2, and 3;

l is selected from the group consisting of 1, 2, 3, 4, and 5;

s is selected from the group consisting of 0, 1, 2, 3, 4, 5, and 6; and m is selected from the group consisting of 5, 6, 7, 8, 9, 10, 11, 12, and 13.

Embodiment 3. The compound of any one of the preceding embodiments, wherein $R^7$ is H.

Embodiment 4. The compound of any of the preceding embodiments, wherein M is —C(O)O— or —OC(O)—.

Embodiment 5. The compound of any of the preceding embodiments, wherein M' is —C(O)O— or —OC(O)—.

Embodiment 6. A compound of Formula (A):

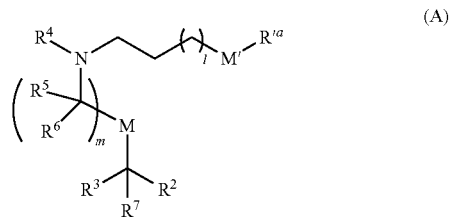

or its N-oxide, or a salt or isomer thereof, wherein $R^{'a}$ is $R^{'branched}$ or $R^{'cyclic}$; wherein $R^{'branched}$ is:

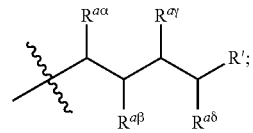

$R^{'cyclic}$ is:

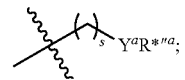

wherein denotes a point of attachment;
wherein $R^{a\alpha}$ is H, and $R^{a\beta}$, $R^{a\gamma}$, and $R^{a\delta}$ are each independently selected from the group consisting of H, $C_{2-12}$ alkyl, and $C_{2-12}$ alkenyl, wherein at least one of $R^{a\beta}$, $R^{a\gamma}$, and $R^{a\delta}$ is selected from the group consisting of $C_{2-12}$ alkyl and $C_{2-12}$ alkenyl;

$R^2$ and $R^3$ are each $C_{1-14}$ alkyl;

$R^4$ is selected from the group consisting of —$(CH_2)_2OH$, —$(CH_2)_3OH$, —$(CH_2)_4OH$, —$(CH_2)_5OH$ and wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

$R^7$ is H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*na}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

Embodiment 7. A compound of Formula (B):

(B)

or its N-oxide, or a salt or isomer thereof,
wherein $R^{'a}$ is $R^{'branched}$ or $R^{'cyclic}$; wherein $R^{'branched}$ is:

$R^{'cyclic}$ is:

wherein denotes a point of attachment;
wherein $R^{a\alpha}$ and $R^{a\beta}$ are each H, and $R^{a\gamma}$ and $R^{a\delta}$ are each independently selected from the group consisting of H, $C_{2-12}$ alkyl, and $C_{2-12}$ alkenyl, wherein at least one of $R^{a\gamma}$ and $R^{a\delta}$ is selected from the group consisting of $C_{2-12}$ alkyl and $C_{2-12}$ alkenyl;

$R^{b\alpha}$, $R^{b\beta}$, $R^{b\gamma}$, and $R^{b\delta}$ are each independently selected from the group consisting of H, $C_2$ alkyl, and $C_{5-20}$ alkenyl, wherein at least one of $R^{b\alpha}$, $R^{b\beta}$, $R^{b\gamma}$, and $R^{b\delta}$ is selected from the group consisting of $C_{2-30}$ alkyl and $C_{5-20}$ alkenyl;

$R^4$ is selected from the group consisting of —$(CH_2)_2OH$, —$(CH_2)_3OH$, —$(CH_2)_4OH$, —$(CH_2)_5OH$ and wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*na}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

Embodiment 8. The compound of any one of the preceding embodiments, each $R^5$ is independently selected from the group consisting of $C_{1-3}$ alkyl, $C_{2-3}$ alkenyl, and H.

Embodiment 9. The compound of any one of the preceding embodiments, wherein each $R^6$ is independently selected from the group consisting of $C_{1-3}$ alkyl, $C_{2-3}$ alkenyl, and H.

Embodiment 10. The compound of any one of the preceding embodiments, wherein $R^5$ and $R^6$ are each H.

Embodiment 11. A compound of Formula (1-1):

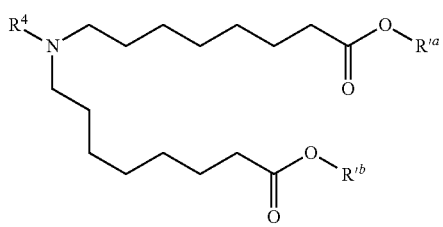
(1-1)

or its N-oxide, or a salt or isomer thereof,
wherein $R'^a$ is $R'^{branched}$ or $R'^{cyclic}$; wherein $R'^{branched}$ is

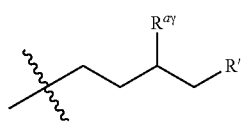

and $R'^{cyclic}$ is:

and
$R'^b$ is:

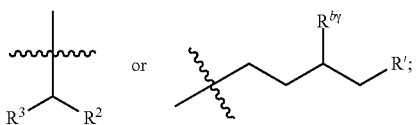

wherein

denotes a point of attachment;
wherein $R^{a\gamma}$ and $R^{b\gamma}$ are each independently a $C_{2-12}$ alkyl or $C_{2-12}$ alkenyl;
$R^2$ and $R^3$ are each independently selected from the group consisting of $C_{1-14}$ alkyl and $C_{2-14}$ alkenyl;

$R^4$ is $—(CH_2)_2OH$, wherein

denotes a point of attachment;
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
each R' independently is a $C_{1-12}$ alkyl or $C_{2-12}$ alkenyl;
$Y^a$ is a $C_{3-6}$ carbocycle;
$R^{*''a}$ is selected from the group consisting of $C_{1-15}$ alkyl and $C_{2-15}$ alkenyl; and
s is 2 or 3.

Embodiment 12. A compound of Formula (2-1):

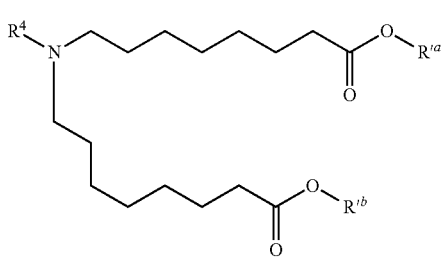
(2-1)

or its N-oxide, or a salt or isomer thereof,
wherein $R'^a$ is $R'^{branched}$ or $R'^{cyclic}$; wherein $R'^{branched}$ is:

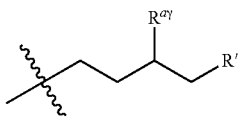

and $R'^{cyclic}$ is:

and
$R'^b$ is:

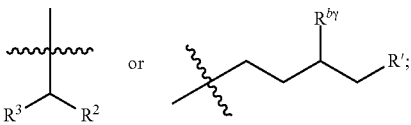

wherein

denotes a point of attachment;

wherein $R^{a\gamma}$ and $R^{b\gamma}$ are each independently a $C_{2-12}$ alkyl or $C_{2-12}$ alkenyl;

$R^2$ and $R^3$ are each independently selected from the group consisting of $C_{1-14}$ alkyl and $C_{2-14}$ alkenyl;

$R^4$ is

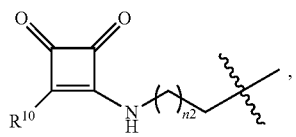

wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl; and s is 2 or 3.

Embodiment 13. The compound of any one of the preceding embodiments, having the following structure:

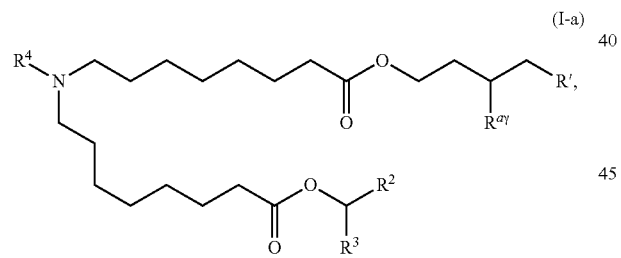

(I-a)

wherein $R^{a\gamma}$ is a $C_{2-6}$ alkyl.

Embodiment 14. The compound of any one of the preceding embodiments, having the following structure:

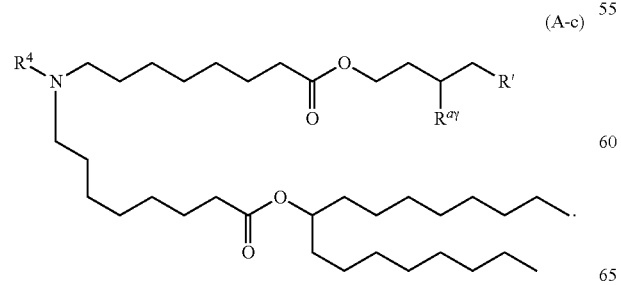

(A-c)

Embodiment 15. The compound of any one of the preceding embodiments, having the following structure:

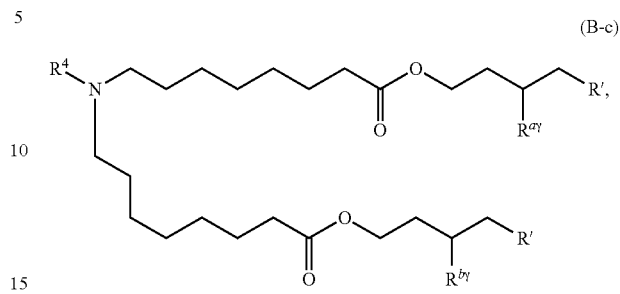

(B-c)

Embodiment 16. The compound of any one of the preceding embodiments, wherein $R^{a\gamma}$ is a $C_{2-6}$ alkyl.

Embodiment 17. The compound of any one of the preceding embodiments, wherein $R^{b\gamma}$ is a $C_{2-6}$ alkyl.

Embodiment 18. The compound of any one of the preceding embodiments, wherein $R^{a\gamma}$ and $R^{b\gamma}$ are each independently a $C_{2-6}$ alkyl.

Embodiment 19. The compound of any one of the preceding embodiments, wherein $R^4$ is $-(CH_2)_2OH$.

Embodiment 20. The compound of any one of the preceding embodiments, wherein $R^4$ is

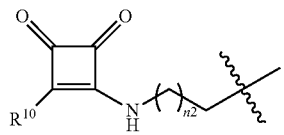

Embodiment 21. The compound of any one of the preceding embodiments, wherein $R^{1a}$ is $R^{1branched}$.

Embodiment 22. The compound of any one of the preceding embodiments, wherein $R^{1a}$ is $R^{1cyclic}$.

Embodiment 23. The compound of any one of the preceding embodiments, wherein $R^{1b}$ is

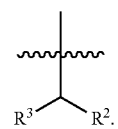

Embodiment 24. The compound of any one of the preceding embodiments, wherein $R^{1b}$ is

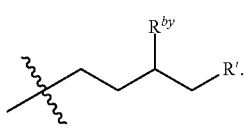

Embodiment 25. A compound of Formula (A-1):

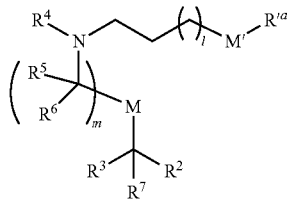

or its N-oxide, or a salt or isomer thereof,
wherein $R^{\prime a}$ is $R^{\prime branched}$ or $R^{\prime cyclic}$; wherein $R^{\prime branched}$ is:

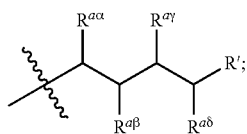

$R^{\prime cyclic}$ is:

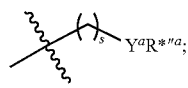

wherein

denotes a point of attachment;
wherein $R^{a\alpha}$, $R^{a\gamma}$ and $R^{a\delta}$ are each independently selected from the group consisting of H, $C_{2-12}$ alkyl, and $C_{2-12}$ alkenyl; and $R^{a\beta}$ is a $C_2$ alkyl, $C_3$ alkyl, $C_4$ alkyl, $C_5$ alkyl, or $C_6$ alkyl;
$R^2$ and $R^3$ are each $C_{1-14}$ alkyl;
$R^4$ is —$(CH_2)_2OH$ or

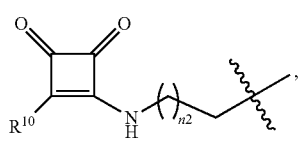

wherein
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
$R^5$ and $R^6$ are each H;
$R^7$ is H;
M and M' are each independently selected from the group consisting of —C(O)O— and —OC(O)—;
R' is a $C_{1-12}$ alkyl or $C_{2-12}$ alkenyl;
$Y^a$ is a $C_{3-6}$ carbocycle;
$R^{*\prime\prime a}$ is selected from the group consisting of $C_{1-15}$ alkyl and $C_{2-15}$ alkenyl;

l is selected from the group consisting of 1, 2, 3, 4, and 5;
s is 2 or 3; and
m is selected from the group consisting of 5, 6, 7, 8, 9, 10, 11, 12, and 13.

Embodiment 26. A compound of Formula (A-2):

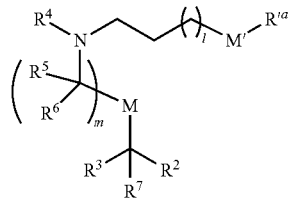

or its N-oxide, or a salt or isomer thereof,
wherein $R^{\prime a}$ is $R^{\prime branched}$ or $R^{\prime cyclic}$; wherein $R^{\prime branched}$ is:

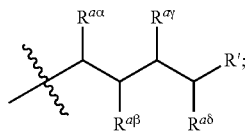

$R^{\prime cyclic}$ is:

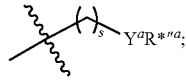

wherein

denotes a point of attachment;
wherein $R^{a\alpha}$, $R^{a\beta}$, and $R^{a\delta}$ are each independently selected from the group consisting of H, $C_{2-12}$ alkyl, and $C_{2-12}$ alkenyl; and $R^{a\gamma}$ is a $C_2$ alkyl, $C_3$ alkyl, $C_4$ alkyl, $C_5$ alkyl, or $C_6$ alkyl;
$R^2$ and $R^3$ are each $C_{1-14}$ alkyl;
$R^4$ is —$(CH_2)_2OH$ or

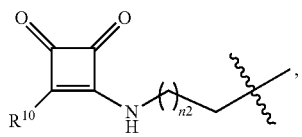

wherein
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
$R^5$ and $R^6$ are each H;
$R^7$ is H;
M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

Embodiment 27. A compound of Formula (A-3):

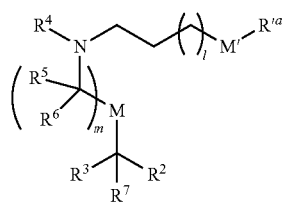
(A-3)

or its N-oxide, or a salt or isomer thereof, wherein $R'^a$ is $R'^{branched}$ or $R'^{cyclic}$; wherein $R'^{branched}$ is:

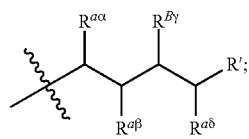

$R'^{cyclic}$ is:

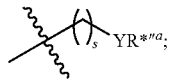

wherein

denotes a point of attachment;

wherein $R^{a\alpha}$, $R^{a\gamma}$ and $R^{a\beta}$ are each independently selected from the group consisting of H, $C_{2-12}$ alkyl, and $C_{2-12}$ alkenyl; and $R^{a\delta}$ is a $C_2$ alkyl, $C_3$ alkyl, $C_4$ alkyl, $C_5$ alkyl, or $C_6$ alkyl;

$R^2$ and $R^3$ are each $C_{1-14}$ alkyl;

$R^4$ is $-(CH_2)_2OH$ or

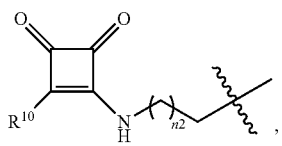

wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

$R^7$ is H;

M and M' are each independently selected from the group consisting of $-C(O)O-$ and $-OC(O)-$;

R' is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

Embodiment 28. The compound of any one of the preceding embodiments, wherein $R^2$ and $R^3$ are each $C_{1-14}$ alkyl.

Embodiment 29. The compound of any one of the preceding embodiments, wherein $R^2$ and $R^3$ are each $C_8$ alkyl.

Embodiment 30. The compound of any one of the preceding embodiments, wherein one of $R^2$ and $R^3$ is $C_2$ alkyl and the other is $C_8$ alkyl.

Embodiment 31. A compound of any one of the preceding embodiments, having the following structure:

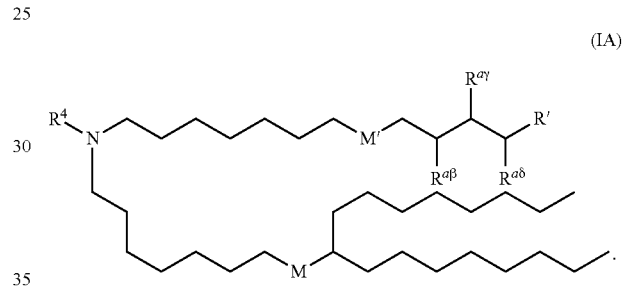
(IA)

Embodiment 32. A compound of any one of the preceding embodiments, having the following structure:

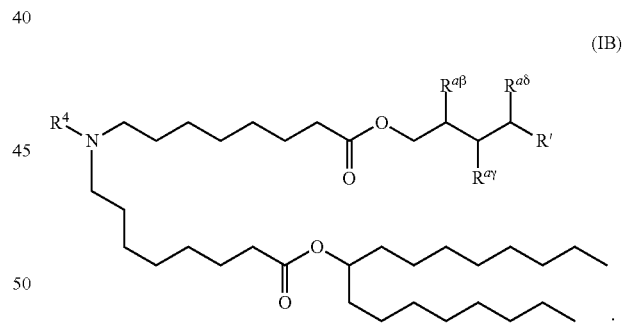
(IB)

Embodiment 33. A compound of Formula (B-1):

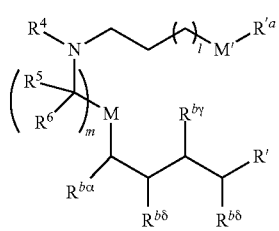
(B-1)

or its N-oxide, or a salt or isomer thereof,
wherein $R^{ia}$ is $R^{ibranched}$ or $R^{icyclic}$; wherein $R^{ibranched}$ is:

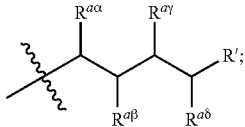

$R^{icyclic}$ is:

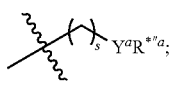

wherein

denotes a point of attachment;
wherein $R^{a\alpha}$, $R^{a\gamma}$, and $R^{a\delta}$ are each independently selected from the group consisting of H, $C_{2-12}$ alkyl, and $C_{2-12}$ alkenyl; and $R^a$ is a $C_2$ alkyl, $C_3$ alkyl, $C_4$ alkyl, $C_5$ alkyl, or $C_6$ alkyl;

$R^{b\alpha}$, $R^{b\gamma}$, and $R^{b\delta}$ are each independently selected from the group consisting of H, $C_{2-30}$ alkyl, and $C_{5-20}$ alkenyl; and $R^{b\beta}$ is a $C_2$ alkyl, $C_3$ alkyl, $C_4$ alkyl, $C_5$ alkyl, or $C_6$ alkyl;

$R^4$ is

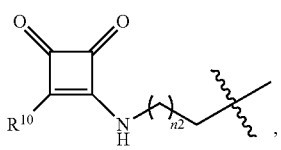

wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*\prime\prime a}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

Embodiment 34. A compound of Formula (B-2):

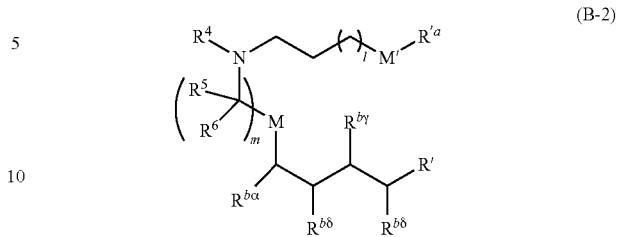

(B-2)

or its N-oxide, or a salt or isomer thereof,
wherein $R^{ia}$ is $R^{ibranched}$ or $R^{icyclic}$; wherein $R^{ibranched}$ is:

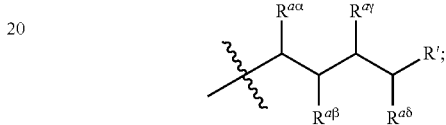

$R^{icyclic}$ is:

wherein

denotes a point of attachment;
wherein $R^{a\alpha}$, $R^{a\beta}$, and $R^{a\delta}$ are each independently selected from the group consisting of H, $C_{2-12}$ alkyl, and $C_{2-12}$ alkenyl; and $R^{a\gamma}$ is a $C_2$ alkyl, $C_3$ alkyl, $C_4$ alkyl, $C_5$ alkyl, or $C_6$ alkyl;

$R^{b\alpha}$, $R^{b\beta}$, and $R^{b\delta}$ are each independently selected from the group consisting of H, $C_{2-30}$ alkyl, and $C_{5-20}$ alkenyl; and $R^{b\gamma}$ is a $C_2$ alkyl, $C_3$ alkyl, $C_4$ alkyl, $C_5$ alkyl, or $C_6$ alkyl;

$R^4$ is —$(CH_2)_2OH$ or

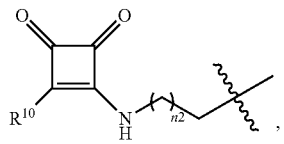

wherein
$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*na}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

Embodiment 35. A compound of Formula (B-3):

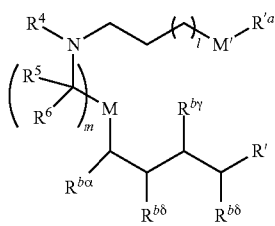

(B-3)

or its N-oxide, or a salt or isomer thereof, wherein $R'^a$ is $R'^{branched}$ or $R'^{cyclic}$; wherein $R'^{branched}$ is:

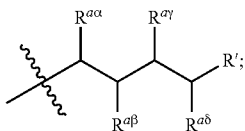

$R'^{cyclic}$ is:

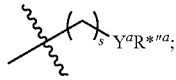

wherein

denotes a point of attachment;

wherein $R^{a\alpha}$, $R^{a\beta}$, and $R^{a\gamma}$ are each independently selected from the group consisting of H, $C_{2-12}$ alkyl, and $C_{2-12}$ alkenyl; and $R^{a\delta}$ is a $C_2$ alkyl, $C_3$ alkyl, $C_4$ alkyl, $C_5$ alkyl, or $C_6$ alkyl;

$R^{b\alpha}$, $R^{b\beta}$, and $R^{b\gamma}$ are each independently selected from the group consisting of H, $C_{2-30}$ alkyl, and $C_{5-20}$ alkenyl; and $R^{b\delta}$ is a $C_2$ alkyl, $C_3$ alkyl, $C_4$ alkyl, $C_5$ alkyl, or $C_6$ alkyl;

$R^4$ is —$(CH_2)_2OH$ or

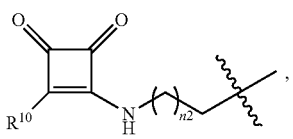

wherein

denotes a point of attachment;

$R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

$R^5$ and $R^6$ are each H;

M and M' are each independently selected from the group consisting of —C(O)O— and —OC(O)—;

R' is a $C_{1-12}$ alkyl or $C_{2-12}$ alkenyl;

$Y^a$ is a $C_{3-6}$ carbocycle;

$R^{*na}$ is selected from the group consisting of $C_{1-15}$ alkyl and $C_{2-15}$ alkenyl;

l is selected from the group consisting of 1, 2, 3, 4, and 5;

s is 2 or 3; and m is selected from the group consisting of 5, 6, 7, 8, 9, 10, 11, 12, and 13.

Embodiment 36. The compound of any one of the preceding embodiments wherein $R'^a$ is $R'^{cyclic}$.

Embodiment 37. The compound of any one of the preceding embodiments, wherein s is 2 or 3.

Embodiment 38. The compound of any one of the preceding embodiments, wherein $Y^a$ is cyclohexyl.

Embodiment 39. The compound of any one of the preceding embodiments, wherein $Y^aR^{*na}$ is

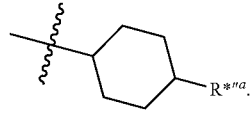

Embodiment 40. The compound of any one of the preceding embodiments, wherein $Y^a$ is cyclopentyl.

Embodiment 41. The compound of any one of the preceding embodiments, wherein $Y^aR^{*na}$ is

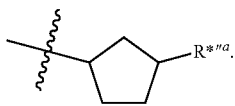

Embodiment 42. The compound of any one of the preceding embodiments, wherein $R^{*na}$ is a $C_2$-alkyl or $C_3$-alkyl.

Embodiment 43. The compound of any one of the preceding embodiments wherein $R'^a$ is $R'^{branched}$.

Embodiment 44. A compound any one of the preceding embodiments, wherein $R^{a\alpha}$, $R^{a\beta}$ and $R^{a\delta}$ are each H; and $R^{a\gamma}$ is a $C_2$ alkyl, $C_3$ alkyl, $C_4$ alkyl, $C_5$ alkyl, or $C_6$ alkyl.

Embodiment 45. A compound any one of the preceding embodiments, wherein $R^{b\alpha}$, $R^{b\gamma}$ and $R^{b\delta}$ are each H, and $R^{b\beta}$ is a $C_2$ alkyl, $C_3$ alkyl, $C_4$ alkyl, $C_5$ alkyl, or $C_6$ alkyl.

Embodiment 46. A compound any one of the preceding embodiments, wherein $R^{b\alpha}$, $R^{b\beta}$ and $R^{b\delta}$ are each H; $R^{b\gamma}$ is a $C_2$ alkyl, $C_3$ alkyl, $C_4$ alkyl, $C_5$ alkyl, or $C_6$ alkyl.

Embodiment 47. A compound any one of the preceding embodiments, wherein $R^{b\alpha}$, $R^{b\beta}$ and $R^{b\gamma}$ are each H, and $R^{b\delta}$ is a $C_2$ alkyl, $C_3$ alkyl, $C_4$ alkyl, $C_5$ alkyl, or $C_6$ alkyl.

Embodiment 48. A compound of Formula (A-a):

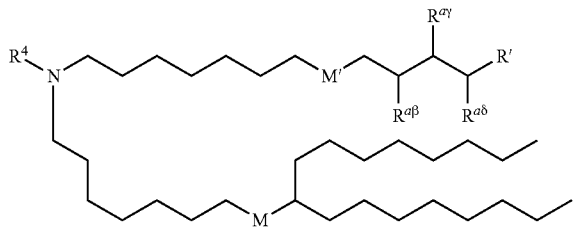

(A-a)

or its N-oxide, or a salt or isomer thereof, wherein $R^{a\beta}$, $R^{a\gamma}$ and $R^{a\delta}$ are each independently selected from the group consisting of H, $C_{2-12}$ alkyl, and $C_{2-12}$ alkenyl, wherein at least one of $R^{a\beta}$, $R^{a\gamma}$, and $R^{a\delta}$ is selected from the group consisting of $C_{2-12}$ alkyl and $C_{2-12}$ alkenyl;

$R^4$ is selected from the group consisting of —$(CH_2)_2OH$, —$(CH_2)_3OH$, —$(CH_2)_4OH$, and —$(CH_2)_5OH$;

M and M' are each independently selected from the group consisting of —C(O)O— and —OC(O)—; and R' is a $C_{1-12}$ alkyl or $C_{2-12}$ alkenyl.

Embodiment 49. A compound of Formula (A-a1):

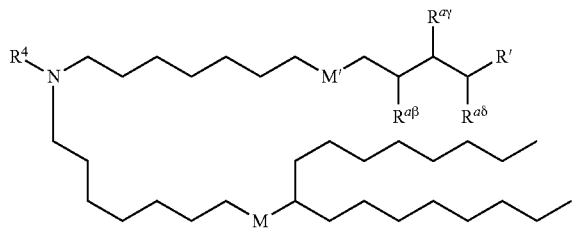

(A-a1)

or its N-oxide, or a salt or isomer thereof, wherein $R^{a\gamma}$ and $R^{a\delta}$ are each independently selected from the group consisting of H, $C_{2-12}$ alkyl, and $C_{2-12}$ alkenyl; and $R^{a\beta}$ is a $C_2$ alkyl, $C_3$ alkyl, $C_4$ alkyl, $C_5$ alkyl, or $C_6$ alkyl;

$R^4$ is —$(CH_2)_2OH$ or

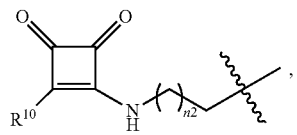

wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

M and M' are each independently selected from the group consisting of —C(O)O— and —OC(O)—; and R' is a $C_{1-12}$ alkyl or $C_{2-12}$ alkenyl.

Embodiment 50. A compound of Formula (A-a2):

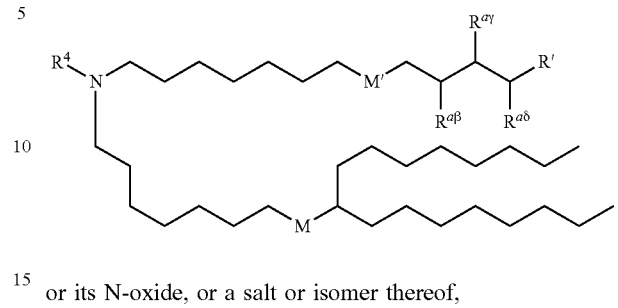

(A-a2)

or its N-oxide, or a salt or isomer thereof, wherein $R^{a\beta}$ and $R^{a\delta}$ are each independently selected from the group consisting of H, $C_{2-12}$ alkyl, and $C_{2-12}$ alkenyl; and $R^{a\gamma}$ is a $C_2$ alkyl, $C_3$ alkyl, $C_4$ alkyl, $C_5$ alkyl, or $C_6$ alkyl;

$R^4$ is —$(CH_2)_2OH$ or

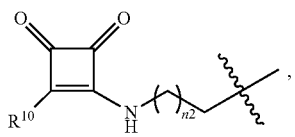

wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

M and M' are each independently selected from the group consisting of —C(O)O— and —OC(O)—; and R' is a $C_{1-12}$ alkyl or $C_{2-12}$ alkenyl.

Embodiment 51. A compound of Formula (A-a3):

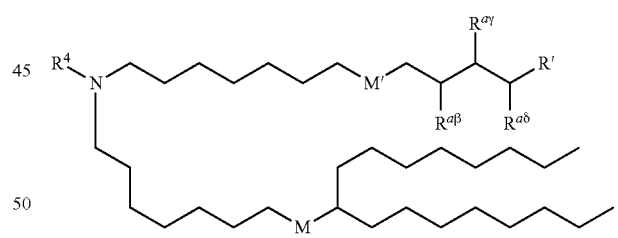

(A-a3)

or its N-oxide, or a salt or isomer thereof, wherein $R^{a\beta}$ and $R^{a\gamma}$ are each independently selected from the group consisting of H, $C_{2-12}$ alkyl, and $C_{2-12}$ alkenyl; and $R^{a\delta}$ is a $C_2$ alkyl, $C_3$ alkyl, $C_4$ alkyl, $C_5$ alkyl, or $C_6$ alkyl;

$R^4$ is —$(CH_2)_2OH$ or

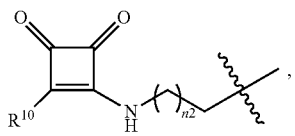

wherein
R$^{10}$ is N(R)$_2$; each R is independently selected from the group consisting of C$_{1-6}$ alkyl, C$_{2-3}$ alkenyl, and H; and n2 is selected from the group consisting of 1, 2, 3, 4, 5, 6, 7, 8, 9, and 10;

M and M' are each independently selected from the group consisting of —C(O)O— and —OC(O)—; and R' is a C$_{1-12}$ alkyl or C$_{2-12}$ alkenyl.

Embodiment 52. A compound of Formula (A-b):

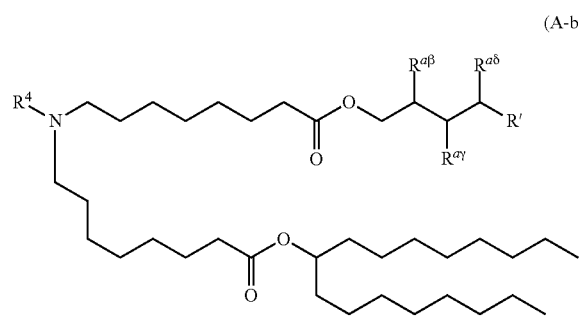

(A-b)

or its N-oxide, or a salt or isomer thereof,
wherein R$^{\alpha\beta}$, R$^{\alpha\gamma}$ and R$^{\alpha\delta}$ are each independently selected from the group consisting of H, C$_{2-12}$ alkyl, and C$_{2-12}$ alkenyl, wherein at least one of R$^{\alpha\beta}$, R$^{\alpha\gamma}$, and R$^{\alpha\delta}$ is selected from the group consisting of C$_{2-12}$ alkyl and C$_{2-12}$ alkenyl;

R$^4$ is selected from the group consisting of —(CH$_2$)$_2$OH, —(CH$_2$)$_3$OH, —(CH$_2$)$_4$OH and —(CH$_2$)$_5$OH; and R' is a C$_{1-12}$ alkyl or C$_{2-12}$ alkenyl.

Embodiment 53. A compound of Formula (A-b1):

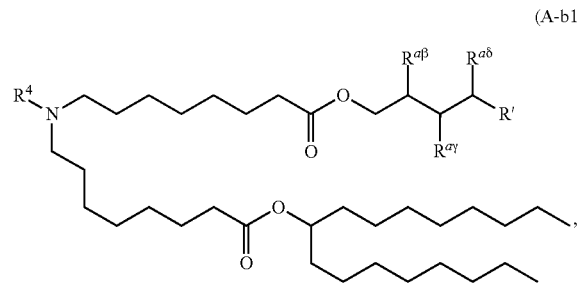

(A-b1)

or its N-oxide, or a salt or isomer thereof,
wherein R$^{\alpha\gamma}$ and R$^{\alpha\delta}$ are each independently selected from the group consisting of H, C$_{2-12}$ alkyl, and C$_{2-12}$ alkenyl; and R$^{\alpha\beta}$ is a C$_2$ alkyl, C$_3$ alkyl, C$_4$ alkyl, C$_5$ alkyl, or C$_6$ alkyl;

R$^4$ is —(CH$_2$)$_2$OH or

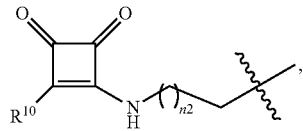

wherein
R$^{10}$ is N(R)$_2$; each R is independently selected from the group consisting of C$_{1-6}$ alkyl, C$_{2-3}$ alkenyl, and H; and n2 is selected from the group consisting of 1, 2, 3, 4, 5, 6, 7, 8, 9, and 10; and R' is a C$_{1-12}$ alkyl or C$_{2-12}$ alkenyl.

Embodiment 54. A compound of Formula (A-b2):

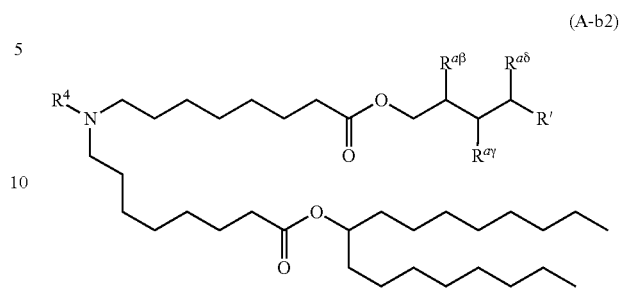

(A-b2)

or its N-oxide, or a salt or isomer thereof,
wherein R$^{\alpha\beta}$ and R$^{\alpha\delta}$ are each independently selected from the group consisting of H, C$_{2-12}$ alkyl, and C$_{2-12}$ alkenyl; and R$^{\alpha\gamma}$ is a C$_2$ alkyl, C$_3$ alkyl, C$_4$ alkyl, C$_5$ alkyl, or C$_6$ alkyl;

R$^4$ is —(CH$_2$)$_2$OH or

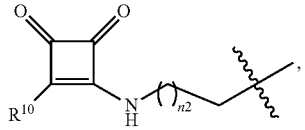

wherein
R$^{10}$ is N(R)$_2$; each R is independently selected from the group consisting of C$_{1-6}$ alkyl, C$_{2-3}$ alkenyl, and H; and n2 is selected from the group consisting of 1, 2, 3, 4, 5, 6, 7, 8, 9, and 10; and R' is a C$_{1-12}$ alkyl or C$_{2-12}$ alkenyl.

Embodiment 55. A compound of Formula (A-b3):

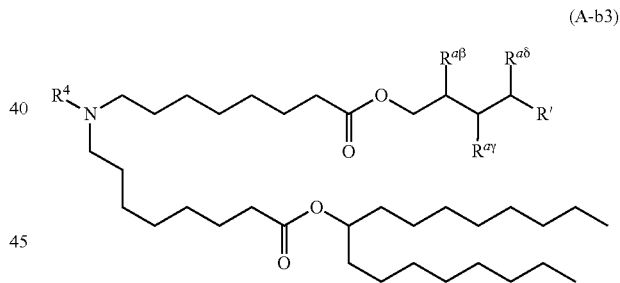

(A-b3)

or its N-oxide, or a salt or isomer thereof,
wherein R$^{\alpha\beta}$ and R$^{\alpha\gamma}$ are each independently selected from the group consisting of H, C$_{2-12}$ alkyl, and C$_{2-12}$ alkenyl; and R$^{\alpha\delta}$ is a C$_2$ alkyl, C$_3$ alkyl, C$_4$ alkyl, C$_5$ alkyl, or C$_6$ alkyl;

R$^4$ is —(CH$_2$)$_2$OH or

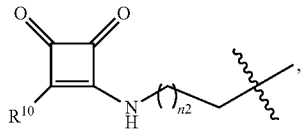

wherein
R$^{10}$ is N(R)$_2$; each R is independently selected from the group consisting of C$_{1-6}$ alkyl, C$_{2-3}$ alkenyl, and H; and n2 is selected from the group consisting of 1, 2, 3, 4, 5, 6, 7, 8, 9, and 10; and R' is a C$_{1-12}$ alkyl or C$_{2-12}$ alkenyl.

Embodiment 56. A compound any one of the preceding embodiments, wherein $R^{a\gamma}$ and $R^{a\delta}$ are each H; and $R^{a\beta}$ is a $C_2$ alkyl, $C_3$ alkyl, $C_4$ alkyl, $C_5$ alkyl, or $C_6$ alkyl.

Embodiment 57. A compound any one of the preceding embodiments, wherein $R^{a\beta}$ and $R^{a\delta}$ are each H; and $R^{a\gamma}$ is a $C_2$ alkyl, $C_3$ alkyl, $C_4$ alkyl, $C_5$ alkyl, or $C_6$ alkyl.

Embodiment 58. A compound any one of the preceding embodiments, wherein $R^{a\beta}$ and $R^{a\gamma}$ are each H; and $R^{a\delta}$ is a $C_2$ alkyl, $C_3$ alkyl, $C_4$ alkyl, $C_5$ alkyl, or $C_6$ alkyl.

Embodiment 59. A compound of Formula (A-c):

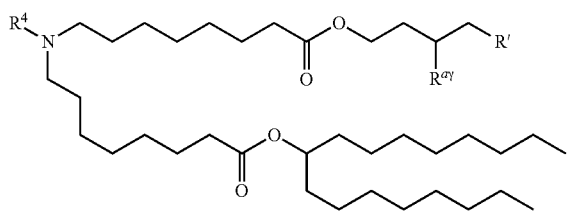

(A-c)

or its N-oxide, or a salt or isomer thereof, wherein $R^{a\gamma}$ is a $C_2$ alkyl, $C_3$ alkyl, $C_4$ alkyl, $C_5$ alkyl, or $C_6$ alkyl; and $R^4$ is —$(CH_2)_2OH$ or

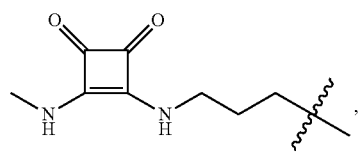 [SMILES: *CCCNc1c(NC)c(=O)c1=O]

and R' is a $C_{1-12}$ alkyl.

Embodiment 60. A compound of Formula (B-c):

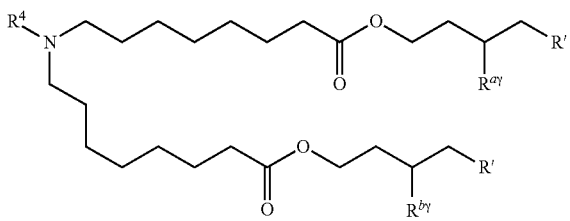

(B-c)

or its N-oxide, or a salt or isomer thereof, wherein
$R^{a\gamma}$ is a $C_2$ alkyl, $C_3$ alkyl, $C_4$ alkyl, $C_5$ alkyl, or $C_6$ alkyl;
$R^{b\gamma}$ is a $C_2$ alkyl, $C_3$ alkyl, $C_4$ alkyl, $C_5$ alkyl, or $C_6$ alkyl; and
$R^4$ is —$(CH_2)_2OH$ or

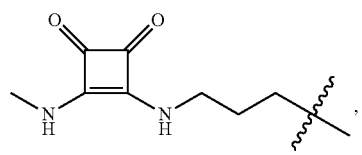 [SMILES: *CCCNc1c(NC)c(=O)c1=O]

and R' is a $C_{1-12}$ alkyl.

Embodiment 61. The compound of any one of the preceding embodiments, wherein $R^4$ is —$(CH_2)_2OH$.

Embodiment 62. The compound of any one of the preceding embodiments, wherein $R^4$ is —$(CH_2)_3OH$.

Embodiment 63. The compound of any one of the preceding embodiments, wherein $R^4$ is —$(CH_2)_4OH$.

Embodiment 64. The compound of any one of the preceding embodiments, wherein $R^4$ is

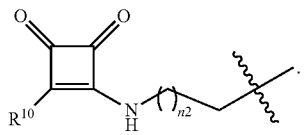

Embodiment 65. The compound of any one of the preceding embodiments, wherein n2 is 2.

Embodiment 66. The compound of any one of the preceding embodiments, wherein $R^{10}$ is —$N(R)_2$.

Embodiment 67. The compound of any one of the preceding embodiments, wherein $R^{10}$ is —$NHCH_3$.

Embodiment 68. The compound of any one of the preceding embodiments, wherein $R^4$ is

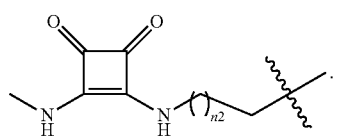

Embodiment 69. The compound of any one of the preceding embodiments, wherein $R^4$ is

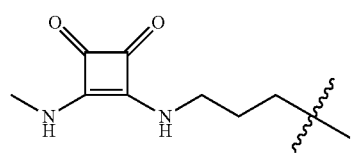

Embodiment 70. The compound of any of the preceding embodiments, wherein M' and M are each —C(O)O—.

Embodiment 71. The compound of any of the preceding embodiments, wherein M' is —C(O)O— and M is —OC(O)—.

Embodiment 72. The compound of any of the preceding embodiments, wherein M' is —OC(O)— and M is —C(O)O—.

Embodiment 73. The compound of any one of the preceding embodiments, wherein l is 5.

Embodiment 74. The compound of any one of the preceding embodiments, wherein m is 7.

Embodiment 75. The compound of any one of the preceding embodiments, wherein R' is a $C_{1-12}$ alkyl or $C_{2-12}$ alkenyl.

Embodiment 76. The compound of any one of the preceding embodiments, wherein R' is a $C_2$ alkyl.

Embodiment 77. The compound of any one of the preceding embodiments, wherein R' is a $C_3$ or $C_4$ alkyl.

Embodiment 78. The compound of any one of the preceding embodiments, wherein R' is a $C_3$ alkyl.

Embodiment 79. The compound of any one of the preceding embodiments, wherein R' is a $C_5$ alkyl.

Embodiment 80. The compound of any one of the preceding embodiments, wherein $R^{a\gamma}$ is a $C_{2-6}$ alkyl and R' is a $C_3$ alkyl.

Embodiment 81. The compound of any one of the preceding embodiments, wherein $R^{a\gamma}$ is a $C_{2-6}$ alkyl and R' is a $C_4$ alkyl.

Embodiment 82. The compound of any one of the preceding embodiments, wherein $R^{a\beta}$ is H.

Embodiment 83. The compound of any one of the preceding embodiments, wherein $R^{a\beta}$ is a $C_2$-$C_4$ alkyl.

Embodiment 84. The compound of any one of the preceding embodiments, wherein $R^a$ is n-propyl or n-butyl.

Embodiment 85.

Embodiment 86. The compound of any one of the preceding embodiments, wherein $R^{a\beta}$ is i-propyl, sec-butyl, or tert-butyl.

Embodiment 87. The compound of any one of the preceding embodiments, wherein $R^{a\beta}$ is a $C_5$-alkyl or a $C_6$-alkyl.

Embodiment 88. The compound of any one of the preceding embodiments, wherein $R^{a\gamma}$ is H.

Embodiment 89. The compound of any one of the preceding embodiments, wherein $R^{a\gamma}$ is a $C_2$-alkyl, $C_3$-alkyl, or a $C_4$ alkyl.

Embodiment 90. The compound of any one of the preceding embodiments, wherein $R^{a\gamma}$ is n-propyl or n-butyl.

Embodiment 91. The compound of any one of the preceding embodiments, wherein $R^{a\gamma}$ is i-propyl, sec-butyl, or tert-butyl.

Embodiment 92. The compound of any one of the preceding embodiments, wherein $R^{a\gamma}$ is a $C_5$-alkyl or a $C_6$-alkyl.

Embodiment 93. The compound of any one of the preceding embodiments, wherein $R^{a\delta}$ is H.

Embodiment 94. The compound of any one of the preceding embodiments, wherein $R^{a\delta}$ is a $C_2$-alkyl, $C_3$-alkyl, or a $C_4$ alkyl.

Embodiment 95. The compound of any one of the preceding embodiments, wherein $R^{a\delta}$ is n-propyl or n-butyl.

Embodiment 96. The compound of any one of the preceding embodiments, wherein $R^{a\delta}$ is i-propyl, sec-butyl, or tert-butyl.

Embodiment 97. The compound of any one of the preceding embodiments, wherein $R^{a\delta}$ is a $C_5$-alkyl or a $C_6$-alkyl.

Embodiment 98. The compound of any one of the preceding embodiments, wherein $R^{b\beta}$ is H.

Embodiment 99. The compound of any one of the preceding embodiments, wherein $R^{b\beta}$ is a $C_2$-alkyl, $C_3$-alkyl, or a $C_4$ alkyl.

Embodiment 100. The compound of any one of the preceding embodiments, wherein $R^{b\beta}$ is n-propyl or n-butyl.

Embodiment 101. The compound of any one of the preceding embodiments, wherein $R^{b\beta}$ is i-propyl, sec-butyl, or tert-butyl.

Embodiment 102. The compound of any one of the preceding embodiments, wherein $R^{b\beta}$ is a $C_5$-alkyl or a $C_6$-alkyl.

Embodiment 103. The compound of any one of the preceding embodiments, wherein $R^{b\gamma}$ is H.

Embodiment 104. The compound of any one of the preceding embodiments, wherein $R^{b\gamma}$ is a $C_2$-alkyl, $C_3$-alkyl, or a $C_4$ alkyl.

Embodiment 105. The compound of any one of the preceding embodiments, wherein $R^{b\gamma}$ is n-propyl or n-butyl.

Embodiment 106. The compound of any one of the preceding embodiments, wherein $R^{b\gamma}$ is i-propyl, sec-butyl, or tert-butyl.

Embodiment 107. The compound of any one of the preceding embodiments, wherein $R^{b\gamma}$ is a $C_5$-alkyl or a $C_6$-alkyl.

Embodiment 108. The compound of any one of the preceding embodiments, wherein $R^{b\delta}$ is H.

Embodiment 109. The compound of any one of the preceding embodiments, wherein $R^{b\delta}$ is a $C_2$-alkyl, $C_3$-alkyl, or a $C_4$ alkyl.

Embodiment 110. The compound of any one of the preceding embodiments, wherein $R^{b\delta}$ is n-propyl or n-butyl.

Embodiment 111. The compound of any one of the preceding embodiments, wherein $R^{b\delta}$ is i-propyl, sec-butyl, or tert-butyl.

Embodiment 112. A compound selected from:

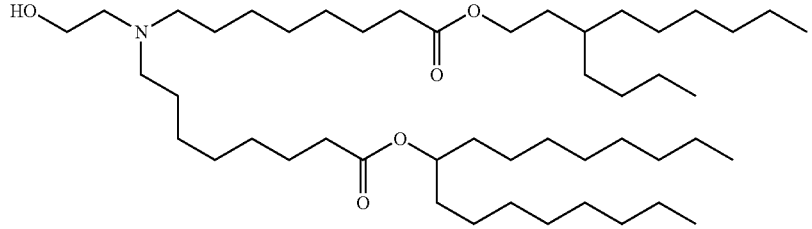

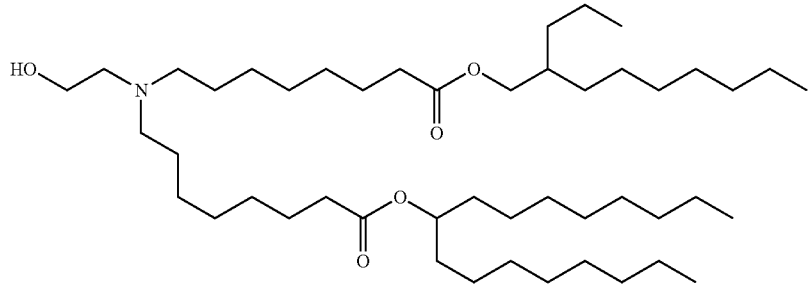

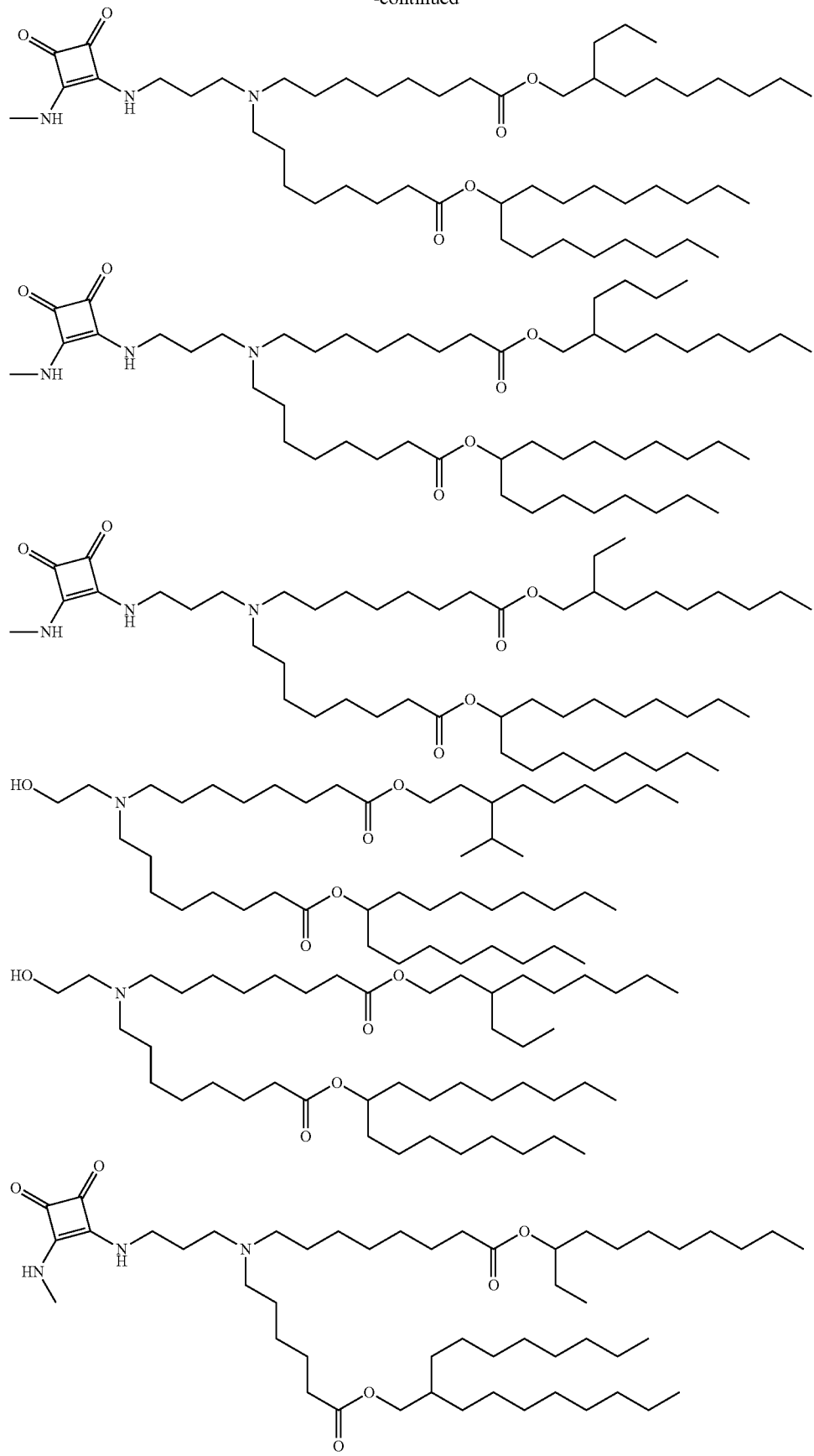

-continued
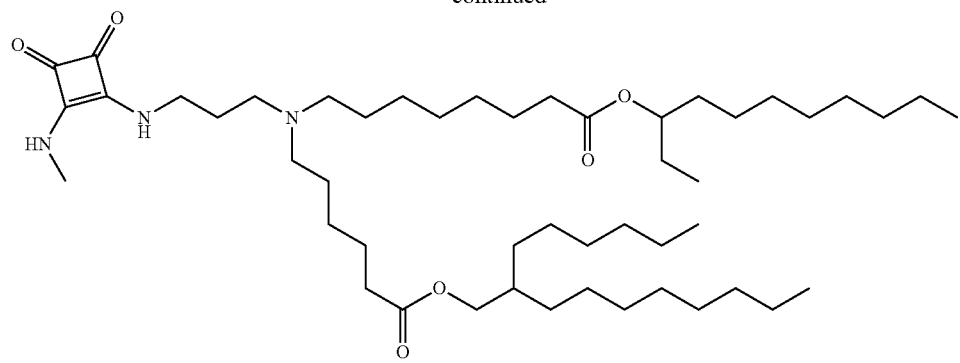
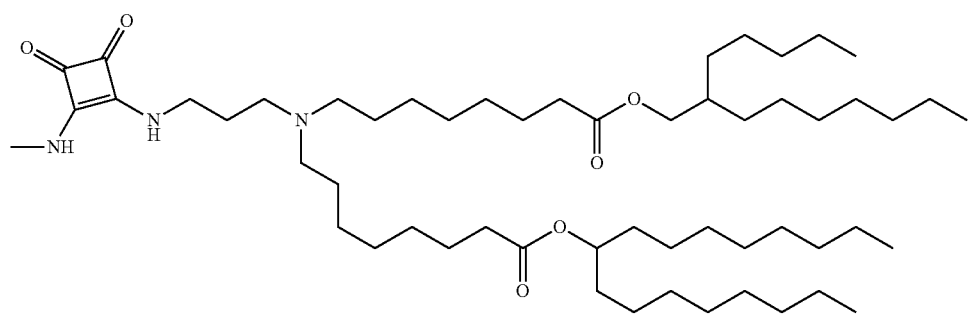
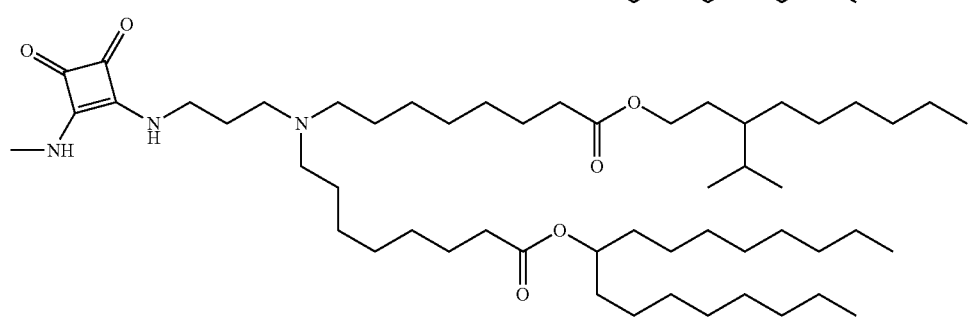
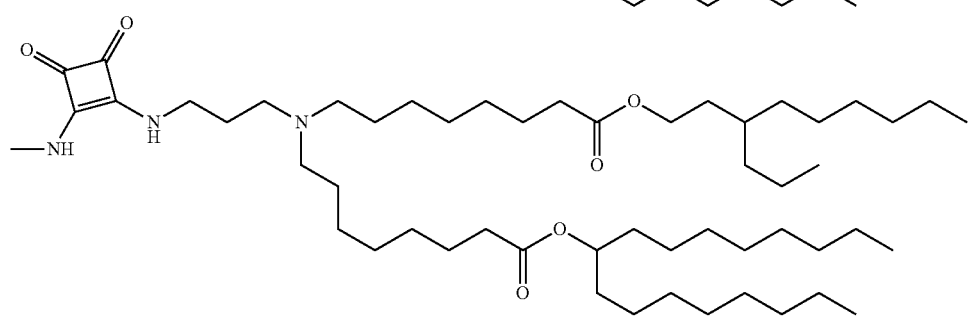
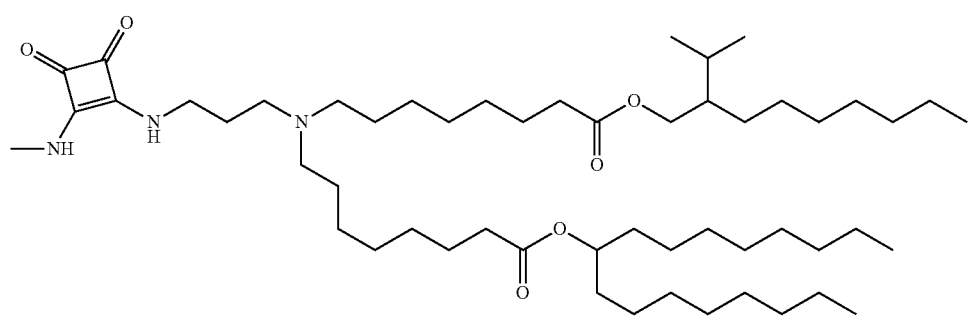

-continued
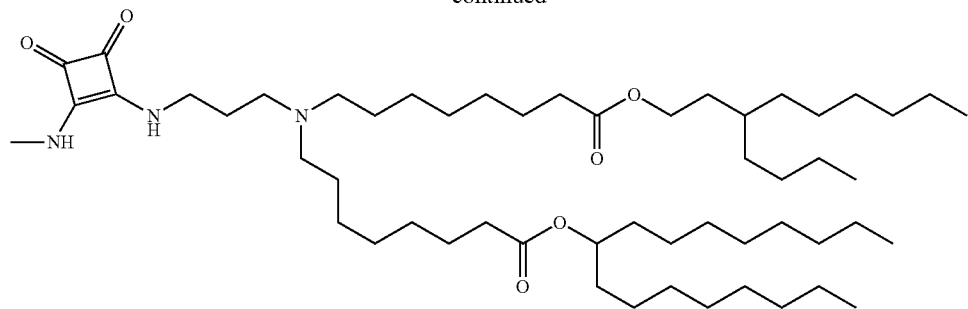
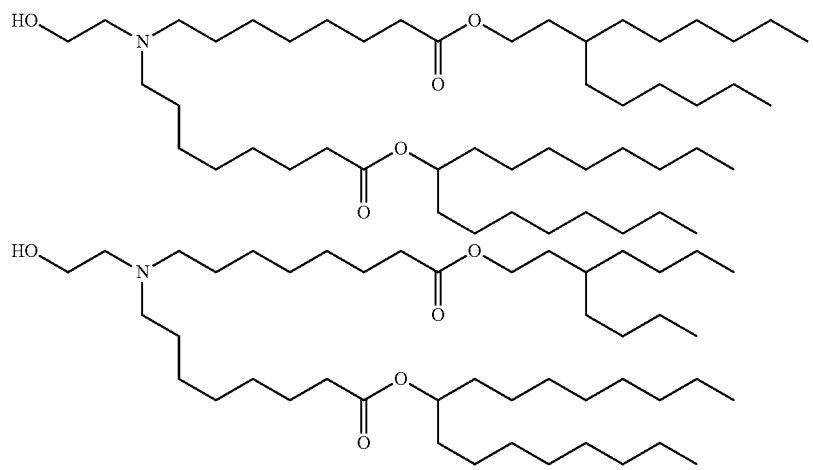
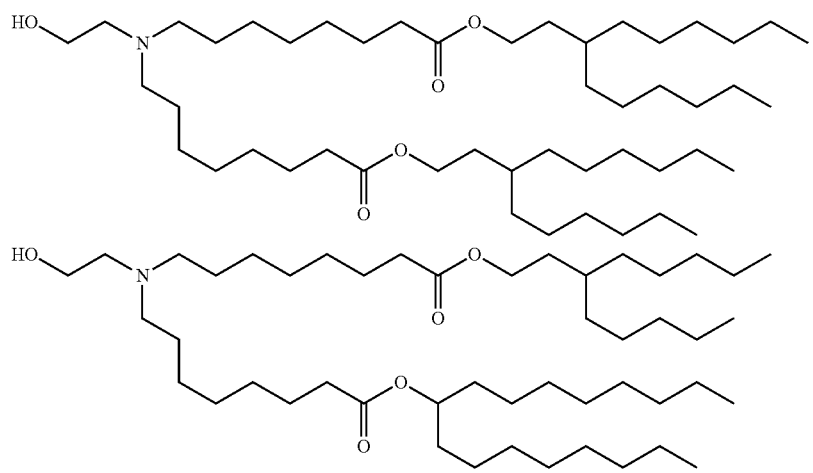
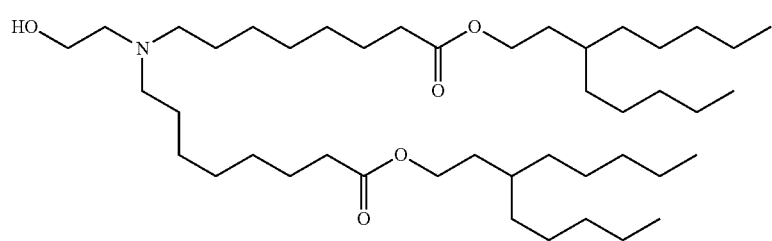

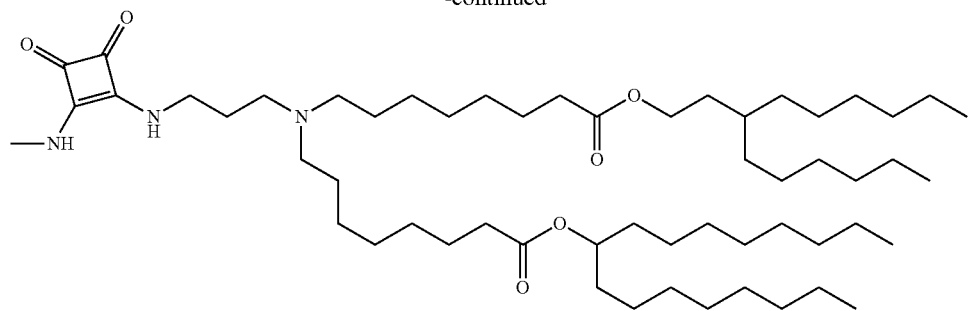
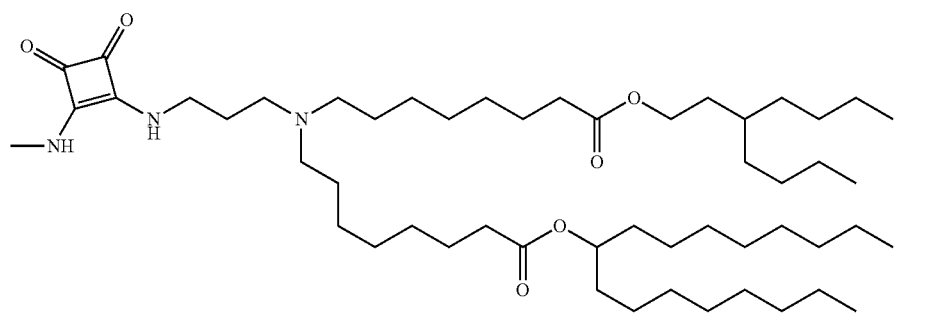
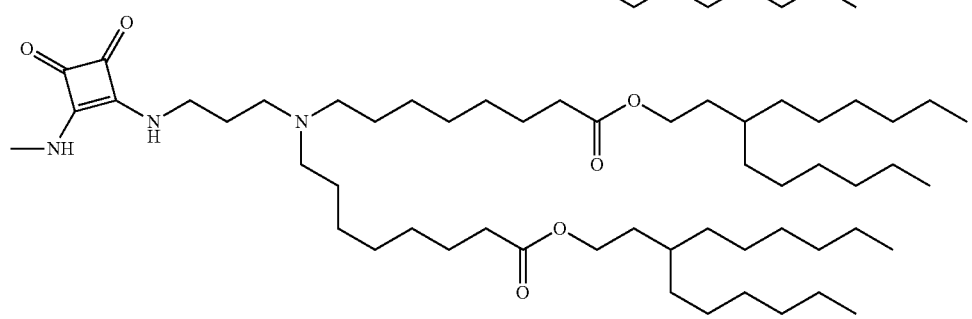
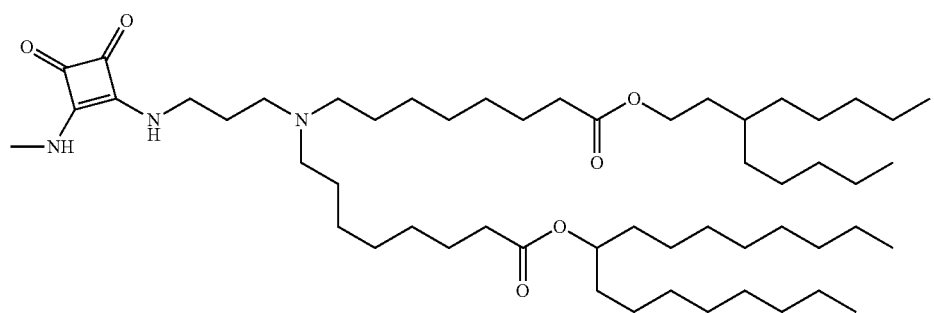
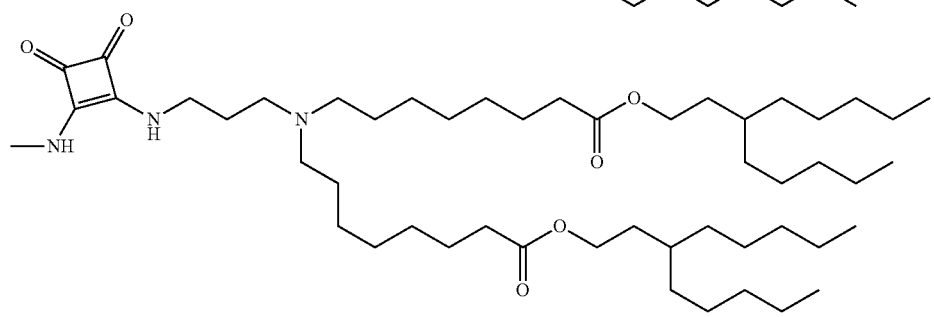

-continued
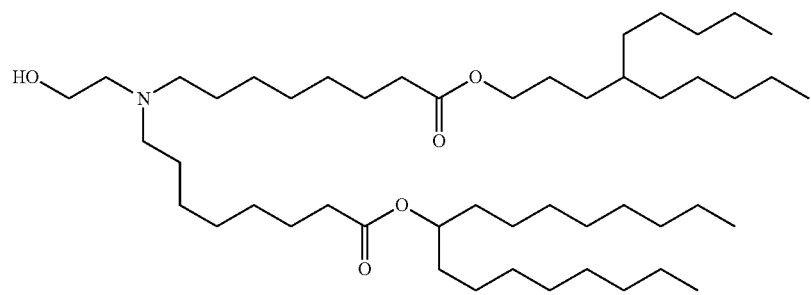
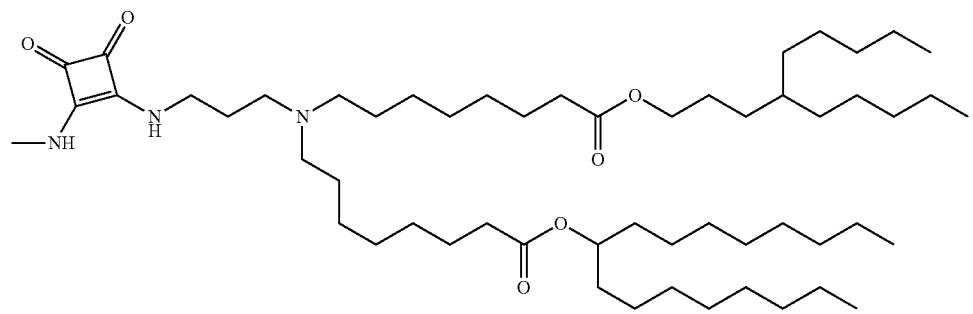
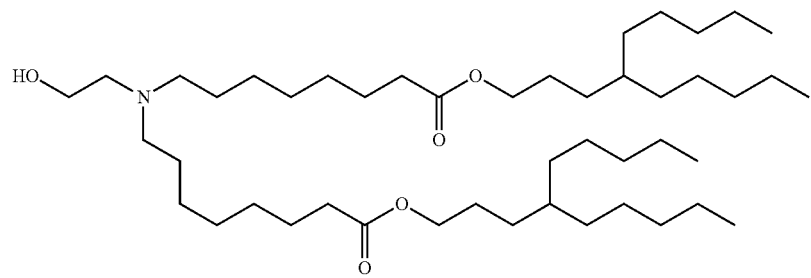
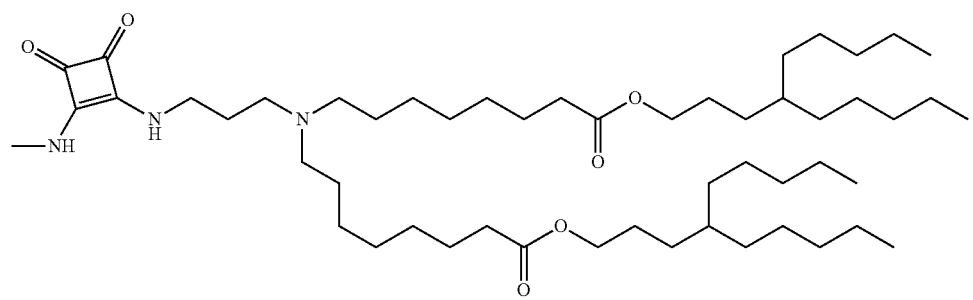
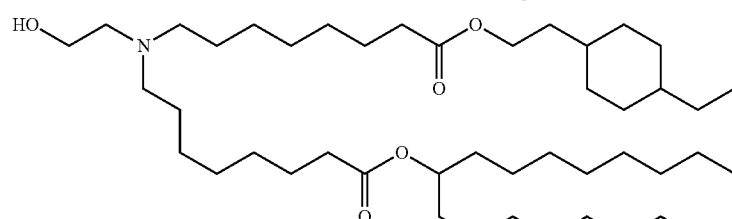
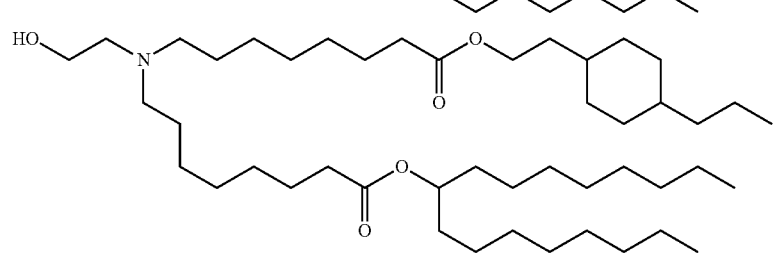

-continued
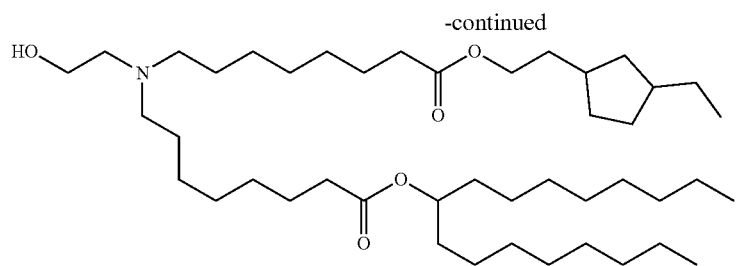
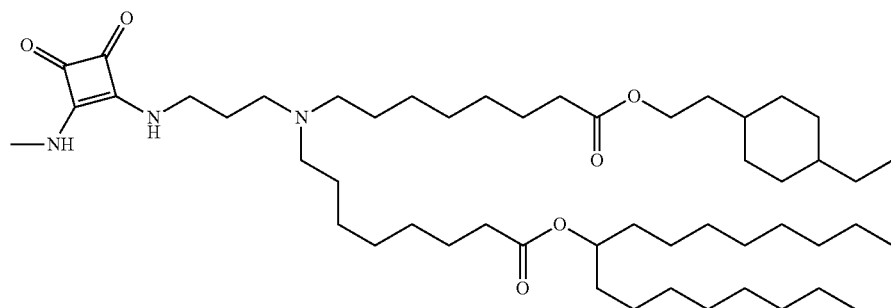
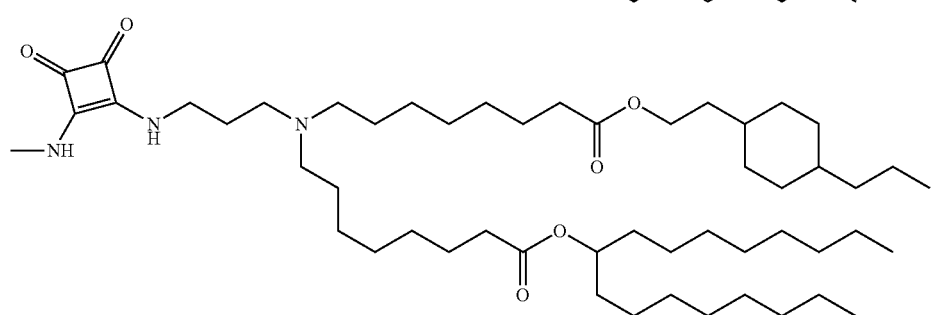
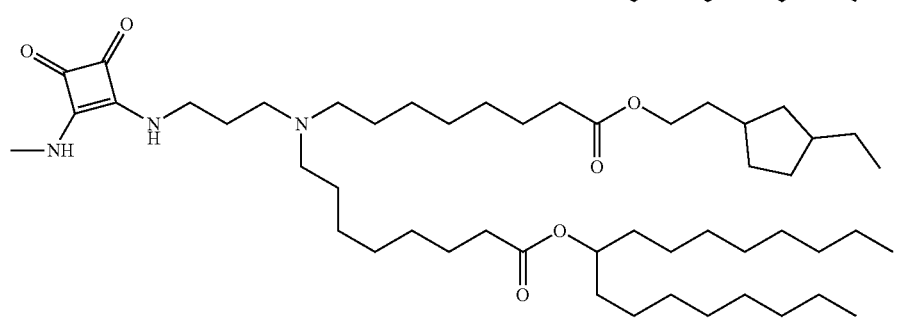
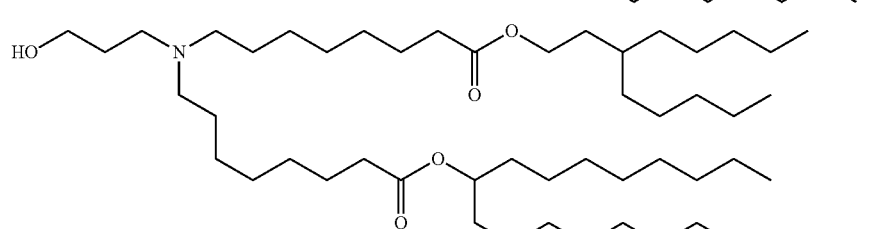
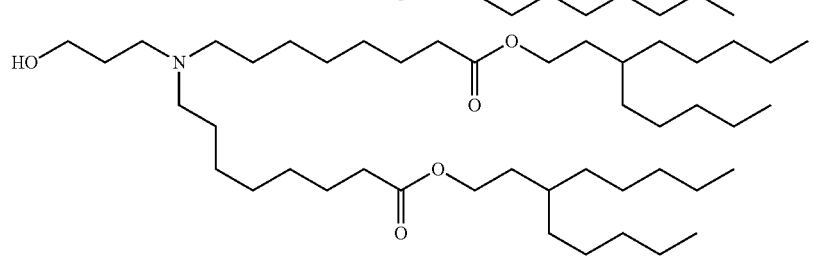

-continued
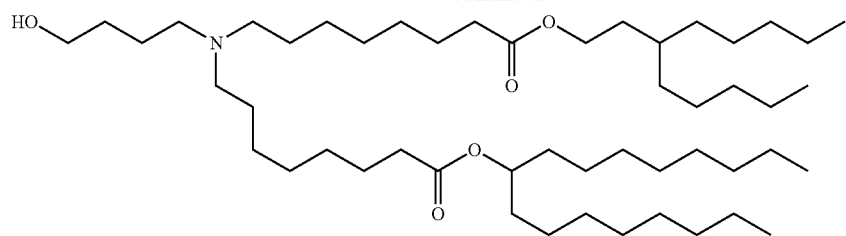
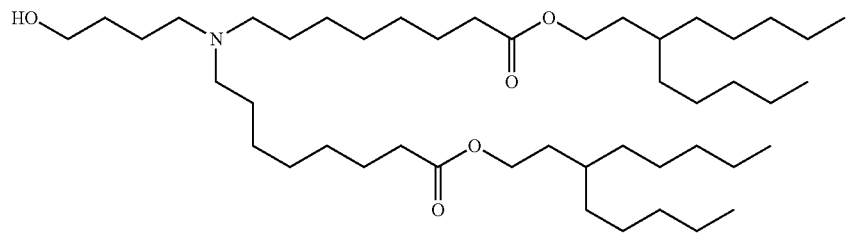
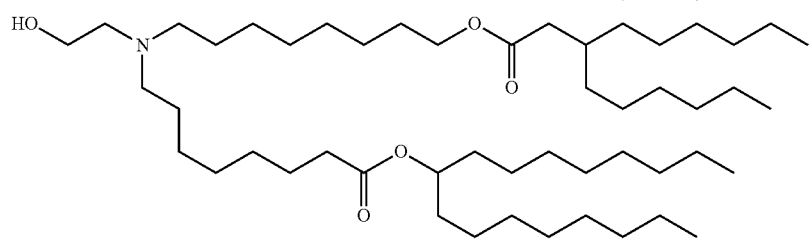
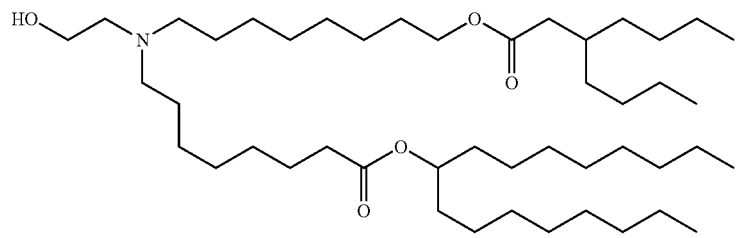
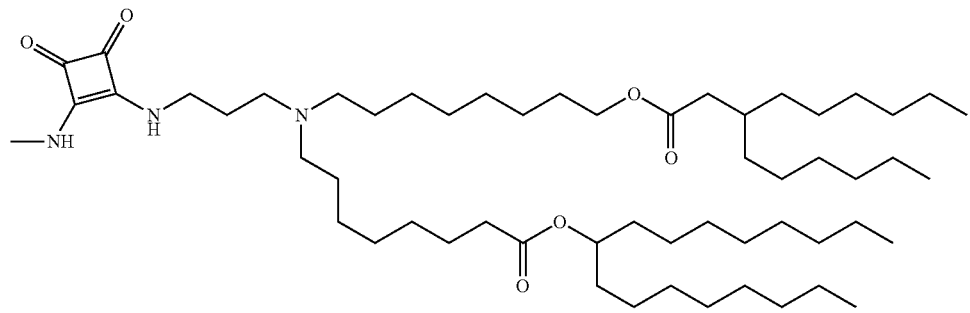
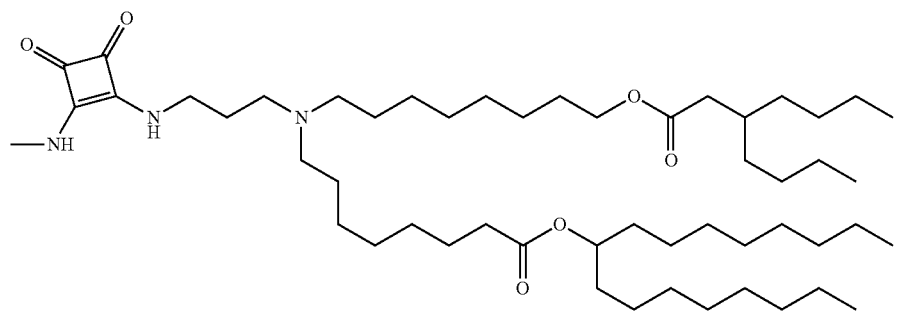

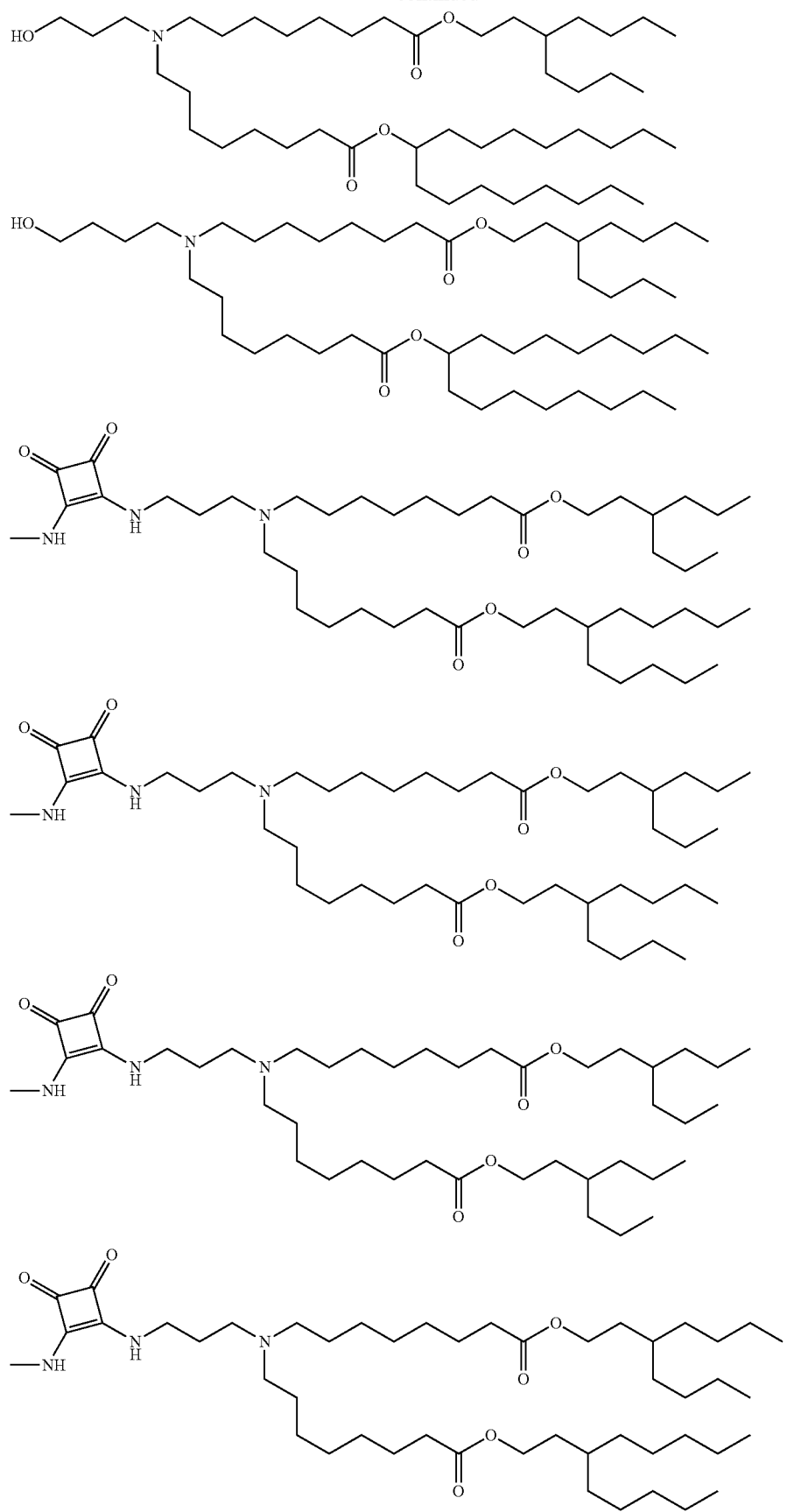

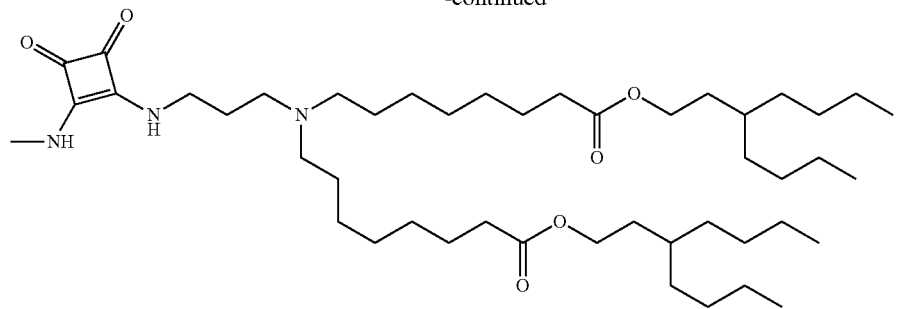
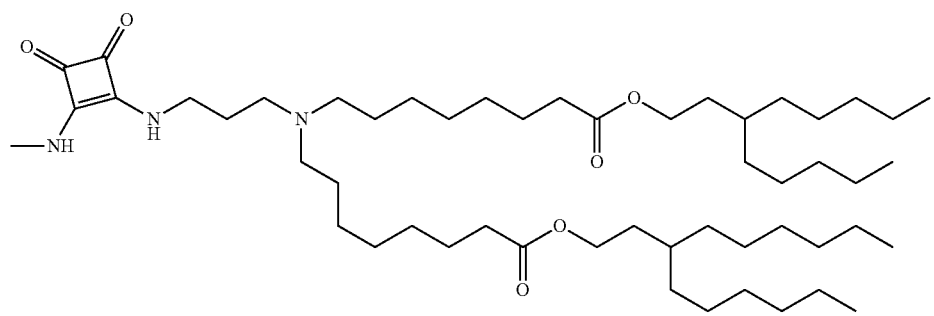
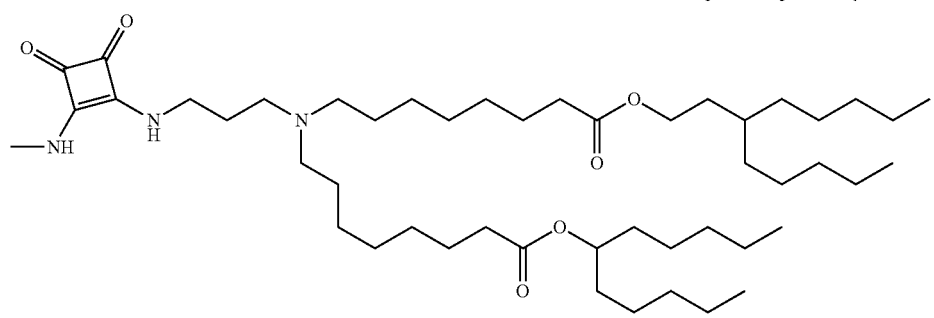
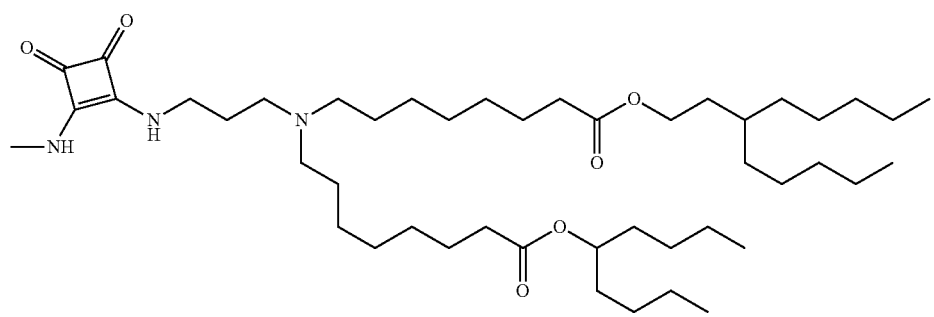
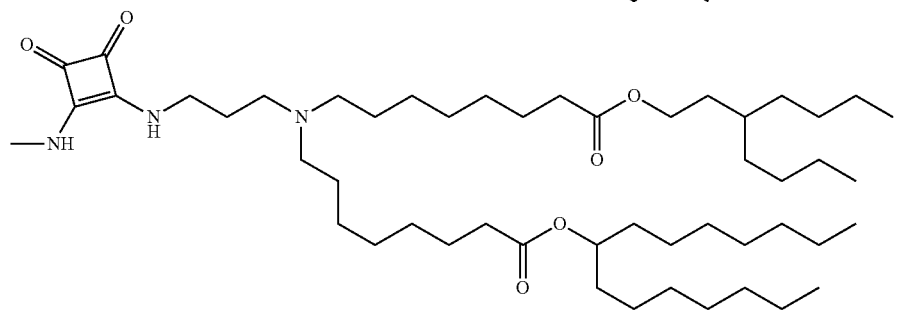

-continued
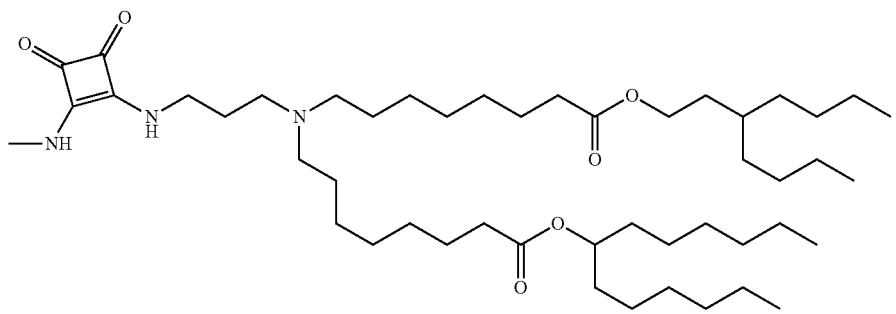
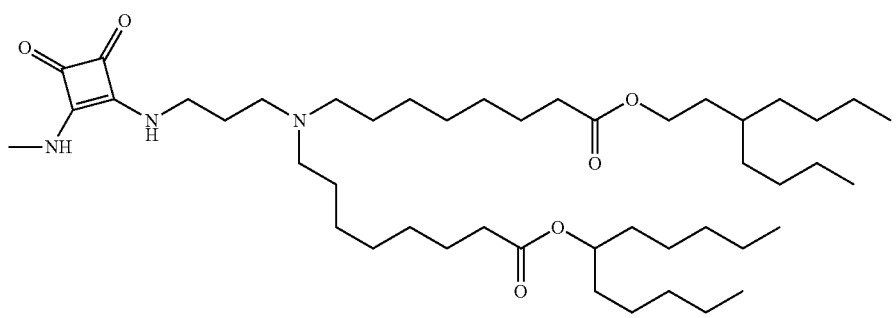
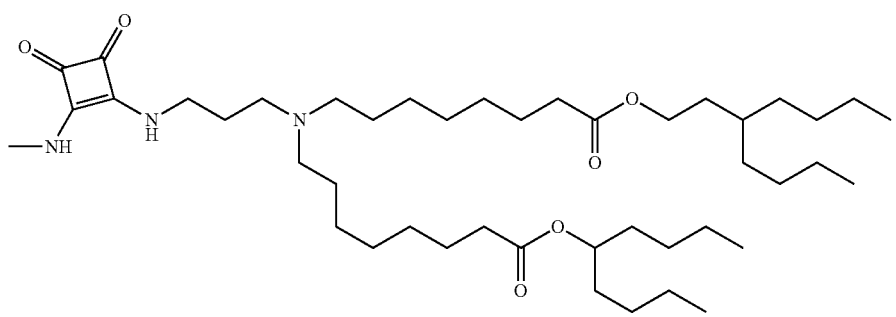
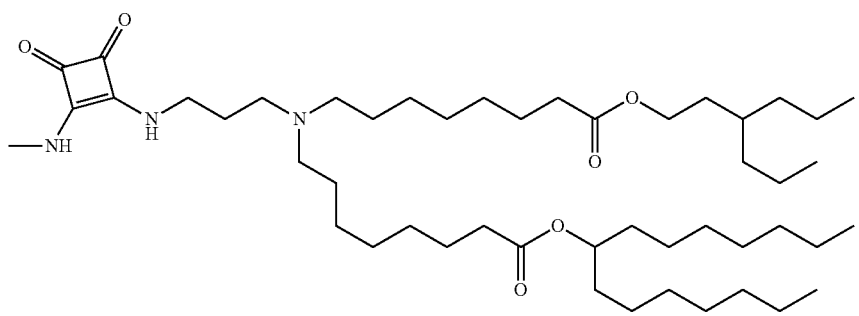
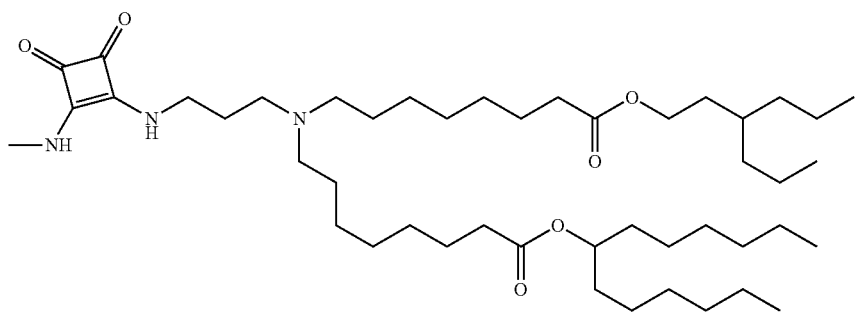

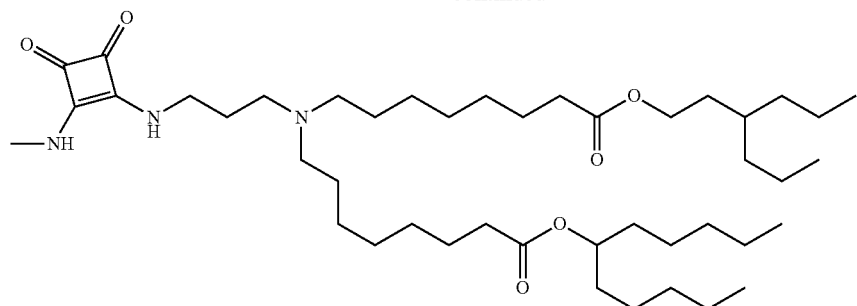
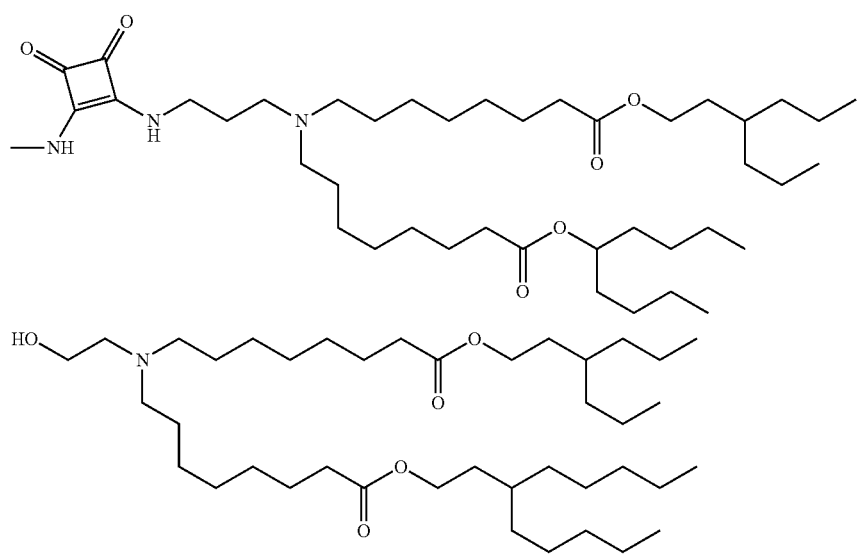
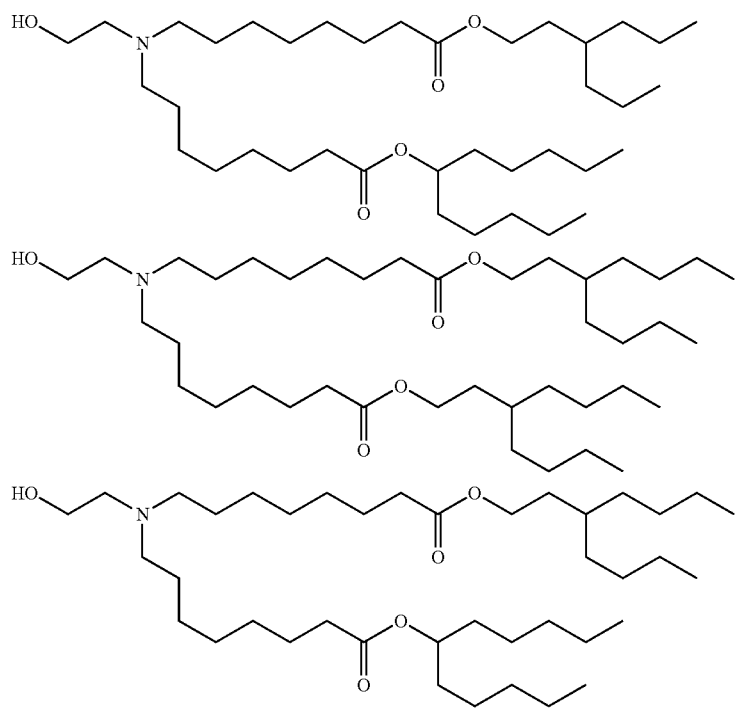

-continued
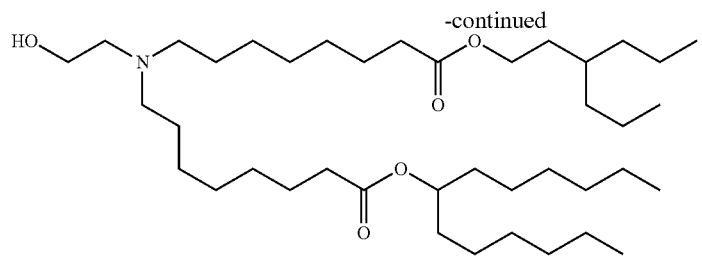
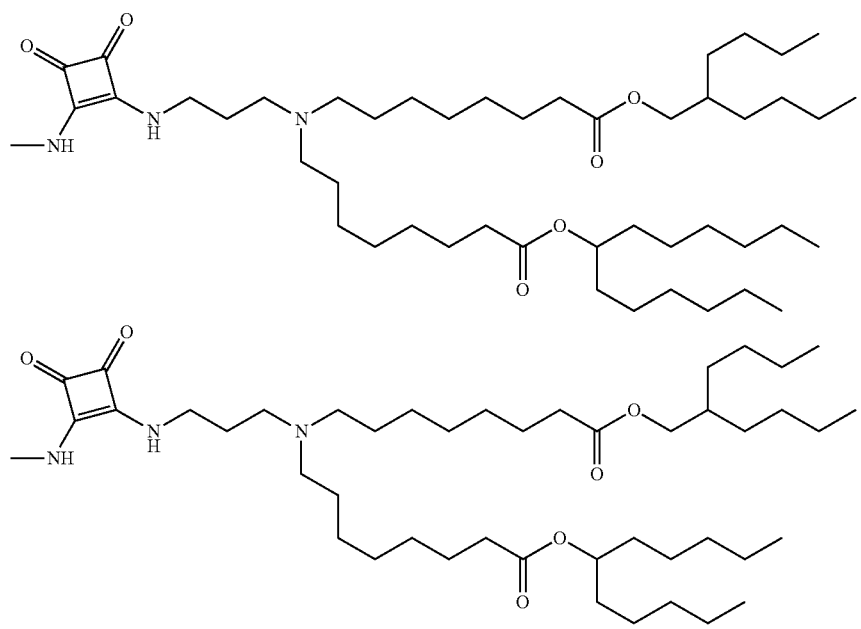
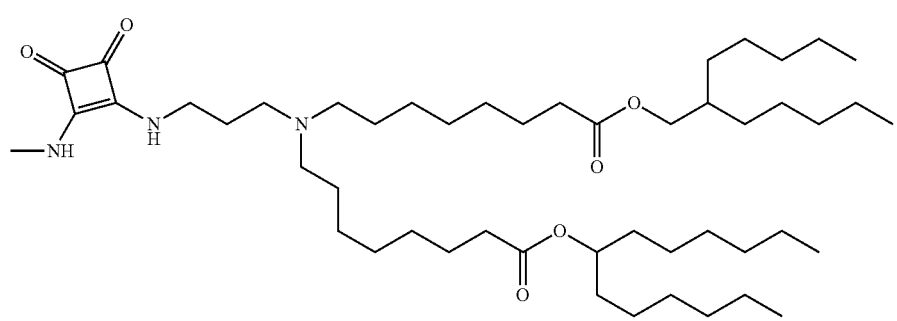
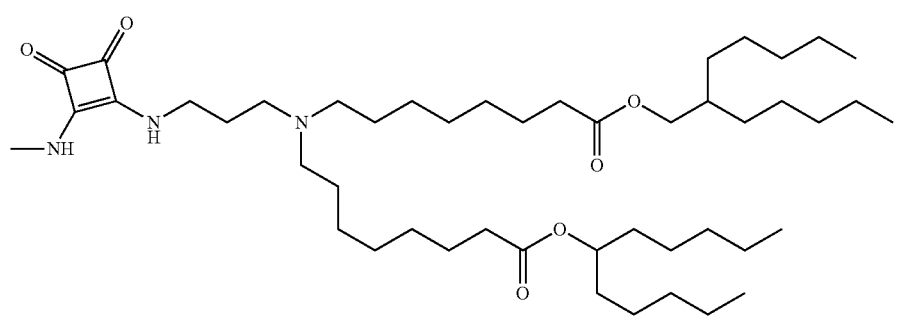

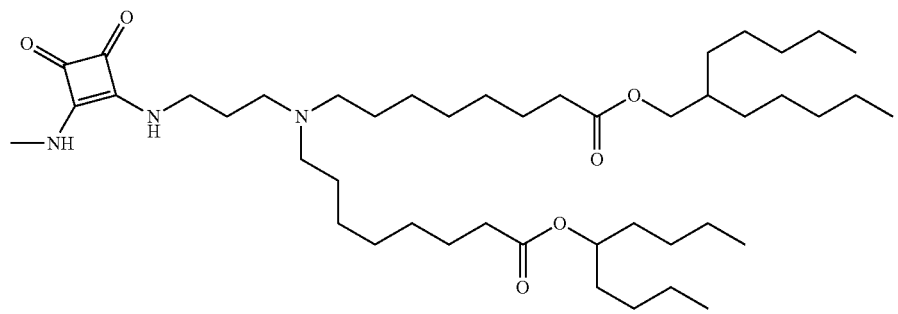
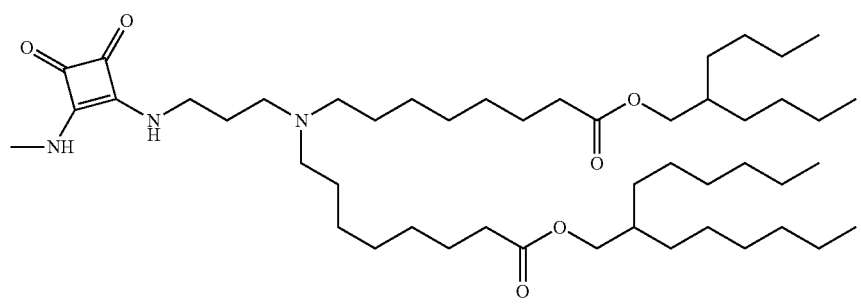
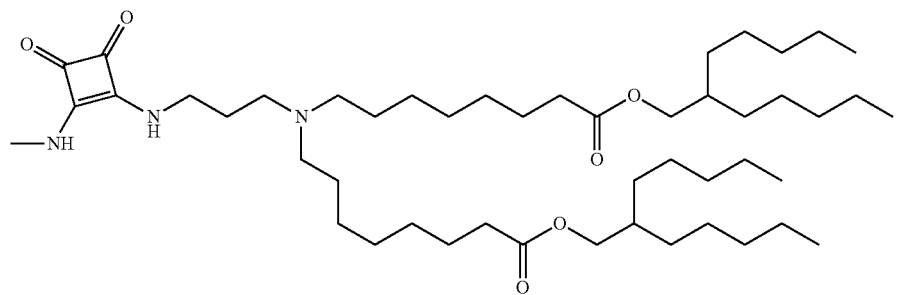
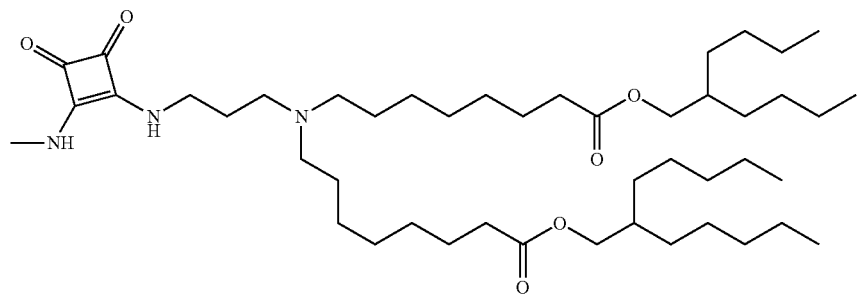
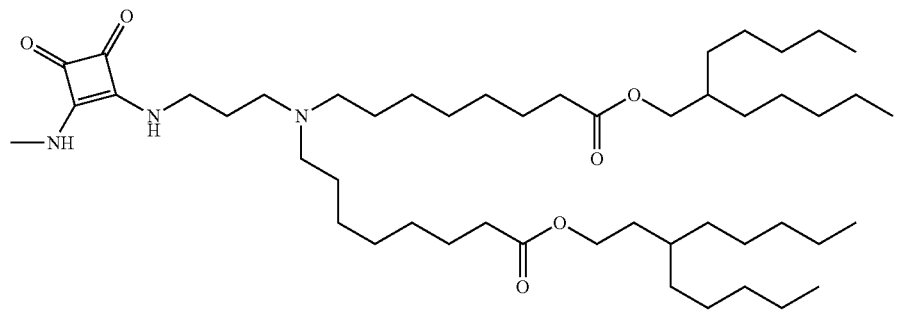

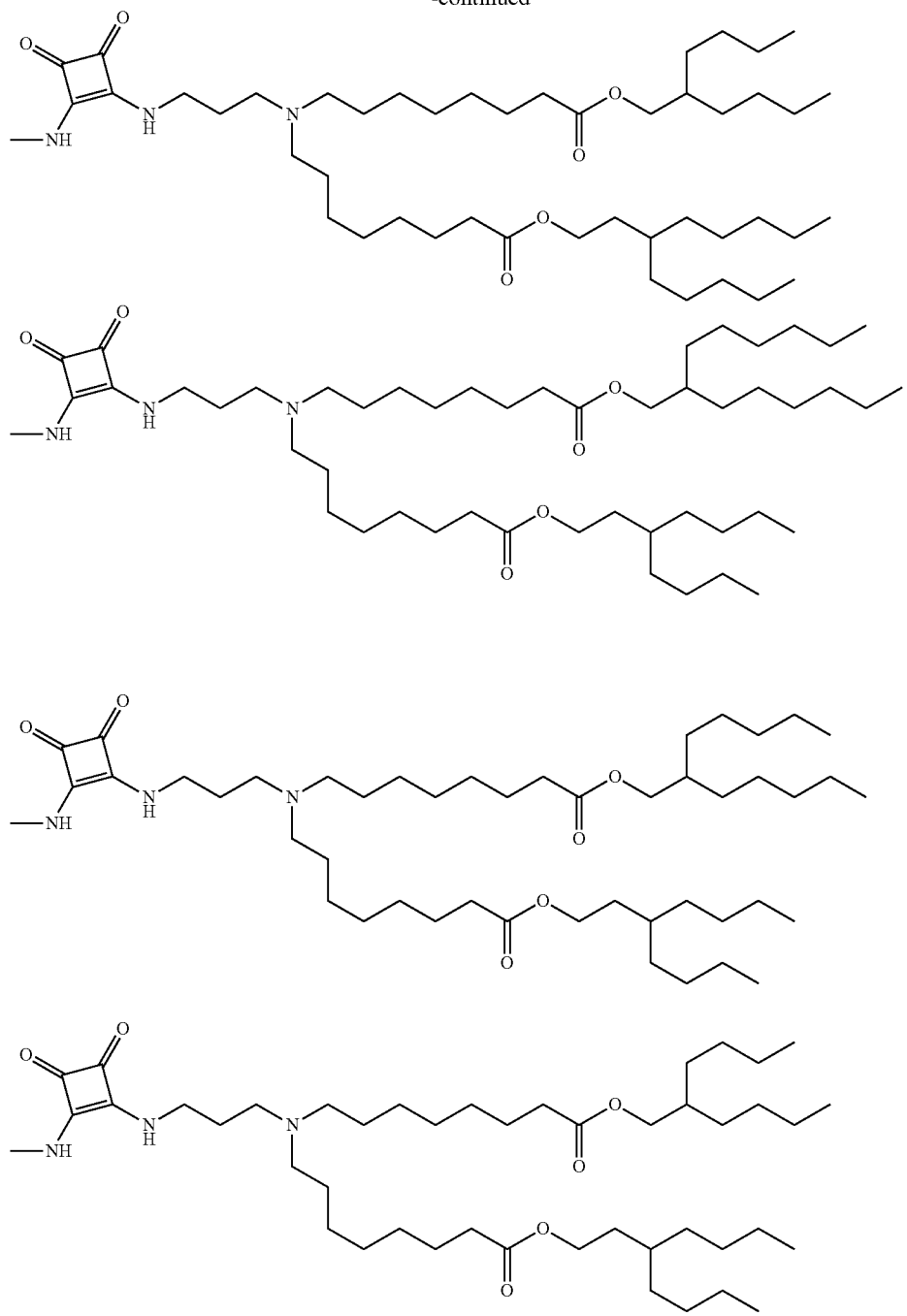
Embodiment 113. A compound selected from:
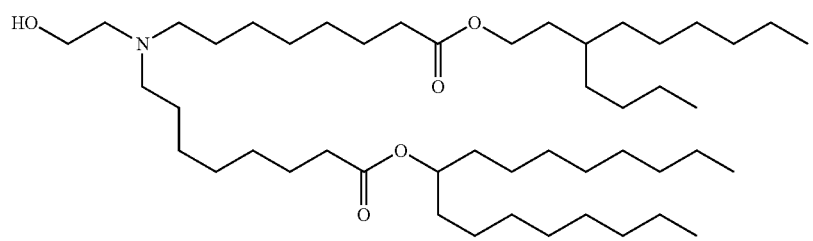

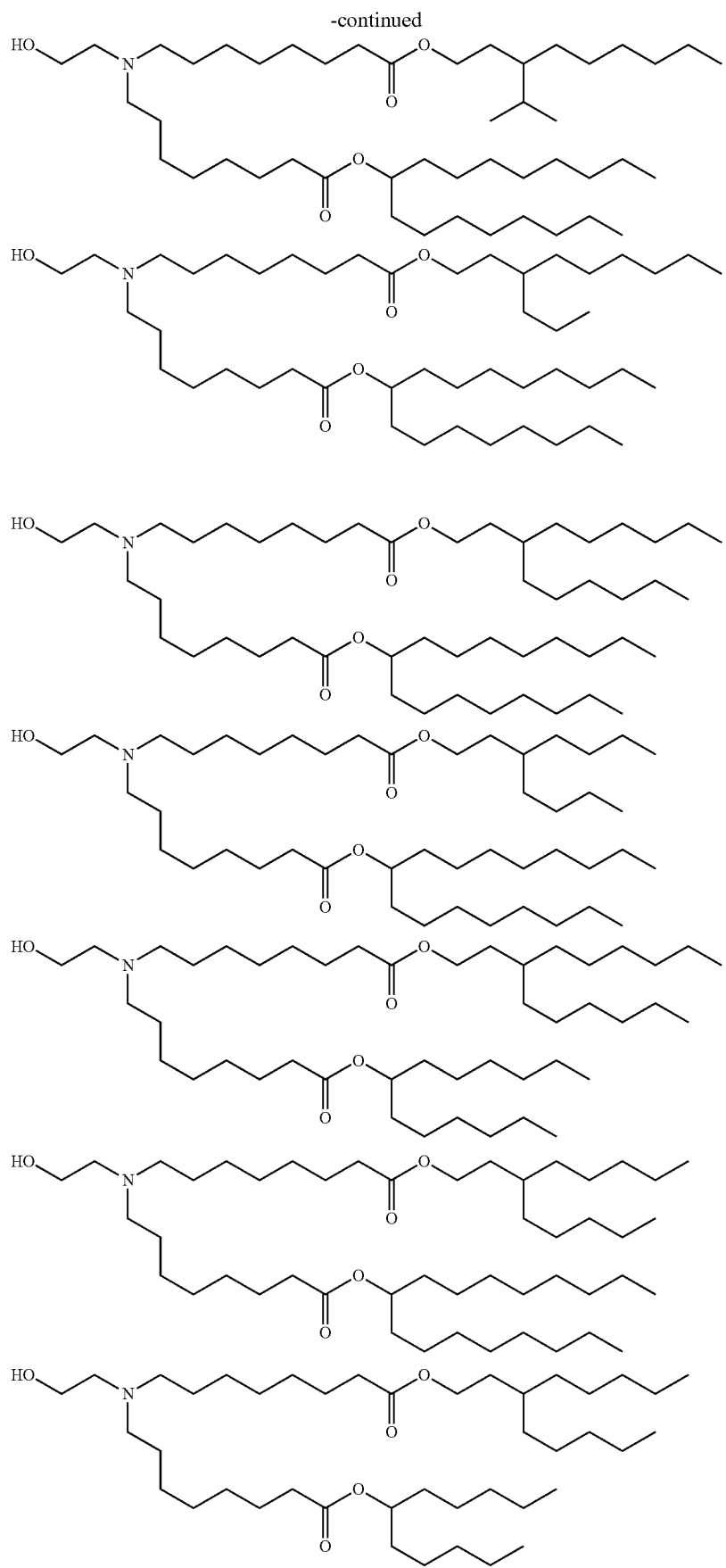

-continued
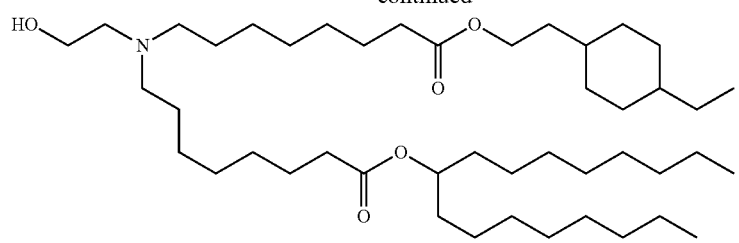
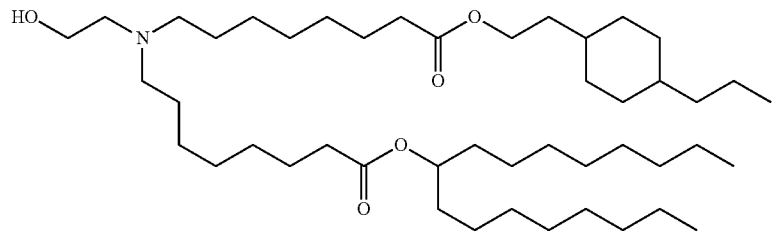
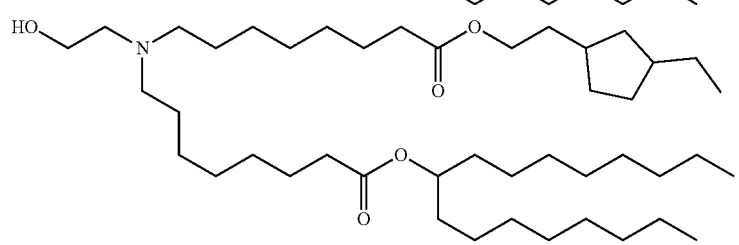
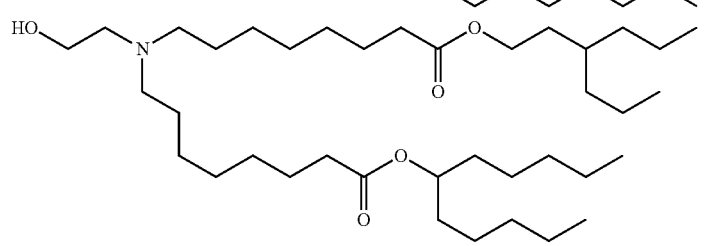
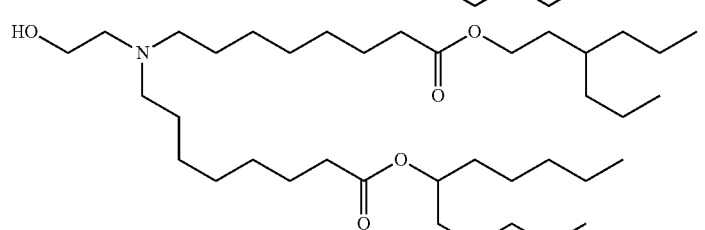
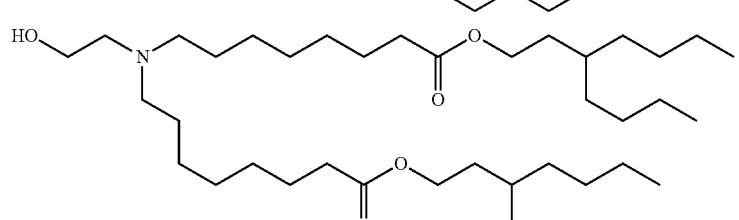
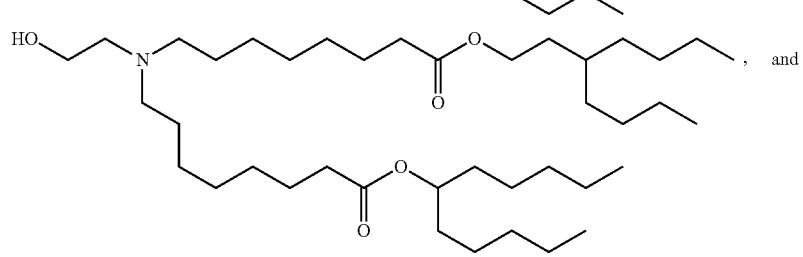, and

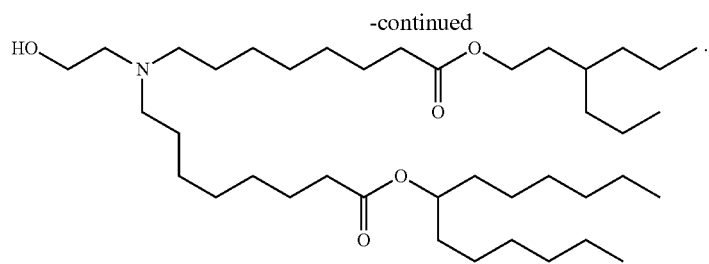
Embodiment 114. A compound selected from:
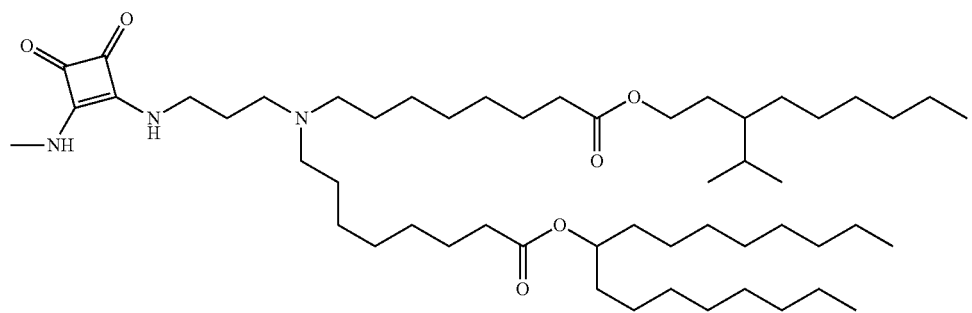
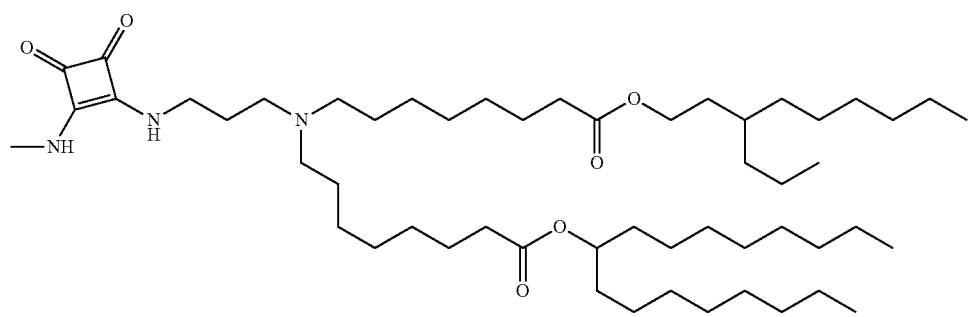
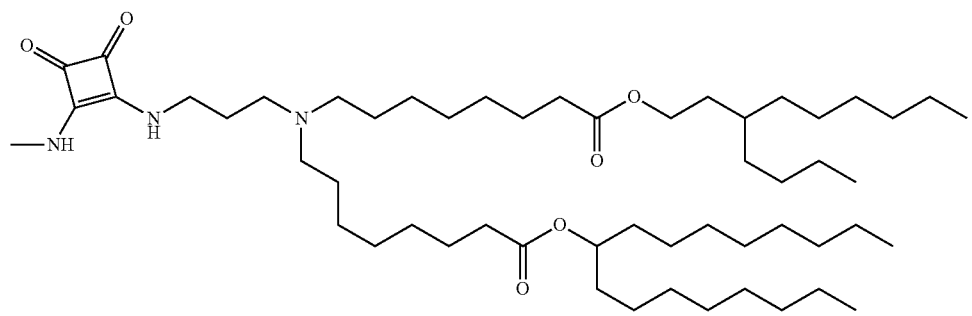
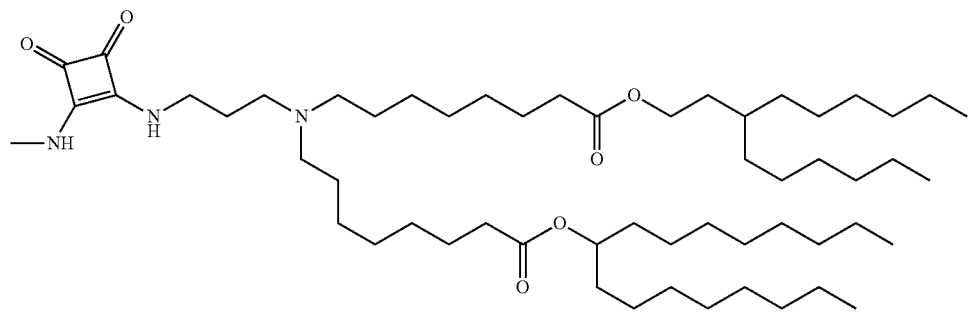

-continued
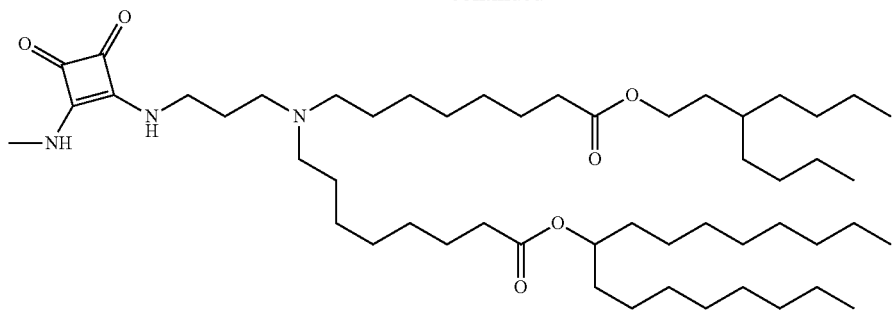
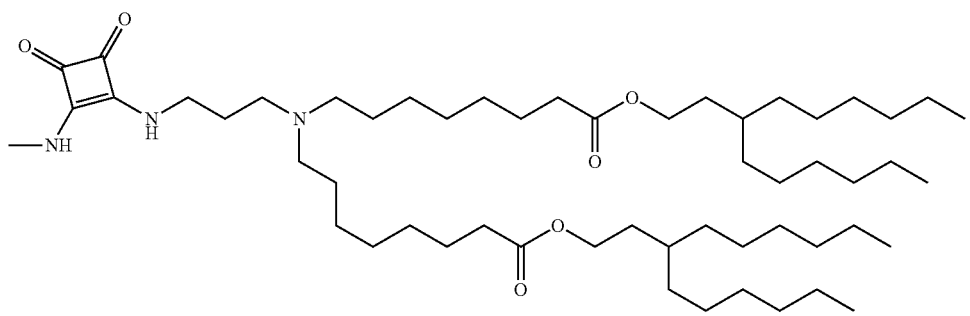
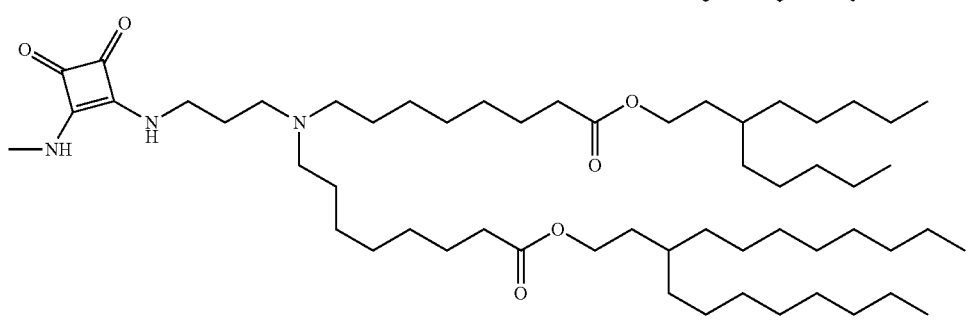
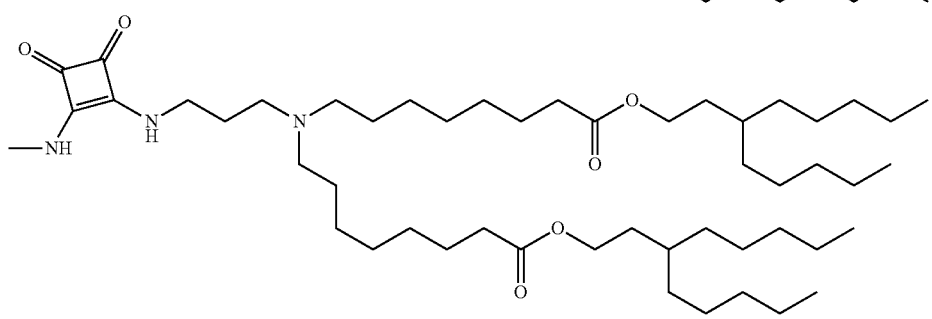
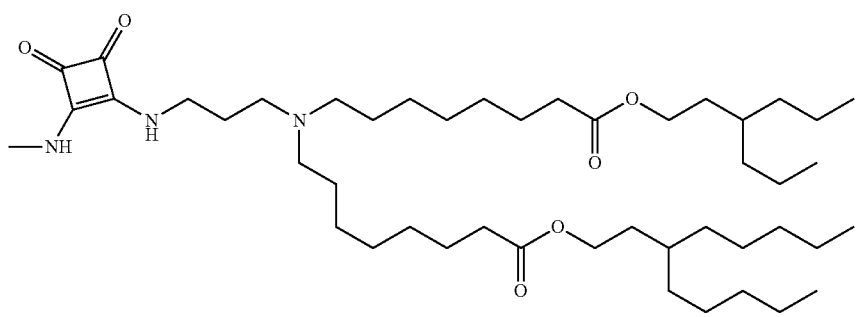

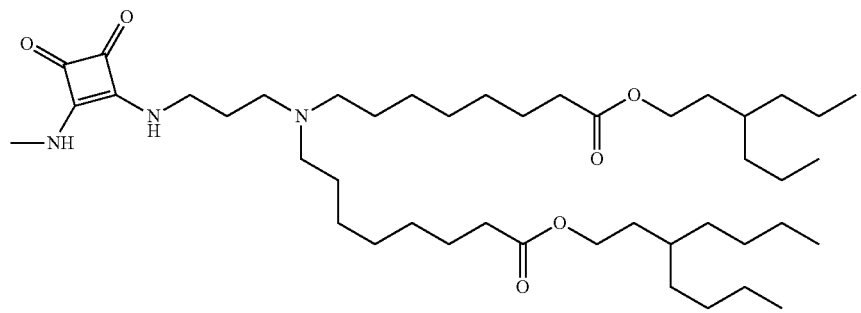
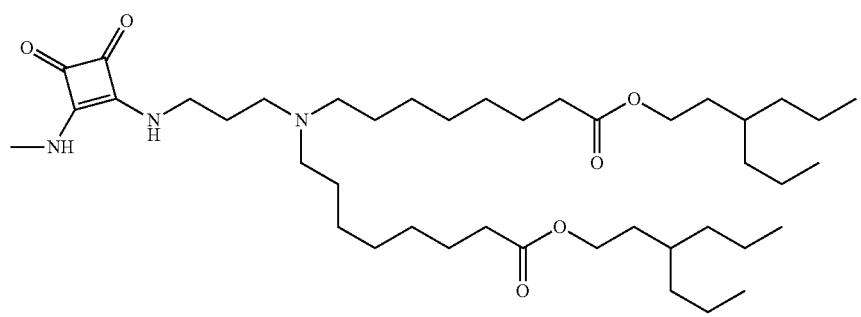
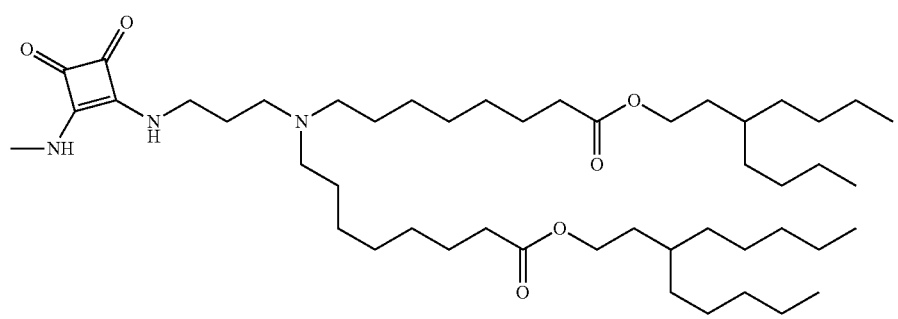
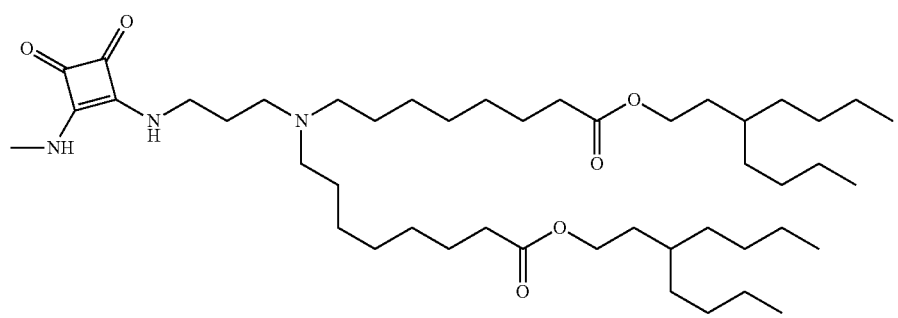
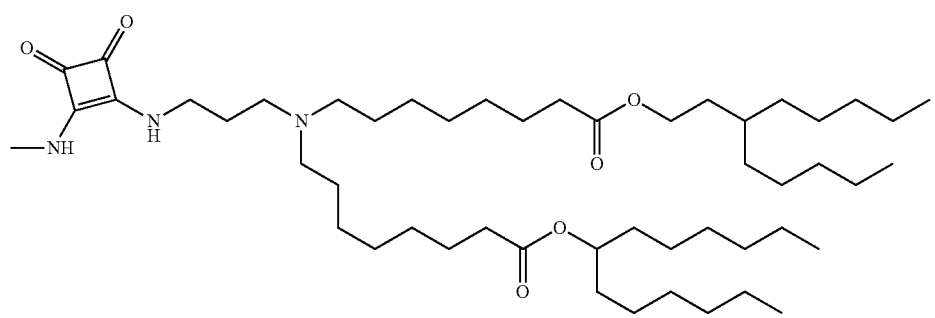

-continued
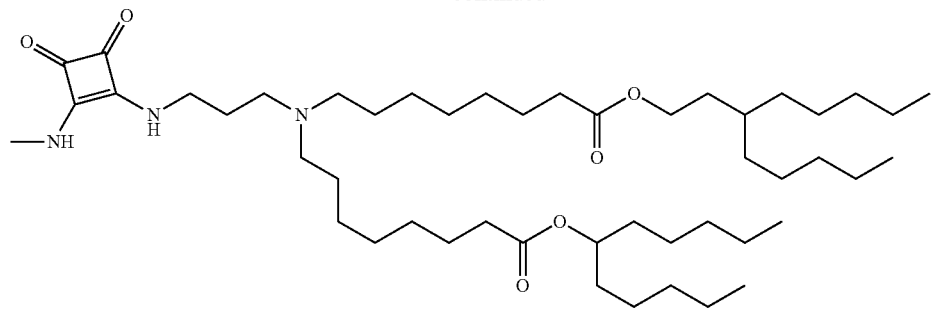
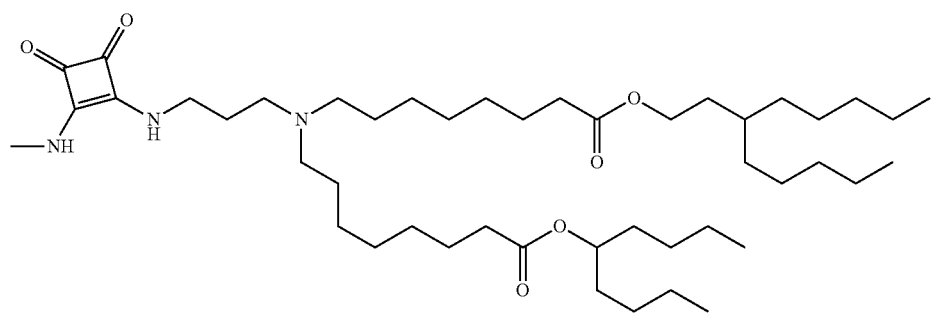
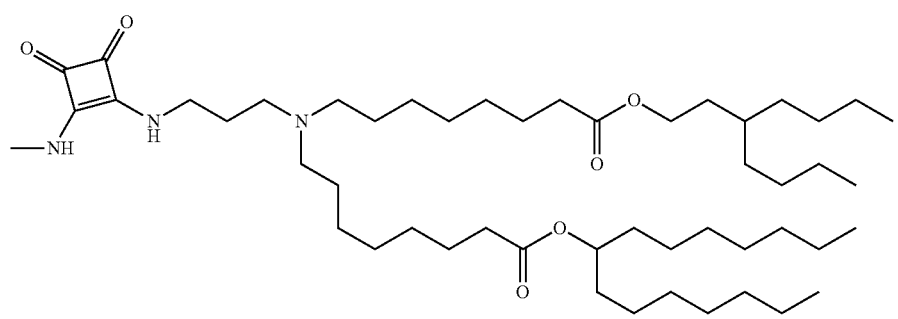
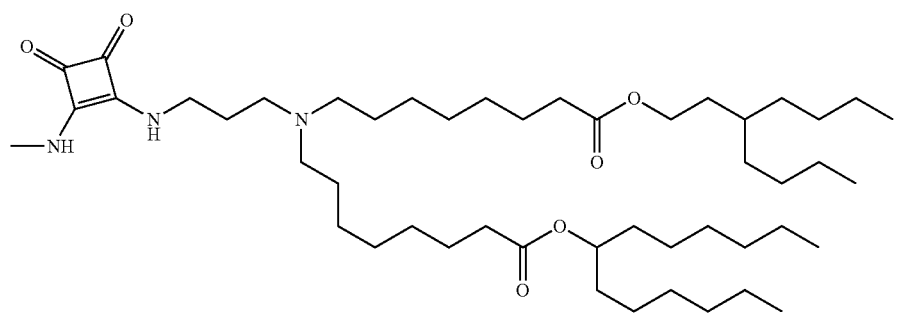
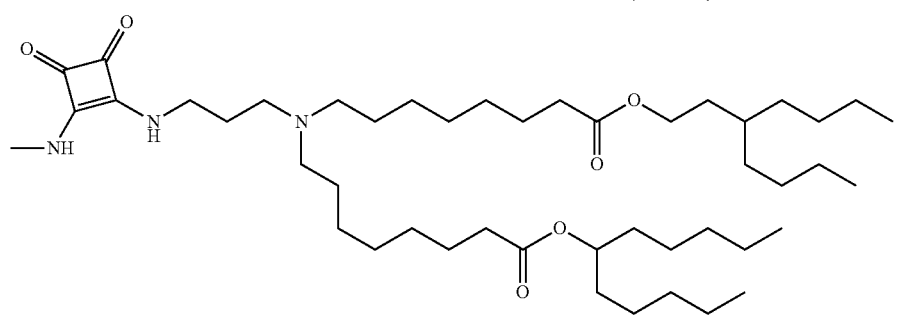

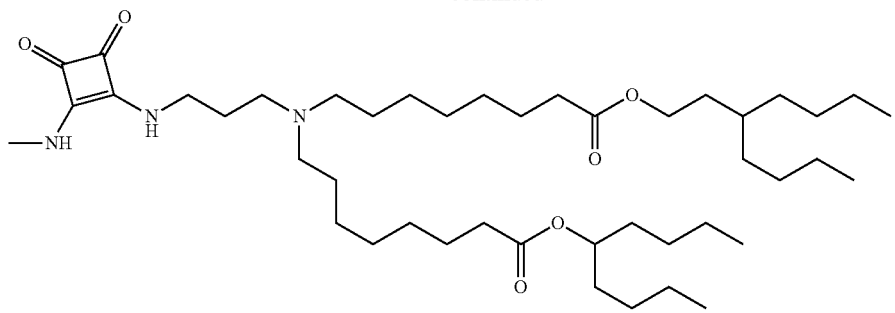
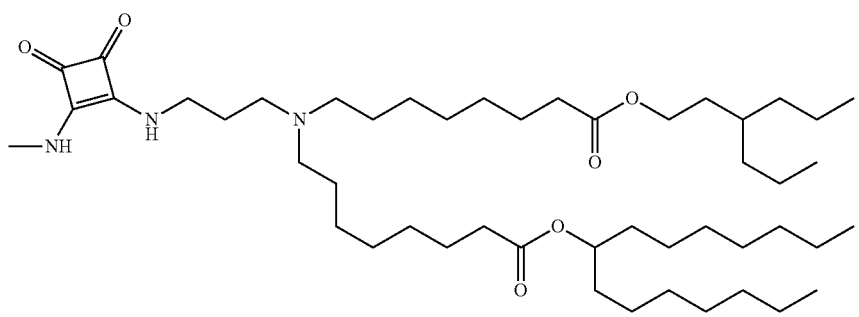
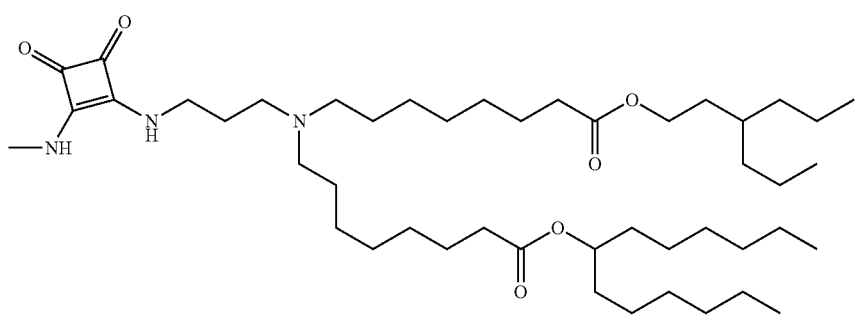
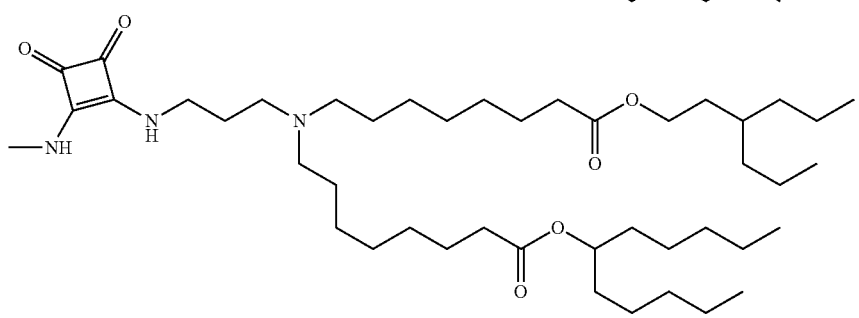
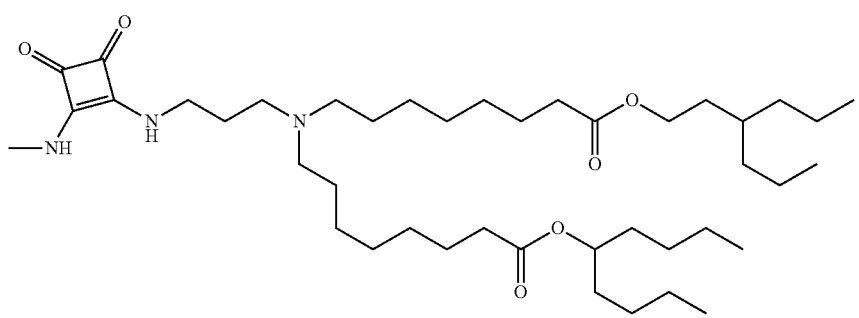

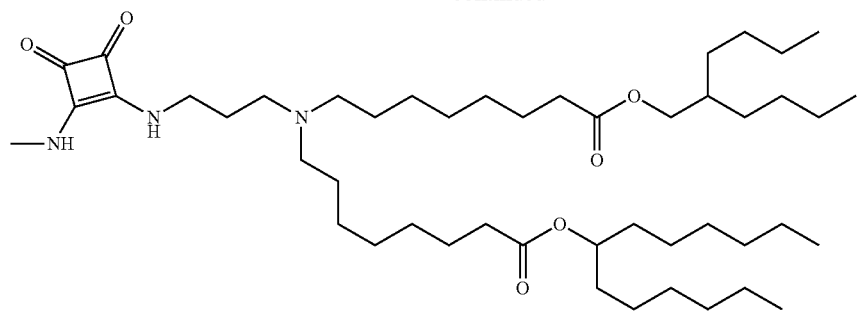
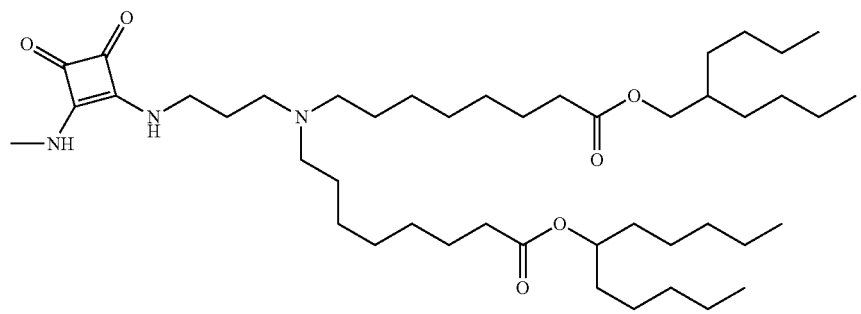
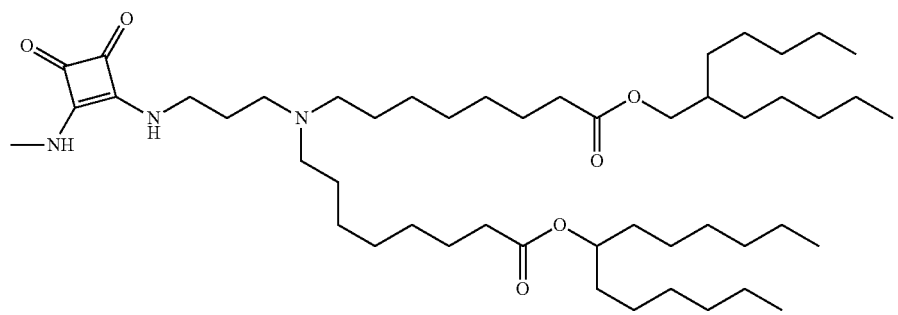
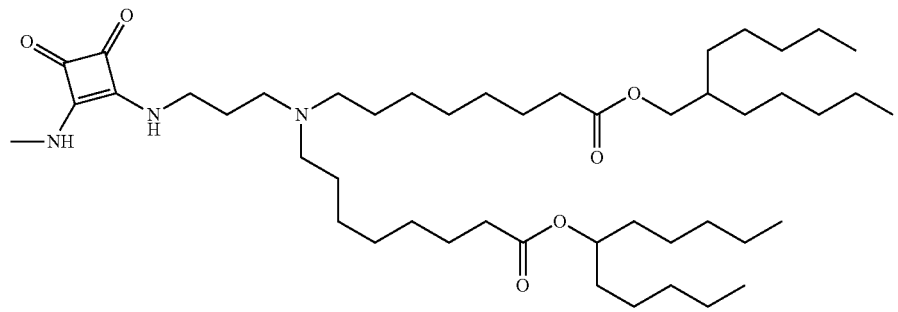
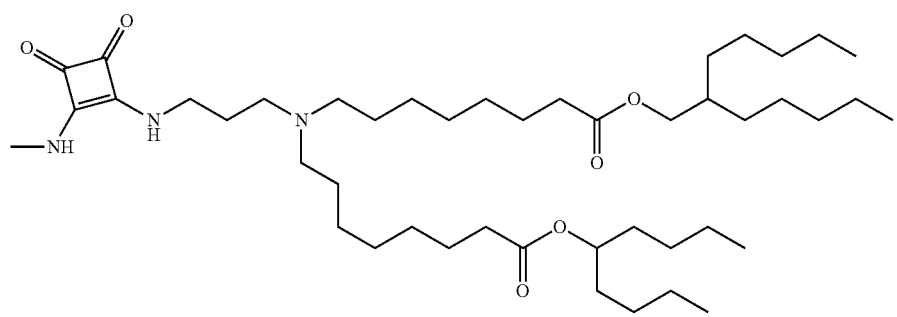

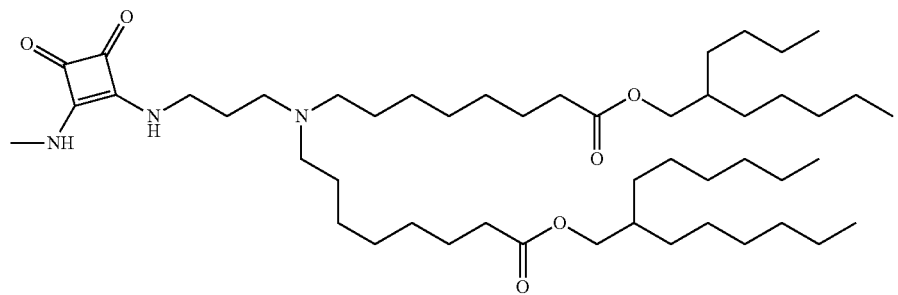
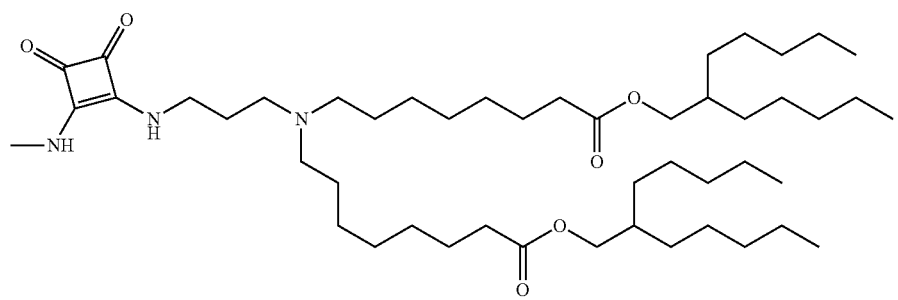
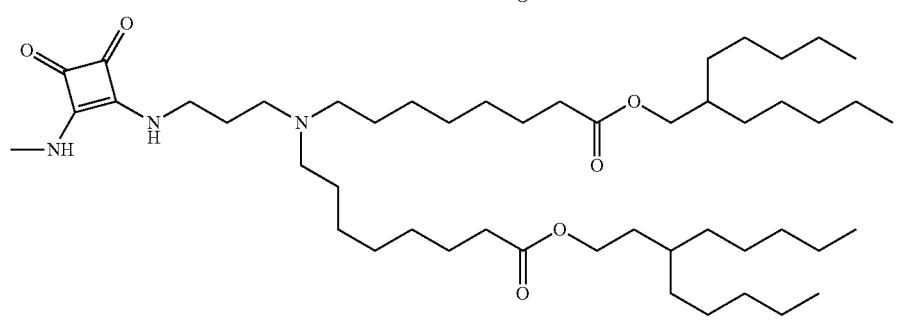
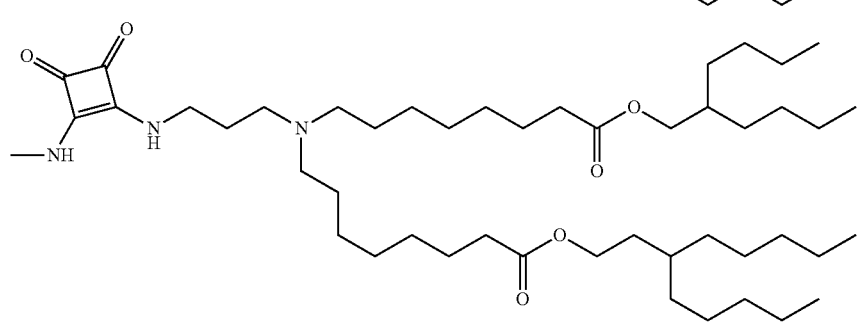
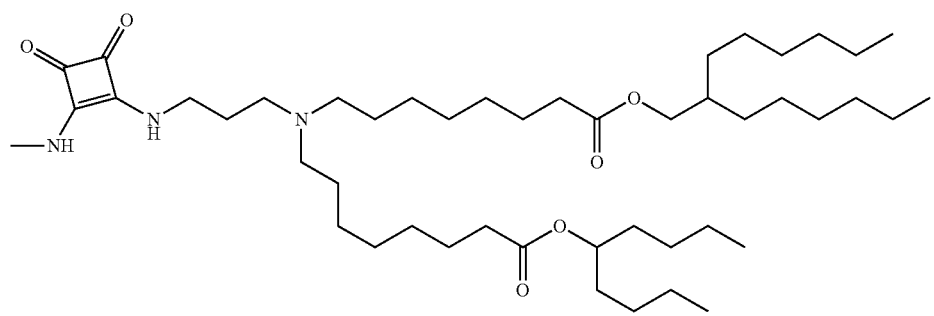

-continued

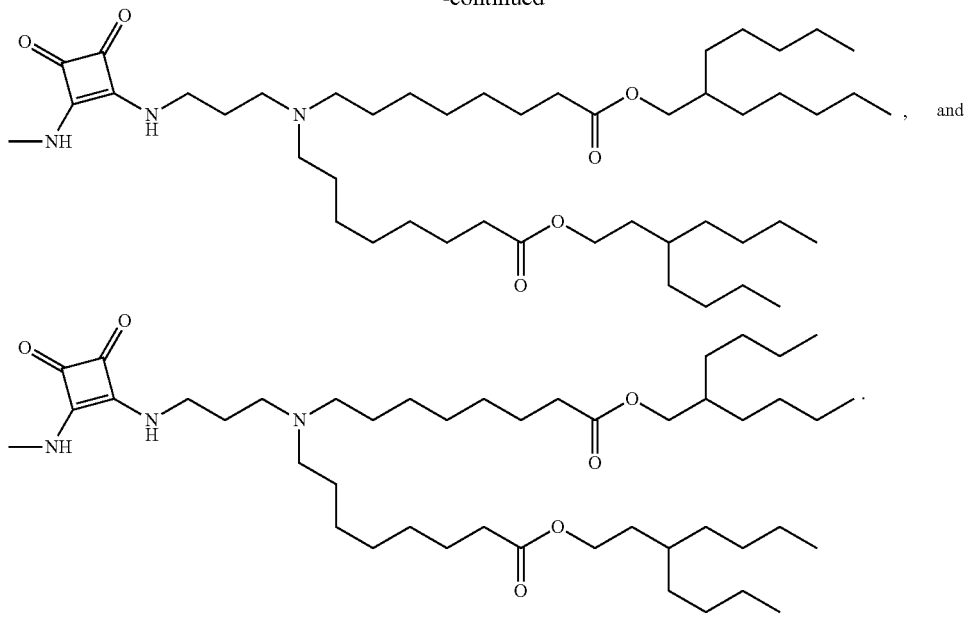

, and

Embodiment 115. An empty lipid nanoparticle (empty LNP) comprising a compound of any one of the preceding embodiments, a phospholipid, a structural lipid, and a PEG lipid.

Embodiment 116. A loaded lipid nanoparticle (loaded LNP) comprising a compound of any one of the preceding embodiments, a phospholipid, a structural lipid, a PEG lipid, and one or more therapeutic and/or prophylactic agents.

Embodiment 117. The empty LNP or loaded LNP of any one of the preceding embodiments, comprising the compound in an amount from about 40% to about 60%.

Embodiment 118. The empty LNP or loaded LNP of any one of the preceding embodiments, comprising the phospholipid in an amount from about 0% to about 20%.

Embodiment 119. The empty LNP or loaded LNP of any one of the preceding embodiments, comprising the structural lipid in an amount from about 30% to about 50%.

Embodiment 120. The empty LNP or loaded LNP of any one of the preceding embodiments, comprising the PEG lipid in an amount from about 0% to about 5%.

Embodiment 121. The empty LNP or loaded LNP of any one of the preceding embodiments, comprising about 40 mol % to about 60 mol % of the compound of any one of the preceding embodiments, about 0 mol % to about 20 mol % phospholipid, about 30 mol % to about 50 mol % structural lipid, and about 0 mol % to about 5 mol % PEG lipid.

Embodiment 122. The empty LNP or loaded LNP of any one of the preceding embodiments, comprising about 30 mol % to about 60 mol % of the compound of any one of the preceding embodiments, about 0 mol % to about 30 mol % phospholipid, about 18.5 mol % to about 48.5 mol % structural lipid, and about 0 mol % to about 10 mol % PEG lipid.

Embodiment 123. The loaded LNP of any one of the preceding embodiments, wherein the one or more therapeutic and/or prophylactic agents is a polynucleotide or a polypeptide. Embodiment 124. The loaded LNP of any one of the preceding embodiments, wherein the one or more therapeutic and/or prophylactic agents is a nucleic acid.

Embodiment 125. The loaded LNP of any one of the preceding embodiments, wherein the one or more therapeutic and/or prophylactic agents is selected from the group consisting of a ribonucleic acid (RNA) and a deoxyribonucleic acid (DNA).

Embodiment 126. The loaded LNP of any one of the preceding embodiments, wherein the DNA is selected from the group consisting of a double-stranded DNA, a single-stranded DNA (ssDNA), a partially double-stranded DNA, a triple stranded DNA, and a partially triple-stranded DNA.

Embodiment 127. The loaded LNP of any one of the preceding embodiments, wherein the DNA is selected from the group consisting of a circular DNA, a linear DNA, and mixtures thereof.

Embodiment 128. The loaded LNP of any one of the preceding embodiments, wherein the one or more therapeutic and/or prophylactic agents is selected from the group consisting of a plasmid expression vector, a viral expression vector, and mixtures thereof.

Embodiment 129. The loaded LNP of any one of the preceding embodiments, wherein the one or more therapeutic and/or prophylactic agents is a RNA.

Embodiment 130. The loaded LNP of any one of the preceding embodiments, wherein the RNA is selected from the group consisting of a single-stranded RNA, a double-stranded RNA (dsRNA), a partially double-stranded RNA, and mixtures thereof.

Embodiment 131. The loaded LNP of any one of the preceding embodiments, wherein the RNA is selected from the group consisting of a circular RNA, a linear RNA, and mixtures thereof.

Embodiment 132. The loaded LNP of any one of the preceding embodiments, wherein the RNA is selected from the group consisting of is selected from the group consisting of a short interfering RNA (siRNA), an asymmetrical interfering RNA (aiRNA), a RNA interference (RNAi) molecule, a microRNA (miRNA), an antagomir, an antisense RNA, a ribozyme, a Dicer-substrate RNA (dsRNA), a small hairpin RNA (shRNA), a messenger RNA (mRNA), and mixtures thereof.

Embodiment 133. The loaded LNP of any one of the preceding embodiments, wherein the RNA is an mRNA.

Embodiment 134. The loaded LNP of any one of the preceding embodiments, wherein the mRNA is a modified mRNA (mmRNA).

Embodiment 135. The loaded LNP of any one of the preceding embodiments, wherein the mRNA incorporates a micro-RNA binding site (miR binding site).

Embodiment 136. The loaded LNP of any one of the preceding embodiments, wherein the mRNA includes one or more of a stem loop, a chain terminating nucleoside, a polyA sequence, a polyadenylation signal, and/or a 5' cap structure.

Embodiment 137. The empty LNP or loaded LNP of any one of the preceding embodiments, wherein the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine,1,2-dioleoyl-sn-glycero-3-phosphoethanola mine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

Embodiment 138. The empty LNP or loaded LNP of any one of the preceding embodiments, wherein the phospholipid is 1,2-distearoyl-sn-glycero-3-phosphocholine (DSPC).

Embodiment 139. The empty LNP or loaded LNP of any one of the preceding embodiments, wherein the structural lipid is selected from the group consisting of cholesterol, fecosterol, sitosterol, ergosterol, campesterol, stigmasterol, brassicasterol, tomatidine, ursolic acid, alpha-tocopherol, and mixtures thereof.

Embodiment 140. The empty LNP or loaded LNP of any one of the preceding embodiments, wherein the structural lipid is

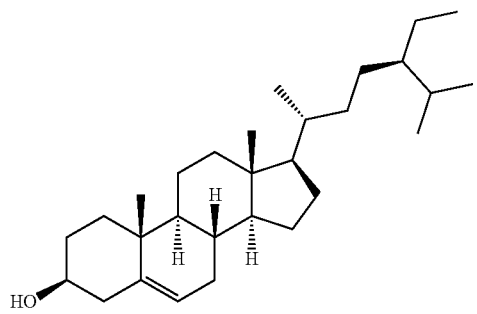

(SL-1)

or a salt thereof.

Embodiment 141. The empty LNP or loaded LNP of any one of the preceding embodiments, wherein the structural lipid is cholesterol:

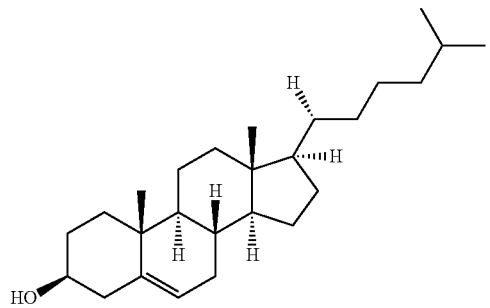

or a salt thereof.

Embodiment 142. The empty LNP or loaded LNP of any one of the preceding embodiments, wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, and a PEG-modified dialkylglycerol, and mixtures thereof.

Embodiment 143. The empty LNP or loaded LNP of any one of the preceding embodiments, wherein the PEG lipid is selected from the group consisting of 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

Embodiment 144. The empty LNP or loaded LNP of any one of the preceding embodiments, wherein the PEG lipid is PEG-DMG.

Embodiment 145. The empty LNP or loaded LNP of any one of the preceding embodiments, wherein the PEG lipid is a compound of Formula (PL-I):

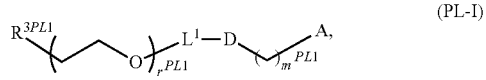

(PL-I)

or a salt thereof, wherein:

$R^{3PL1}$ is $-OR^{OPL1}$.

$R^{OPL1}$ is hydrogen, optionally substituted alkyl, or an oxygen protecting group;

$r^{PL1}$ is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, N($R^{NPL1}$), S, C(O), C(O)N($R^{NPL1}$), $NR^{NPL1}C(O)$, C(O)O, OC(O), OC(O)O, OC(O)N($R^{NPL1}$), $NR^{NPL1}C(O)O$, or $NR^{NPL1}C(O)N(R^{NPL1})$;

D is a moiety obtained by click chemistry or a moiety cleavable under physiological conditions;

$m^{PL1}$ is 0, 1, 2, 3, 4, 5, 6, 7, 8, 9, or 10;

A is of the formula:

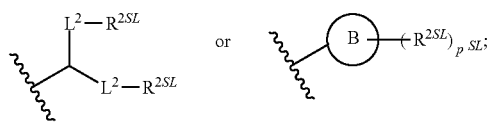

each instance of of $L^2$ is independently a bond or optionally substituted $C_{1-6}$ alkylene, wherein one methylene unit of the optionally substituted $C_{1-6}$ alkylene is optionally replaced with O, N($R^{NPL1}$), S, C(O), C(O)N($R^{NPL1}$), $NR^{NPL1}C(O)$, C(O)O, OC(O), OC(O)O, OC(O)N($R^{NPL1}$), $NR^{NPL1}C(O)O$, or $NR^{NPL1}C(O)N(R^{NPL1})$;

each instance of $R^{2SL}$ is independently optionally substituted $C_{1-30}$ alkyl, optionally substituted $C_{1-30}$ alkenyl, or optionally substituted $C_{1-30}$ alkynyl; optionally wherein one or more methylene units of $R^{2SL}$ are independently replaced with optionally substituted carbocyclylene, optionally substituted heterocyclylene, optionally substituted arylene, optionally substituted heteroarylene, N($R^{NPL1}$), O, S, C(O), C(O)N($R^{NPL1}$), $NR^{NPL1}C(O)$, $NR^{NPL1}C(O)N(R^{NPL1})$, C(O)O, OC(O), OC(O)O, OC(O)N($R^{NPL1}$), $NR^{NPL1}C(O)O$, C(O)S, SC(O), C(=$NR^{NPL1}$), —C(=$NR^{NPL1}$)N($R^{NPL1}$), $NR^{NPL1}C(=NR^{NPL1})$, $NR^{NPL1}C(=NR^{NPL1})N(R^{NPL1})$, C(S), C(S)N($R^{NPL1}$), $NR^{NPL1}C(S)$ $NR^{NPL1}C(S)N(R^{NPL1})$, S(O), OS(O), S(O)O, OS(O)O, S(O)$_2$, S(O)$_2$O, OS(O)$_2$O, N($R^{NPL1}$)S(O) S(O)N($R^{NPL1}$), N($R^{NPL1}$)S(O)N($R^{NPL1}$), OS(O)N($R^{NPL1}$), N($R^{NPL1}$)S(O)O, (O)$_2$, N($R^{NPL1}$)S(O)$_2$, S(O)$_2$N($R^{NPL1}$), N($R^{NPL1}$)S(O)$_2$N($R^{NPL1}$) OS(O)$_2$N ($R^{NPL1}$), or N($R^{NPL1}$)S(O)$_2$O;

each instance of $R^{NPL1}$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and $p^{SL}$ is 1 or 2.

Embodiment 146. The empty LNP or loaded LNP of any one of the preceding embodiments, wherein the PEG lipid is a compound of Formula (PL-I—OH):

(PL-I—OH), or a salt thereof.

Embodiment 147. The empty LNP or loaded LNP of any one of the preceding embodiments, wherein the PEG lipid is a compound of Formula (PL-II-OH):

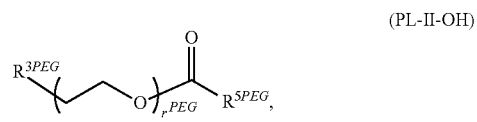

(PL-II-OH)

or a salt or isomer thereof, wherein:

$R^{3PEG}$ is $-OR^O$;

$R^O$ is hydrogen, $C_{1-6}$ alkyl or an oxygen protecting group;

r PEG is an integer between 1 and 100;

$R^{5PEG}$ is $C_{10-40}$ alkyl, $C_{10-40}$ alkenyl, or $C_{10-40}$ alkynyl; and optionally one or more methylene groups of $R^{5PEG}$ are independently replaced with $C_{3-10}$ carbocyclylene, 4 to 10 membered heterocyclylene, $C_{6-10}$ arylene, 4 to 10 membered heteroarylene, —N($R^{NPEG}$)—, —O—, —S—, —C(O)—, —C(O)N($R^{NPEG}$)—, —$NR^{NPEG}$C(O)—, —$NR^{NPEG}$C(O)N ($R^{NPEG}$)—, —C(O)O—, —OC(O)—, —OC(O)O—, —OC (O)N($R^{NPEG}$)—, —$NR^{NPEG}$C(O)O—, —C(O)S—, —SC (O)—, —C(=$NR^{NPEG}$)—, —C(=$NR^{NPEG}$)N($R^{NPEG}$)—, —$NR^{NPEG}$C(=$NR^{NPEG}$)—, —$NR^{NPEG}$C(=$NR^{NPEG}$)N ($R^{NPEG}$)—, —C(S)—, —C(S)N($R^{NPEG}$)—, —$NR^{NPEG}$C (S)—, —$NR^{NPEG}$C(S)N($R^{NPEG}$)—, —S(O)—, —OS(O)—, —S(O)O—, —OS(O)O—, —OS(O)$_2$—, —S(O)$_2$O—, —OS(O)$_2$O—, —N($R^{NPEG}$)S(O)—, —S(O)N($R^{NPEG}$)—, —N($R^{NPEG}$)S(O)N($R^{NPEG}$)—, —OS(O)N($R^{NPEG}$)—, —N($R^{NPEG}$)S(O)O—, —S(O)$_2$—, —N($R^{NPEG}$)S(O)$_2$—, —S(O)$_2$N($R^{NPEG}$)—, —N($R^{NPEG}$)S(O)$_2$N($R^{NPEG}$)—, —OS(O)$_2$N($R^{NPEG}$)—, or —N($R^{NPEG}$)S(O)$_2$O—; and each instance of $R^{NPEG}$ is independently hydrogen, $C_{1-6}$ alkyl, or a nitrogen protecting group.

Embodiment 148. The empty LNP or loaded LNP of any one of the preceding embodiments, wherein in the PEG lipid of Formula (PL-II-OH), r is an integer between 40 and 50.

Embodiment 149. The empty LNP or loaded LNP of any one of the preceding embodiments, wherein in the PEG lipid of Formula (PL-II-OH), r is 45.

Embodiment 150. The empty LNP or loaded LNP of any one of the preceding embodiments, wherein in the PEG lipid of Formula (PL-II-OH), $R^5$ is $C_{17}$ alkyl.

Embodiment 151. The empty LNP or loaded LNP of any one of the preceding embodiments, wherein the PEG lipid is a compound of Formula (PL-II):

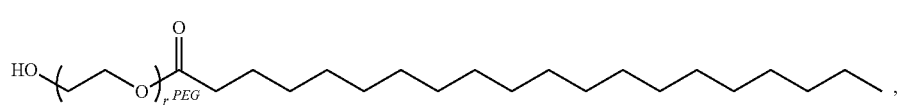

(PL-II)

wherein $r^{PEG}$ is an integer between 1 and 100.

Embodiment 152. The empty LNP or loaded LNP of any one of the preceding embodiments, wherein the PEG lipid is a compound of Formula (PEG-1):

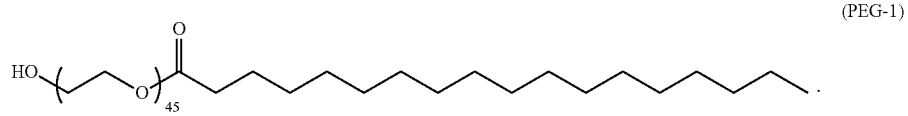

(PEG-1)

Embodiment 153. The empty LNP or loaded LNP of any one of the preceding embodiments, wherein the PEG lipid is a compound of Formula (PL-III):

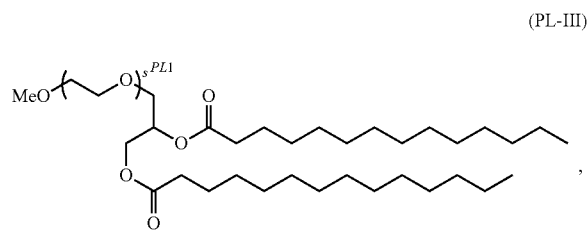

(PL-III)

or a salt or isomer thereof, wherein $s^{PL1}$ is an integer between 1 and 100.

Embodiment 154. The empty LNP or loaded LNP of any one of the preceding embodiments, wherein the PEG lipid is a compound of following formula:

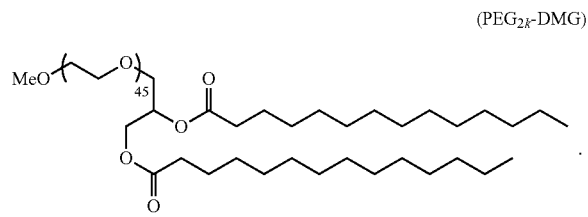

(PEG$_{2k}$-DMG)

Embodiment 155. An empty lipid nanoparticle (empty LNP) comprising a compound of any one of the preceding embodiments, a phospholipid, a structural lipid, and a PEG lipid, wherein the phospholipid is DSPC and the structural lipid is cholesterol.

Embodiment 156. An empty lipid nanoparticle (empty LNP) comprising a compound of any one of the preceding embodiments, a phospholipid, a structural lipid, and a PEG lipid, wherein the structural lipid is cholesterol and the PEG lipid is PEG$_{2k}$-DMG.

Embodiment 157. An empty lipid nanoparticle (empty LNP) comprising a compound of any one of the preceding embodiments, a phospholipid, a structural lipid, and a PEG lipid, wherein the structural lipid is cholesterol and the PEG lipid is PEG-1.

Embodiment 158. An empty lipid nanoparticle (empty LNP) comprising a compound of any one of the preceding embodiments, a phospholipid, a structural lipid, and a PEG lipid, wherein the phospholipid is DSPC and the PEG lipid is PEG$_{2k}$-DMG.

Embodiment 159. An empty lipid nanoparticle (empty LNP) comprising a compound of any one of the preceding embodiments, a phospholipid, a structural lipid, and a PEG lipid, wherein the phospholipid is DSPC and the PEG lipid is PEG-1.

Embodiment 160. An empty lipid nanoparticle (empty LNP) comprising a compound of any one of the preceding embodiments, a phospholipid, a structural lipid, and a PEG lipid, wherein the phospholipid is DSPC, the structural lipid is cholesterol, and the PEG lipid is PEG$_{2k}$-DMG.

Embodiment 161. An empty lipid nanoparticle (empty LNP) comprising a compound of any one of the preceding embodiments, a phospholipid, a structural lipid, and a PEG lipid, wherein the phospholipid is DSPC, the structural lipid is cholesterol, and the PEG lipid is PEG-1.

Embodiment 162. A loaded lipid nanoparticle (loaded LNP) comprising a compound of any one of the preceding embodiments, a phospholipid, a structural lipid, and a PEG lipid, wherein the phospholipid is DSPC and the structural lipid is cholesterol, and one or more therapeutic and/or prophylactic agents.

Embodiment 163. A loaded lipid nanoparticle (loaded LNP) comprising a compound of any one of the preceding embodiments, a phospholipid, a structural lipid, and a PEG lipid, wherein the structural lipid is cholesterol and the PEG lipid is PEG$_{2k}$-DMG, and one or more therapeutic and/or prophylactic agents.

Embodiment 164. A loaded lipid nanoparticle (loaded LNP) comprising a compound of any one of the preceding embodiments, a phospholipid, a structural lipid, and a PEG lipid, wherein the structural lipid is cholesterol and the PEG lipid is PEG-1, and one or more therapeutic and/or prophylactic agents.

Embodiment 165. A loaded lipid nanoparticle (loaded LNP) comprising a compound of any one of the preceding embodiments, a phospholipid, a structural lipid, and a PEG lipid, wherein the phospholipid is DSPC and the PEG lipid is PEG$_{2k}$-DMG, and one or more therapeutic and/or prophylactic agents.

Embodiment 166. A loaded lipid nanoparticle (loaded LNP) comprising a compound of any one of the preceding embodiments, a phospholipid, a structural lipid, and a PEG lipid, wherein the phospholipid is DSPC and the PEG lipid is PEG-1, and one or more therapeutic and/or prophylactic agents.

Embodiment 167. A loaded lipid nanoparticle (loaded LNP) comprising a compound of any one of the preceding embodiments, a phospholipid, a structural lipid, and a PEG lipid, wherein the phospholipid is DSPC, the structural lipid is cholesterol, and the PEG lipid is PEG$_{2k}$-DMG, and one or more therapeutic and/or prophylactic agents.

Embodiment 168. A loaded lipid nanoparticle (loaded LNP) comprising a compound of any one of the preceding embodiments, a phospholipid, a structural lipid, and a PEG lipid, wherein the phospholipid is DSPC, the structural lipid is cholesterol, and the PEG lipid is PEG-1, and one or more therapeutic and/or prophylactic agents.

Embodiment 169. The empty LNP or loaded LNP of any one of the preceding embodiments, comprising DSPC in an amount from about 0% to about 20%.

Embodiment 170. The empty LNP or loaded LNP of any one of the preceding embodiments, comprising cholesterol in an amount from about 30% to about 50%.

Embodiment 171. The empty LNP or loaded LNP of any one of the preceding embodiments, comprising $PEG_{2k}$-DMG in an amount from about 0% to about 5%.

Embodiment 172. The empty LNP or loaded LNP of any one of the preceding embodiments, comprising PEG-1 in an amount from about 0% to about 5%.

Embodiment 173. The empty LNP or loaded LNP of any one of the preceding embodiments, comprising about 40 mol % to about 60 mol % of the compound of any one of the preceding embodiments, about 0 mol % to about 20 mol % DSPC, about 30 mol % to about 50 mol % cholesterol, and about 0 mol % to about 5 mol % $PEG_{2k}$-DMG.

Embodiment 174. The empty LNP or loaded LNP of any one of the preceding embodiments, comprising about 40 mol % to about 60 mol % of the compound of any one of the preceding embodiments, about 0 mol % to about 20 mol % DSPC, about 30 mol % to about 50 mol % cholesterol, and about 0 mol % to about 5 mol % PEG-1.

Embodiment 175. The loaded LNP of any one of the preceding embodiments the encapsulation efficiency of the therapeutic and/or prophylactic agent is between 80% and 100%.

Embodiment 176. The loaded LNP of any one of the preceding embodiments, wherein the wt/wt ratio of the lipid component to the mRNA is from about 10:1 to about 60:1.

Embodiment 177. The loaded LNP of any one of the preceding embodiments, wherein the wt/wt ratio of the lipid component to the mRNA is about 20:1.

Embodiment 178. The loaded LNP of any one of the preceding embodiments, wherein the N:P ratio is from about 5:1 to about 8:1.

Embodiment 179. A pharmaceutical composition comprising the loaded LNP of any one of the preceding embodiments and a pharmaceutically acceptable carrier.

Embodiment 180. The pharmaceutical composition of any one of the preceding embodiments, further comprising a cryoprotectant, a buffer, or a combination thereof.

Embodiment 181. The pharmaceutical composition of any one of the preceding embodiments, wherein the cryoprotectant comprises sucrose.

Embodiment 182. The pharmaceutical composition of any one of the preceding embodiments, wherein the cryoprotectant comprises sodium acetate.

Embodiment 183. The pharmaceutical composition of any one of the preceding embodiments, wherein the cryoprotectant comprises sucrose and sodium acetate.

Embodiment 184. The pharmaceutical composition of any one of the preceding embodiments, wherein the buffer is selected from the group consisting of an acetate buffer, a citrate buffer, a phosphate buffer, and a tris buffer.

Embodiment 185. A method of delivering a therapeutic and/or prophylactic agent to a cell within a subject, the method comprising administering to the subject the loaded LNP of any one of the preceding embodiments.

Embodiment 186. A method of specifically delivering a therapeutic and/or prophylactic agent to an organ of a subject, the method comprising administering to the subject the loaded LNP of any one of the preceding embodiments.

Embodiment 187. A method for the enhanced delivery of a therapeutic and/or prophylactic to a target tissue of a subject, the method comprising administering to the subject the loaded LNP of any one of the preceding embodiments.

Embodiment 188. A method of producing a polypeptide of interest in a cell within a subject, the method comprising administering to the subject the loaded LNP of any one of the preceding embodiments.

Embodiment 189. A method of treating a disease or disorder in a subject in need thereof, the method comprising administering to the subject a therapeutically effective amount of the loaded LNP of any one of the preceding embodiments.

Embodiment 190. Use of a loaded LNP of any one of the preceding embodiments, in the manufacture of a medicament for delivering a therapeutic and/or prophylactic agent to a cell within a subject.

Embodiment 191. Use of a loaded LNP of any one of the preceding embodiments, in the manufacture of a medicament for specifically delivering a therapeutic and/or prophylactic agent to an organ of a subject.

Embodiment 192. Use of a loaded LNP of any one of the preceding embodiments, in the manufacture of a medicament for the enhanced delivery of a therapeutic and/or prophylactic to a target tissue of a subject.

Embodiment 193. Use of a loaded LNP of any one of the preceding embodiments, in the manufacture of a medicament for producing a polypeptide of interest in a cell within a subject.

Embodiment 194. Use of a loaded LNP of any one of the preceding embodiments, in the manufacture of a medicament for treating a disease or disorder in a subject in need thereof.

Embodiment 195. A loaded LNP of any one of the preceding embodiments, for use in delivering a therapeutic and/or prophylactic agent to a cell within a subject, wherein the delivering comprises administering a therapeutically effective amount of the loaded LNP to the subject.

Embodiment 196. A loaded LNP of any one of the preceding embodiments, for use in specifically delivering a therapeutic and/or prophylactic agent to an organ of a subject, wherein the delivering comprises administering a therapeutically effective amount of the loaded LNP to the subject.

Embodiment 197. A loaded LNP of any one of the preceding embodiments, for use in the enhanced delivery of a therapeutic and/or prophylactic to a target tissue of a subject, wherein the use comprises administering to the subject the loaded LNP of any one of the preceding embodiments.

Embodiment 198. A loaded LNP of any one of the preceding embodiments, for use in producing a polypeptide of interest in a cell within a subject, the use comprises administering to the subject the loaded LNP of any one of the preceding embodiments.

Embodiment 199. A loaded LNP of any one of the preceding embodiments, for use in the treatment of a disease or disorder in a subject in need thereof, wherein the treatment comprises administering a therapeutically effective amount of the loaded LNP to a subject.

Embodiment 200. A method of delivering a therapeutic and/or prophylactic agent to a cell within a subject, the method comprising administering to the subject the pharmaceutical composition of any one of the preceding embodiments.

Embodiment 201. A method of specifically delivering a therapeutic and/or prophylactic agent to an organ of a subject, the method comprising administering to the subject the pharmaceutical composition of any one of the preceding embodiments.

Embodiment 202. A method for the enhanced delivery of a therapeutic and/or prophylactic to a target tissue of a subject, the method comprising administering to the subject the pharmaceutical composition of any one of the preceding embodiments.

Embodiment 203. A method of producing a polypeptide of interest in a cell within a subject, the method comprising administering to the subject the loaded LNP of any one of the preceding embodiments.

Embodiment 204. A method of treating a disease or disorder in a subject in need thereof, the method comprising administering to the subject a therapeutically effective amount of the pharmaceutical composition of any one of the preceding embodiments.

Embodiment 205. Use of a pharmaceutical composition of any one of the preceding embodiments, in the manufacture of a medicament for delivering a therapeutic and/or prophylactic agent to a cell within a subject.

Embodiment 206. Use of a pharmaceutical composition of any one of the preceding embodiments, in the manufacture of a medicament for specifically delivering a therapeutic and/or prophylactic agent to an organ of a subject.

Embodiment 207. Use of a pharmaceutical composition of any one of the preceding embodiments, in the manufacture of a medicament for the enhanced delivery of a therapeutic and/or prophylactic to a target tissue of a subject, the method comprising administering to the subject the pharmaceutical composition of any one of the preceding embodiments.

Embodiment 208. Use of a pharmaceutical composition of any one of the preceding embodiments, in the manufacture of a medicament for producing a polypeptide of interest in a cell within a subject.

Embodiment 209. Use of a pharmaceutical composition of any one of the preceding embodiments, in the manufacture of a medicament for treating a disease or disorder in a subject in need thereof.

Embodiment 210. A pharmaceutical composition of any one of the preceding embodiments, for use in delivering a therapeutic and/or prophylactic agent to a cell within a subject, wherein the delivering comprises administering a therapeutically effective amount of the pharmaceutical composition to the subject.

Embodiment 211. A pharmaceutical composition of any one of the preceding embodiments, for use in specifically delivering a therapeutic and/or prophylactic agent to an organ of a subject, wherein the delivering comprises administering a therapeutically effective amount of the pharmaceutical composition to the subject.

Embodiment 212. A pharmaceutical composition of any one of the preceding embodiments, for use in the enhanced delivery of a therapeutic and/or prophylactic to a target tissue of a subject, wherein the use comprises administering to the subject the pharmaceutical composition of any one of the preceding embodiments.

Embodiment 213. A pharmaceutical composition of any one of the preceding embodiments, for use in producing a polypeptide of interest in a cell within a subject, the use comprises administering to the subject the pharmaceutical composition of any one of the preceding embodiments Embodiment 214. A pharmaceutical composition of any one of the preceding embodiments, for use in the treatment of a disease or disorder in a subject in need thereof, wherein the treatment comprises administering a therapeutically effective amount of the pharmaceutical composition to a subject.

Embodiment 215. The method, use, or loaded LNP or pharmaceutical composition for use, of any one of the preceding embodiments, wherein the organ is selected from the group consisting of liver, kidney, lung, and spleen.

Embodiment 216. The method, use, or loaded LNP or pharmaceutical composition for use, of any one of the preceding embodiments, wherein the target tissue is selected from the group consisting of liver, kidney, lung, and spleen.

Embodiment 217. The method or loaded LNP or pharmaceutical composition for use of any one of the preceding embodiments, wherein the administering is performed parenterally.

Embodiment 218. The method or loaded LNP or pharmaceutical composition for use wherein the administering is performed intramuscularly, intradermally, subcutaneously, and/or intravenously.

Embodiment 219. The use of any one of the preceding claims, wherein the medicament is for parenteral administration.

Embodiment 220. The use of any one of the preceding claims, wherein the medicament is for intramuscular, intradermal, subcutaneous, and/or intravenous administration.

Embodiment 221. The method, use, or loaded LNP or pharmaceutical composition for use, of any one of the preceding embodiments, wherein the subject is human.

EQUIVALENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A compound of Formula (A-a):

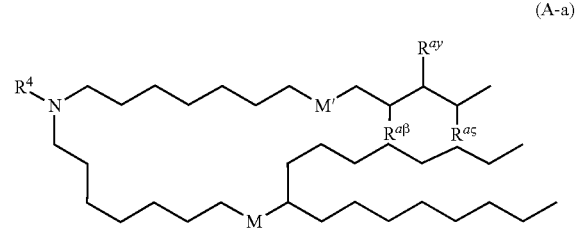

(A-a)

or its N-oxide, or a salt or isomer thereof, wherein:
  $R^{\alpha\beta}$, $R^{\alpha\gamma}$ and $R^{\alpha\delta}$ are each independently selected from the group consisting of H, $C_{2-12}$ alkyl, and $C_{2-12}$ alkenyl, wherein at least one of $R^{\alpha\beta}$, $R^{\alpha\gamma}$, and $R^{\alpha\delta}$ is selected from the group consisting of $C_{2-12}$ alkyl and $C_{2-12}$ alkenyl;
  $R^4$ is selected from the group consisting of —(CH$_2$)$_2$OH, —(CH$_2$)$_3$OH, —(CH$_2$)$_4$OH, and —(CH$_2$)$_5$OH;
  M and M' are each independently selected from the group consisting of —C(O)O— and —OC(O)—; and
  R' is a $C_{1-12}$ alkyl or $C_{2-12}$ alkenyl.

2. A compound of Formula (A-a2):

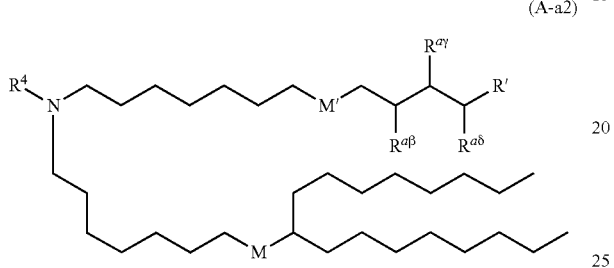

(A-a2)

or its N-oxide, or a salt or isomer thereof, wherein $R^{\alpha\beta}$ and $R^{\alpha\delta}$ are each independently selected from the group consisting of H, $C_{2-12}$ alkyl, and $C_{2-12}$ alkenyl; and $R^{\alpha\gamma}$ is a $C_2$ alkyl, $C_3$ alkyl, $C_4$ alkyl, $C_5$ alkyl, or $C_6$ alkyl;
  $R^4$ is —(CH$_2$)$_2$OH or

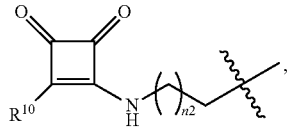

wherein
  $R^{10}$ is N(R)$_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;
  M and M' are each independently selected from the group consisting of —C(O)O— and —OC(O)—; and
  R' is a $C_{1-12}$ alkyl or $C_{2-12}$ alkenyl.

3. The compound of claim 1, wherein $R^4$ is —(CH$_2$)$_2$OH.

4. The compound of claim 1, wherein M' and M are each —C(O)O—.

5. The compound of claim 1, wherein R' is a $C_3$ or $C_4$ alkyl.

6. The compound of claim 1, wherein $R^{\alpha\gamma}$ is a $C_{2-6}$ alkyl and R' is a $C_3$ alkyl.

7. The compound of claim 1, wherein $R^{\alpha\beta}$ and $R^{\alpha\delta}$ are each H.

8. The compound of claim 1, wherein $R^{\alpha\gamma}$ is a $C_2$-alkyl, $C_3$-alkyl, or a $C_4$ alkyl.

9. An empty lipid nanoparticle (empty LNP) comprising a compound of claim 1, a phospholipid, a structural lipid, and a PEG lipid.

10. The empty LNP of claim 9, comprising about 40 mol % to about 60 mol % said compound, about 0 mol % to about 20 mol % phospholipid, about 30 mol % to about 50 mol % structural lipid, and about 0 mol % to about 5 mol % PEG lipid.

11. The empty LNP of claim 9, wherein:
  (i) the phospholipid is selected from the group consisting of:
    1,2-dilinoleoyl-sn-glycero-3-phosphocholine (DLPC),
    1,2-dimyristoyl-sn-glycero-phosphocholine (DMPC),
    1,2-dioleoyl-sn-glycero-3-phosphocholine (DOPC),
    1,2-dipalmitoyl-sn-glycero-3-phosphocholine (DPPC),
    1,2-distearoyl-sn-glycero-3-phosphocholine (DSPC),
    1,2-diundecanoyl-sn-glycero-phosphocholine (DUPC),
    1-palmitoyl-2-oleoyl-sn-glycero-3-phosphocholine (POPC),
    1,2-di-O-octadecenyl-sn-glycero-3-phosphocholine (18:0 Diether PC),
    1-oleoyl-2-cholesterylhemisuccinoyl-sn-glycero-3-phosphocholine (OChemsPC),
    1-hexadecyl-sn-glycero-3-phosphocholine (C16 Lyso PC),
    1,2-dilinolenoyl-sn-glycero-3-phosphocholine,
    1,2-diarachidonoyl-sn-glycero-3-phosphocholine,
    1,2-didocosahexaenoyl-sn-glycero-3-phosphocholine,
    1,2-dioleoyl-sn-glycero-3-phosphoethanolamine (DOPE),
    1,2-diphytanoyl-sn-glycero-3-phosphoethanolamine (ME 16.0 PE),
    1,2-distearoyl-sn-glycero-3-phosphoethanolamine,
    1,2-dilinoleoyl-sn-glycero-3-phosphoethanolamine,
    1,2-dilinolenoyl-sn-glycero-3-phosphoethanolamine,
    1,2-diarachidonoyl-sn-glycero-3-phosphoethanolamine,
    1,2-didocosahexaenoyl-sn-glycero-3-phosphoethanolamine,
    1,2-dioleoyl-sn-glycero-3-phospho-rac-(1-glycerol) sodium salt (DOPG), sphingomyelin, and mixtures thereof,
  (ii) the structural lipid is selected from the group consisting of cholesterol, fecosterol, sitosterol, ergosterol, campesterol, stigmasterol, brassicasterol, and mixtures thereof;
  (iii) the PEG lipid is selected from the group consisting of a PEG-modified phosphatidylethanolamine, a PEG-modified phosphatidic acid, a PE(G-modified ceramide, a PEG-modified dialkylamine, a PEG-modified diacylglycerol, a PEG-modified dialkylglycerol, and mixtures thereof; and/or
  (iv) the PEG lipid is selected from PEG2k-DMG and PEG-1:

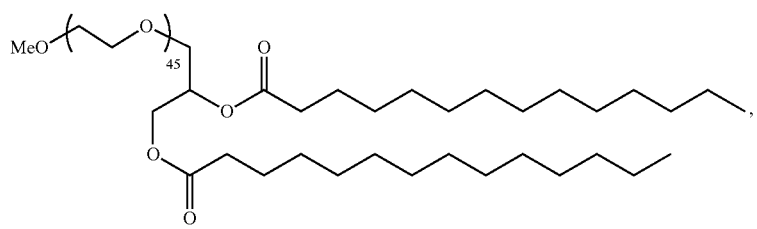

(PEG$_{2k}$-DMG)

(PEG-1)

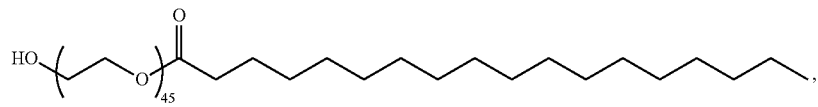

and mixtures thereof.

12. A loaded lipid nanoparticle (loaded LNP), which comprises the empty LNP of claim 9, and one or more therapeutic and/or prophylactic agents.

13. The loaded LNP of claim 12, wherein the one or more therapeutic and/or prophylactic agents is a nucleic acid.

14. The loaded LNP of claim 12, wherein the RNA is an mRNA.

15. A pharmaceutical composition comprising the loaded LNP of claim 12 and a pharmaceutically acceptable carrier.

16. A method of delivering a therapeutic and/or prophylactic agent to a cell within a subject, the method comprising administering to the subject the loaded LNP of claim 12.

17. A method of specifically delivering a therapeutic and/or prophylactic agent to an organ of a subject, the method comprising administering to the subject the loaded LNP of claim 12.

18. A method of producing a polypeptide of interest in a cell within a subject, the method comprising administering to the subject the loaded LNP of claim 12.

19. A method of treating a disease or disorder in a subject in need thereof, the method comprising administering to the subject a therapeutically effective amount of the loaded LNP of claim 12.

20. The method of claim 17, wherein:

(i) the organ is selected from the group consisting of liver, kidney, lung, and spleen; and/or (ii) the administering is performed parenterally, intramuscularly, intradermally, subcutaneously, and/or intravenously.

* * * * *